(12) United States Patent
Goldberg et al.

(10) Patent No.: US 11,345,666 B2
(45) Date of Patent: May 31, 2022

(54) PHENYL AND PYRIDINYL SUBSTITUTED IMIDAZOLES AS MODULATORS OF RORγT

(71) Applicant: Janssen Pharmaceutica NV, Beerse (BE)

(72) Inventors: Steven Goldberg, Carlsbad, CA (US); Connor L. Martin, San Diego, CA (US); Elizabeth G. Fennema, La Mesa, CA (US); David A. Kummer, San Diego, CA (US); Rachel T. Nishimura, San Diego, CA (US); Virginia M. Tanis, Vista, CA (US); Craig R. Woods, San Diego, CA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 16/442,864

(22) Filed: Jun. 17, 2019

(65) Prior Publication Data
US 2019/0382354 A1    Dec. 19, 2019

Related U.S. Application Data

(60) Provisional application No. 62/686,323, filed on Jun. 18, 2018.

(51) Int. Cl.
| C07D 233/54 | (2006.01) |
| C07D 233/90 | (2006.01) |
| C07D 401/04 | (2006.01) |

(52) U.S. Cl.
CPC ......... *C07D 233/90* (2013.01); *C07D 401/04* (2013.01)

(58) Field of Classification Search
CPC .................................................. C07D 233/54
See application file for complete search history.

(56) References Cited

U.S. PATENT DOCUMENTS

| 5,342,835 | A  | 8/1994  | Pepin et al. |
| 8,809,547 | B2 | 8/2014  | Bretschneider et al. |
| 10,369,146 | B2 | 8/2019  | Leonard et al. |
| 2005/0014805 | A1 | 1/2005  | Zhang et al. |
| 2005/0065189 | A1 | 3/2005  | Lange et al. |
| 2012/0245137 | A1 | 9/2012  | Pajouhesh |
| 2014/0163001 | A1 | 6/2014  | Yamamoto |
| 2015/0038350 | A1 | 2/2015  | Nishinaga et al. |
| 2015/0072890 | A1 | 3/2015  | James |
| 2015/0111870 | A1 | 4/2015  | Leonard |
| 2015/0266824 | A1 | 9/2015  | Beck |
| 2016/0120850 | A1 | 5/2016  | Goldberg et al. |
| 2016/0122326 | A1 | 5/2016  | Goldberg et al. |
| 2016/0122335 | A1 | 5/2016  | Goldberg et al. |
| 2016/0122336 | A1 | 5/2016  | Goldberg et al. |
| 2016/0304476 | A1 | 10/2016 | Aicher |
| 2016/0304505 | A1 | 10/2016 | Aicher |
| 2017/0253591 | A1 | 9/2017  | Yammamoto |
| 2017/0313691 | A1 | 11/2017 | Goldberg |
| 2019/0269134 | A1* | 9/2019 | Bayer .................. A01N 43/56 |
| 2019/0382349 | A1 | 12/2019 | Goldberg et al. |
| 2019/0382350 | A1 | 12/2019 | Goldberg et al. |
| 2019/0382354 | A1 | 12/2019 | Goldberg et al. |
| 2019/0382373 | A1 | 12/2019 | Goldberg et al. |

FOREIGN PATENT DOCUMENTS

| CL | 201102650 | 10/2011 |
| CL | 201200534 | 2/2012 |
| CL | 201803050 | 10/2018 |
| CL | 201901343 | 5/2019 |
| CN | 1033333168 | 10/2013 |
| CN | 103833672 | 6/2014 |
| CN | 104926733 | 9/2015 |
| EP | 360701 A1 | 3/1990 |
| EP | 2433938 | 3/2012 |
| EP | 2474543 | 7/2012 |
| EP | 2738170 | 6/2014 |
| JP | 2005507932 | 3/2005 |

(Continued)

OTHER PUBLICATIONS

Sanis Health Inc. Product Monograph. "ENALAPRIL: Enalapril Maleate." Revision Date Jun. 10, 2016. Accessed on Jul. 3, 2021. Available from: «https://pdf.hres.ca/dpd_pm/00035279.PDF». (Year: 2016).*

Angew. Chem. Int. Ed. Engl. 1982, 21, 567-583.

Barczyk, A., W. Pierzchala, et al. (2003). "Interleukin-17 in sputum correlates with airway hyperresponsiveness to methacholine." Respir Med 97(6): 726-33.

(Continued)

*Primary Examiner* — John S Kenyon
(74) *Attorney, Agent, or Firm* — Yuriy P. Stercho

(57) ABSTRACT

The present invention comprises compounds of Formula I.

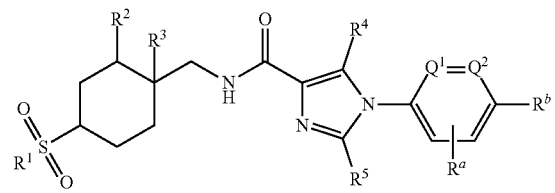

Formula I wherein:
$R^1$, $R^2$, $R^3$, $R^4$, $R^5$, $R^a$, $R^b$, $Q^1$, and $Q^2$ are defined in the specification.

The invention also comprises a method of treating or ameliorating a ROR-γ-t mediated syndrome, disorder or disease, including wherein the syndrome, disorder or disease is selected from the group consisting of rheumatoid arthritis, psoriatic arthritis, and psoriasis. The invention also comprises a method of modulating RORγt activity in a mammal by administration of a therapeutically effective amount of at least one compound of Formula I.

8 Claims, No Drawings

Specification includes a Sequence Listing.

(56) References Cited

FOREIGN PATENT DOCUMENTS

| WO | WO 1996003392 A1 | 2/1996 |
|---|---|---|
| WO | WO 2002083111 A2 | 10/2002 |
| WO | WO 2003015776 A1 | 2/2003 |
| WO | WO 2006087355 | 8/2006 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |
| WO | WO 2011053948 A1 | 5/2011 |
| WO | WO 2011/107248 | 9/2011 |
| WO | WO 2011112263 A1 | 9/2011 |
| WO | WO 2011112264 A1 | 9/2011 |
| WO | WO 2011115892 A1 | 9/2011 |
| WO | WO 2012027965 | 3/2012 |
| WO | WO 2012074547 A2 | 6/2012 |
| WO | WO 2012129491 | 9/2012 |
| WO | WO 2012158784 A2 | 11/2012 |
| WO | WO 2012174362 | 12/2012 |
| WO | WO 2013/029338 | 3/2013 |
| WO | WO 2013036912 A2 | 3/2013 |
| WO | WO 2013/045431 | 4/2013 |
| WO | WO 2013079223 A | 6/2013 |
| WO | WO 2013092939 A1 | 6/2013 |
| WO | WO 2013/171729 | 11/2013 |
| WO | WO 2013178362 A1 | 12/2013 |
| WO | WO 2014023367 | 2/2014 |
| WO | WO 2014093191 | 6/2014 |
| WO | WO 2015035278 A1 | 3/2015 |
| WO | WO 2015042212 A1 | 3/2015 |
| WO | WO 2015/057200 | 4/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015/139619 | 9/2015 |
| WO | WO 2015145371 A1 | 10/2015 |
| WO | WO 2016069974 | 5/2016 |
| WO | WO 2017/189823 | 11/2017 |
| WO | WO 2017/189829 | 11/2017 |
| WO | WO 2018123918 | 7/2018 |
| WO | WO 2018/185236 | 10/2018 |

OTHER PUBLICATIONS

Beurel, E., Harrington, L. E., Jope, R. S. (2013) "Inflammatory T helper 17 cells promote depression-like behavior in mice." Biol Psychiatry 73(7): 622-30.

Bimekizumab demonstrates impressive joint and skin responses for psoriatic arthritis patients. Dec. 20, 2017. https://www.ucb.com/stories-media/Press-Releases/article/Bimekizumab-demonstrates-impressive-joint-and-skin-responses-for-psoriatic-arthritis-patients-nbsp.

Bowes, J. and A. Barton "The genetics of psoriatic arthritis: lessons from genome-wide association studies." Discov Med 10(52): 177-83 (2010).

Chang M, "Pharmacologic Repression of Retinoic Acid Receptor-Related Orphan Nuclear Receptor Is Therapeutic in the Collagen-Induced Arthritis Experimental Model", Arthritis & Rheumatology (2014), 66(3), 579-588.

Chang, M. R. et al. (2015) "Antiobesity Effect of a Small Molecule Repressor of RORγ." Mol Pharmacol. 88(1): 48-56.

Chen, Y., et al. (2011). "Emerging tendency towards autoimmune process in major depressive patients: A novel insight from Th17 cells." Psychiatry Research 188(2): 224-230.

Cheng, Chia-Chung et al., The Friedlander synthesis of quinolines, Organic Reactions, 1982, 28, pp. 37-201.

Cua, D. J., J. Sherlock, et al. (2003). "Interleukin-23 rather than interleukin-12 is the critical cytokine for autoimmune inflammation of the brain." Nature 421(6924): 744-8.

De Wit et al., RORγt inhibitors suppress TH17 responses in inflammatory arthritis and inflammatory bowel disease. Journal of Allergy and Clinical Immunology, vol. 137, Issue 3, (2016), 960-963.

Dolff S et al., Disturbed Th1, Th2, Th17 and T-reg balance in patients with systemic lupus erythematosus, Clinical Immunology 141(2):197-204 • Aug. 2011.

Dong, C. (2006). "Diversification of T-helper-cell lineages: finding the family root of IL-17-producing cells." Nat Rev Immunol 6(4): 329-33.

Fauber et al., J. Med. Chem. 2014, 57, 5871-5892.

Feagan BG, et al. Ustekinumab as induction and maintenance therapy for Crohn's disease. N Engl J Med. 2016;375(20):1946-60.

Fitzpatrick, Leo Robert. Ror-gamma T inhibition as a Pharmacological Approach for Inflammatory Bowel Disease. Medical Research Archives, [S.1.], v. 2, n. 2, Aug. 2015.

Fujino, S., A. Andoh, et al. (2003). "Increased expression of interleukin 17 in inflammatory bowel disease." Gut 52(1): 65-70.

Garber K. (2011). "Psoriasis: from bed to bench and back" Nat Biotech 29, 563-566.

Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).

Hodgson et al., Ustekinumab for Treating Moderately to Severely Active Crohn's Disease after Prior Therapy: An Evidence Review Group Perspective of a NICE Single Technology Appraisal. PharmacoEconomics (2018) 36:4, 387-398.

Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N.S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.

Innovimmune: ROR Gamma Inhibitor (INV-17) Tested in Lupus Model. 2015 Eular Congress News. https://static1.squarespace.com/static/577aff0015db17f97d2d57/t/584f44f9725e254d6b032644/148159004360/150611_INV-17+Lupus+Thursday_EULAR_2015+small+size.pdf.

Ivanov, II, B. S. McKenzie, et al. (2006). "The orphan nuclear receptor RORgammat directs the differentiation program of proinflammatory IL-17+ T helper cells." Cell 126(6): 1121-33.

Jethwa H at al., The interleukin (IL)-23/IL-17 axis in ankylosing spondylitis: new advances and potentials for treatment, Clinical and Experimental Immunology, 2015, 183: 30-36.

Kochi, Y., Y. Okada, et al. (2010) "A regulatory variant in CCR6 is associated with rheumatoid arthritis susceptibility." Nat Genet 42(6): 515-9.

Kolls, J. K. and A. Linden (2004). "Interleukin-17 family members and inflammation." Immunity 21(4): 467-76.

Korn, T., E. Bettelli, et al. (2009). "IL-17 and Th17 Cells." Annu Rev Immunol 27: 485-517.

Krueger, J. G., S. Fretzin, et al. "IL-17A is essential for cell activation and inflammatory gene circuits in subjects with psoriasis." J Allergy Clin Immunol 130(1): 145-154 e9 (2012).

Kumar N, "The Benzenesulfoamide T0901317 [N-(2,2,2-Trifluoroethyl)-N-[4-[2,2,2-trifluoro-1-hydroxy-1-(trifluoromethyl)ethyl]phenyl]-benzenesulfonamide] Is a Novel Retinoic Acid Receptor-Related Orphan Receptor-Inverse Agonist", Molecular Pharmacology (2010), 77(2), 228-236.

Langrish, C. L., Y. Chen, et al. (2005). "IL-23 drives a pathogenic T cell population that induces autoimmune inflammation." J Exp Med 201(2): 233-40.

Leonardi, C., R. Matheson, et al. "Anti-interleukin-17 monoclonal antibody ixekizumab in chronic plaque psoriasis." N Engl J Med 366(13): 1190-9 (2012).

Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.

Lock, C., G. Hermans, et al. (2002). "Gene-microarray analysis of multiple sclerosis lesions yields new targets validated in autoimmune encephalomyelitis." Nat Med 8(5): 500-8.

(56) References Cited

OTHER PUBLICATIONS

Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66.

McGinley et al., (2018) Th17 cells, γδ T cells and their interplay in EAE and multiple sclerosis. *Journal of Autoimmunity* 87, 97-108.

McKenzie, B. S., R. A. Kastelein, et al. (2006). "Understanding the IL-23-IL-17 immune pathway." Trends Immunol 27(1): 17-23.

Mease, P. J. et al. Brodalumab, an anti-IL17RA monoclonal antibody, in psoriatic arthritis, The New England Journal of Medicine 370, 2295-2306 (2014).

Meissburger, B. et al. (2011) "Adipogenesis and insulin sensitivity in obesity are regulated by retinoid-related orphan receptor gamma." EMBO Mol Med. 3(11): 637-651.

Nunez, C., B. Dema, et al. (2008). "IL23R: a susceptibility locus for celiac disease and multiple sclerosis?" Genes Immun 9(4): 289-93.

Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40.

Papp, K. A., "Brodalumab, an anti-interleukin-17-receptor antibody for psoriasis." N Engl J Med 2012 366(13): 1181-9.

Poddhubnyy et al., Ann Rheum Dis 2014;0:1-7.

Pure & Appl. Chem. 45, 1976, 11-30.

Qian et al., Clin. Invest. (2012) 2(4), 417-421.

Registry(STN)[online], [Search Date: May 13, 2019]CAS Registration No. 791058-42-9,263386-02-3.

Sandborn WJ et al. Ustekinumab Induction and Maintenance Therapy in Refractory Crohn's Disease N Engl J Med 2012; 367:1519-1528.

Silva MJ et al, Glucocorticoid Resistant Asthma: The Potential Contribution of IL-17. Biomark J. 2016, 1:6.

Stamp, L. K., M. J. James, et al. (2004). "Interleukin-17: the missing link between T-cell accumulation and effector cell actions in rheumatoid arthritis" Immunol Cell Biol 82(1): 1-9.

Tonel, G., C. Conrad, et al. "Cutting edge: A critical functional role for IL-23 in psoriasis." J Immunol 185(10): 5688-91 (2010).

Wang X, Wei Y, Xiao H, et al. A novel IL-23p19/Ebi3 (IL-39) cytokine mediates inflammation in Lupus-like mice. Eur J Immunol. 2016;46(6):1343-1350.

Weitz JE et al., Ustekinumab: Targeting the IL-17 Pathway to Improve Outcomes in Psoriatic Arthritis. Expert Opin Biol Ther 2104 14, 515-526.

Withers DR, et al. Transient inhibition of ROR-γt therapeutically limits intestinal inflammation by reducing TH17 cells and preserving group 3 innate lymphoid cells Nature Medicine 2016, 22, 319.

Yang et al., Trends in Pharmacological Sciences, Oct. 2014, vol. 35, No. 10, 493-500.

Yang X et al. Does IL-17 Respond to the Disordered Lung Microbiome and Contribute to the Neutrophilic Phenotype in Asthma? Mediators of Inflammation. vol. 2016 (2016), Article ID 6470364, pp. 1-7.

Yao, et al, "Preparation Method of N-butyl-5-phenylthiazole-4-Formamide Derivative Via Coupling Reaction Under Catalysis of Copper Catalyst", Database accession No. 2014:924023.

Yen, D., J. Cheung, et al. (2006). "IL-23 is essential for T cell-mediated colitis and promotes inflammation via IL-17 and IL-6." J Clin Invest 116(5): 1310-6.

Zhang, et al., "Decarboxylative Cross-Coupling of Azoyl Carboxylic Acids with Aryl Halides", Organic Letters, (2010) vol. 12, No. 21, pp. 4745-47457.

PCT/US2015/058193, Written Opinion dated Jan. 26, 2016.

PCT/US2015/058198, Written Opinion dated Jan. 21, 2016.

PCT/US2015/058200, Written Opinion dated Jan. 27, 2016.

PCT/US2015/058193, International Search Report, dated Jan. 26, 2016.

PCT/US2015/058198, International Search Report, dated Jan. 21, 2016.

PCT/US2015/058200, International Search Report, dated Jan. 27, 2016.

PCT/US2017/029531, International Search Report, dated Sep. 15, 2017.

PCT/US2017/029531, International Preliminary Report on Patentability, dated Oct. 30, 2018.

PCT/IB2019/055043, International Search Report, dated Sep. 30, 2019.

PCT/IB2019/055045, International Search Report, dated Sep. 30, 2019.

PCT/IB2019/055046, International Search Report, dated Oct. 4, 2019.

PCT/IB2019/055048, International Search Report, dated Sep. 27, 2019.

Eastman; Oncotarget. 2017, 8, 8854-8866. DOI: 10.18632/oncotarget.12673 (Year: 2017).

Guendisch; PLoS ONE 2017, 12, e0188391. DOI: 10.1371/journal.pone.0188391 (Year: 2017).

Huh; Eur. J. Immunol. 2012. 42, 2232-2237. DOI: 10.1002/eji.201242740 (Year: 2012).

Isono; Drug Discovery Today, 2014, 19, 1205-1211. DOI: 10.1016/j.drudis.2014.04.012 (Year: 2014).

Kiaei; Basic Clin Neurosci. 2013, 4, 3-4. URL: http://bcn.jurns.ac.ir/article-1-307-en.html (Year: 2013).

Xue; Scientific Reports 2016, 6, Article No. 37977. DOI: 10.1038/srep37977 (Year: 2016).

Yao Chongzheng et al., Hydrolysis of carboxylate, Principles of Fine Chemical Product Synthesis, published on Dec. 31, 2000 (see English translation as provided).

\* cited by examiner

PHENYL AND PYRIDINYL SUBSTITUTED IMIDAZOLES AS MODULATORS OF RORγT

CROSS REFERENCE TO RELATED APPLICATIONS

This application claims priority from U.S. Provisional Application 62/686,323, filed on Jun. 18, 2018, which is incorporated by reference herein in its entirety.

SEQUENCE LISTING

The instant application contains a Sequence Listing which has been filed electronically in ASCII format and is hereby incorporated by reference in its entirety. Said ASCII copy, created on Jun. 11, 2019, is named PRD3478USNP.txt and is 8,223 bytes in size.

FIELD OF THE INVENTION

The invention is directed to substituted imidazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4+ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8.; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

RORγT deficient mice exhibited resistance to learned helplessness. Treatment with the RORγT inhibitor SR1001, or anti-interleukin-17A antibodies reduced Th17-dependent learned helplessness (Beurel, E., Harrington, L. E., Jope, R. S. (2013) "Inflammatory T helper 17 cells promote depression-like behavior in mice." Biol Psychiatry 73(7): 622-30). In human patients with major depressive disorder, both peripheral blood lymphocyte RORγT mRNA expression and peripheral Th17 cells were found to be elevated relative to the control group (Chen, Y., et al. (2011). "Emerging tendency towards autoimmune process in major depressive patients: A novel insight from Th17 cells." Psychiatry Research 188(2): 224-230).

Administration of RORγ inverse agonist SR1555 to obese diabetic mice resulted in a modest reduction in food intake accompanied with significant reduction in fat mass, resulting in reduced body weight and improved insulin sensitivity (Chang, M. R. et al. (2015) "Antiobesity Effect of a Small Molecule Repressor of RORγ." Mol Pharmacol. 88(1): 48-56). In addition, Rorγ–/– mice are protected from hyperglycemia and insulin resistance in the state of obesity (Meissburger, B. et al. (2011) "Adipogenesis and insulin sensitivity in obesity are regulated by retinoid-related orphan receptor gamma." EMBO Mol Med. 3(11): 637-651).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33.; Fujino, S., A. Andoh, et al. (2003). "Increased expression of interleukin 17 in inflammatory bowel disease." Gut 52(1): 65-70.; Lock, C., G. Hermans, et al. (2002). "Gene-microarray analysis of multiple sclerosis lesions yields new targets validated in autoimmune encephalomyelitis." Nat Med 8(5): 500-8.; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93.; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9.; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises a compound of Formula I:

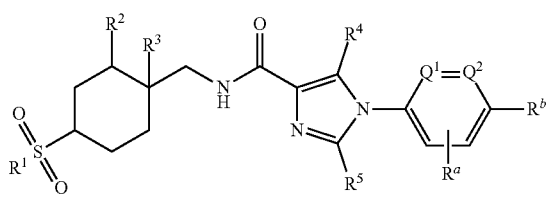

Formula I wherein
$R^1$ is —$C_{(1-4)}$alkyl, —$NH_2$, —$NHC_{(1-4)}$alkyl, —$N(C_{(1-4)}$alkyl$)_2$, —NHC(O)$NH_2$, NHC(O)$C_{(1-4)}$alkyl, —NHC(O)H, or —NHC(O)NH$C_{(1-4)}$alkyl;

$R^2$ is H, —OH, or —$NH_2$;

$R^3$ is —H, —OH, —CN, —$NH_2$, —$CONH_2$, —$CO_2$H, —$CO_2C_{(1-4)}$alkyl, —$CH_2$OH, —$CH_2NH_2$, —$CH_2$CN, —$NHC_{(1-4)}$alkyl, or —$CONHC_{(1-4)}$alkyl;

$R^4$ is —H, —Cl, —$C_{(1-4)}$alkyl, —F, —CN, —C(O)$NH_2$, or

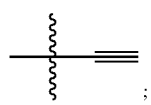

;

wherein said —$C_{(1-4)}$alkyl is optionally substituted with up to six fluorine atoms;

$R^5$ is —$C_{(1-4)}$alkyl, wherein said —$C_{(1-4)}$alkyl is optionally substituted with —CN, —OH, —$OCH_3$, —$OCF_3$, or up to six fluorine atoms;

$Q^1$ is N or CRC;

$Q^2$ is N or CH; provided that $Q^2$ is not N if $Q^1$ is N;

$R^a$ is —F, —Cl, —$OCD_3$, —CN, —$OC_{(1-3)}$alkyl, or —$C_{(1-3)}$alkyl, wherein said —$C_{(1-3)}$alkyl and said $OC_{(1-3)}$alkyl are optionally substituted with up to three fluorine atoms;

$R^b$ is —$NA^1A^2$ (including

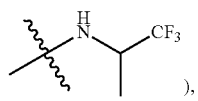

),

—$C_{(3-6)}$alkyl (including

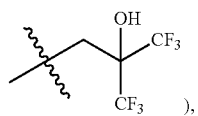

), or —$OC_{(1-3)}$alkyl, wherein said —$C_{(3-6)}$alkyl is optionally substituted with —OH or oxo, and the —$C_{(3-6)}$alkyl may additionally be substituted with up to six fluorine atoms, and said —$OC_{(1-3)}$alkyl is optionally substituted with up to three fluorine atoms;

$R^c$ is —H, —$OCH_3$, —F, —$CH_3$, —$CF_3$, —$OCF_3$, or —Cl;

$A^1$ is —$C_{(2-3)}$alkyl, wherein said —$C_{(2-3)}$alkyl is optionally substituted with up to six fluorine atoms;

$A^2$ is H, or $A^1$ and $A^2$ are taken together with their attached nitrogen to form

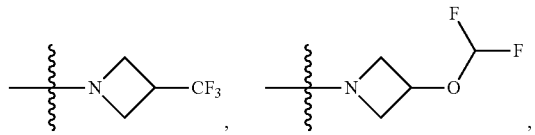

,

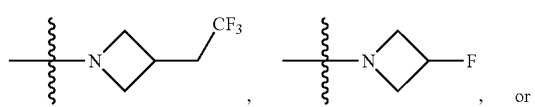

, or

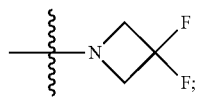

;

and pharmaceutically acceptable salts thereof.

DETAILED DESCRIPTION OF THE INVENTION

The present invention comprises a compound of Formula I:

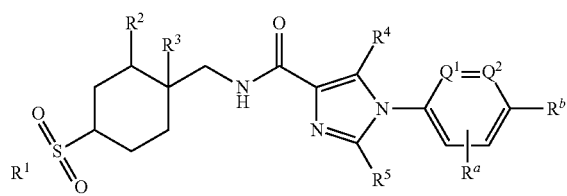

Formula I wherein
R$^1$ is —C$_{(1-4)}$alkyl, —NH$_2$, —NHC$_{(1-4)}$alkyl, —N(C$_{(1-4)}$alkyl)$_2$, —NHC(O)NH$_2$, NHC(O)C$_{(1-4)}$alkyl, —NHC(O)H, or —NHC(O)NHC$_{(1-4)}$alkyl;
R$^2$ is H, —OH, or —NH$_2$;
R$^3$ is —H, —OH, —CN, —NH$_2$, —CONH$_2$, —CO$_2$H, —CO$_2$C$_{(1-4)}$alkyl, —CH$_2$OH, —CH$_2$NH$_2$, —CH$_2$CN, —NHC$_{(1-4)}$alkyl, or —CONHC$_{(1-4)}$alkyl;
R$^4$ is —H, —Cl, —C$_{(1-4)}$alkyl, —F, —CN, —C(O)NH$_2$, or

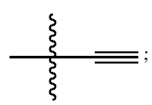

wherein said —C$_{(1-4)}$alkyl is optionally substituted with up to six fluorine atoms;
R$^5$ is —C$_{(1-4)}$alkyl, wherein said —C$_{(1-4)}$alkyl is optionally substituted with —CN, —OH, —OCH$_3$, —OCF$_3$, or up to six fluorine atoms;
Q$^1$ is N or CR$^c$;
Q$^2$ is N or CH; provided that Q$^2$ is not N if Q$^1$ is N;
R$^a$ is —F, —Cl, —OCD$_3$, —CN, —OC$_{(1-3)}$alkyl, or —C$_{(1-3)}$alkyl, wherein said —C$_{(1-3)}$alkyl and said OC$_{(1-3)}$alkyl are optionally substituted with up to three fluorine atoms;
R$^b$ is —NA$^1$A$^2$ (including

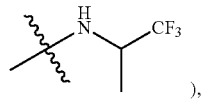

),

—C$_{(3-6)}$alkyl (including

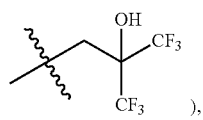

), or —OC$_{(1-3)}$alkyl, wherein said —C$_{(3-6)}$alkyl is optionally substituted with —OH or oxo, and the —C$_{(3-6)}$alkyl may additionally be substituted with up to six fluorine atoms, and said —OC$_{(1-3)}$alkyl is optionally substituted with up to three fluorine atoms;

R$^c$ is —H, —OCH$_3$, —F, —CH$_3$, —CF$_3$, —OCF$_3$, or —Cl;
A$^1$ is —C$_{(2-3)}$alkyl, wherein said —C$_{(2-3)}$alkyl is optionally substituted with up to six fluorine atoms;
A$^2$ is H, or A$^1$ and A$^2$ are taken together with their attached nitrogen to form

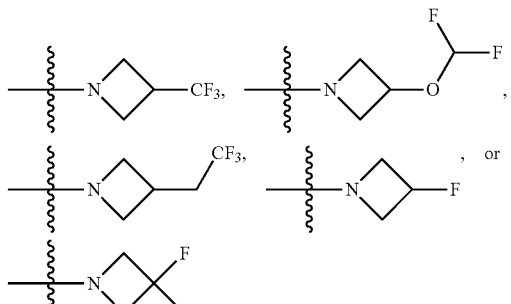

and pharmaceutically acceptable salts thereof.
In another embodiment of the invention:
R$^1$ is —C$_{(1-3)}$alkyl, —NH$_2$, —NHC$_{(1-2)}$alkyl, —N(C$_{(1-2)}$alkyl)$_2$, —NHC(O)NH$_2$, NHC(O)C$_{(1-2)}$alkyl, —NHC(O)H, or —NHC(O)NHCH$_3$;
R$^2$ is H, —OH, or —NH$_2$;
R$^3$ is —H, —OH, —CN, —NH$_2$, —CONH$_2$, —CO$_2$H, —CO$_2$CH$_2$CH$_3$, or —CH$_2$OH;
R$^4$ is —H, —Cl, —C$_{(1-4)}$alkyl, —F, —CN, —C(O)NH$_2$,

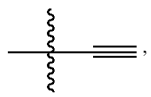 [SMILES: *C#C]

or —CF$_3$;
R$^5$ is —C$_{(1-4)}$alkyl, wherein said —C$_{(1-4)}$alkyl is optionally substituted with —CN, —OH, or —OCH$_3$;
Q$^1$ is N or CR$^c$;
Q$^2$ is N or CH; provided that Q$^2$ is not N if Q$^1$ is N;
R$^a$ is —F, —Cl, —OCD$_3$, —CN, —OC$_{(1-3)}$alkyl, or —C$_{(1-3)}$alkyl, wherein said —C$_{(1-3)}$alkyl and said OC$_{(1-3)}$alkyl are optionally substituted with up to three fluorine atoms;
R$^b$ is —NA$^1$A$^2$ (including

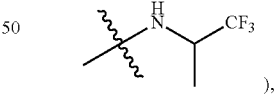

),

—C$_{(3-6)}$alkyl (including

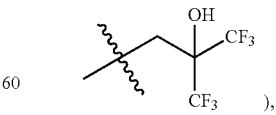

), or —OC$_{(1-3)}$alkyl, wherein said —C$_{(3-6)}$alkyl is optionally substituted with —OH or oxo, and the —C$_{(3-6)}$alkyl may additionally be substituted with up to six fluorine atoms, and said —OC$_{(1-3)}$alkyl is optionally substituted with up to three fluorine atoms;

$R^c$ is —H, —OCH$_3$, —F, —CH$_3$, —CF$_3$, or —OCF$_3$;
$A^1$ is —C$_{(2-3)}$alkyl, wherein said —C$_{(2-3)}$alkyl is optionally substituted with up to six fluorine atoms;
$A^2$ is H;
and pharmaceutically acceptable salts thereof.

In another embodiment of the invention:
$R^1$ is —C$_{(1-3)}$alkyl, —NH$_2$, —NHC$_{(1-2)}$alkyl, or —N(C$_{(1-2)}$alkyl)$_2$;
$R^2$ is —H or —OH;
$R^3$ is —H, —OH, —CN, or —NH$_2$;
$R^4$ is —H, —Cl, —C$_{(1-4)}$alkyl, —F, —CN, —C(O)NH$_2$,

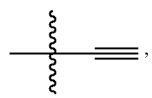 [SMILES: *C#C]

or —CF$_3$;
$R^5$ is —C$_{(1-4)}$alkyl;
$Q^1$ is N or CRC;
$Q^2$ is N or CH; provided that $Q^2$ is not N if $Q^1$ is N;
$R^a$ is —F, —OCD$_3$, —OC$_{(1-3)}$alkyl, or —C$_{(1-3)}$alkyl, wherein said —C$_{(1-3)}$alkyl and said OC$_{(1-3)}$alkyl are optionally substituted with up to three fluorine atoms;
$R^b$ is

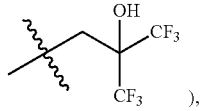 [SMILES: *CC(O)(C(F)(F)F)C(F)(F)F]

—C$_{(3-6)}$alkyl (including

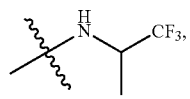

or —OC$_{(1-3)}$alkyl, wherein said —C$_{(3-6)}$alkyl is optionally substituted with —OH or oxo, and the —C$_{(3-6)}$alkyl may additionally be substituted with up to six fluorine atoms, and said —OC$_{(1-3)}$alkyl is optionally substituted with up to three fluorine atoms;
$R^c$ is —H, —OCH$_3$, —F, or —CH$_3$;
and pharmaceutically acceptable salts thereof.

In another embodiment of the invention:
$R^1$ is —C$_{(1-2)}$alkyl, —NH$_2$, —NHC$_{(1-2)}$alkyl, or —N(C$_{(1-2)}$alkyl)$_2$;
$R^2$ is —H or —OH;
$R^3$ is —H, —OH, —CN, or —NH$_2$;
$R^4$ is —H, —Cl, —C$_{(1-4)}$alkyl, —F, —CN, —C(O)NH$_2$, or

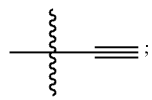 [SMILES: *C#C]

$R^5$ is —C$_{(1-4)}$alkyl;
$Q^1$ is N or CRC;
$Q^2$ is N or CH; provided that $Q^2$ is not N if $Q^1$ is N;

$R^a$ is —F, —OCH$_3$, —OCD$_3$, —OCHF$_2$, —OCF$_3$, or —C$_{(1-3)}$alkyl, wherein said —C$_{(1-3)}$alkyl is optionally substituted with up to three fluorine atoms;
$R^b$ is

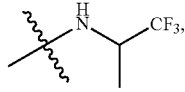 [SMILES: *NC(C)C(F)(F)F]

or —C$_{(3-6)}$alkyl (including

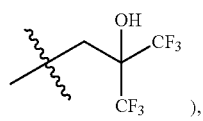

wherein said —C$_{(3-6)}$alkyl is optionally substituted with —OH or oxo, and the —C$_{(3-6)}$alkyl may additionally be substituted with up to six fluorine atoms;
$R^c$ is —H, —OCH$_3$, or —F;
and pharmaceutically acceptable salts thereof.

In another embodiment of the invention:
$R^1$ is —CH$_3$, —NH$_2$, —NHCH$_3$, or —N(CH$_3$)$_2$;
$R^2$ is —H or —OH;
$R^3$ is —H, —OH, or —CN;
$R^4$ is —H, —Cl, —CH$_3$, —F, —CN, —C(O)NH$_2$, or

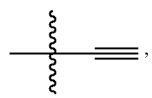 [SMILES: *C#C]

$R^5$ is —C$_{(1-4)}$alkyl;
$Q^1$ is N or CRC;
$Q^2$ is N or CH; provided that $Q^2$ is not N if $Q^1$ is N;
$R^a$ is —F, —OCH$_3$, —OCD$_3$, —OCHF$_2$, —OCF$_3$, or —C$_{(1-2)}$alkyl;
$R^b$ is

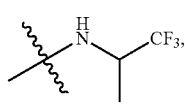 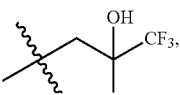

or —C$_{(3-6)}$alkyl, wherein said —C$_{(3-6)}$alkyl is optionally substituted with up to six fluorine atoms;
$R^c$ is —H or —F;
and pharmaceutically acceptable salts thereof.

Another embodiment of the invention is a compound selected from the group consisting of:

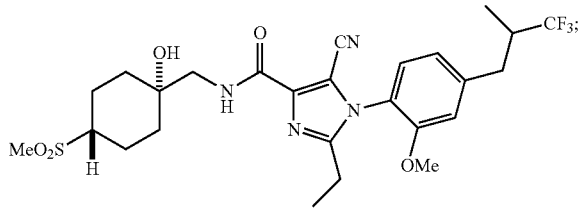

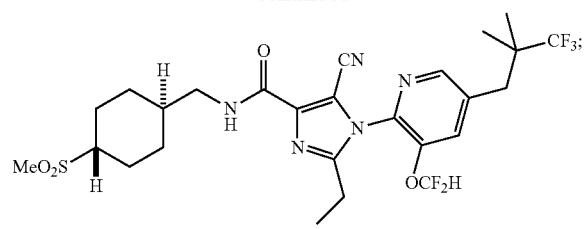
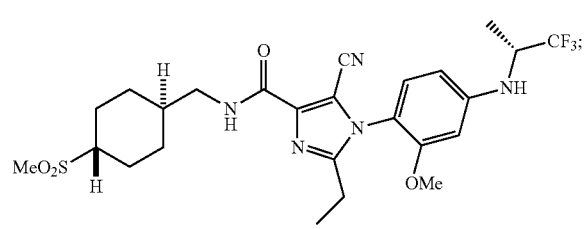
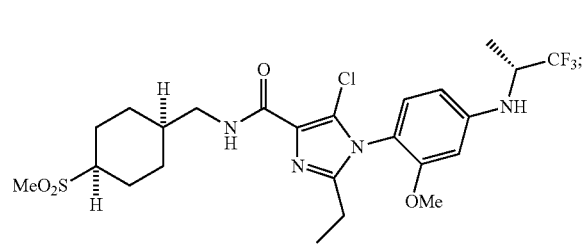
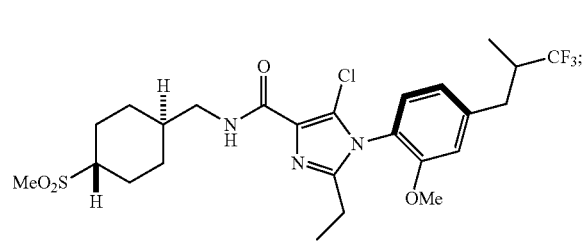
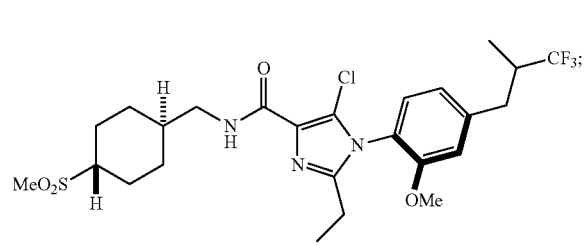
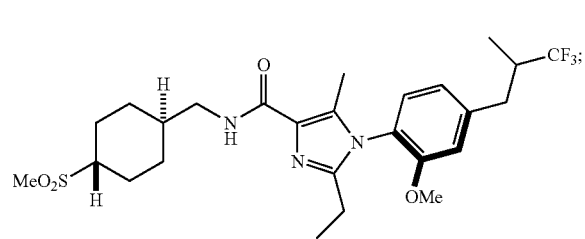
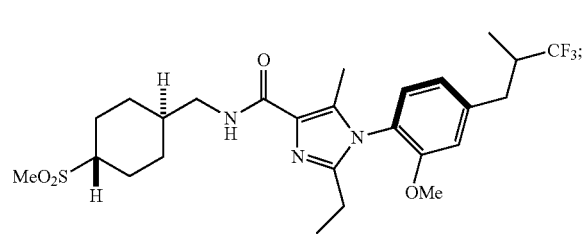
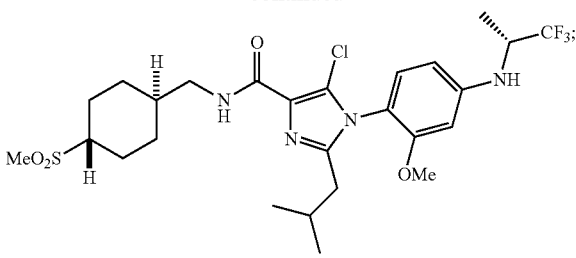
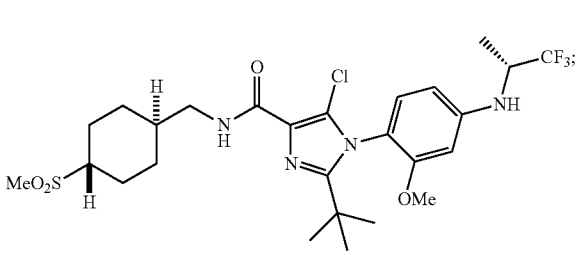
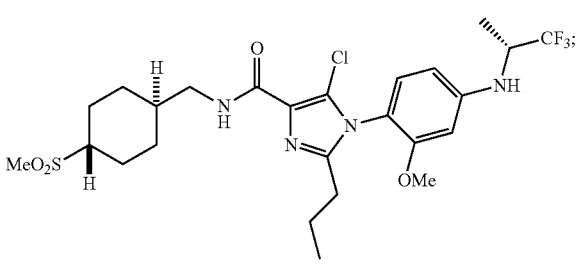
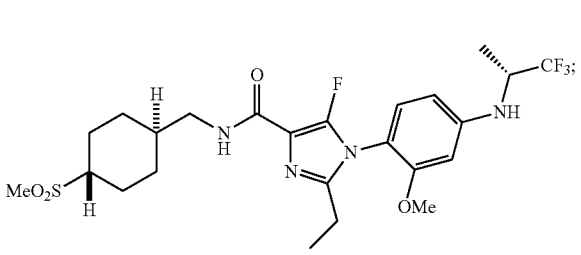
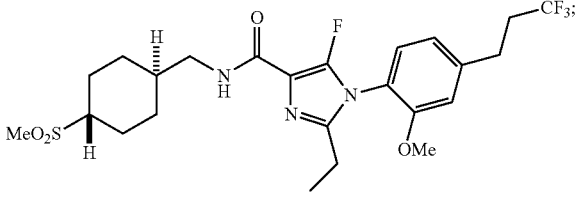
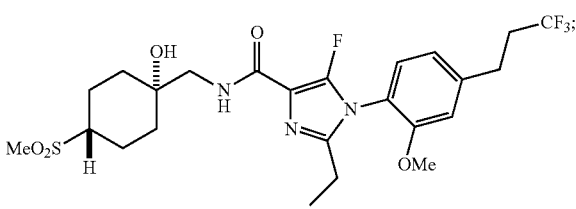
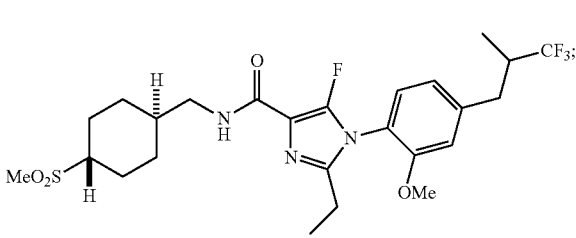

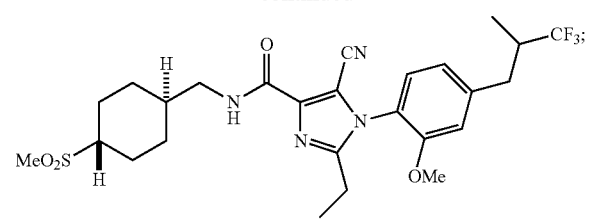
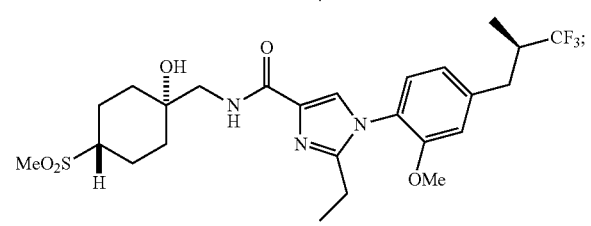
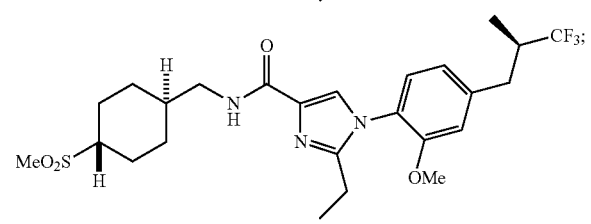
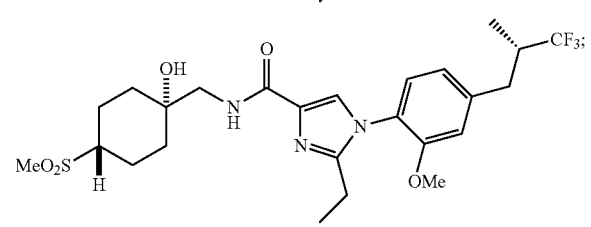
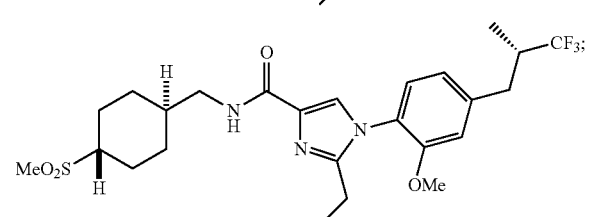
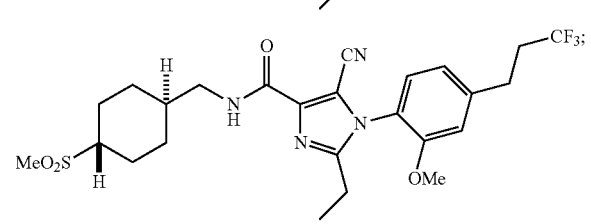
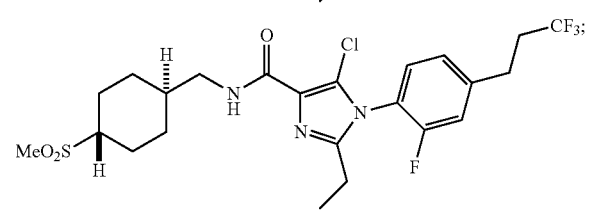
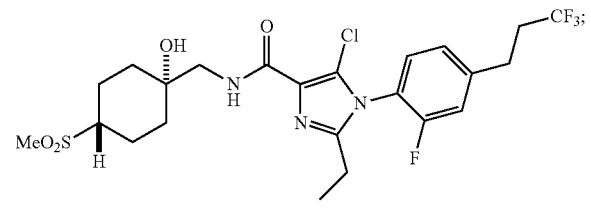
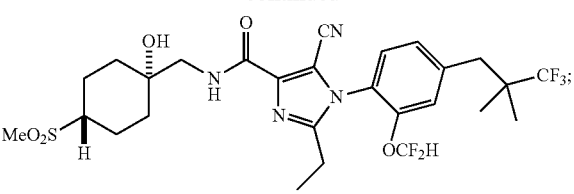
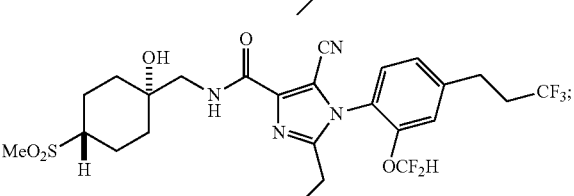
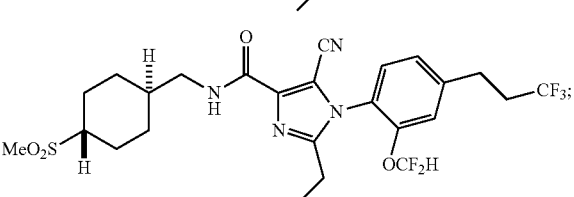
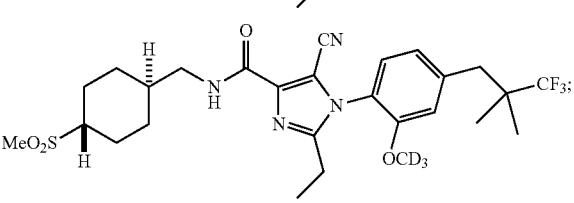
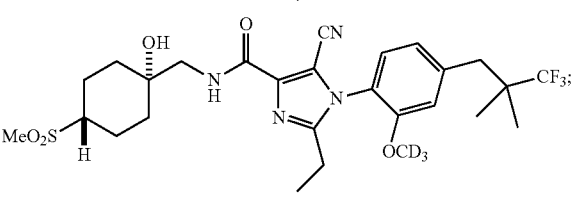
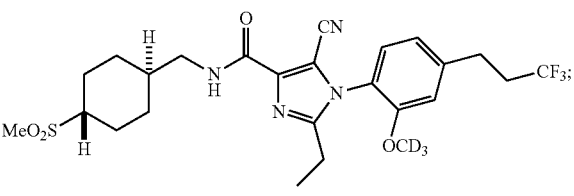
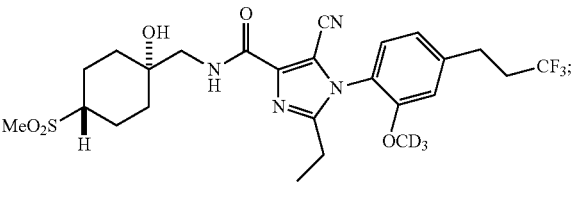
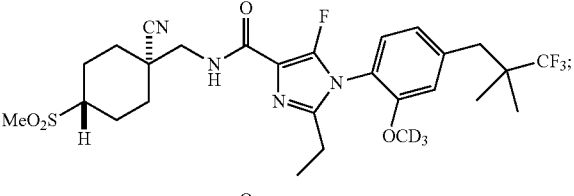
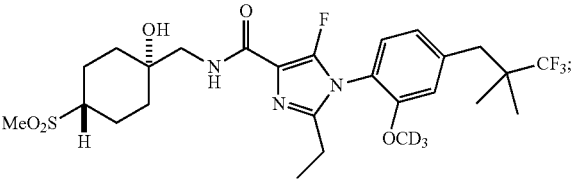

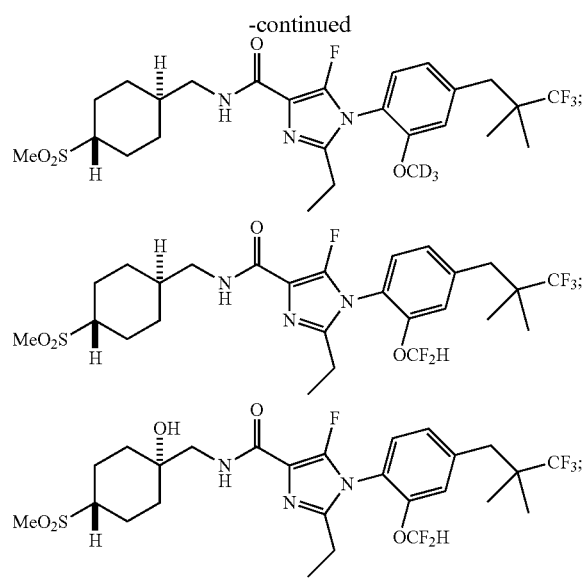
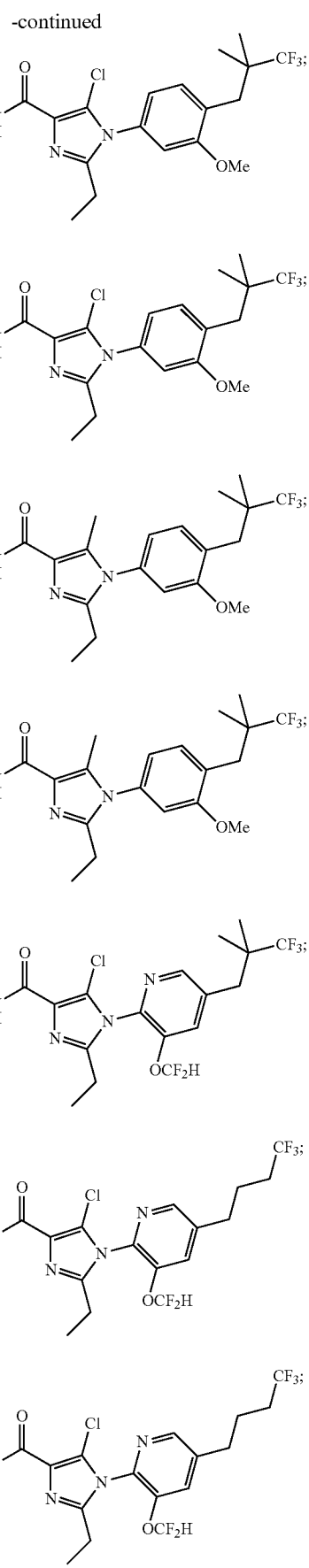

-continued
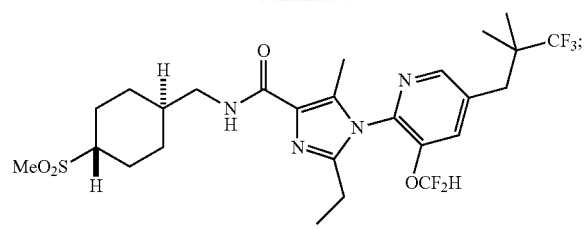
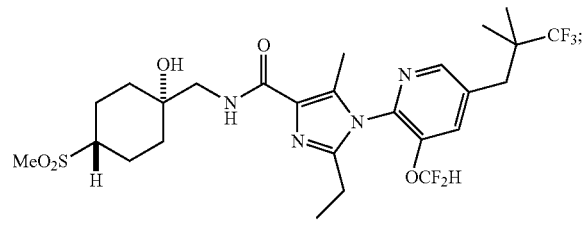
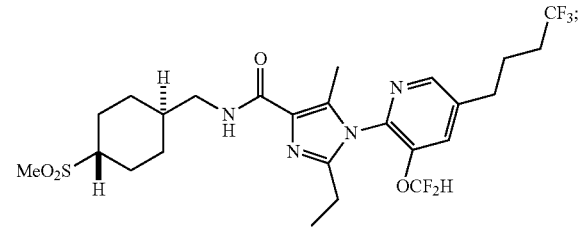
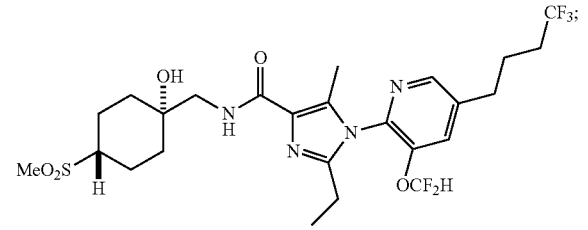
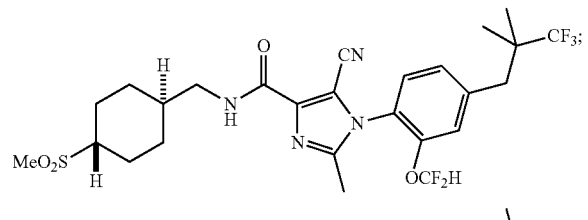
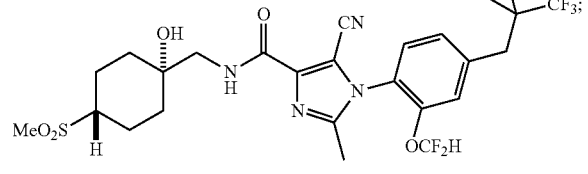
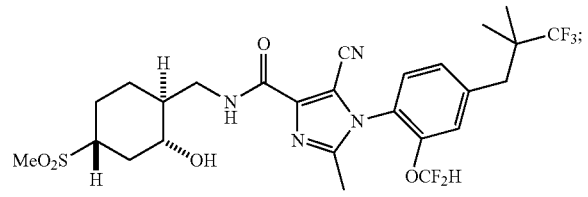
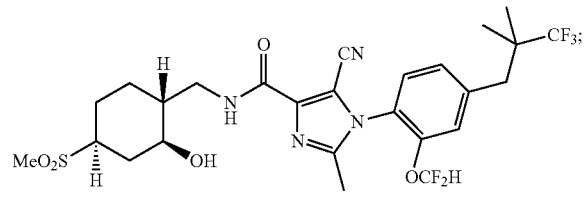
-continued
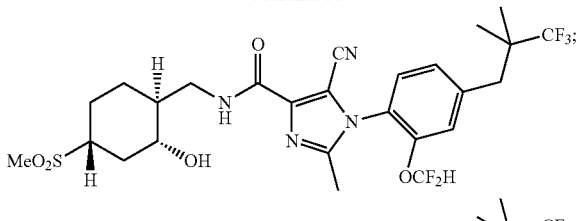
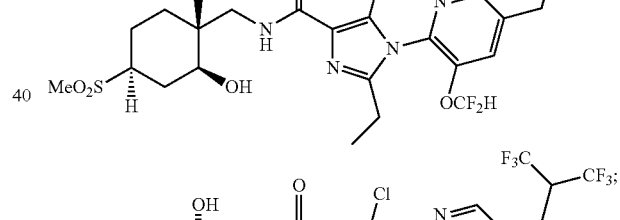
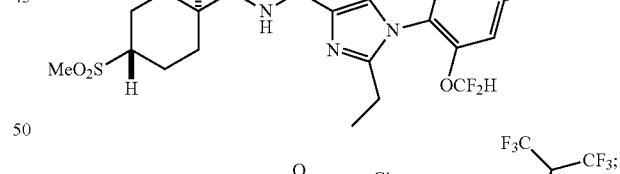

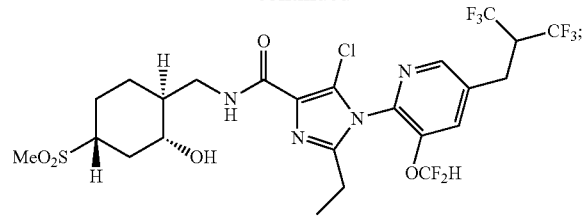
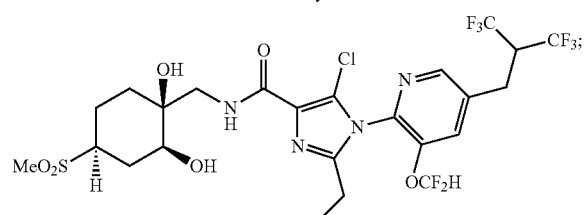
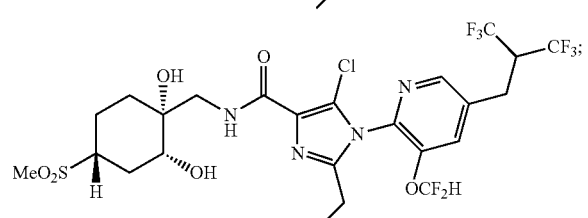
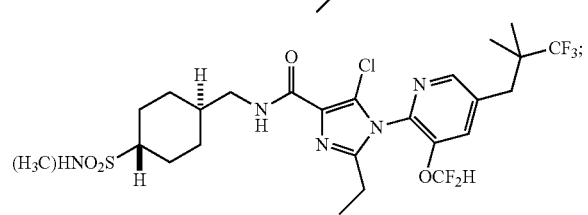
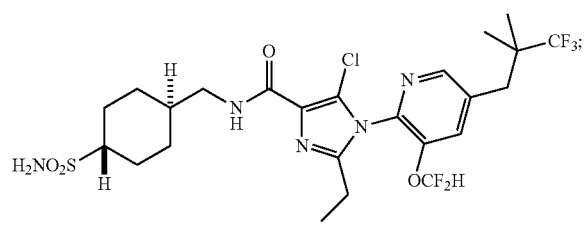
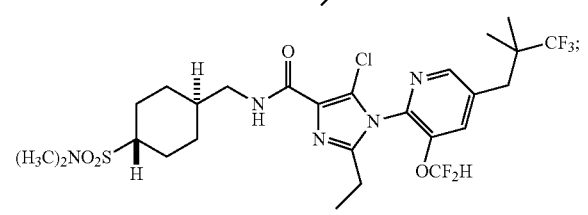
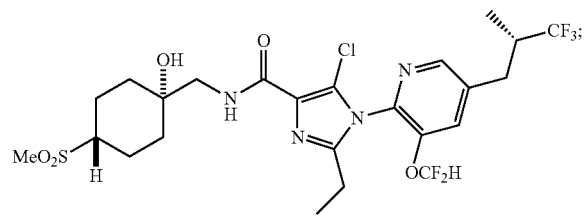
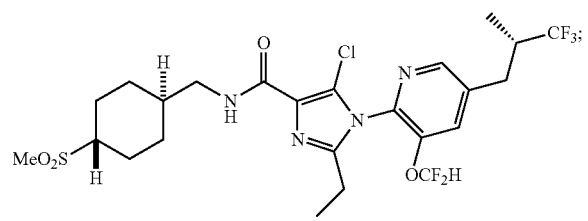
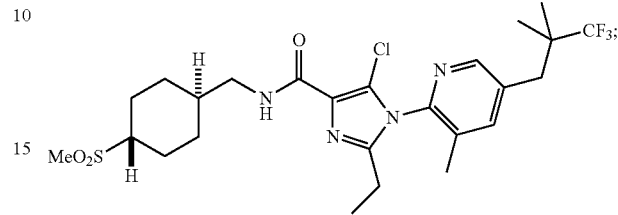
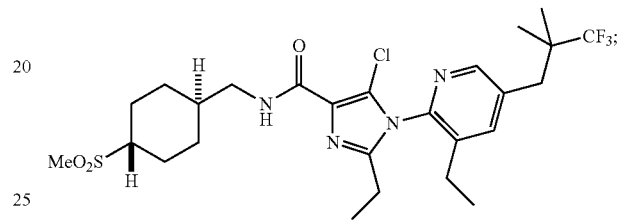
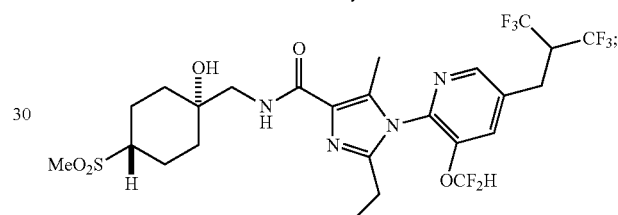
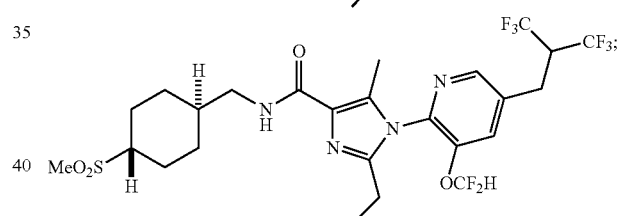
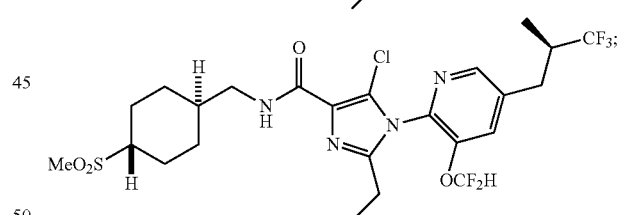
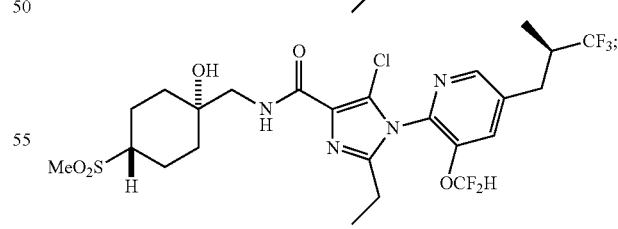
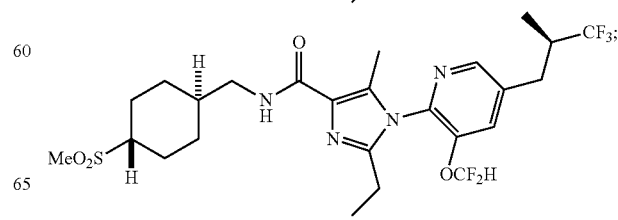

-continued
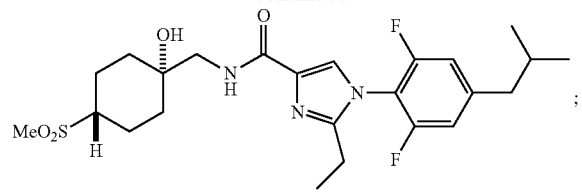
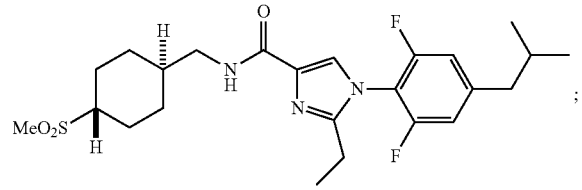
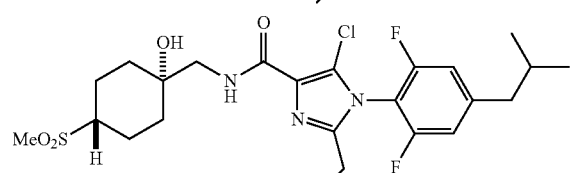
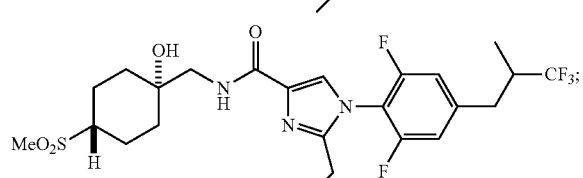
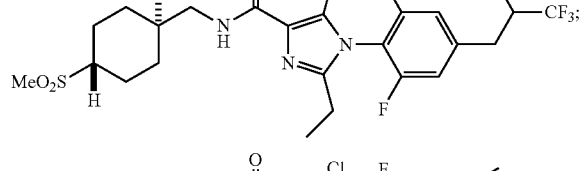
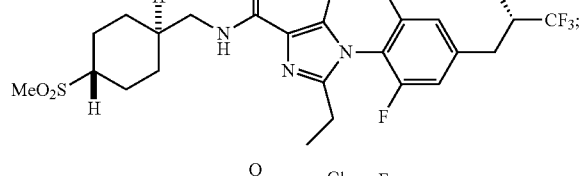
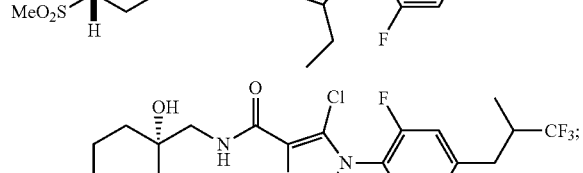
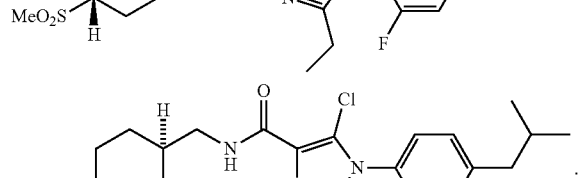
-continued
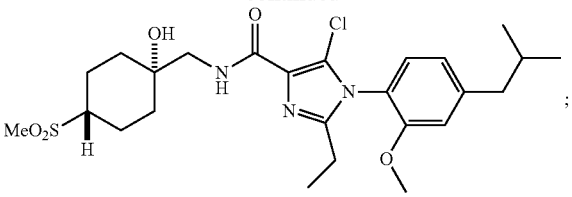
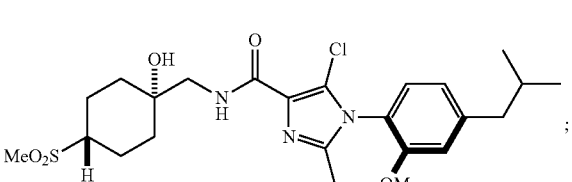
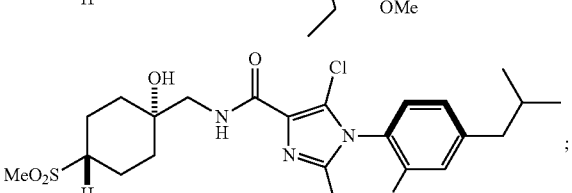
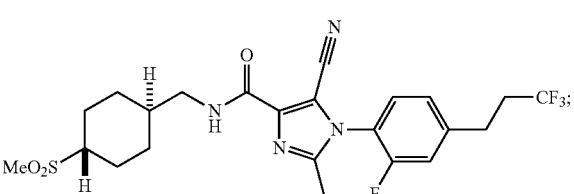
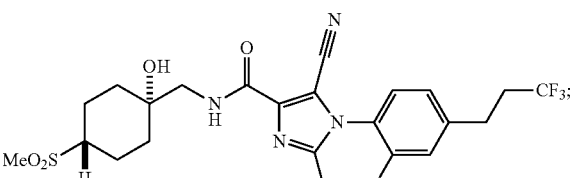
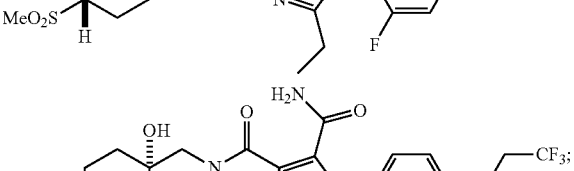
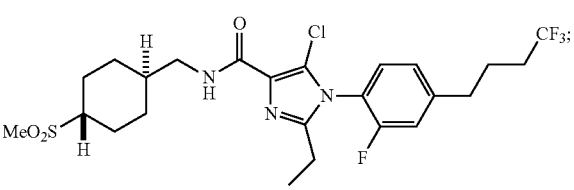

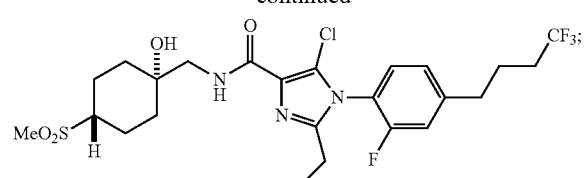
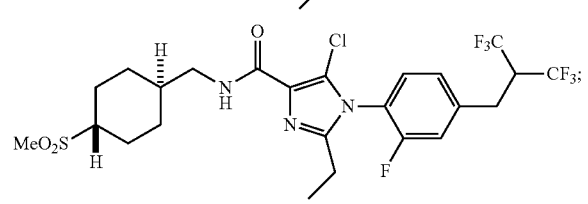
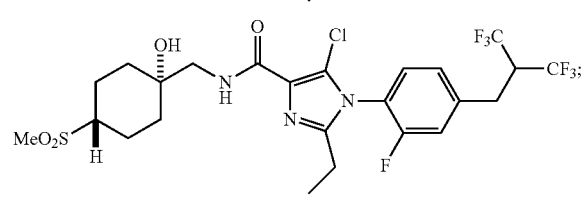
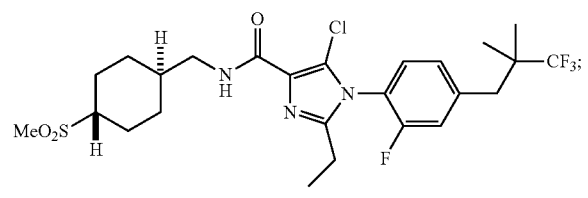
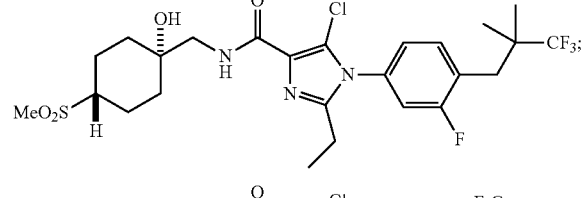
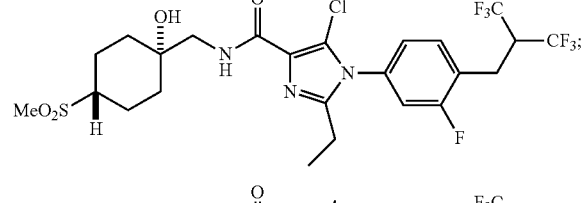
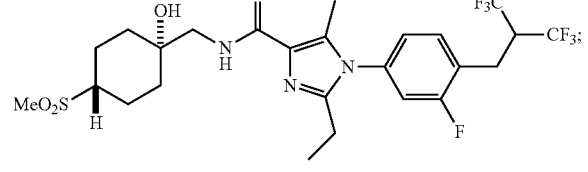
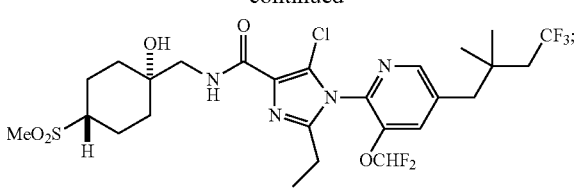
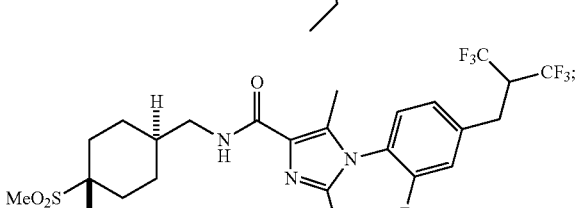
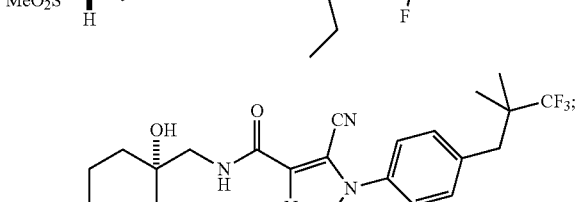
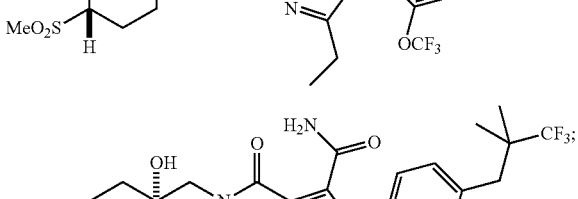
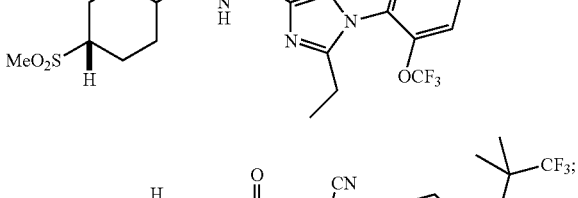
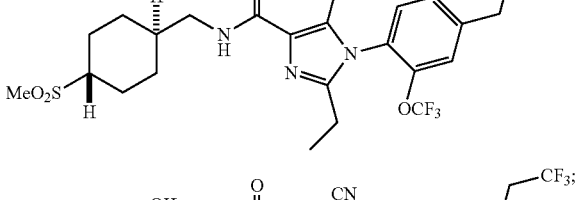
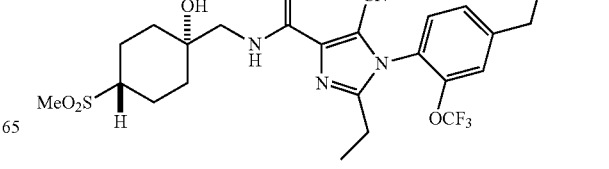

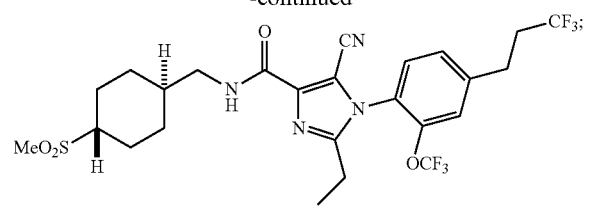

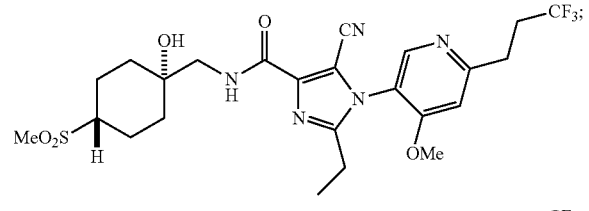
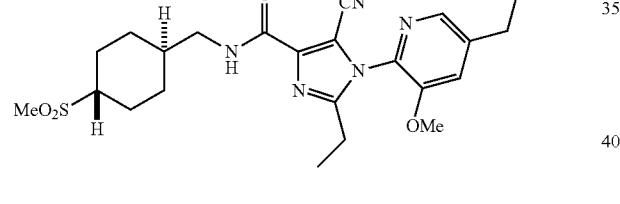
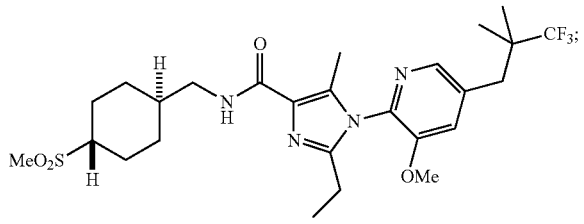
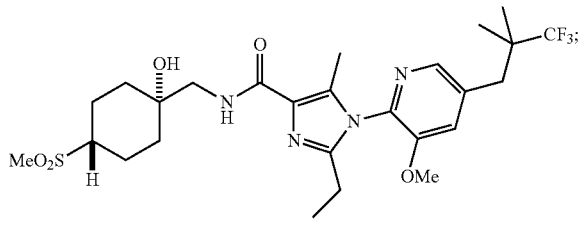
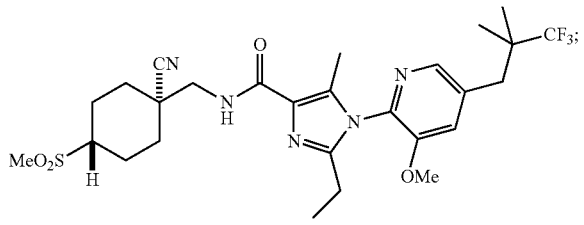
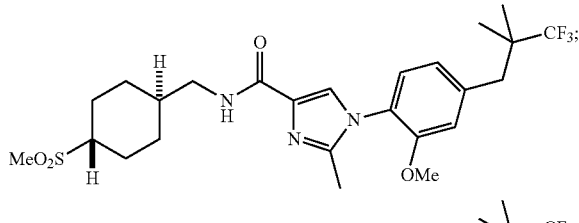
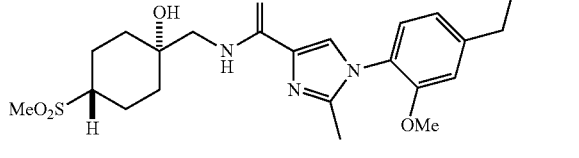

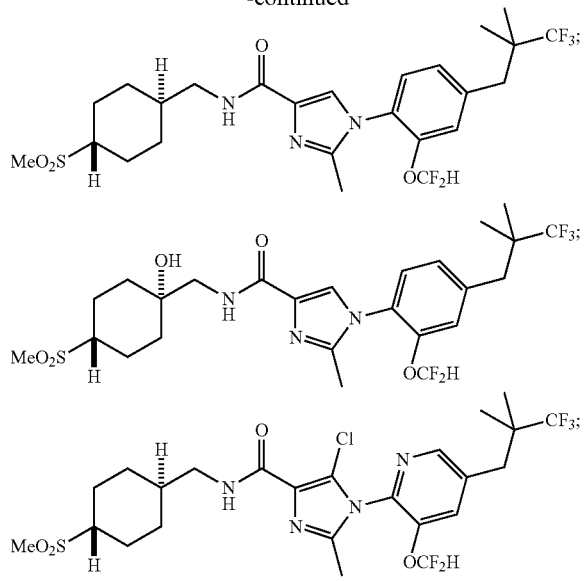

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: depression and metabolic syndrome.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, systemic lupus erythematosus, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: psoriatic arthritis and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: depression and metabolic syndrome comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: psoriatic arthritis and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: depression and metabolic syndrome.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is depression comprising administering to a subject in need thereof an effective amount of a compound of Formula I or a form, composition or medicament thereof.

The present invention provides a method of treating or ameliorating a syndrome, disorder or disease, wherein said syndrome, disorder or disease is metabolic syndrome comprising administering to a subject in need thereof an effective amount of a compound of Formula I or a form, composition or medicament thereof.

The invention also relates to methods of modulating RORγt activity in a mammal by administration of an effective amount of at least one compound of Formula I.

Another embodiment of the invention is a method of inhibiting production of interleukin-17, comprising administering to a subject in need thereof an effective amount of a compound of Formula I.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "oxo" refers to a substituent on an alkyl group, wherein two hydrogen atoms on the same carbon atom have been replaced with a single oxygen atom. Said oxygen atom is double bonded to said carbon atom, replacing the pair of single bonds to hydrogen atoms.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of Formula I may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by 1H NMR leading to complex multiplets and peak integration in the 1H NMR spectrum.

Chiral centers, of which the absolute configurations are known, are labelled by prefixes R and S, assigned by the standard sequence-rule procedure, and preceded when necessary by the appropriate locants. Chiral centers, of which the relative but not the absolute configurations are known, are labelled arbitrarily by prefixes R* and S*, preceded when necessary by the appropriate locants. These prefixes are assigned by the standard sequence-rule procedure on the arbitrary assumption that the center of chirality with the lowest locant has chirality R. When a compound contains chiral centers with known absolute configurations and a sterically unrelated set of chiral centers with known relative configurations but unknown absolute configurations, then R* and S* are used to designate the latter. (Pure & Appl. Chem. 45, 1976, 11-30). Racemates containing a single chiral center are labelled RS or are not labelled. For racemates with more than one chiral center, the chiral center with the lowest locant is labelled RS and the others are labelled RS or SR according to whether they are R or S when the chiral center with the lowest locant is R. Pseudoasymmetric stereogenic centers are treated in the same way as chiral centers, but are given lower-case symbols, r or s (Angew. Chem. Int. Ed. Engl. 1982, 21, 567-583).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

ABBREVIATIONS

Herein and throughout the application, the following abbreviations may be used.
Ac acetyl
9-BBN 9-borabicyclo[3.3.1]nonane
Boc tert-butyloxycarbonyl br broad
Bu butyl
Cbz carboxybenzyl
δ NMR chemical shift in parts per million downfield from a standard
d doublet
DABSO 1,4-diazabicyclo[2.2.2]octane bis(sulfur dioxide) adduct
DAST (diethylamino)sulfur trifluoride
DBU 1,8-diazabicyclo[5.4.0]undec-7-ene
DCE dichloroethane
DCM dichloromethane
Deoxo-Fluor® bis(2-methoxyethyl)aminosulfur trifluoride
DIPEA N,N-diisopropylethylamine (Hünig's base)
DMA N,N-dimethylacetamide
DMAP 4-(dimethylamino)pyridine
DME 1,2-dimethoxyethane
DMEN N,N-dimethylethylenediamine
DMF N,N-dimethylformamide
DMI 1,3-dimethyl-2-imidazolidinone
DMSO dimethyl sulfoxide
dppf 1,1'-bis(diphenylphosphino)ferrocene
dtbpf 1,1'-bis(di-tert-butylphosphino)ferrocene
EDCI 1-ethyl-3-(3-dimethylaminopropyl) carbodiimide hydrochloride
ESI electrospray ionization
Et ethyl
g grams(s)
h hour(s)
HATU O-(7-azabenzotriazol-1-yl)-N,N,N',N'-tetramethyluronium hexafluorophosphate
HOBt 1-hydroxybenzotriazole
HPLC high pressure liquid chromatography
Hz Hertz
i iso
IPA isopropanol
J coupling constant (NMR spectroscopy)
L liter(s)
LAH lithium aluminum hydride
LC liquid chromatography
LDA lithium diisopropylamide
m milli or multiplet
m/z mass-to-charge ratio
M+ parent molecular ion
M molar (moles/liter) or mega
mCPBA 3-chloroperbenzoic acid
Me methyl
MeCN acetonitrile
min minute(s)
μ micro
MS mass spectrometry
MTBE tert-butyl methyl ether
n normal (chemical nomenclature prefix)
n nano
N normal (equivalent concentration)
NBS N-bromosuccinimide
NCS N-chlorosuccinimide
NFSI N-fluorobenzenesulfonimide
NIS N-iodosuccinimide
NMO 4-methylmorpholine N-oxide
NMR nuclear magnetic resonance
Pd/C palladium on carbon
PEPPSI-IPr [1,3-bis(2,6-diisopropylphenyl)imidazol-2-ylidene](3-chloropyridyl)palladium(II) dichloride
Ph phenyl
Pr propyl
Pt/C platinum on carbon
q quartet
rt room temperature
RuPhos 2-dicyclohexylphosphino-2',6'-diisopropoxybiphenyl
RuPhos G1 chloro-(2-dicyclohexylphosphino-2',6'-diisopropoxy-1,1'-biphenyl) [2-(2-aminoethyl)phenyl]palladium(II)
RuPhos G2 chloro(2-dicyclohexylphosphino-2',6'-diisopropoxy-1,1'-biphenyl)[2-(2'-amino-1,1'-biphenyl)]palladium(II)
s singlet
SFC supercritical fluid chromatography
t tert
t triplet
TEA triethylamine
TFA trifluoroacetic acid
THF tetrahydrofuran
TMP 2,2,6,6-tetramethylpiperidine
TMS trimethylsilyl
TosMIC p-toluenesulfonylmethyl isocyanide
Ts p-toluenesulfonyl
T3P propanephosphonic acid anhydride
v/v volume-to-volume ratio
wt % weight percent
w/w weight-to-weigh ratio General Schemes Compounds of Formula I in the present invention can be synthesized in accordance with the general synthetic methods known to those who are skilled in the art. The following reaction schemes are only meant to represent examples of the invention and are in no way meant to be a limit of the invention.

Compounds of Formula I can be prepared according to Scheme 1. Palladium-catalyzed cross coupling of haloarenes A-I (Y=alkyl, X=Cl or Br) with C- or N-nucleophiles (e.g., organoboron reagents, organozinc reagents, or amines) can give imidazole esters A-II. If A-II are methyl or ethyl esters, ester hydrolysis using aqueous hydroxide solution in a cosolvent such as 1,4-dioxane or THF can give imidazole carboxylic acids A-III. If A-II are a tert-butyl esters, ester dealkylation using an acid such as TFA in a solvent such as DCE can give A-III. Amides of Formula I can be formed by reaction of A-III with amines or amine salts promoted by a reagent such as HATU or EDCI and a base such as DIPEA in a solvent such as DMF, MeCN, or DCM. Amides of Formula I ($R^4$=Cl) can undergo Suzuki cross-coupling reaction with organoboron reagents such as trimethylboroxine using a palladium precatalyst and ligand combination such as RuPhos G1/RuPhos and a carbonate base such as $K_2CO_3$ in a solvent such as 1,4-dioxane to give amides of Formula I ($R^4$=alkyl).

Scheme 1

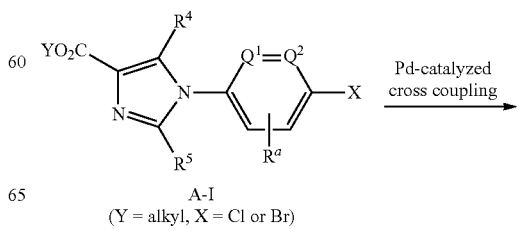

A-I
(Y = alkyl, X = Cl or Br)

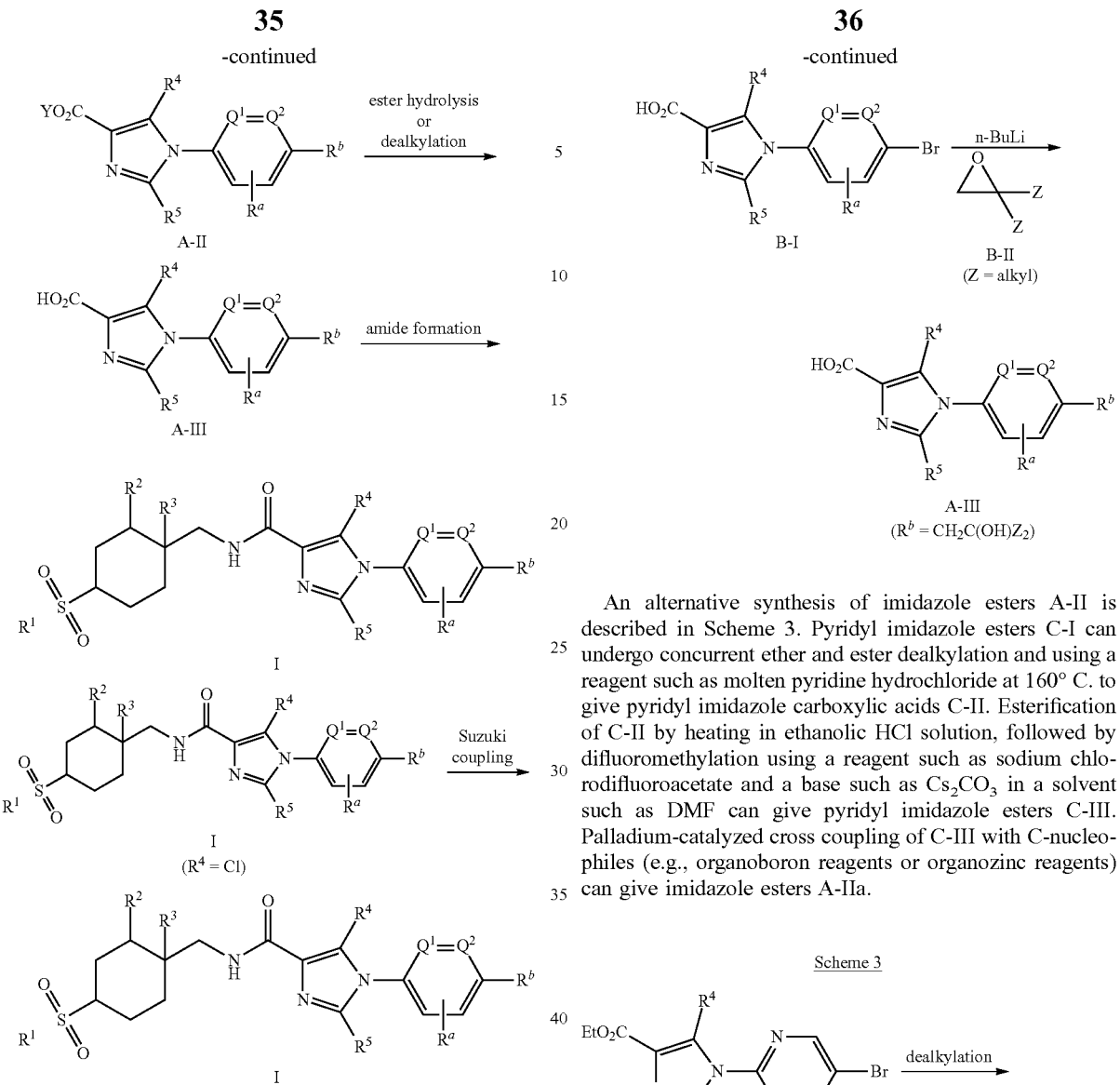

An alternative synthesis of imidazole carboxylic acids A-III is described in Scheme 2. Haloarenes A-I (Y=alkyl, X=Br) can undergo ester hydrolysis using aqueous hydroxide solution in a cosolvent such as 1,4-dioxane or THF to give haloarene carboxylic acids B-I. Treatment of B-I with n-BuLi in an ethereal solvent such as THF, followed by trapping of the resulting aryllithium intermediate with oxiranes B-II (Z=alkyl) can give A-III ($R^b$=CH$_2$C(OH)Z$_2$).

An alternative synthesis of imidazole esters A-II is described in Scheme 3. Pyridyl imidazole esters C-I can undergo concurrent ether and ester dealkylation and using a reagent such as molten pyridine hydrochloride at 160° C. to give pyridyl imidazole carboxylic acids C-II. Esterification of C-II by heating in ethanolic HCl solution, followed by difluoromethylation using a reagent such as sodium chlorodifluoroacetate and a base such as Cs$_2$CO$_3$ in a solvent such as DMF can give pyridyl imidazole esters C-III. Palladium-catalyzed cross coupling of C-III with C-nucleophiles (e.g., organoboron reagents or organozinc reagents) can give imidazole esters A-IIa.

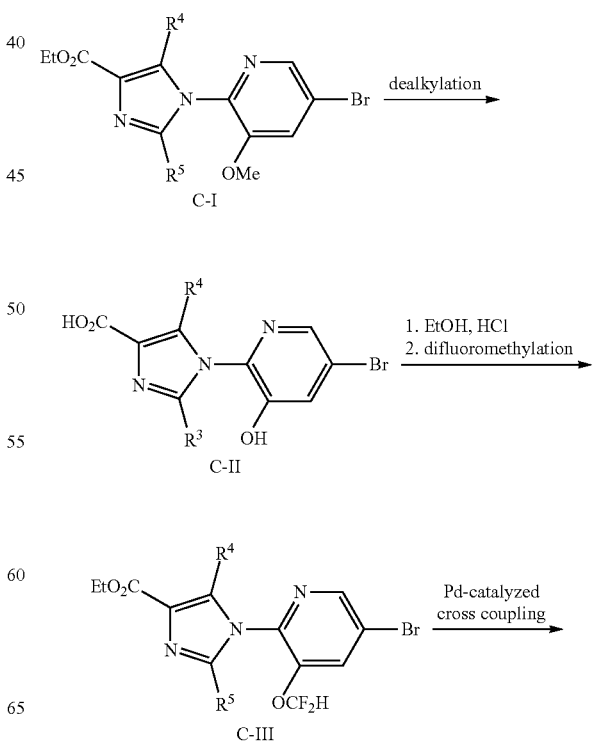

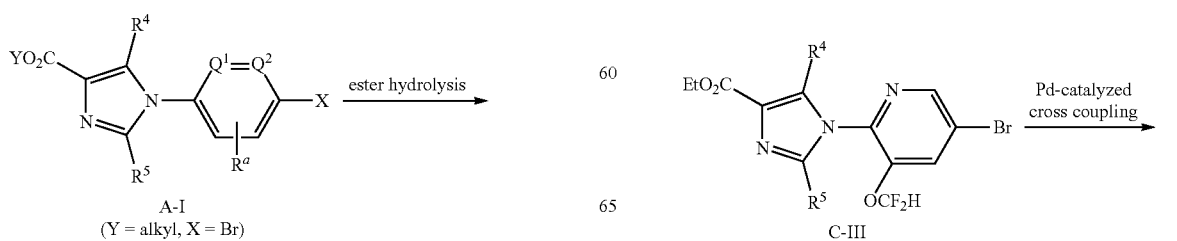

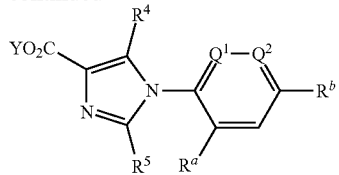

A-IIa
(Q¹ = N, Q² = CH, Rᵃ = OCF₂H)

The ethyl ester group of haloarenes A-I (Y=Et, X=Br) can be transformed into a tert-butyl ester group according to Scheme 4. Ester hydrolysis of A-I (Y=Et, X=Br) using aqueous hydroxide solution in a cosolvent such as 1,4-dioxane or THF can give the corresponding carboxylic acids. Alkylation of the carboxylic acids using Boc₂O and a nucleophilic catalyst such as DMAP in a solvent such as benzene can give haloarenes A-I (Y=t-Bu, X=Br).

Scheme 4

An alkyl substituent can be introduced at the 5-position of the imidazole ring of haloarenes A-II according Scheme 5. Haloarenes A-II (R⁴=Cl) can undergo Suzuki cross-coupling reaction with organoboron reagents such as trimethylboroxine using a palladium precatalyst and ligand combination such as RuPhos G1/RuPhos and a carbonate base such as K₂CO₃ in a solvent such as 1,4-dioxane to give haloarenes A-II (R⁴=alkyl).

Scheme 5

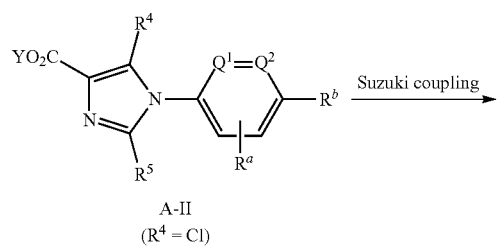

Substituents can be introduced at the 5-position of the imidazole ring of haloarenes A-I according to Scheme 6. Electrophilic chlorination of A-I (Y=alkyl, X=Cl or Br, R⁴=H) using a reagent such as NCS in a solvent such as DMF can give 5-chloroimidazoles A-I (R⁴=Cl). Deprotonation of A-I (Y=alkyl, X=Cl or Br, R⁴=H) using a base such as LDA, followed by reaction with an electrophilic fluorinating reagent such as NFSI can give 5-fluoroimidazoles A-I (R⁴=F). Deprotonation of A-I (Y=alkyl, X=Cl or Br, R⁴=H) using a base such as TMPMgCl.LiCl, followed by reaction with an electrophilic cyanating reagent such as TsCN can give 5-cyanoimidazoles A-I (R⁴=CN). Electrophilic iodination of A-I (Y=alkyl, X=Cl or Br, R⁴=H) using NIS in a solvent such as AcOH, followed by Sonogashira coupling of the resulting 5-iodoimidazoles with acetylenes can give A-I (R⁴=alkynyl).

Scheme 6

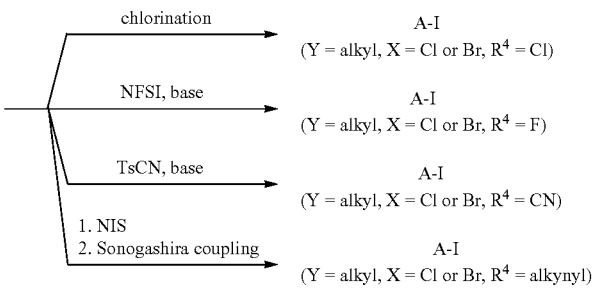

Haloarenes A-I with methyl or fluoro substituents at the 5-position of the imidazole ring can be constructed according to Scheme 7. Cyclocondensation of amidines D-I (X=Br) with ethyl 3-bromo-2-oxobutanoate using a carbonate base such as NaHCO$_3$ in an alcoholic solvent such as i-PrOH can give A-I (Y=Et, X=Br, R$^4$=Me). Cyclocondensation of amidines D-I (X=Br) with methyl 2,3-dibromo-3,3-difluoropropanoate using a carbonate base such as Cs$_2$CO$_3$ in a solvent such as DMF can give A-I (Y=Me, X=Br, R$^4$=F).

Scheme 7

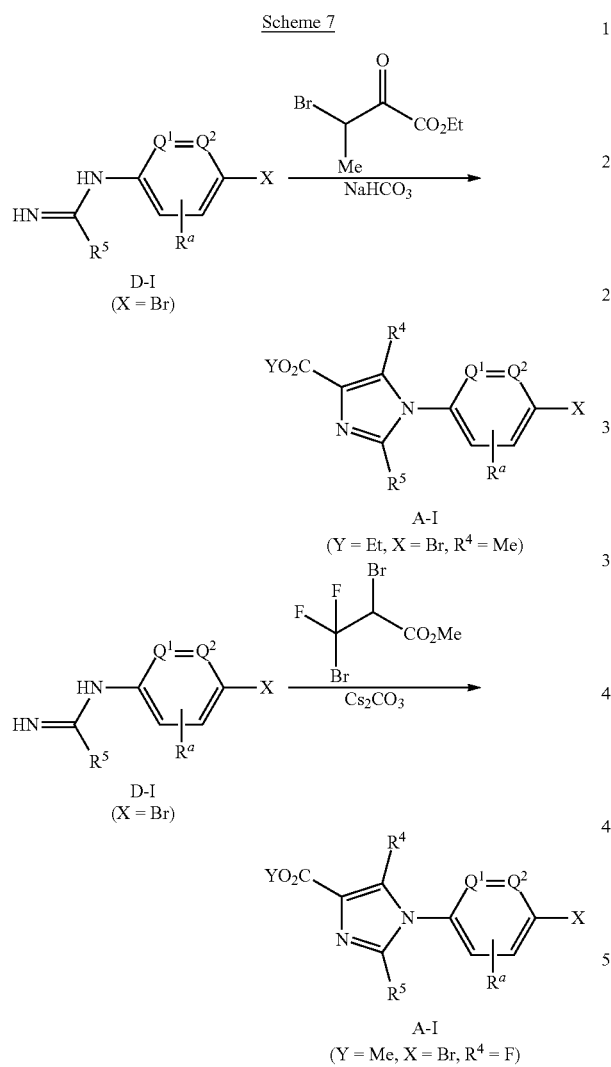

Haloarenes A-I without substituents at the 5-position of the imidazole ring can be constructed according to Scheme 8. Cyclocondensation of amidines D-I (X=Cl or Br) with ethyl 2-bromoacrylate using a carbonate base such as NaHCO$_3$ or Cs$_2$CO$_3$ in a solvent such as EtOH or DMF can give imidazoline ester intermediates. These intermediates can undergo oxidation using reagents or combinations of reagents such as Pb(OAc)$_4$ in THF, BrCCl$_3$ and DBU in DCM, or CCl$_4$ and DBU in pyridine/MeCN to give A-I (Y=Et, X=Cl or Br, R$^4$=H). An alternative preparation starts with condensation of aminoarenes E-I (X=Br) with ethyl 3,3-diethoxy-2-nitropropanoate in a solvent such as AcOH to give enamines E-II. Nitro group reduction can be accomplished using Pt/C-catalyzed hydrogenation conditions or by using reducing agents such as iron or zinc. Condensation of the resulting diamines with orthoformates can be accomplished in situ during hydrogenation step or in a subsequent step to give A-I (Y=Et, X=Br, R$^4$=H).

Scheme 8

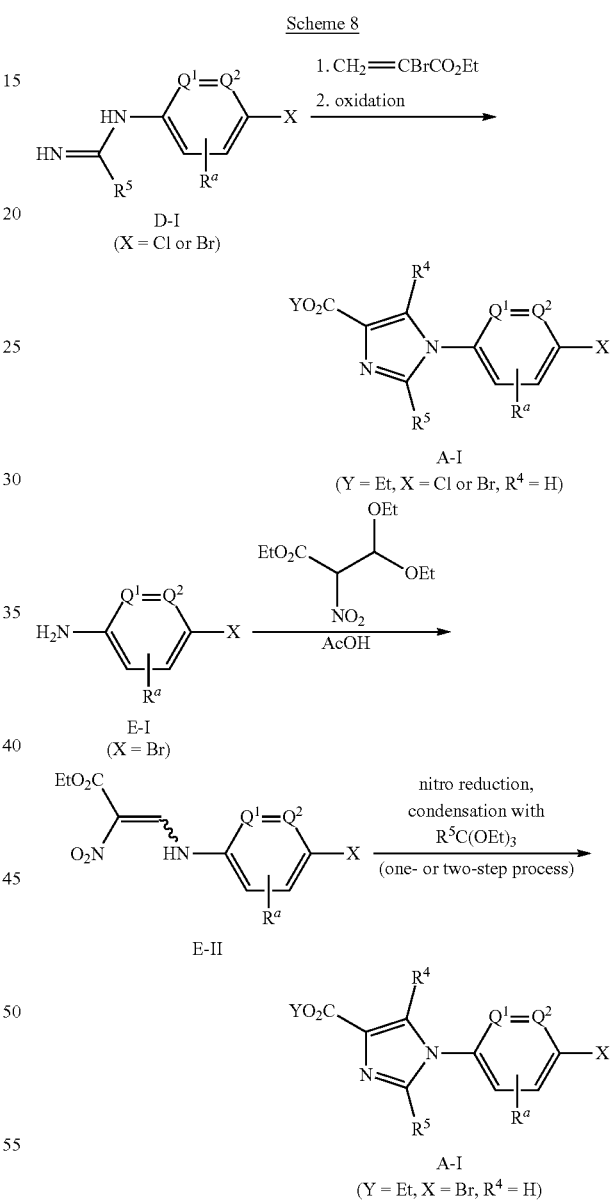

Amidines D-I (X=Cl or Br) can be prepared according to Scheme 9. Reaction of aminoarenes E-I (X=Cl or Br) with alkyl nitriles promoted by Lewis acids such as AlMe$_3$ or SnCl$_4$ in a hydrocarbon solvent such as toluene can give amidines D-I (X=Cl or Br). An alternative preparation starts with reaction of E-I (X=Cl or Br) with aliphatic acid chlorides to give the corresponding amides. Treatment of the amides with PCl₅ in a solvent such as DCM, followed by reaction of the resulting imidoyl chlorides with ammonia can give D-I (X=Cl or Br).

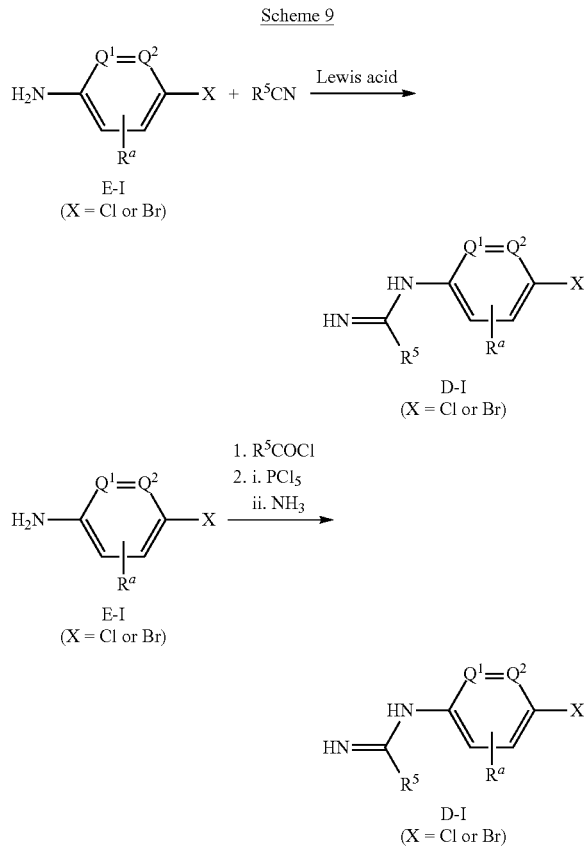

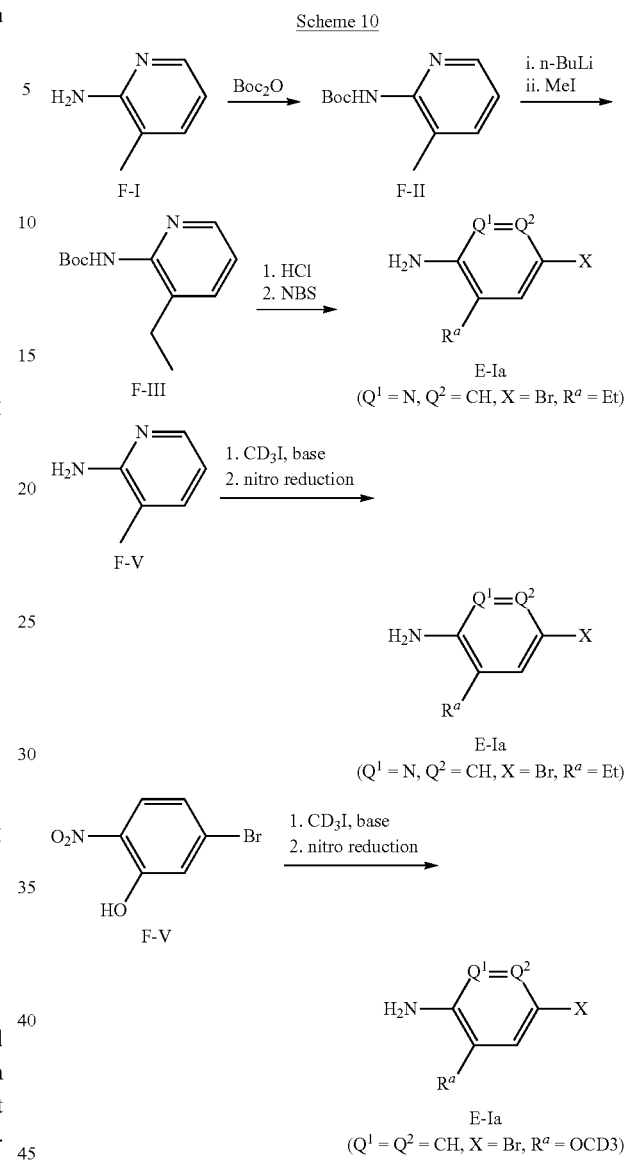

Aminoarenes E1 can be purchased from commercial suppliers or prepared as described in Scheme 10. Reaction of 3-methylpyridin-2-amine (F-I) with Boc₂O in a solvent such as EtOAc/hexanes can give tert-butyl (3-methylpyridin-2-yl)carbamate (F-II). Lithiation of F-II using n-BuLi in a solvent such as THF, followed by trapping of the organolithium intermediate with MeI can give tert-butyl (3-ethylpyridin-2-yl)carbamate (F-III). Treatment of F-III with a strong acid such as HCl in a solvent such as EtOAc, followed bromination of the resulting aminopyridine intermediate with NBS in a solvent mixture such as 1,4-dioxane/water can give 5-bromo-3-ethylpyridin-2-amine (E-Ia; Q¹=N, Q²=CH, X=Br, Rᵃ=Et). 5-Bromo-3-methylpyridin-2-amine (E-Ia; Q¹=N, Q²=CH, X=Br, Rᵃ=Me) can be prepared by bromination of 3-methylpyridin-2-amine (F-IV) using molecular bromine in a solvent such as DCM. 4-Bromo-2-(methoxy-d₃)aniline (E-Ia; Q¹=Q²=CH, X=Br, Rᵃ=OCD₃) can be prepared by first alkylating 5-bromo-2-nitrophenol (F-V) using CD₃I and a base such as K₂CO₃ in a solvent such as DMF. Reducing the nitro group with a reductant such as SnCl₂·2H₂O in a solvents such as EtOAc can give E-Ia (Q¹=Q²=CH, X=Br, Rᵃ=OCD₃).

Ethyl 2-bromoacrylate (G-II), methyl 2,3-dibromo-3,3-difluoropropanoate (G-IV), and ethyl 3-bromo-2-oxobutanoate (G-VI) can be prepared according to Scheme 11. Treating a solution of ethyl 2,3-dibromopropanoate (G-I) with a base such as TEA in a solvent mixture such as Et₂O/hexanes can give G-1I. Treating methyl 3,3-difluoroacrylate (G-III) with bromine in a solvent such as DCM can give G-IV. Treating ethyl 2-oxobutanoate (G-V) with bromine in a solvent such as DCM can give G-VI.

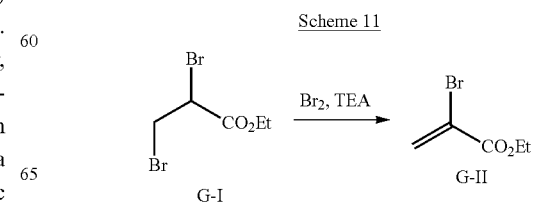

-continued

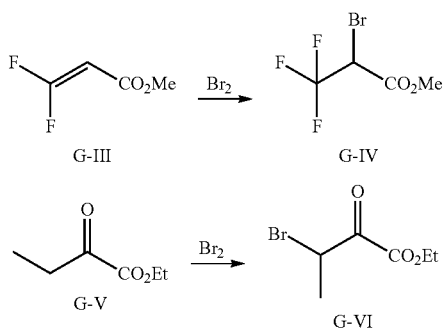

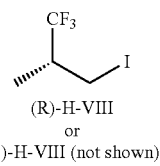

(R)-H-VIII
or
(S)-H-VIII (not shown)

Reagents, or precursors to reagents, for use in palladium-catalyzed cross-coupling reactions can be prepared according to Scheme 12. Alkenes H-I can undergo hydroboration reaction with 9-BBN to give borane reagents H-II. Carboxylic acids H-III can undergo reduction promoted by LAH in an ethereal solvent to give primary alcohols H-IV. These alcohols can be converted to iodides H-V by heating them with triphenyl phosphite and iodomethane or by heating them with a combination of reagents such as iodine, triphenylphosphine, and imidazole in a solvent such as NMP. Chiral, enantioenriched iodides can be prepared by enantioselective hydrogenation of acrylate H-VI, optionally followed by classical resolution of the resulting carboxylic acids H-VII. Reduction of H-VII with LAH in an ethereal solvent followed by treatment of the resulting alcohol intermediates with combination of reagents such as iodine, triphenylphosphine, and imidazole can give enantioenriched iodides H-VIII.

(1s,4s)-1-(Aminomethyl)-4-(methylsulfonyl)cyclohexan-1-ol hydrochloride ((s,s)-I-VI) can be prepared according to Scheme 13. Reduction of 1,4-dioxaspiro[4.5]decan-8-one (I-I) with a reagent such as NaBH$_4$, followed by mesylation of the resulting secondary alcohol can give cyclohexane mesylate I-II. Reaction of I-II with sodium thiomethoxide in a polar aprotic solvent, followed by hydrolytic cleavage of the 1,3-dioxolane group promoted by an aqueous acid such as HCl can give cyclohexanone sulfide I-III. Oxidation of the sulfide of with a reagent such as mCPBA can give cyclohexanone sulfone I-IV. Cyanosilylation of I-IV using TMSCN and TEA can give nitrile I-V. Reduction of I-V with borane followed by quenching with HCl can give a diastereomeric mixture of amino alcohol HCl salts, I-VI. Equilibration of the isomeric mixture can be promoted by heating with an alkoxide base, such as t-BuONa, in THF/t-BuOH to enrich the mixture in the s,s isomer. Once the thermodynamic ratio is reached, the mixture can undergo reaction with Boc$_2$O, and the resulting product can be triturated with EtOAc/n-heptane to provide the stereochemically pure hydroxy carbamate (s,s)-I-VII. Removal of the Boc group under acidic conditions, such as ethanolic HCl, can give amine salt (s,s)-I-VI.

Scheme 12

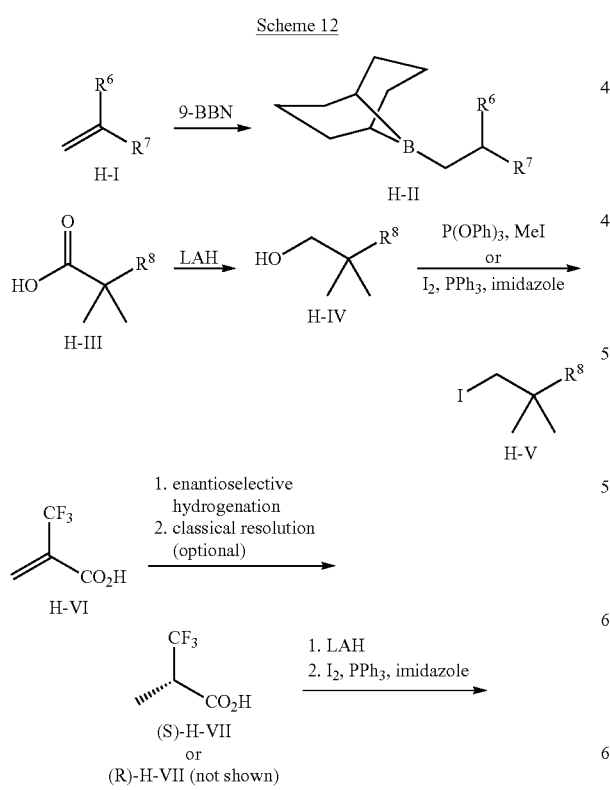

Scheme 13

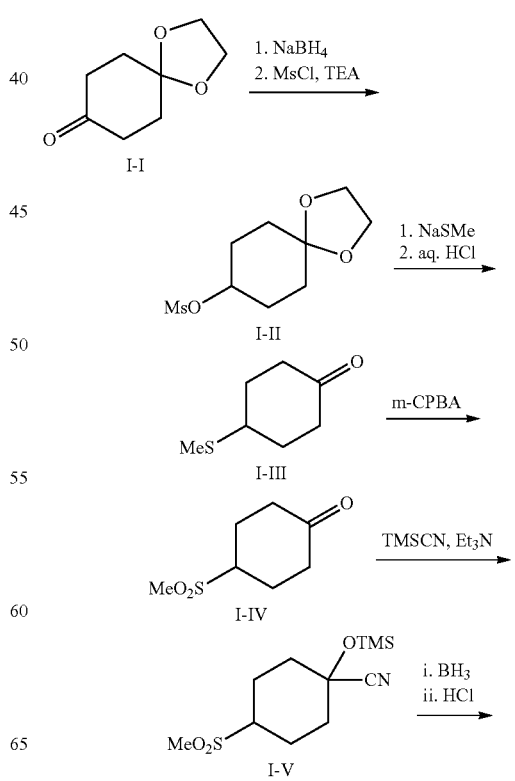

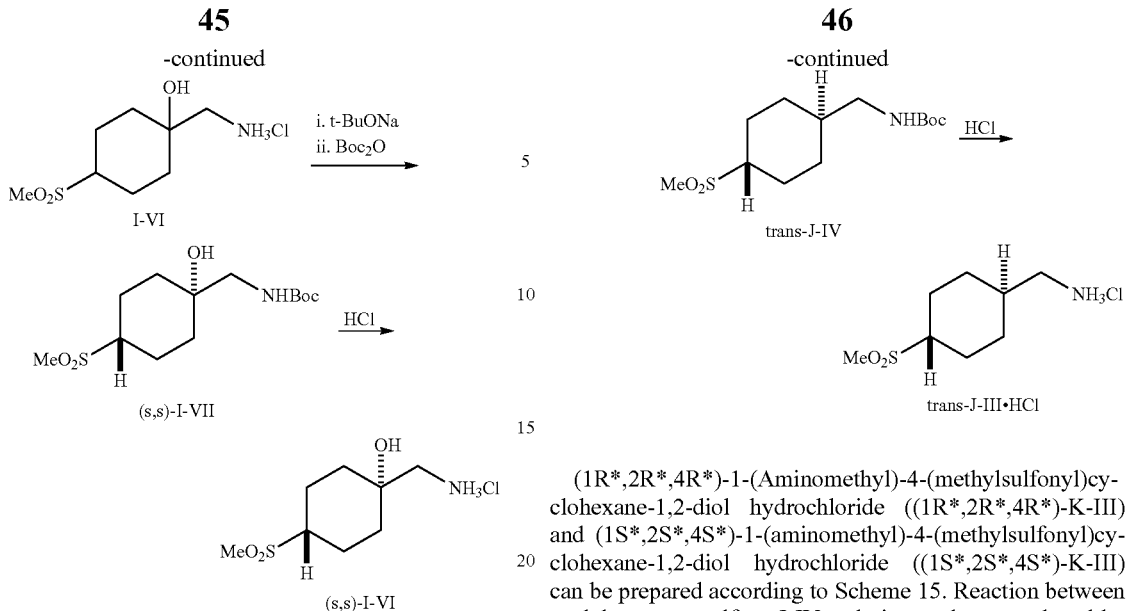

((1r,4r)-4-(Methylsulfonyl)cyclohexyl)methanamine hydrochloride (trans-J-III·HCl) can be prepared according to Scheme 14. Reductive cyanation of cyclohexanone sulfide I-III using TosMIC with an alkoxide base, such as t-BuONa, in an ethereal solvent can give cyanocyclohexane sulfide J-I. Oxidation of J-I with a reagent system such as Oxone in acetone/water can give cyanocyclohexane sulfone J-II. Reduction of J-II with LAH in an ethereal solvent can give amine J-III as a mixture of cis and trans isomers. The corresponding Boc carbamate intermediate, J-IV, can be prepared if J-III is not isolated, but instead Boc$_2$O is added to the solution generated after quenching and filtering the LAH reduction reaction mixture. Isolation of J-IV followed by sequential triturations using IPA/n-heptanes and then EtOAc/n-heptanes can provide stereochemically pure trans-J-IV. Removal of the Boc group under acidic conditions, such as ethanolic HCl, can give amine salt trans-J-III·HCl.

(1R*,2R*,4R*)-1-(Aminomethyl)-4-(methylsulfonyl)cyclohexane-1,2-diol hydrochloride ((1R*,2R*,4R*)-K-III) and (1S*,2S*,4S*)-1-(aminomethyl)-4-(methylsulfonyl)cyclohexane-1,2-diol hydrochloride ((1S*,2S*,4S*)-K-III) can be prepared according to Scheme 15. Reaction between cyclohexanone sulfone I-IV and nitromethane catalyzed by DMEN can give nitro cyclohexene K-I. Reduction of K-I using zinc metal in AcOH, followed by reaction of the resulting amine salt intermediate with Boc$_2$O in a solvent mixture containing THF and aqueous NaHCO$_3$ can give cyclohexene carbamate K-II. Dihydroxylation of K-II using a catalyst such as K$_2$OsO$_4$·2H$_2$O and a terminal reductant such as NMO in acetone/water can give a diol intermediate, which can undergo TFA-promoted cleavage of the Boc group, followed by treatment with HCl to give amino diol HCl salt (1RS,2RS)-K-III as a mixture of C4 epimers. Equilibration of the isomeric mixture can be promoted by heating with an alkoxide base, such as t-BuOK, in t-BuOH to enrich the mixture in the 1RS,2RS,4RS isomer. Reaction of this equilibrated mixture with CbzCl in aqueous NaHCO$_3$ solution, followed by trituration of the product with EtOAc/hexanes can give (1RS,2RS,4RS)-K-IV as a single diastereomer. Resolution of (1RS,2RS,4RS)-K-IV by SFC using a chiral stationary phase can give (1R*,2R*,4R*)-K-IV and (1S*,2S*,4S*)-K-IV in stereochemically pure form. Hydrogenolysis of the Cbz carbamates with hydrogen gas using a catalyst such as Pd/C, followed by treatment of the resulting amines with HCl can give amino diol salts (1R*,2R*,4R*)-K-III and (1S*,2S*,4S*)-K-III.

Scheme 14

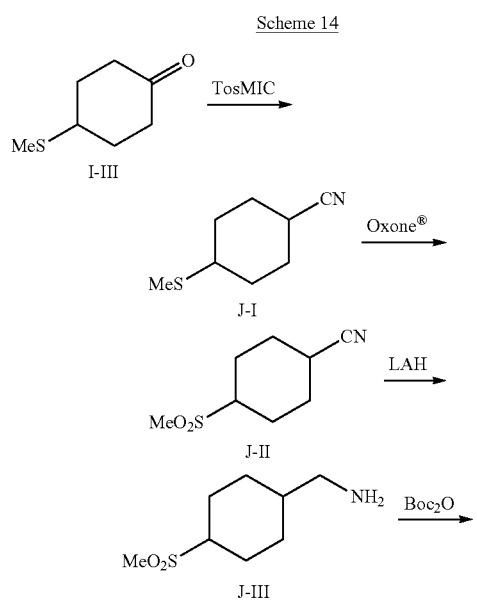

Scheme 15

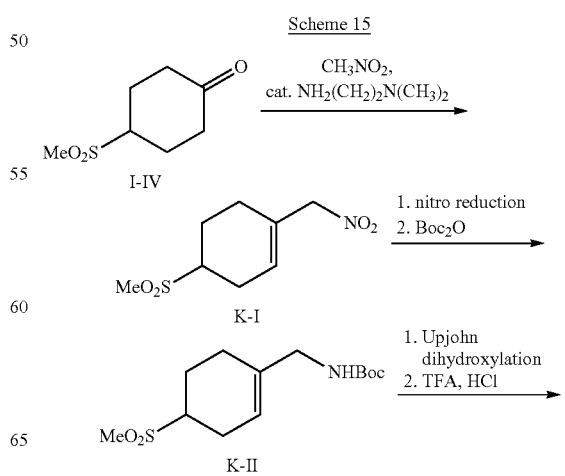

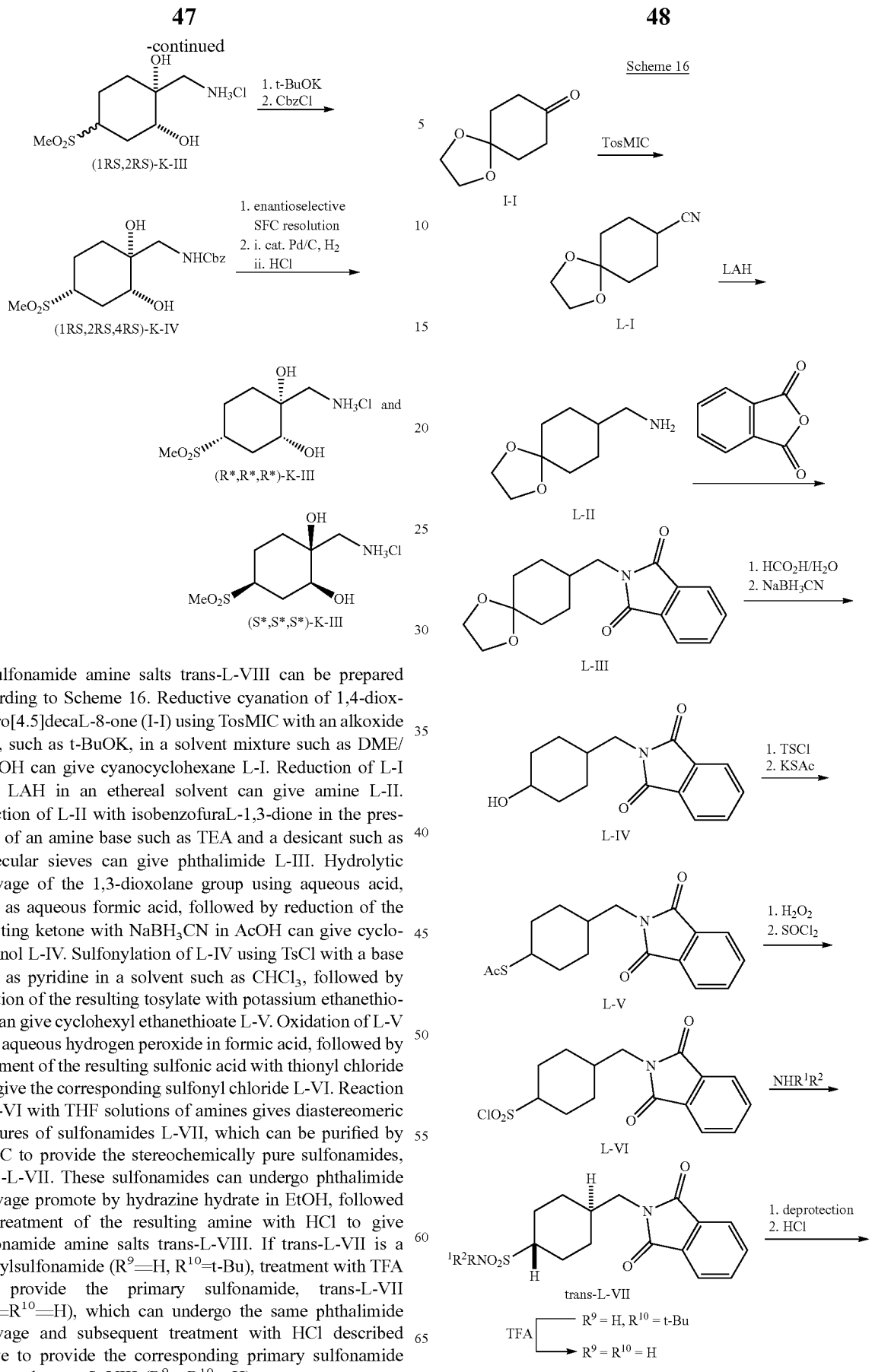

Sulfonamide amine salts trans-L-VIII can be prepared according to Scheme 16. Reductive cyanation of 1,4-dioxaspiro[4.5]decaL-8-one (I-I) using TosMIC with an alkoxide base, such as t-BuOK, in a solvent mixture such as DME/t-BuOH can give cyanocyclohexane L-I. Reduction of L-I with LAH in an ethereal solvent can give amine L-II. Reaction of L-II with isobenzofuraL-1,3-dione in the presence of an amine base such as TEA and a desiccant such as molecular sieves can give phthalimide L-III. Hydrolytic cleavage of the 1,3-dioxolane group using aqueous acid, such as aqueous formic acid, followed by reduction of the resulting ketone with $NaBH_3CN$ in AcOH can give cyclohexanol L-IV. Sulfonylation of L-IV using TsCl with a base such as pyridine in a solvent such as $CHCl_3$, followed by reaction of the resulting tosylate with potassium ethanethioate can give cyclohexyl ethanethioate L-V. Oxidation of L-V with aqueous hydrogen peroxide in formic acid, followed by treatment of the resulting sulfonic acid with thionyl chloride can give the corresponding sulfonyl chloride L-VI. Reaction of L-VI with THF solutions of amines gives diastereomeric mixtures of sulfonamides L-VII, which can be purified by HPLC to provide the stereochemically pure sulfonamides, trans-L-VII. These sulfonamides can undergo phthalimide cleavage promote by hydrazine hydrate in EtOH, followed by treatment of the resulting amine with HCl to give sulfonamide amine salts trans-L-VIII. If trans-L-VII is a t-butylsulfonamide ($R^9$=H, $R^{10}$=t-Bu), treatment with TFA can provide the primary sulfonamide, trans-L-VII ($R^9$=$R^{10}$=H), which can undergo the same phthalimide cleavage and subsequent treatment with HCl described above to provide the corresponding primary sulfonamide amine salt trans-L-VIII ($R^9$=$R^{10}$=H).

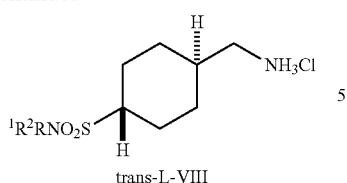

trans-L-VIII

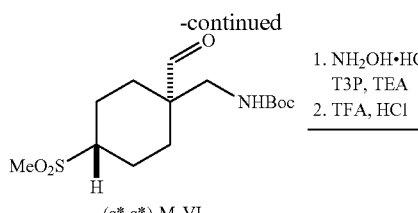

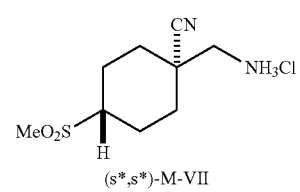

(1s*,4s*)-1-(Aminomethyl)-4-(methylsulfonyl)cyclohexane-1-carbonitrile hydrochloride ((s,s)-M-VII) can be prepared can be prepared according Scheme 17. Conjugate addition of sodium methanesulfinate to 5,6-dihydro-2H-pyran-2-one (M-I) promoted by an organic acid, such as AcOH, in MeCN can give lactone sulfone M-II. Reduction of the lactone with LAH in an ethereal solvent, followed by transformation of the resulting diol to the corresponding dibromide using $PBr_3$ can give M-III. Reaction of M-III with methyl cyanoacetate promoted by a carbonate base such as $Cs_2CO_3$ in a solvent such as DMF can give cyclohexane M-IV. Treatment of M-IV with LAH in an ethereal solvent, followed by reaction of the resulting amino alcohol with $Boc_2O$ can give carbamate alcohol M-V. Swern oxidation of this alcohol, followed by separation of the diastereomers by silica gel chromatography can give (s*,s*)-M-VI. Conversion of (s*,s*)-M-VI to the corresponding nitrile by treatment with a combination of reagents such as hydroxylamine.HCl, TEA, and T3P in a solvent such as DMF, followed by treatment of the nitrile intermediate with TFA and then HCl can give amino nitrile salt (s*,s*)-M-VII.

(1RS,2SR,5RS)-2-(Aminomethyl)-5-(methylsulfonyl)cyclohexan-1-ol hydrochloride ((1RS,2SR,5RS)-N-II) can be prepared according to Scheme 18. Sequential hydroboration and oxidation of cyclohexene carbamate K-II in THF using first $BH_3$.THF and then aqueous hydrogen peroxide and sodium hydroxide can give secondary alcohol (1RS,2SR)-N-I as a mixture of C4 epimers. Chromatographic separation of the epimers can give (1RS,2SR,4SR)-N-I. Treatment of (1RS,2SR,4SR)-N-I with TFA and HCl can give amino alcohol salt (1RS,2SR,5RS)-N-II.

Scheme 18

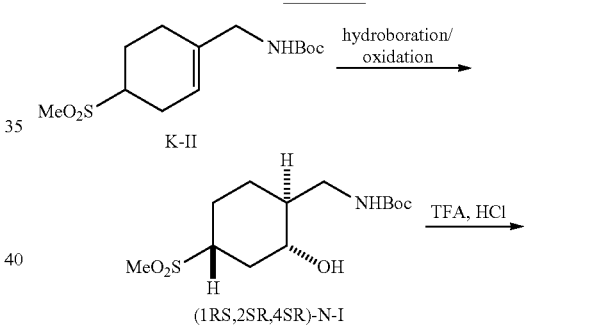

Scheme 17

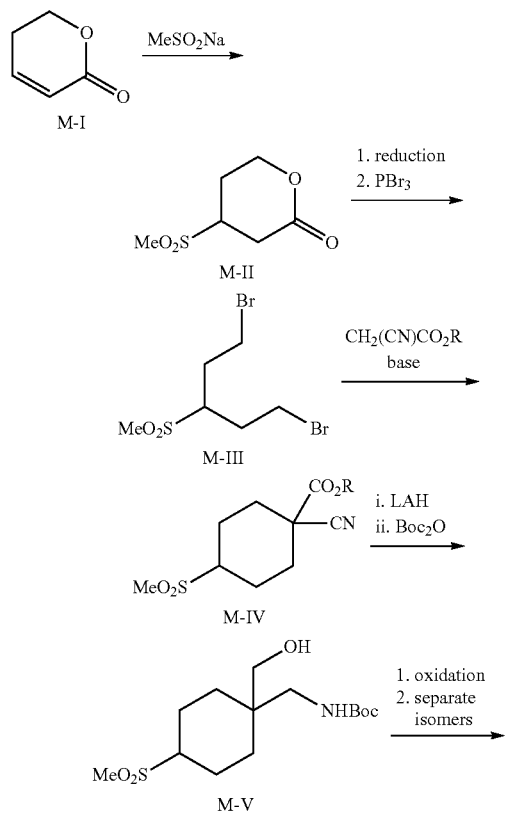

Intermediate 1

1,4-Dioxaspiro[4.5]decan-8-ol

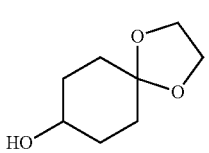

Sodium borohydride (83.4 g, 2.21 mol) was added in portions over 2 h to a stirring 0-5° C. solution of 1,4-dioxaspiro[4.5]decan-8-one (1150 g, 7.36 mol) and MeOH (7 L) at a rate that maintained the internal temperature below 5° C. After the reaction went to completion, water was added, and the mixture was concentrated. The residue was then diluted with DCM and water, the layers were separated, and the aqueous layer was extracted twice with DCM. The combined organic layers was washed with brine, dried with anhydrous Na$_2$SO$_4$, and then concentrated to afford the title compound as a colorless liquid (65.9% w/w).

Intermediate 2

1,4-Dioxaspiro[4.5]decan-8-yl methanesulfonate

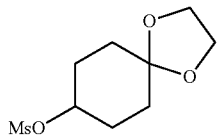 [SMILES: CSC1CCC2(CC1)OCCO2]

Methanesulfonyl chloride (1000 g, 8.790 mol) was added dropwise to a stirring solution of 1,4-dioxaspiro[4.5]decan-8-ol (1722 g, 65.9% w/w, 7.17 mol, Intermediate 1) and TEA (2178 g, 21.52 mol) in DCM (10 L) at a rate that maintained the internal temperature between 10 and 20° C. After the reaction went to completion, it was combined with another mixture prepared in a similar way. The combined mixture was washed with water and then concentrated. The residue was slurried in n-heptane and EtOH (10:1 v/v) at room temperature, and the suspension was filtered. The filter cake was dried under vacuum to afford the title compound as a yellow solid.

Intermediate 3

8-(Methylthio)-1,4-dioxaspiro[4.5]decane

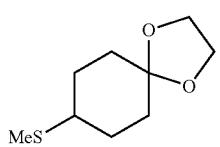

Sodium thiomethoxide (249 g, 3.56 mol) was added in five portions to a stirring 0-5° C. solution of 1,4-dioxaspiro[4.5]decan-8-yl methanesulfonate (800 g, 3.39 mol, Intermediate 2) in DMF (4.8 L), and the reaction mixture was allowed to warm to 15-20° C. over 24 h. An additional portion of NaSMe (23.7 g, 0.339 mol) was then added, and stirring was continued until the reaction went to completion. Water and MTBE were then added, and the layers were separated. The organic layer was washed three times with water, concentrated, and then dried under vacuum to afford the title compound as a yellow oil.

Intermediate 4

4-(Methylthio)cyclohexan-1-one

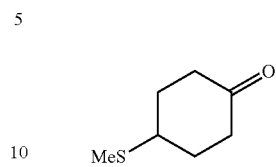

A mixture of 8-(methylthio)-1,4-dioxaspiro[4.5]decane (680 g, 3.61 mol, Intermediate 3), i-PrOAc (6.8 L), and 3 N aqueous HCl (680 mL) was stirred at 20-25° C. for 30 min. After this time, the layers were separated. The organic layer was washed with a 3 N aqueous HCl (680 mL) as described above eight additional times. During the final washing, the mixture was stirred for 1 h. The organic layer was then concentrated to afford the title compound as a yellow oil.

Intermediate 5

4-(Methylsulfonyl)cyclohexan-1-one

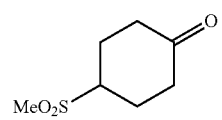

m-Chloroperbenzoic acid (1151 g, 85% w/w, 5.668 mol) was added in portions to a stirring −5 to 5° C. solution of 4-(methylthio)cyclohexan-1-one (545 g, 3.78 mol, Intermediate 4) in DCM (11 L) at a rate that maintained the internal temperature below 5° C. After the addition was complete, stirring was continued for 45 min before an additional portion of mCPBA (231 g, 85% w/w, 1.13 mol) was added, and stirring was continued for 30 min. A third portion of mCPBA (76.9 g, 85% w/w, 0.378 mol) was added, and stirring was continued at −5 to 5° C. for 30 min. The reaction mixture was then filtered. The filter cake was rinsed with DCM, and the combined filtrate and rinse was concentrated. The concentrate was then diluted with MTBE and stirred at 50° C. for 1 h before it was allowed to cool to rt and stir for 16 h. The slurry was then filtered, and the filter cake was rinsed with MTBE and dried under vacuum to afford the title compound as a colorless solid.

Intermediate 6

4-(Methylsulfonyl)-1-((trimethylsilyl)oxy)cyclohexane-1-carbonitrile

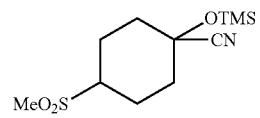

Trimethylsilyl cyanide (410 g, 4.13 mol) was added dropwise to a stirring solution of 4-(methylsulfonyl)cyclohexan-1-one (560 g, 3.18 mol, Intermediate 5) and TEA (113 g, 1.11 mol) in DCM (5.6 L) at a rate that maintained the internal temperature of 25-30° C., and the resulting mixture was stirred for 30 min. After this time, a saturated aqueous NaHCO$_3$ solution was added, and the layers were separated. The organic layer was washed with brine and then concentrated. The residual DCM was then removed by two cycles of sequential dilution with n-heptane and concentration. The concentrate was then stirred as a slurry in n-heptane at rt for 16 h before it was filtered. The filter cake was rinsed with n-heptane and then dried under vacuum to afford the title compound as a colorless solid.

Intermediate 7

1-(Aminomethyl)-4-(methylsulfonyl)cyclohexan-1-ol hydrochloride

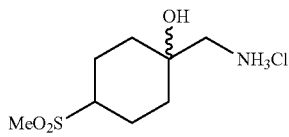

Borane (1.74 L, 1.0 M in THF, 1.74 mol) was added dropwise to a stirring 60° C. solution of 4-(methylsulfonyl)-1-((trimethylsilyl)oxy)cyclohexane-1-carbonitrile (400 g, 1.45 mol, Intermediate 6) in THF (1.6 L), and the solution was stirred until the reaction went to completion. The solution was then cooled in an ice-water bath and quenched by carefully adding MeOH. After the quench was completed, the mixture was acidified with 33% ethanolic HCl solution (200 mL) and stirred for 30 min. The mixture was then filtered, and the filter cake was rinsed with MTBE and then dried under vacuum to afford the title compound as a colorless solid.

Intermediate 8 tert-Butyl (((1s,4s)-1-hydroxy-4-(methylsulfonyl)cyclohexyl)methyl)carbamate

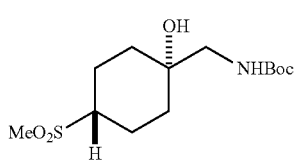

Sodium tert-butoxide (118 g, 1.05 mol) was added in portions to a stirring solution of 1-(aminomethyl)-4-(methylsulfonyl)cyclohexan-1-ol hydrochloride (170 g, 0.70 mol, Intermediate 7) in t-BuOH (850 mL) and THF (850 mL) at rt. The resulting mixture was then heated to 60° C. and stirred until the cis and trans isomers reached equilibrium as judged by HPLC analysis. The reaction mixture was then allowed to cool to rt before 3 N aqueous HCl (70 mL, 0.21 mol) was added. A solution of Boc$_2$O (159 g, 0.728 mol) in THF (510 mL) was then added dropwise at rt, and the mixture was stirred until the reaction went to completion. The resulting mixture was combined with another mixture prepared in a similar way on a similar scale. The combined mixture was filtered, and the filter cake was rinsed with DCM. The filtrate and wash were combined and then concentrated to afford an off-white solid, which was stirred as a slurry in EtOAc/n-heptane (0.8 L, 1:1 v/v) at 60° C. for 1 h. The suspension was allowed to cool and then filtered. The filter cake was rinsed with EtOAc/n-heptane (1:1 v/v) and then dried under vacuum to afford the title compound as a colorless solid.

Intermediate 9

(1s,4s)-1-(Aminomethyl)-4-(methylsulfonyl)cyclohexan-1-ol hydrochloride

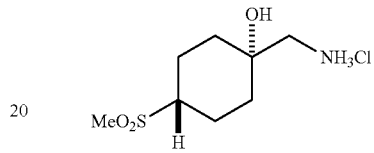

Ethanolic HCl (0.9 L, 33 wt %) was added dropwise to a solution of tert-butyl (((1s,4s)-1-hydroxy-4-(methylsulfonyl)cyclohexyl)methyl)carbamate (290 g, 0.94 mol, Intermediate 8) in EtOH (0.9 L), and the mixture was stirred at rt. After the reaction went to completion, the suspension was filtered, and the filter cake was rinsed with EtOH. The filter cake was then stirred as a slurry in EtOH at reflux temperature for 2 h before it was allowed to cool to rt. The suspension was then filtered, and the filter cake was washed three times with EtOH. The filter cake was then dried at under vacuum at 50° C. the title compound as a colorless solid.

Intermediate 10

4-(Methylthio)cyclohexane-1-carbonitrile

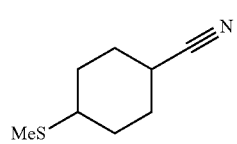

Sodium tert-butoxide (655 g, 5.82 mol) was added in portions to a stirring −38° C. mixture of 4-(methylthio)cyclohexan-1-one (350 g, 2.43 mol, Intermediate 4), TosMIC (616 g, 3.15 mol) and EtOH (263 mL, 4.50 mol) in MTBE (7.0 L) at a rate that maintained the internal temperature between −40 and −35° C., and the resulting mixture was stirred for 1 h. After this time, the mixture was allowed to warm to 3° C., and then it was filtered. The filter cake was washed with water, and the layers of the combined filtrate and wash were separated. The filter cake was then suspended in the aqueous layer, and the resulting mixture was filtered. The filter cake was washed with MTBE. Then the layers of the combined filtrate and wash were separated, and the aqueous layer was extracted with MTBE. The organic layers were combined, washed with water, washed with brine, and then concentrated. The concentrate was purified by vacuum distillation to afford the title compound as a light-yellow oil.

Intermediate 11

4-(Methylsulfonyl)cyclohexane-1-carbonitrile

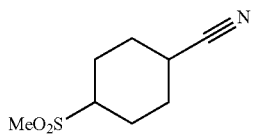

Oxone (2238 g, 3.640 mol) was added to a stirring −10° C. mixture of 4-(methylthio)cyclohexane-1-carbonitrile (255 g, 1.64 mol, Intermediate 10), acetone (2.5 L), and water (2.5 L) over 45 min at a rate that maintained the internal temperature below 2° C., and the resulting mixture was stirred for 40 min. The reaction mixture was then filtered, and the filter cake was washed with acetone. The filtrate was concentrated to remove most of acetone, and the residue was extracted with five times with EtOAc. The organic layers were combined, dried over anhydrous Na$_2$SO$_4$, filtered, and concentrated to afford a colorless solid. This solid was stirred as a slurry in n-heptane at rt overnight, and then the suspension was filtered. The filter cake was dried under vacuum to afford the title compound as a colorless solid.

Intermediate 12 tert-Butyl (((1r,4r)-4-(methylsulfonyl)cyclohexyl)methyl)carbamate

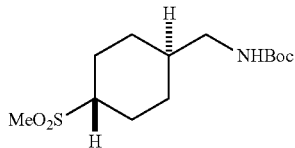

A solution of 4-(methylsulfonyl)cyclohexane-1-carbonitrile (200 g, 1.07 mol, Intermediate 11) in THF (3.0 L) was added dropwise to a stirring −10 to −5° C. suspension of LAH (123 g, 3.24 mol) in THF (1.0 L) over 3 h at a rate that maintained an internal temperature of −10 to 10° C., and the resulting mixture stirred for 2 h. After the reaction went to completion, a solution of THF and water (246 g, 1:1 w/w), 15% aqueous NaOH (123 g), and water (369 g) were sequentially added. The mixture was then filtered, and the filter cake was rinsed with THF. Di-tert-butyl dicarbonate (245 g, 3.40 mol) was then added to the combined filtrate and rinse, and the mixture was stirred at rt overnight. The mixture was then concentrated. The residue was diluted with water, and the mixture was extracted three times with EtOAc. The organic layers were combined, washed with brine, dried with anhydrous Na2SO4, filtered, and then concentrated. This concentrate was combined with an additional concentrate prepared in a similar way on a similar scale, diluted with i-PrOH (0.6 L), and stirred at 85° C. for 30 min. n-Heptane (1.2 L) was added dropwise, and the resulting mixture was stirred for 30 min. The mixture was allowed to cool to 25° C., and stirring was continued for 2 h. The mixture was then filtered, and the filter cake was washed with n-heptane and dried under vacuum at 45° C. to give a colorless solid. This solid was combined with another batch prepared in a similar way but on one-fourth scale, dissolved in EtOAc (0.6 L), and stirred at 60° C. for about 2 h. n-Heptane (2.4 L) was then added dropwise over 2 h, and stirring was continued at 60° C. for 1 h. The resulting mixture was then allowed to cool to 25° C. and was stirred for 2 h. The mixture was then filtered, and the filter cake was washed with n-heptane and dried under vacuum at 40° C. to afford the title compound as a colorless solid.

Intermediate 13

((1r,4r)-4-(Methylsulfonyl)cyclohexyl)methanamine hydrochloride

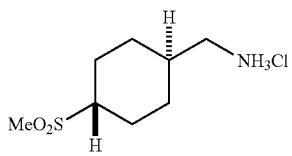

Ethanolic HCl (684 g, 33 wt %, 6.27 mol) was added dropwise to a solution of tert-butyl (((1r,4r)-4-(methylsulfonyl)cyclohexyl)methyl)carbamate (180 g, 0.62 mol, Intermediate 12) in EtOH (0.6 L), and the resulting mixture was stirred at rt. After the reaction went to completion, MTBE (2.5 L) was added, and the suspension was filtered. The filter cake was rinsed with MTBE and then dried under vacuum at 50° C. to afford the title compound as a colorless solid.

Intermediate 14

4-(Methylsulfonyl)-1-(nitromethyl)cyclohex-1-ene

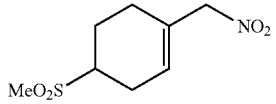

A solution of 4-(methylsulfonyl)cyclohexanone (15.27 g, 86.65 mmol, Intermediate 5), nitromethane (15 mL, 350 mmol), and DMEN (2.8 mL, 26 mmol) in benzene (220 mL) was stirred at reflux temperature for 16 h in a reactor fitted with a Dean-Stark trap. After this time, the solution was allowed to cool and then diluted with 1 N aqueous HCl (200 mL). The layers of the resulting mixture were mixed then separated, and the aqueous layer was extracted EtOAc. The organic layers were combined, washed with brine, dried with anhydrous MgSO$_4$, filtered, and then concentrated to afford the title compound as a colorless solid.

Intermediate 15

(4-(Methylsulfonyl)cyclohex-1-en-1-yl)methanamine hydrochloride

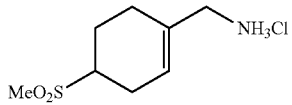

A warm solution of 4-(methylsulfonyl)-1-(nitromethyl) cyclohex-1-ene (15.52 g, 70.78 mmol, Intermediate 14) in AcOH (80 mL) was added dropwise over 1.5 h to a stirring suspension of zinc (50 g, 760 mmol) in AcOH (100 mL), which was submerged in a 70° C. bath. The drip rate was periodically adjusted to maintain the internal reaction temperature below 85° C. After the addition was complete, stirring was continued at 70° C. for 4 h before the reaction mixture was allowed to cool. The mixture was then diluted with an equal volume of EtOAc and filtered through Celite®. The filtrate was concentrated, diluted with IPA (300 mL), and filtered. The filtrate was then concentrated to half its original volume before a 1,4-dioxane solution of HCl (18 mL, 4.0 M, 72 mmol) was added. The resulting mixture was concentrated, diluted with MeOH (200 mL), and stirred until the solids were well-dispersed. The resulting suspension was concentrated to half the original volume, diluted with an equal volume of EtOAc, and then filtered. The filter cake was dried by aspiration to afford the title compound as a colorless solid.

Intermediate 16 tert-Butyl ((4-(methylsulfonyl)cyclohex-1-en-1-yl) methyl)carbamate

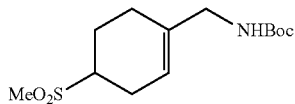

A solution of (4-methylsulfonylcyclohexen-1-yl)methanamine hydrochloride (22.0 g, 97.5 mmol, Intermediate 15) in THF (100 mL) was diluted with a saturated aqueous NaHCO$_3$ solution, Boc$_2$O (20.9 mL, 97.5 mmol) was added, and then the mixture was stirred at rt for 16 h. After this time, the mixture was diluted with EtOAc and filtered. The layers were separated, and the aqueous layer was extracted with EtOAc. The organic layers were combined, washed with brine, dried with anhydrous MgSO$_4$, filtered, and then concentrated to afford the title compound as a tan solid.

Intermediate 17 tert-Butyl ((((1RS,2RS)-1,2-dihydroxy-4-(methylsulfonyl)cyclohexyl)methyl)carbamate

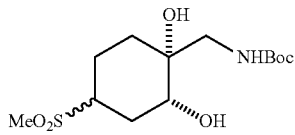

Potassium osmate(VI) dihydrate (470 mg, 1.3 mmol) was added to a solution of tert-butyl ((4-(methylsulfonyl)cyclohex-1-en-1-yl)methyl)carbamate (17.55 g, 57.01 mmol, 94%, Intermediate 16) and NMO (8.7 g, 61 mmol) in acetone/water (250 mL, 4:1 v/v), and the mixture was stirred at rt for 20 h. After this time, a solution of Na$_2$S$_2$O$_4$ (3.1 g, 15 mmol) in water (15 mL) was added, and the mixture was stirred for 30 min. After this time, the mixture was concentrated to one-third its original volume. The concentrate was diluted with EtOAc and enough hexanes to make the mixture biphasic. The pH of the aqueous layer was adjusted to pH<4 with 10 M aqueous H$_2$SO$_4$, and the layers were mixed and then separated. The aqueous layer was extracted four times with EtOAc, and then the organic layers were combined, dried anhydrous MgSO$_4$, filtered, and concentrated to afford the title compound as a pale-purple gum.

Intermediate 18

(1RS,2RS)-1-(Aminomethyl)-4-(methylsulfonyl) cyclohexane-1,2-diol hydrochloride

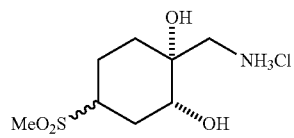

Trifluoroacetic acid (48 mL, 0.63 mol) was added to a solution of tert-butyl ((((1RS,2RS)-1,2-dihydroxy-4-(methylsulfonyl)cyclohexyl)methyl)carbamate (17.77 g, 94% w/w, 51.65 mmol, Intermediate 17) in DCM (180 mL), and the resulting solution was maintained at rt for 2 h. After this time, the solution was concentrated, MeOH was added, and the solution was concentrated again. The concentrate was dissolved in MeOH (50 mL), a solution of HCl in 1,4-dioxane (14.2 mL, 4.0 M, 56.8 mmol) was added, and the solution was concentrated to give a brown oil. This oil was dissolved in MeOH (50 mL) and then EtOAc (200 mL) was added over 30 min to induce crystallization. The resulting slurry was filtered, and the solids were washed with EtOAc and then dried by aspiration to afford the title compound as a tan solid (dr=1.6:1.0 according to NMR analysis).

Intermediate 19

(1RS,2RS,4RS)-1-(Aminomethyl)-4-(methylsulfonyl)cyclohexane-1,2-diol hydrochloride

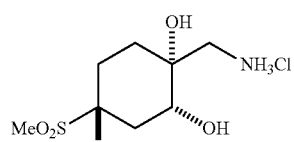

Potassium tert-butoxide (7.7 g, 68 mmol) was added to a suspension of (1RS,2RS)-1-(aminomethyl)-4-(methylsulfonyl)cyclohexane-1,2-diol hydrochloride (11.84 g, 45.58 mmol, Intermediate 18) in t-BuOH (120 mL), and the resulting thick, heterogeneous mixture was stirred at 60° C. for 65 h. After this time, the mixture was allowed to cool, and then a solution of HCl in 1,4-dioxane (18.2 mL, 4.0 M, 72.9 mmol) was added. The mixture was then concentrated to afford the title compound as a tan solid (dr=10:1.0 according to NMR analysis).

Intermediate 20

Benzyl (((1RS,2RS,4RS)-1,2-dihydroxy-4-(methylsulfonyl)cyclohexyl)methyl)carbamate

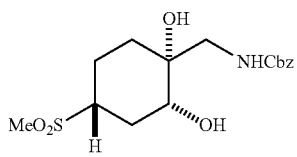 [SMILES: CS(=O)(=O)[C@@H]1CC[C@@](O)(CNC(=O)OCc2ccccc2)[C@H](O)C1]

Benzyl chloroformate (16.6 mL, 112 mmol) was added to a 0-5° C. mixture of (1RS,2RS,4RS)-1-(aminomethyl)-4-(methylsulfonyl)cyclohexane-1,2-diol hydrochloride (19.81 g, 56.05 mmol, Intermediate 19) and NaHCO$_3$ (14.1 g, 168 mmol) in water (160 mL), and the resulting mixture was stirred vigorously and allowed to gradually warm to rt over 24 h. After this time, the resulting suspension was filtered, and the filter cake was washed with water and then dried by aspiration.

The solids were diluted with hexanes and EtOAc (100 mL, 3:1 v/v) and stirred for 3 h. The slurry was filtered, and the filter cake was washed with hexanes and then dried by aspiration to afford the title compound as a light-tan solid (dr>100:1 according to NMR analysis).

Intermediate 21

Benzyl (((1S*,2S*,4S*)-1,2-dihydroxy-4-(methylsulfonyl)cyclohexyl)methyl)carbamate

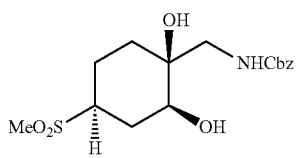 [SMILES: CS(=O)(=O)[C@H]1CC[C@](O)(CNC(=O)OCc2ccccc2)[C@@H](O)C1]

Intermediate 22

Benzyl (((1R*,2R*,4R*)-1,2-dihydroxy-4-(methylsulfonyl)cyclohexyl)methyl)carbamate

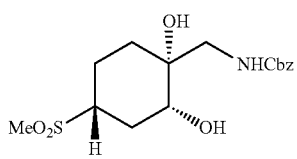 [SMILES: CS(=O)(=O)[C@@H]1CC[C@@](O)(CNC(=O)OCc2ccccc2)[C@H](O)C1]

Intermediate 20 was purified by SFC using a chiral stationary phase (Chiralpak IA, 60% CO$_2$, 40% EtOH/i-PrOH (1:1 v/v)) to give a pair of enantiomers. The first-eluting enantiomer was Intermediate 21, and the second-eluting enantiomer was Intermediate 22.

Intermediate 23

(1R*,2R*,4R*)-1-(Aminomethyl)-4-(methylsulfonyl)cyclohexane-1,2-diol hydrochloride

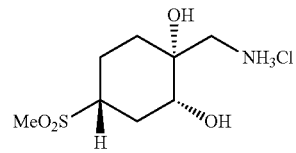

A vessel containing benzyl (((1R*,2R*,4R*)-1,2-dihydroxy-4-(methylsulfonyl)cyclohexyl)methyl)carbamate (4.22 g, 11.8 mmol, Intermediate 22) and Pd/C (10% Pd, 50% water, Degussa E101 NE/W) (2.5 g, 1.2 mmol Pd) was evacuated and backfilled three times with nitrogen before EtOH (130 mL) was added, and the mixture was stirred under an atmosphere of hydrogen at rt for 16 h. After this time, the suspension was diluted with enough water to dissolve the newly-formed precipitate, filtered through Celite®, and then concentrated. This concentrate was dissolved in MeOH and water (30 mL, 1:1 v/v) before a solution of HCl in 1,4-dioxane (3.0 mL, 4.0 M, 12 mmol) was added, and the resulting mixture was concentrated. The oily residue was diluted with EtOH and concentrated again to afford a colorless solid. This solid was suspended in EtOAc and then isolated by filtration. The moist filter cake was dried under vacuum to afford the title compound as a colorless solid. $[\alpha]_{589}^{20}$+1.9, $[\alpha]_{436}^{20}$+5.2, $[\alpha]_{365}^{20}$+10 (c 1.1, MeOH).

Intermediate 24

(1S*,2S*,4S*)-1-(Aminomethyl)-4-(methylsulfonyl)cyclohexane-1,2-diol hydrochloride

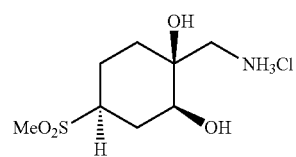

The title compound was prepared as described for the synthesis of Intermediate 23, using benzyl (((1S*,2S*,4S*)-1,2-dihydroxy-4-(methylsulfonyl)cyclohexyl)methyl)carbamate (Intermediate 21) in place of benzyl (((1R*,2R*,4R*)-1,2-dihydroxy-4-(methylsulfonyl)cyclohexyl)methyl)carbamate. $[\alpha]_{589}^{20}$-1.7, $[\alpha]_{436}^{20}$-5.1, $[\alpha]_{365}^{20}$-10 (c 1.7, MeOH).

Intermediate 25

1,4-Dioxaspiro[4.5]decane-8-carbonitrile

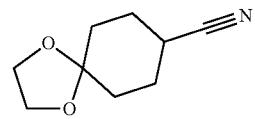 [SMILES: N#CC1CCC2(CC1)OCCO2]

A solution of t-BuOK (147 g, 1.31 mol) in t-BuOH and DME (2.0 L, 1:1 v/v) was added dropwise to a 0-5° C. solution of 1,4-dioxaspiro[4.5]decan-8-one (100 g, 640 mmol) and TosMIC (131 g, 672 mmol) in 1,2-dimethoxyethane (2.0 L), and the resulting mixture was stirred at 0-5° C. for 1 h before it was allowed to warm to rt over 12 h. After this time, the mixture was poured into water and then extracted three timed with MTBE. The organic layers were combined, washed with brine, dried with anhydrous Na$_2$SO$_4$, filtered, and then concentrated to afford the title compound, which was used in the next step without further purification.

Intermediate 26

(1,4-Dioxaspiro[4.5]decan-8-yl)methanamine

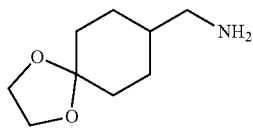

A solution of 1,4-dioxaspiro[4.5]decane-8-carbonitrile (130 g, 0.777 mmol, Intermediate 25) in THF (500 mL) was added dropwise to a 0-5° C. suspension of LAH (44.3 g, 1.17 mol) in THF (2.0 L), and the resulting mixture was stirred at 65° C. for 12 h. After this time, the mixture was allowed to cool to rt and stirred for another 12 h. The mixture was then cooled to 0-5° C. before water (45 mL) and 15% aqueous NaOH (135 mL) were sequentially added dropwise. The resulting mixture was allowed to warm to rt over 1 h with stirring before anhydrous MgSO$_4$ was added, and the suspension was stirred for another 1 h at rt. The mixture was then filtered through a pad of Celite®, and the pad was washed with EtOAc. The filtrate and wash were combined, concentrated, and then purified by distillation to afford the title compound as a colorless oil.

Intermediate 27

2-(1,4-Dioxaspiro[4.5]decan-8-ylmethyl)isoindoline-1,3-dione

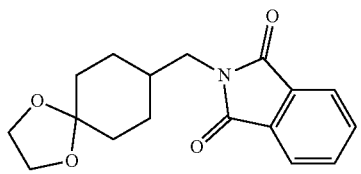 [SMILES: O=C1c2ccccc2C(=O)N1CC1CCC2(CC1)OCCO2]

A mixture of isobenzofuran-1,3-dione (64.2 g, 433 mmol), 1,4-dioxaspiro[4.5]decan-8-ylmethanamine (90.0 g, 433 mmol, Intermediate 26), TEA (52.6 g, 0.519 mol), and 4 Å molecular sieves (90 g) in toluene and DMF (990 mL, 10:1 v/v) was stirred at 110° C. for 12 h. After this time, the suspension was allowed to cool to rt and then filtered through a pad of Celite®. The pad was washed with EtOAc, and the filtrate and wash were combined, concentrated, and then purified by silica gel chromatography (10→50% EtOAc/petroleum ether) to afford the title compound as a colorless solid.

Intermediate 28

2-((4-Oxocyclohexyl)methyl)isoindoline-1,3-dione

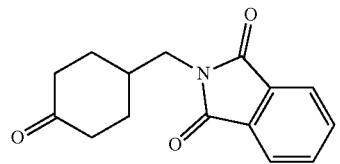 [SMILES: O=C1CCC(CN2C(=O)c3ccccc3C2=O)CC1]

Water (11.0 mL, 611 mmol) was added to a solution of 2-(1,4-dioxaspiro[4.5]decan-8-ylmethyl)isoindoline-1,3-dione (122 g, 405 mmol, Intermediate 27) in formic acid (900 mL), and the resulting solution was maintained at rt for 16 h. After this time, the solution was concentrated and then diluted with EtOAc. The resulting solution washed twice with a saturated aqueous NaHCO$_3$ solution, dried with anhydrous Na$_2$SO$_4$, filtered, and then concentrated to afford the title compound as a colorless solid.

Intermediate 29

2-((4-Hydroxycyclohexyl)methyl)isoindoline-1,3-dione

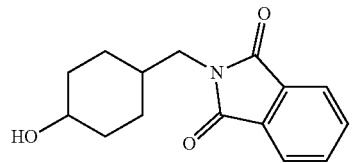 [SMILES: O=C1c2ccccc2C(=O)N1CC1CCC(O)CC1]

Sodium cyanoborohydride (48.5 g, 772 mmol) was added portionwise to a solution of 2-((4-oxocyclohexyl)methyl)isoindoline-1,3-dione (100 g, 389 mmol, Intermediate 28) in AcOH (1.0 L), and the resulting mixture was stirred at rt for 16 h. After this time, the mixture was concentrated, and the concentrate was dissolved in EtOAc. The resulting solution washed twice with a saturated aqueous NaHCO$_3$ solution, dried with anhydrous Na$_2$SO$_4$, filtered, and concentrated to afford the title compound as a colorless solid, which was used in the next step without further purification.

Intermediate 30

4-((1,3-Dioxoisoindolin-2-yl)methyl)cyclohexyl 4-methylbenzenesulfonate

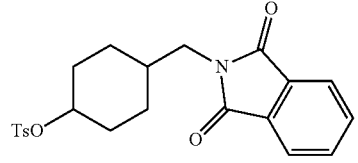 [SMILES: Cc1ccc(S(=O)(=O)OC2CCC(CN3C(=O)c4ccccc4C3=O)CC2)cc1]

4-Methylbenzene-1-sulfonyl chloride (199 g, 1.04 mol) was added to a 0-5° C. solution of 2-((4-hydroxycyclohexyl)-methyl)isoindoline-1,3-dione (135 g, 0.521 mol, Intermediate 29), and pyridine (165 g, 2.08 mol) in CHCl₃ (800 mL), and the resulting mixture was allowed to warm to rt over 12 h with stirring. After this time, the mixture was concentrated, and the concentrate was dissolved in EtOAc, washed with 2 N aqueous HCl, dried with anhydrous Na₂SO₄, filtered, and then concentrated. The concentrate was purified by silica gel chromatography (5→25% EtOAc/petroleum ether) to afford the title compound as a colorless solid.

Intermediate 31

S-(4-((1,3-dioxoisoindolin-2-yl)methyl)cyclohexyl) ethanethioate

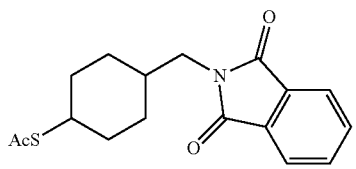

Potassium ethanethioate (27.6 g, 242 mmol) was added to a solution of 4-((1,3-dioxoisoindolin-2-yl)methyl)cyclohexyl 4-methylbenzenesulfonate (40.0 g, 96.7 mmol, Intermediate 30) in DMF (600 mL), and the resulting mixture was stirred at 75° C. for 12 h. After this time, the mixture was allowed to cool to rt and then concentrated. The concentrate was dissolved in EtOAc, washed with brine, dried with anhydrous Na₂SO₄, filtered, and then concentrated. The concentrate was purified by silica gel chromatography (5→25% EtOAc/petroleum ether) to afford the title compound as a yellow solid.

Intermediate 32

4-((1,3-Dioxoisoindolin-2-yl)methyl)cyclohexane-1-sulfonic acid

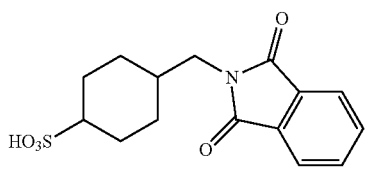 [SMILES: O=C1c2ccccc2C(=O)N1CC1CCC(S(=O)(=O)O)CC1]

A solution of H₂O₂ in water (20 mL, 30-34% w/w, 19 mmol) was added to formic acid (200 mL) at 0-5° C., and the solution was maintained at 0-5° C. for 1 h. A solution of S-(4-((1,3-dioxoisoindolin-2-yl)methyl)cyclohexyl) ethanethioate (10.0 g, 31.5 mmol, Intermediate 31) in formic acid and DCM (100 mL, 1:1 v/v) was then added, the mixture was allowed to warm to rt over 12 h with stirring. After this time, the mixture was cooled to 0-5° C. before solid Na₂SO₃ was added. The resulting mixture was filtered, concentrated, and then purified by silica gel chromatography (5→25% MeOH/DCM) to afford the title compound as a colorless solid.

Intermediate 33

4-((1,3-Dioxoisoindolin-2-yl)methyl)cyclohexane-1-sulfonyl chloride

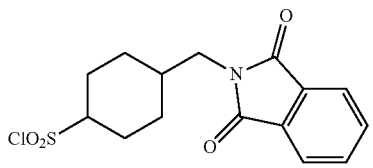 [SMILES: O=C1c2ccccc2C(=O)N1CC1CCC(S(=O)(=O)Cl)CC1]

Thionyl chloride (44.2 g, 371 mmol) and DMF (1.0 mL, 13 mmol) were added to a solution of 4-((1,3-dioxoisoindolin-2-yl)methyl)cyclohexane-1-sulfonic acid (24.0 g, 74.2 mmol, Intermediate 32) in CHCl₃ (300 mL), and the resulting mixture was stirred at 75° C. for 12 h. After this time, the mixture was allowed to cool to rt, and then it was concentrated. The concentrate underwent two cycles of sequential dilution with toluene and concentration to afford the title compound as a colorless solid.

Intermediate 34

4-((1,3-Dioxoisoindolin-2-yl)methyl)-N,N-dimethyl-cyclohexane-1-sulfonamide

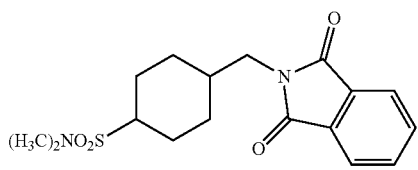

A mixture of dimethylamine (161 mL, 2.0 M in THF, 321 mmol) and 4 Å molecular sieves (20 g) in THF (300 mL) was added to a 0-5° C. solution of 4-((1,3-dioxoisoindolin-2-yl)methyl)cyclohexane-1-sulfonyl chloride (11 g, 32 mmol, Intermediate 33) in THF (300 mL), and the resulting mixture was allowed to warm to rt over 12 h with stirring. After this time, the mixture was filtered, concentrated, and then purified by silica gel chromatography (3→25% MeOH/DCM) to afford the title compound as a colorless solid.

Intermediate 35

(1r,4r)-4-((1,3-Dioxoisoindolin-2-yl)methyl)-N,N-dimethylcyclohexane-1-sulfonamide

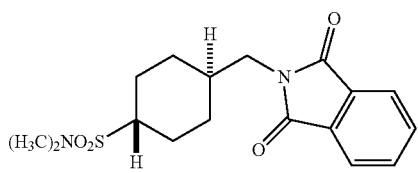

Intermediate 34 was purified by SFC (Chiralpak AD-3, 5→40% i-PrOH/CO₂ with 0.05% Et₂NH) to give the title compound as a colorless solid.

Intermediate 36

(1r,4r)-4-(Aminomethyl)-N,N-dimethylcyclohexane-1-sulfonamide

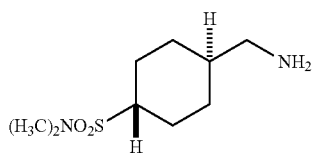

(1r,4r)-4-((1,3-Dioxoisoindolin-2-yl)methyl)-N,N-dimethylcyclohexane-1-sulfonamide (200 mg, 0.571 mmol, Intermediate 35) was suspended in EtOH (2.3 mL) before hydrazine hydrate (0.090 mL, 65% w/w, 1.0 mmol) was added, and the resulting mixture was stirred at 80° C. for 14 h. After this time, the thick suspension was allowed to cool to rt and then was concentrated to afford the title compound as a colorless solid.

Intermediate 37

4-((1,3-Dioxoisoindolin-2-yl)methyl)-N-methylcyclohexane-1-sulfonamide

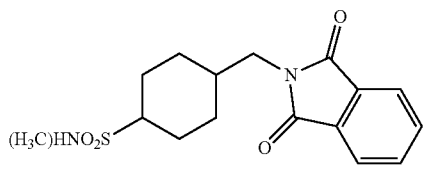

The title compound was prepared as described for the synthesis of Intermediate 34, using methylamine (2.0 M in THF) in place of dimethylamine solution.

Intermediate 38

(1r,4r)-4-((1,3-Dioxoisoindolin-2-yl)methyl)-N-methylcyclohexane-1-sulfonamide

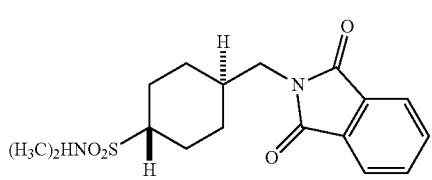

Intermediate 37 was purified by SFC (Chiralpak IA, 70% CO$_2$, 30% MeOH) to give the title compound as a colorless solid.

Intermediate 39

(1r,4r)-4-(Aminomethyl)-N-methylcyclohexane-1-sulfonamide

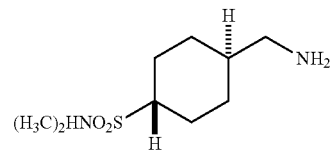

(1r,4r)-4-((1,3-Dioxoisoindolin-2-yl)methyl)-N-methylcyclohexane-1-sulfonamide (200 mg, 0.595 mmol, Intermediate 38) and hydrazine hydrate (0.089 mL, 65% w/w, 1.2 mmol) were combined EtOH (4.8 mL), and the resulting thick mixture was stirred at 80° C. for 14 h. After this time, the hot mixture was filtered, and the filter cake was washed with boiling EtOH. The filtrate and wash were combined, allowed to cool, and refiltered. The filter cake was washed with EtOH, and the filtrate and wash were combined and then concentrated to afford the title compound as a colorless solid.

Intermediate 40

N-(tert-Butyl)-4-((1,3-dioxoisoindolin-2-yl)methyl)cyclohexane-1-sulfonamide

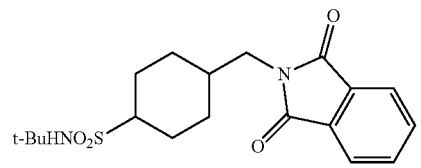

The title compound was prepared as described for the synthesis of Intermediate 34, using neat tert-butylamine in place of dimethanamine solution.

Intermediate 41

4-((1,3-Dioxoisoindolin-2-yl)methyl)cyclohexane-1-sulfonamide

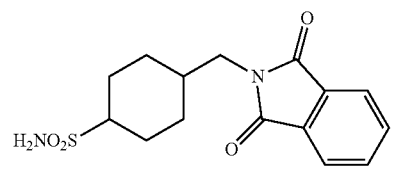 [SMILES: NS(=O)(=O)C1CCC(CN2C(=O)c3ccccc3C2=O)CC1]

2,2,2-Trifluoroacetic acid (10 mL, 130 mmol) was added dropwise to a 0-5° C. solution of N-(tert-butyl)-4-((1,3-dioxoisoindolin-2-yl)methyl)cyclohexane-1-sulfonamide (2.0 g, 5.3 mmol, Intermediate 40) in DCM (10 mL), and the resulting mixture was stirred at 0-5° C. for 12 h before it was concentrated. The concentrate was purified by preparative HPLC (Phenomenex Synergi Max-RP, 12%→52% MeCN/H₂O, 10 mM NH₄HCO₃) to afford the title compound as a colorless solid.

Intermediate 42

(1r,4r)-4-((1,3-Dioxoisoindolin-2-yl)methyl)cyclohexane-1-sulfonamide

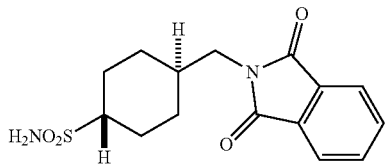 [SMILES: NS(=O)(=O)[C@H]1CC[C@H](CN2C(=O)c3ccccc3C2=O)CC1]

Intermediate 41 was purified by SFC (Chiralcel OJ-H, 80% CO₂, 20% MeOH) to give the title compound as a colorless solid.

Intermediate 43

(1r,4r)-4-(Aminomethyl)cyclohexane-1-sulfonamide hydrochloride

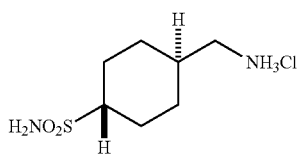

(1r,4r)-4-((1,3-Dioxoisoindolin-2-yl)methyl)cyclohexane-1-sulfonamide (1.1 g, 3.4 mmol, Intermediate 42) was suspended in EtOH (20 mL), hydrazine hydrate (0.51 mL, 65% w/w, 6.9 mmol) was added, and the resulting mixture was stirred at 80° C. for 16 h. After this time, the thick suspension was allowed to cool to rt and then was concentrated to afford a colorless solid. This solid was suspended in THF (20 mL), Boc₂O (3.7 mL, 17 mmol) and enough water to dissolve the solids, and the mixture was stirred at rt overnight. The mixture was then concentrated to afford a colorless solid. This solid was diluted with acetone (15 mL), mixed, and then filtered. The filter cake was discarded. The filtrate was diluted with enough hexanes to promote formation of a precipitate, and the resulting suspension was stirred for 10 min and then filtered. The filter cake was washed with hexanes and dried by aspiration to afford tert-butyl (((1r,4r)-4-sulfamoylcyclohexyl)methyl)carbamate as a colorless solid. This solid was diluted with DCM (10 mL), TFA (2.6 mL, 34 mmol) was added, and the resulting solution was maintained at rt for 2 h. After this time, the solution was concentrated to afford a colorless solid. This solid was dissolved in MeOH, a dioxane solution of HCl (0.77 mL, 4.0 M, 3.1 mmol) was added, and then the solution was concentrated. The resulting solid residue was suspended in EtOAc, and the solids were collected by filtration, washed with EtOAc, and dried by aspiration to afford the title compound as a colorless solid.

Intermediate 44

4-(Methylsulfonyl)tetrahydro-2H-pyran-2-one

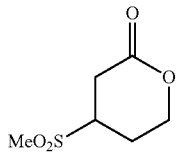

Acetic acid (11.2 mL, 196 mmol) and then 5,6-dihydro-2h-pyran-2-one (15.0 mL, 157 mmol) were added to a suspension of sodium methanesulfinate (23.1 g, 204 mmol) in MeCN (200 mL), and the resulting suspension was stirred at 70° C. for 48 h. After this time, the warm mixture was filtered. The filter cake was rinsed with MeCN, and the combined filtrate and rinse were concentrated to afford an off-white solid. This solid was briefly triturated with 20 mL of boiling DCM, cooled to 0° C. for 1 h, and then filtered. The filter cake was washed with DCM and then dried under vacuum to afford the title compound as an off-white solid.

Intermediate 45

3-(Methylsulfonyl)pentane-1,5-diol

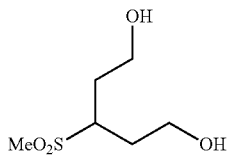

4-(Methylsulfonyl)tetrahydro-2H-pyran-2-one (10 g, 0.056 mol, Intermediate 44) was added portionwise over 5 min to a 0-5° C. suspension of LAH (6.4 g, 0.17 mol) in THF (170 mL) at a rate that maintained the internal temperature below 20° C. The resulting mixture was allowed to warm to rt and stir over 16 h. After this time, the mixture was diluted with THF (170 mL) and cooled in an ice bath. Water (6.4 mL), 15% aqueous NaOH (6.4 mL), and then more water (19 mL) were added dropwise, and the resulting mixture was allowed to warm to rt over 15 min. Celite® and anhydrous MgSO₄ were then added, and the mixture was filtered and then concentrated to afford the title compound as a colorless oil.

Intermediate 46

1,5-Dibromo-3-(methylsulfonyl)pentane

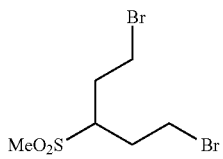

Phosphorus tribromide (6.8 mL, 72 mmol) was added to mixture of 3-(methylsulfonyl)pentane-1,5-diol (6.25 g, 34.3 mmol, Intermediate 45) in benzene (11 mL), and the resulting mixture was stirred at 60° C. for 20 h. After this time, the mixture was allowed to cool and then poured into a stirring DCM and ice mixture. The layers were mixed and then separated, and the aqueous layer was extracted with DCM. The organic layers were combined, washed with brine, dried with anhydrous MgSO$_4$, filtered, and then concentrated to afford the title compound as a colorless solid.

Intermediate 47

Methyl 1-cyano-4-(methylsulfonyl)cyclohexane-1-carboxylate

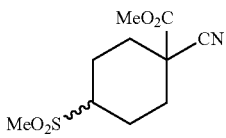

Methyl cyanoacetate (14 g, 0.14 mol) and then 1,5-dibromo-3-(methylsulfonyl)pentane (36 g, 0.12 mol, Intermediate 46) were added to a suspension of Cs$_2$CO$_3$ (115 g, 353 mmol) in DMF (800 mL), and the resulting mixture was stirred at rt for 20 h. After this time, the mixture was filtered, and the filter cake was rinsed with DMF. The combined filtrate and rinse were then concentrated to afford an oily solid. This residue was diluted with DCM, triturated, and then filtered. The filtrate was concentrated to afford the title compound a yellow solid.

Intermediate 48 tert-Butyl ((1-(hydroxymethyl)-4-(methylsulfonyl) cyclohexyl)methyl)carbamate

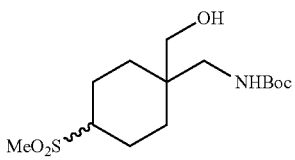

Methyl 1-cyano-4-(methylsulfonyl)cyclohexanecarboxylate (86 g, 0.35 mol, Intermediate 47) in THF (200 mL) was added to a 0° C. suspension of LAH (53.2 g, 1.40 mol) in THF (800 mL), and the resulting suspension was allowed to warm to rt over 16 h. After this time, mixture was cooled in an ice bath and diluted with THF (500 mL). Water (53 mL), 15% aqueous NaOH (53 mL), and then more water (160 mL) were added dropwise, and the mixture was stirred for 20 min. The mixture was then filtered through Celite®, Boc$_2$O (76.5 g, 351 mmol) was added to the filtrate, and the resulting mixture was stirred overnight. The layers were then separated, and the aqueous layer was extracted twice with EtOAc. The organic layers were combined, dried with anhydrous MgSO$_4$, filtered, and then concentrated to afford the title compound as a colorless solid.

Intermediate 49 tert-Butyl (((1s*,4s*)-1-formyl-4-(methylsulfonyl) cyclohexyl)methyl)carbamate

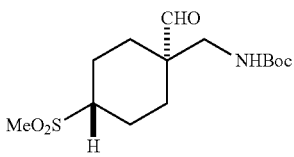

A solution of DMSO (2.2 mL, 31 mmol) in DCM (5 mL) was added dropwise to a −78° C. solution of oxalyl chloride (1.3 mL, 15 mmol) in DCM (25 mL), and this solution was maintained at −78° C. for 15 min. After this time, a solution of tert-butyl ((1-(hydroxymethyl)-4-(methylsulfonyl)cyclohexyl)methyl)carbamate (3.95 g, 12.3 mmol, Intermediate 48) in DCM (10 mL) was added, and the resulting opaque mixture was stirred for an additional 15 min. After this time, TEA (8.5 mL, 61 mmol) was added, and the mixture was allowed to warm to rt over 30 min with stirring. The suspension was then diluted with DCM, washed with a 1 N aqueous HCl solution, dried with anhydrous MgSO$_4$, filtered, and then concentrated. The residue was purified by silica gel chromatography (50→100% EtOAc/hexanes) to give a separable pair of diastereomers (dr=3:1). Intermediate 49 was the major diastereomer: $^1$H NMR (500 MHz, CDCl$_3$) δ 9.54 (s, 1H), 4.63 (t, J=6.5 Hz, 1H), 3.21 (d, J=6.7 Hz, 2H), 2.82-2.73 (m, 1H), 2.79 (s, 3H), 2.38-2.28 (m, 2H), 2.24-2.16 (m, 2H), 1.57 (qd, J=13.0, 3.7 Hz, 2H), 1.42 (s, 9H), 1.32 (td, J=14.0, 4.2 Hz, 2H).

Intermediate 50 tert-Butyl (((1s*,4s*)-1-cyano-4-(methylsulfonyl) cyclohexyl)methyl)carbamate

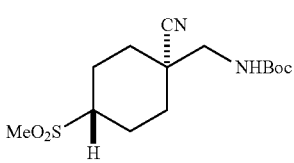

Triethylamine (1.5 mL, 11 mmol) was added to a mixture of tert-butyl (((1s*,4s*)-1-formyl-4-(methylsulfonyl)cyclohexyl)methyl)carbamate (1.06 g, 3.32 mmol, Intermediate 49) and hydroxylamine hydrochloride (254 mg, 3.65 mmol) in DMF (5.3 mL), and the mixture was stirred for 5 min. After this time, T3P (2.2 mL, 3.7 mmol) was added, and the mixture was stirred at 100° C. for 4 h. Additional T3P (1.0 mL, 1.7 mmol) was then added, and stirring was continued for 20 h. After this time, the mixture was cooled to 0° C. and then filtered. The filter cake was rinsed with EtOAc, and the filtrate and rinse were combined and concentrated. The concentrate was diluted with EtOAc and a saturated aqueous NaHCO$_3$ solution, and the layers were mixed and then separated. The aqueous layer was extracted with EtOAc, and the organic layers combined, washed with brine, dried with MgSO$_4$, filtered, and then concentrated. The residue was purified by silica gel chromatography (50→100% EtOAc/hexanes) to afford the title compound as a colorless solid.

Intermediate 51

(1s*,4s*)-1-(Aminomethyl)-4-(methylsulfonyl)cyclohexane-1-carbonitrile hydrochloride

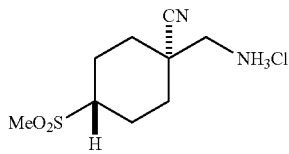

A solution of tert-butyl (((1r*,4r*)-1-cyano-4-(methylsulfonyl)cyclohexyl)methyl)carbamate (150 mg, 0.474 mmol, Intermediate 50) in DCM (1.6 mL) and TFA (0.41 mL, 5.4 mmol) was maintained at rt for 2 h. After this time, the solution was concentrated and then dissolved in in enough DCM and MeOH (1:1 v/v) to make a solution. A 1,4-dioxane solution of HCl (0.13 mL, 4.0 M, 0.52 mmol) was then added, and the resulting suspension was concentrated. The solid residue was suspended in EtOAc, filtered, rinsed with additional EtOAc, and then dried under vacuum to afford the title compound as a colorless solid.

Intermediate 52

(4-(Methylsulfonyl)cyclohexyl)methanamine

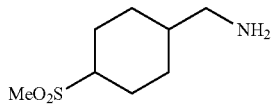

4-(Methylsulfonyl)cyclohexane-1-carbonitrile (5.29 g, 97% w/w, 27.3 mmol, Intermediate 11) was added in portions over 5 min to a 0-5° C. solution of LAH (82 mL, 1.0 M in THF, 82 mmol), and the residual solid on the walls of the nitrile-containing flask was washed into the reaction solution with THF (20 mL). The resulting solution was stirred at 0-5° C. for 10 min before it was allowed to warm to rt over 16 h. After this time, the resulting heterogeneous mixture was diluted with THF (100 mL) and cooled in an ice bath. Water (3.3 mL), 15% aqueous NaOH (3.3 mL), and more water (9.9 mL) were sequentially added at a rate that maintained the internal temperature below 30° C., and then the mixture was allowed to warm to rt with stirring over 20 min. Celite® was added, and the mixture was filtered and then concentrated to afford the title compound as a colorless oil that eventually solidified (trans:cis=7.7:1.0).

Intermediate 53 tert-Butyl (((1RS,2SR,4SR)-2-hydroxy-4-(methylsulfonyl)cyclohexyl)methyl)carbamate

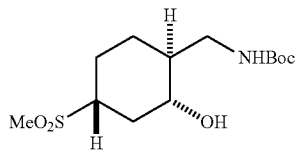

A solution of BH$_3$.THF in THF (30 mL, 1.0 M, 30 mmol) was added to a 0-5° C. solution of tert-butyl ((4-(methylsulfonyl)cyclohex-1-en-1-yl)methyl)carbamate (2.9 g, 10 mmol, Intermediate 16) in THF (30 mL), and the resulting solution was allowed to warm to rt over 16 h with stirring. After this time, the resulting mixture was cooled to 0-5° C. and then quenched with drops of water. When the bubbling ceased, 10% aqueous NaOH (8.0 mL, 22 mmol) and then H$_2$O$_2$ (2.5 mL, 50% w/w, 43 mmol) were added, and the mixture was stirred at rt for 5 h. After this time, the mixture was diluted with brine, and the layers were mixed then separated. The aqueous layer was extracted twice with EtOAc, and the combined organic layers were dried with anhydrous MgSO$_4$, filtered, and then concentrated to afford a colorless gum. This residue was purified by silica gel chromatography (75→100% EtOAc/hexanes) to afford the first-eluting diastereomer as a colorless solid. This solid was purified further by crystallization from boiling i-PrOAc (12 mL) to afford the title compound as a colorless solid.

Intermediate 54

(1RS,2SR,5RS)-2-(Aminomethyl)-5-(methylsulfonyl)cyclohexan-1-ol hydrochloride

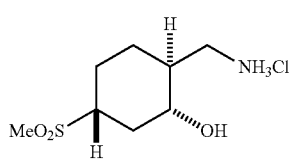

The title compound was prepared as described for the synthesis of Intermediate 51, using tert-butyl (((1RS,2SR,4SR)-2-hydroxy-4-(methylsulfonyl)cyclohexyl)methyl)carbamate (Intermediate 53) in place of tert-butyl (((1r*,4r*)-1-cyano-4-(methylsulfonyl)cyclohexyl)methyl)carbamate.

Intermediate 55

Ethyl 3-bromo-2-oxobutanoate

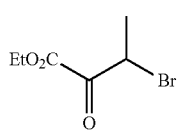

Bromine (2.2 mL, 43 mmol) was added dropwise to a 0-5° C. solution of the ethyl 2-oxobutanoate (4.8 mL, 46 mmol)

in DCM (25 mL), and the resulting mixture was allowed to warm to rt over 14 h. After this time, the mixture was washed with a saturated aqueous NaHCO₃ solution, washed with an aqueous Na₂S₂O₃ solution, dried with anhydrous MgSO₄, filtered, and then concentrated to afford the title compound as a yellow oil.

Intermediate 56

Ethyl 2-bromoacrylate

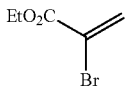

A solution of TEA (33 mL, 240 mmol) in Et₂O (50 mL) was added over 30 min to a solution of the ethyl 2,3-dibromopropanoate (15.0 mL, 103 mmol) in hexanes (100 mL), and the resulting suspension was stirred at rt for 1 h. After this time, the mixture was filtered, and the filter cake was washed with hexanes. The filtrate and wash were combined and then concentrated to afford the title compound as a yellow oil.

Intermediate 57

Methyl 2,3-dibromo-3,3-difluoropropanoate

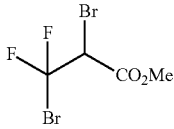

Bromine (1.4 mL, 28 mmol) was added dropwise to a solution of methyl 3,3-difluoroacrylate (3.42 g, 28.0 mmol) in DCM (13 mL), and the resulting solution was maintained at rt for 14 h. The solution was then concentrated to afford the title compound as an orange oil.

Intermediate 58

3,3,3-Trifluoro-2,2-dimethylpropan-1-ol

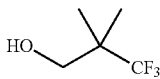

A solution of 3,3,3-trifluoro-2,2-dimethylpropanoic acid (340 g, 2.18 mol) in Et₂O (340 mL) was added dropwise to a −15 to −5° C. suspension of LAH (108 g, 2.83 mol) in Et₂O (3.1 L), and the mixture was stirred for 15 min. After this time, water (108 mL), 15% aqueous NaOH (108 mL), and more water (324 mL) were added at a rate that maintained the internal temperature at 0-10° C. Anhydrous MgSO₄ was then added, and the mixture was stirred for 30 min. The mixture was then filtered, and the filter cake was washed with Et₂O. The filtrate and wash were combined and then concentrated to afford the title compound as a pale-yellow liquid.

Intermediate 59

1,1,1-Trifluoro-3-iodo-2,2-dimethylpropane

Iodine (536 g, 2.11 mol) was added in five portions to a stirring solution of PPh₃ (554 g, 2.11 mol), 3,3,3-trifluoro-2,2-dimethylpropan-1-ol (200 g, 1.41 mol, Intermediate 58), and imidazole (144 g, 2.11 mol) in NMP (1.0 L) at a rate that maintained the internal temperature between 45 and 50° C. The mixture was then warmed to 95-100° C. and stirred until the reaction went to completion. The reaction mixture was then allowed to cool to 50-65° C. and purified by distillation to give the title compound as a solution in NMP (58% w/w, bp 50-65° C. at 1-2 mmHg).

Intermediate 60

(S*)-3,3,3-Trifluoro-2-methylpropanoic acid

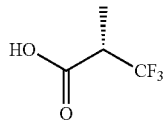

A solution of 2-(trifluoromethyl)acrylic acid (60.0 g, 0.429 mol), dicyclohexylamine (77.6 g, 0.428 mol), and (R)—RuCl[(p-cymene(BINAP)]Cl (3.96 g, 4.26 mmol) in MeOH (1.2 L) was stirred under an atmosphere of H₂ (4-5 MPa) at 35-40° C. for 48 h. After this time, the mixture was filtered, and then the filtrate was concentrated. The concentrate was diluted with MTBE and EtOAc (600 mL, 1:1 v/v), and the solution was washed with a 10% aqueous Na₂CO₃ solution (300 mL×3). The aqueous phases were combined, and the pH was adjusted to pH 2-4 with aqueous HCl. The resulting mixture was filtered, and the filtrate was extracted with three times with MTBE. The organic layers were combined, dried with anhydrous Na₂SO₄, filtered, and then concentrated to give a yellow liquid (82.6% ee).

(S)-(+)-1,2,3,4-Tetrahydronaphthalen-1-amine (14.6 g, 99.2 mmol) was added dropwise to a 30° C. solution of (S*)-3,3,3-trifluoro-2-methylpropanoic acid from the previous step (17.6 g, 0.124 mol) in MTBE (210 mL), and then the mixture was cooled to 20° C. and stirred for 16 h. After this time, the suspension was filtered and the filter cake was dried to give (S)-1,2,3,4-tetrahydronaphthalen-1-amine (S*)-3,3,3-trifluoro-2-methylpropanoic acid salt as a colorless solid (dr=97.4:2.6).

A 5% aqueous KHSO₄ solution (400 mL) was added to a suspension of (S)-1,2,3,4-tetrahydronaphthalen-1-amine (S*)-3,3,3-trifluoro-2-methylpropanoic acid salt (26.7 g, 0.0924 mol) from the previous step in MTBE (260 mL), and the mixture was stirred until the solids dissolved. The layers were then separated, and the aqueous layer was extracted three times with MTBE. The organic layers were combined, washed twice with a 5% aqueous KHSO₄ solution, washed with water, and then concentrated to afford the title compound as yellow liquid (95.0% ee).

Intermediate 61

(S*)-3,3,3-Trifluoro-2-methylpropan-1-ol

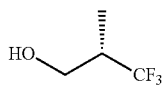

Lithium aluminum hydride (15.0 g, 0.369 mol) was added in portions to a stirring solution of (S*)-3,3,3-trifluoro-2-methylpropanoic acid (34.6 g, 0.244 mol, Intermediate 60) in Et$_2$O (350 mL), which was cooled in an ice bath, at a rate that maintained the internal temperature below 15° C. The mixture was then allowed to warm to 20° C., and stirring was continued for 2 h. After this time, water (25 mL) was carefully added, and then the mixture was dried with anhydrous Na$_2$SO$_4$, filtered, and then concentrated under atmospheric pressure to give the title compound as a colorless liquid (95.8% ee).

Intermediate 62

(R*)-1,1,1-Trifluoro-3-iodo-2-methylpropane

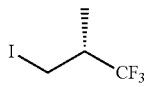

Iodine (44.58 g, 175.6 mmol) was added in five portions to a stirring solution of (S*)-3,3,3-trifluoro-2-methylpropan-1-ol (15.0 g, 117 mmol, Intermediate 61), PPh$_3$ (46.07 g, 175.6 mmol) and imidazole (11.96 g, 175.7 mmol) in NMP (75 mL) at a rate that maintained the internal temperature between 40 and 50° C. The mixture was then warmed to 55-60° C. and stirred until the reaction went to completion. The reaction mixture was then distilled directly to afford the title compound as a solution in NMP (50.5% w/w, bp 50-65° C. at 1-2 mm Hg).

Intermediate 63

(S*)-1,1,1-Trifluoro-3-iodo-2-methylpropane

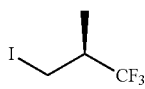

The title compound was prepared as described for the synthesis of Intermediate 62, using (S)—RuCl[(p-cymene(BINAP)]Cl and (S)-(−)-phenylethylamine in place of (R)—RuCl[(p-cymene(BINAP)]Cl and (S)-(+)-1,2,3,4-tetrahydronaphthalen-1-amine.

Intermediate 64

9-(3,3,3-Trifluoro-2-methylpropyl)-9-borabicyclo[3.3.1]nonane (0.5 M in THF)

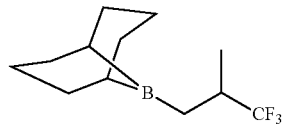

3,3,3-Trifluoro-2-methylprop-1-ene (6.5 g, 59 mmol) was condensed into a pressure vessel at −78° C. before a solution of 9-BBN in THF (100 mL, 0.5 M, 50 mmol) was slowly added. The vessel was then sealed and the suspension was allowed to warm to rt over 2 h. The resulting solution was then maintained at 65° C. for 18 h before it was allowed to cool to rt, sparged with argon, and then transferred to a Schlenk flask for storage.

Intermediate 65

9-(3,3,3-Trifluoropropyl)-9-borabicyclo[3.3.1]nonane (0.5 M in THF)

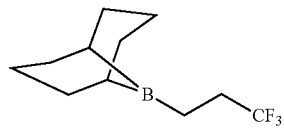 [SMILES: FC(F)(F)CCB1C2CCCC1CCC2]

The title compound was prepared as described for the synthesis of Intermediate 64, using 3,3,3-trifluoroprop-1-ene in place of 3,3,3-trifluoro-2-methylprop-1-ene.

Intermediate 66

9-(4,4,4-Trifluorobutyl)-9-borabicyclo[3.3.1]nonane (0.5 M in THF)

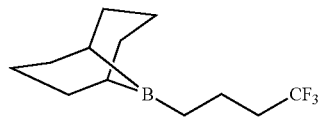 [SMILES: FC(F)(F)CCCB1C2CCCC1CCC2]

The title compound was prepared as described for the synthesis of Intermediate 64, using 4,4,4-trifluorobut-1-ene in place of 3,3,3-trifluoro-2-methylprop-1-ene.

Intermediate 67

N-(4-Bromo-2-methoxyphenyl)propionimidamide

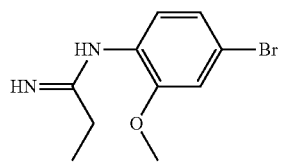

Trimethylaluminum (74 mL, 2.0 M in toluene, 150 mmol) was added over 15 min to a mixture of the 4-bromo-2-methoxyaniline (30 g, 150 mmol) and propionitrile (10.6 mL, 148 mmol) at a rate that maintained the internal temperature near 70° C., and the resulting solution was then heated to 110° C. for 5.5 h. After this time, the solution was allowed to cool to rt, diluted with 70 mL of THF, and cooled to 0-5° C. in an ice bath. Water (5.7 mL), 15% aqueous NaOH (5.7 mL), and then more water (17 mL) were slowly added, and the resulting mixture was allowed to warm to rt over 30 min with stirring. The mixture was then filtered through Celite® and concentrated. The concentrate was diluted with enough 1 N aqueous HCl to give a solution with pH 1-2, and the resulting solution was washed with EtOAc. The organic layer was then separated and discarded. The pH of the aqueous layer was adjusted to pH 5-6, and the solution was washed with EtOAc. The organic layer was again separated and discarded. The pH of the aqueous layer was finally adjusted to pH 13-14, and resulting mixture was extracted three times with DCM. The organic layers were combined, dried with anhydrous MgSO₄, filtered, and then concentrated to afford the title compound as a brown oil, which was used in the next step without further purification.

Intermediate 68

Ethyl 1-(4-bromo-2-methoxyphenyl)-2-ethyl-4,5-dihydro-1H-imidazole-4-carboxylate

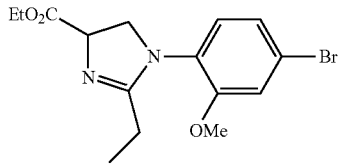 [SMILES: CCOC(=O)C1CN(c2ccc(Br)cc2OC)C(CC)=N1]

Ethyl 2-bromoacrylate (10 g, 56 mmol, Intermediate 56) was added to a 65° C. mixture of N-(4-bromo-2-methoxyphenyl)propionimidamide (13 g, 51 mmol, Intermediate 67) and NaHCO₃ (4.7 g, 56 mmol) in EtOH (250 mL), and the resulting mixture was stirred for 48 h. After this time, the mixture was allowed to cool to rt and then concentrated. The concentrate was diluted with EtOAc and enough 1 N aqueous HCl to make the mixture acidic according to litmus paper. The mixture was shaken, the layers were separated, and the organic layer was discarded. The pH of the aqueous layer was adjusted to pH 13-14, and the resulting mixture was extracted twice with DCM. The organic layers were combined, dried with anhydrous MgSO₄, filtered, and then concentrated to afford the title compound as a brown gum, which was used in the next step without further purification.

Intermediate 69

Ethyl 1-(4-bromo-2-methoxyphenyl)-2-ethyl-1H-imidazole-4-carboxylate

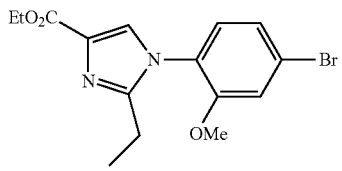

Lead tetraacetate (22.7 g, 51.4 mmol) was added in portions over 5 min to a 60° C. solution of ethyl 1-(4-bromo-2-methoxyphenyl)-2-ethyl-4,5-dihydro-1H-imidazole-4-carboxylate (15.2 g, 42.8 mol, Intermediate 68) in THF (210 mL), and the resulting suspension was stirred at 60° C. for 1 h. After this time, the mixture was allowed to cool, filtered, and then concentrated. The concentrate was diluted with DCM and a saturated aqueous solution of NaHCO₃, and the resulting mixture was shaken and then filtered. The layers of the filtrate were separated, and the aqueous layer was extracted with DCM. The combined organic layers were washed with brine and concentrated to afford a brown oil. This oil was dissolved in THF (100 mL), a saturated aqueous solution of EDTA (100 mL) was added, and then the mixture was stirred at rt for 15 h. After this time, the layers were separated, and the aqueous layer was extracted with EtOAc. The combined organic layers were washed with brine, dried with anhydrous MgSO₄, filtered, and concentrated to afford a brown residue. This residue was loaded onto a pad of silica gel, and the pad was washed thoroughly using EtOAc/hexanes (1:1 v/v). The wash was concentrated to afford the title compound as an amber gum, which was used in the next step without further purification.

Intermediate 70

Ethyl 1-(4-bromo-2-methoxyphenyl)-5-cyano-2-ethyl-1H-imidazole-4-carboxylate

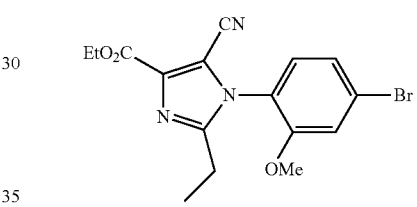

A solution of TMPMgCl.LiCl (0.60 mL, 1 M in THF, 0.60 mmol) was added to a 0-5° C. solution of ethyl 1-(4-bromo-2-methoxyphenyl)-2-ethyl-1H-imidazole-4-carboxylate (192 mg, 0.544 mmol, Intermediate 69) in THF (0.6 mL), and the resulting dark solution was maintained at 0-5° C. for 30 min. After this time, tosyl cyanide (120 mg, 0.65 mmol) was added, and the resulting solution was allowed to warm to rt over 45 min. The solution was then diluted with EtOAc and a saturated aqueous solution of NH₄Cl. Water was added to enable filtration of the resulting thick suspension, and then it was filtered. The layers of the filtrate were separated, and the organic layer was dried with anhydrous MgSO₄, filtered, and then concentrated. The residue was purified by silica gel chromatography (25→50% EtOAc/hexanes) to afford the title compound as a colorless film.

Intermediate 71

Ethyl 5-cyano-2-ethyl-1-(2-methoxy-4-(3,3,3-trifluoro-2-methylpropyl)phenyl)-1H-imidazole-4-carboxylate

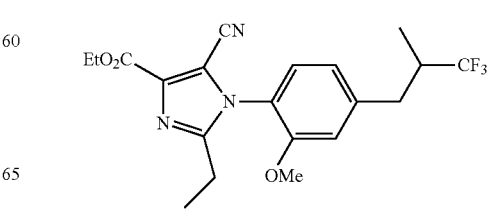

Ethyl 1-(4-bromo-2-methoxyphenyl)-5-cyano-2-ethyl-1H-imidazole-4-carboxylate (119 mg, 0.252 mmol, Intermediate 70), K₂CO₃ (70 mg, 0.50 mmol), and Pd(dppf).DCM (10 mg, 0.013 mmol) were combined in a vessel, and the vessel was evacuated and then backfilled three times with nitrogen. A solution of 9-(3,3,3-trifluoro-2-methylpropyl)-9-borabicyclo[3.3.1]nonane (1.5 mL, 0.5 M in THF, 0.75 mmol, Intermediate 64) and DMF (0.6 mL) were then added, and the resulting mixture was stirred at 65° C. for 1.5 h. After this time, the mixture was allowed to cool and then it was diluted with EtOAc and water. The layers were separated, and the organic layer was washed with water, washed with brine, dried with anhydrous MgSO₄, filtered, and then concentrated. The residue was purified by silica gel chromatography (10→50% EtOAc/hexanes) to afford the title compound as a yellow oil.

Intermediate 72

Ethyl 2-ethyl-1-(2-methoxy-4-(3,3,3-trifluoro-2-methylpropyl)phenyl)-1H-imidazole-4-carboxylate

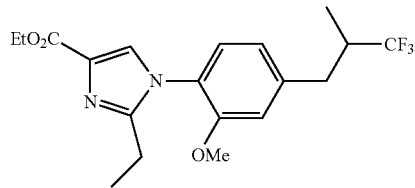 [SMILES: CCOC(=O)c1cn(-c2ccc(CC(C)C(F)(F)F)cc2OC)c(CC)n1]

The title compound was prepared as described for the synthesis of Intermediate 71, using ethyl 1-(4-bromo-2-methoxyphenyl)-2-ethyl-1H-imidazole-4-carboxylate (Intermediate 69) in place of ethyl 1-(4-bromo-2-methoxyphenyl)-5-cyano-2-ethyl-1H-imidazole-4-carboxylate.

Intermediate 73

Ethyl (R*)-2-ethyl-1-(2-methoxy-4-(3,3,3-trifluoro-2-methylpropyl)phenyl)-1H-imidazole-4-carboxylate

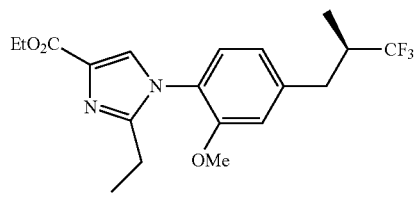 [SMILES: CCOC(=O)c1cn(-c2ccc(C[C@@H](C)C(F)(F)F)cc2OC)c(CC)n1]

Intermediate 74

Ethyl (S*)-2-ethyl-1-(2-methoxy-4-(3,3,3-trifluoro-2-methylpropyl)phenyl)-1H-imidazole-4-carboxylate

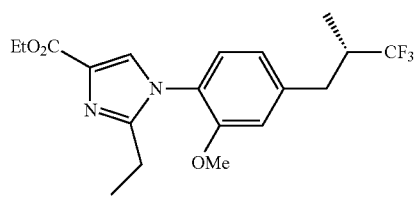 [SMILES: CCOC(=O)c1cn(-c2ccc(C[C@H](C)C(F)(F)F)cc2OC)c(CC)n1]

Intermediate 72 was purified by SFC using a chiral stationary phase (Chiralpak Diacel AS, 96% CO₂, 4% i-PrOH with 0.2% i-PrNH₂) to give a pair of enantiomers. The first-eluting isomer was Intermediate 73, and the second-eluting isomer was Intermediate 74.

Intermediate 75, Step a

N-(4-Bromo-2-(difluoromethoxy)phenyl)propionamide

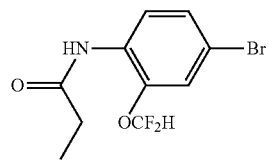

Propionyl chloride (6.0 mL, 69 mmol) in EtOAc (30 mL) was added dropwise over 2 h to a mixture containing 4-bromo-2-(difluoromethoxy)aniline (15 g, 63 mmol) and NaHCO₃ (8.0 g, 95 mmol) in EtOAc (120 mL) and water (48 mL), and the resulting mixture was stirred at rt for 14 h. After this time, the layers were separated. The organic layer was washed with 1 N aqueous HCl, washed with 1 N aqueous NaOH, washed with brine, dried with anhydrous MgSO₄, and then concentrated to afford the title compound as a yellow solid, which was used in the next step without further purification.

Intermediate 75, Step b

N-(4-Bromo-2-(difluoromethoxy)phenyl)propionimidamide

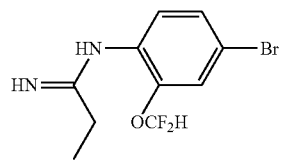

Phosphorous pentachloride (12.3 g, 59.2 mmol) was added in portions over 3 min to a solution of N-(4-bromo-2-(difluoromethoxy)phenyl)propionamide (17.4 g, 59.2 mmol, Intermediate 75, Step a) in DCM (85 mL), and the resulting solution was maintained at rt for 1 h before it was concentrated. The concentrate was then dissolved in THF (55 mL) and added dropwise over 20 min to a solution of ammonia (250 mL, 2.0 M in i-PrOH, 500 mmol). The internal temperature was maintained below 28° C. by submerging the reactor in an ice bath during the last 5 min of the addition. After the addition was complete, the resulting suspension was stirred at rt for 2 h before it was filtered and then concentrated. The residue was diluted with a small volume THF, filtered again, and concentrated to afford the title compound as a brown oil, which was used in the next step without further purification.

Intermediate 76

N-(4-Bromo-2-methoxyphenyl)pivalimidamide

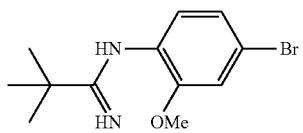 [SMILES: COc1cc(Br)ccc1NC(=N)C(C)(C)C]

The title compound was prepared as described for the synthesis of Intermediate 75, using 4-bromo-2-methoxyaniline and pivaloyl chloride in place of 4-bromo-2-(difluoromethoxy)aniline and propionyl chloride.

Intermediate 77

N-(5-bromo-3-methoxypyridin-2-yl)propionimidamide

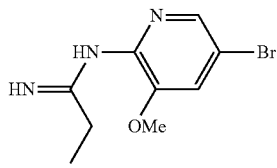

Toluene (8 mL) was added to a mixture of 5-bromo-3-methoxypyridin-2-amine (5.1 g, 25 mmol) and propionitrile (3.3 mL, 28 mmol), and the resulting suspension was warmed to 80° C. in a heavy-walled glass pressure vessel until the mixture became homogeneous. Tin(IV) chloride (3.2 mL, 28 mmol) was then carefully added, (CAUTION: A strong exotherm was observed at the beginning of the addition) and this addition was followed by addition of more toluene (10 mL). The resulting mixture was stirred at 110° C. for 15 h. After this time, additional portions of propionitrile (0.5 mL, 4 mmol) and SnCl$_4$ (0.5 mL, 4 mmol) were added, and stirring was continued at 110° C. for 6 h. The reaction mixture was then allowed to cool before it was diluted with DCM and water. The mixture was made basic with 10% aqueous NaOH, Celite® was added, and then the mixture was filtered. The layers of the filtrate were separated, and the aqueous layer was again made basic with 10% aqueous NaOH and extracted twice with DCM. The combined organic layers were dried with anhydrous MgSO$_4$ and then concentrated. The filter cake was suspended in DCM and the aqueous layer from the previous extraction. The mixture was made basic with 10% aqueous NaOH and stirred vigorously. The mixture was then filtered, and the layers of the filtrate were separated. The aqueous layer was adjusted to pH 13-14 and extracted with DCM. This pH adjustment and extraction process was repeated once more, and the combined organic layers were dried with anhydrous MgSO$_4$, filtered, combined with the concentrate from the first extraction, and then concentrated to afford the title compound as a tan solid.

Intermediate 78

Ethyl 1-(5-bromo-3-methoxypyridin-2-yl)-2-ethyl-4,5-dihydro-1H-imidazole-4-carboxylate

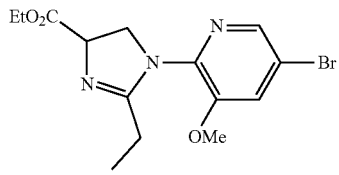 [SMILES: CCOC(=O)C1CN(c2ncc(Br)cc2OC)C(CC)=N1]

Cesium carbonate (16.8 g, 51.5 mmol) and ethyl 2-bromoacrylate (7.7 g, 43 mmol, Intermediate 56) were added to a solution of N-(5-bromo-3-methoxypyridin-2-yl)propionimidamide (12.0 g, 42.9 mmol, Intermediate 77) in DMF (165 mL), and the resulting suspension was stirred at 65° C. for 14 h. After this time, additional Cs$_2$CO$_3$ (2.8 g, 8.6 mmol) and ethyl 2-bromoacrylate (1.5 g, 8.6 mmol, Intermediate 56) were added, and the mixture was stirred for an additional 8 h at 65° C. Third portions of Cs$_2$CO$_3$ (2.8 g, 8.6 mmol) and ethyl 2-bromoacrylate (1.5 g, 8.6 mmol, Intermediate 56) were then added, and the mixture was stirred for an additional 20 h at 65° C. After this time, the mixture was allowed to cool, filtered, and then concentrated to afford a brown oil with some interspersed solids. This mixture was diluted with DCM, filtered, and then concentrated again. This concentrate was used in the next step without further purification.

Intermediate 79

Ethyl 1-(5-bromo-3-methoxypyridin-2-yl)-2-ethyl-1H-imidazole-4-carboxylate

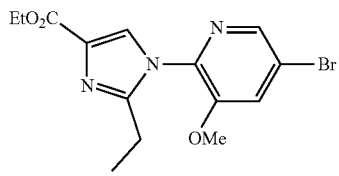 [SMILES: CCOC(=O)c1cn(-c2ncc(Br)cc2OC)c(CC)n1]

Ethyl 1-(5-bromo-3-methoxypyridin-2-yl)-2-ethyl-4,5-dihydro-1H-imidazole-4-carboxylate (15.3 g, 42.9 mmol, Intermediate 78) was sequentially diluted with 130 mL of MeCN, pyridine (65 mL, 810 mmol), 1,8-diazabicyclo[5.4.0]undec-7-ene (26 mL, 170 mmol), and CCl$_4$ (6.2 mL, 64 mmol), and the resulting solution was maintained at 50° C. for 20 h. Additional CCl$_4$ (1.0 mL, 10 mmol) was added, and stirring was continued for an additional 40 h at 50° C. After this time, the reaction mixture was allowed to cool and then concentrated. The concentrate was dissolved in EtOAc and water, and the pH of the aqueous layer was adjusted to pH 5 with intermittent mixing of the layers. The layers were then separated, and the aqueous layer was extracted twice with EtOAc. The combined organic layers were washed with brine, dried with anhydrous MgSO$_4$, filtered, and then concentrated to afford a brown residue. This residue was purified by silica gel chromatography (30→60% EtOAc/hexanes) to afford the title compound as a colorless solid.

Intermediate 80

1-(5-Bromo-3-hydroxypyridin-2-yl)-2-ethyl-1H-imidazole-4-carboxylic acid

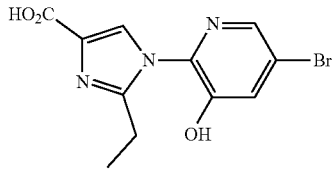

Ethyl 1-(5-bromo-3-methoxypyridin-2-yl)-2-ethyl-1H-imidazole-4-carboxylate (8.46 g, 23.9 mmol, Intermediate 79) was added to 160° C. molten pyridine hydrochloride (42 g, 360 mmol), and the resulting solution was maintained at 160° C. for 3 h. The solution was allowed to cool to rt, at which temperature it solidified. Water (100 mL) was added, and the resulting suspension was stirred for 20 min. The solids were isolated by filtration, washed with water, dried by aspiration, and then azeotropically dried twice with EtOH to afford a tan solid, which was used in the next reaction without further purification.

Intermediate 81

Ethyl 1-(5-bromo-3-hydroxypyridin-2-yl)-2-ethyl-1H-imidazole-4-carboxylate

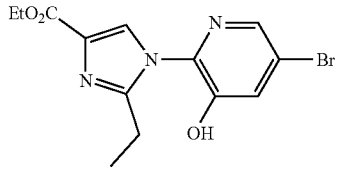 [SMILES: CCc1nc(C(=O)O)cn1-c1ncc(Br)cc1O]

Acetyl chloride (8.5 mL, 120 mmol) was added to EtOH (100 mL) at 0-5° C., and the resulting solution was allowed to warm to rt. 1-(5-Bromo-3-hydroxypyridin-2-yl)-2-ethyl-1H-imidazole-4-carboxylic acid (7.46 g, 23.9 mmol, Intermediate 80) was then added, and the resulting solution was maintained at 90° C. in a sealed tube for 16 h. After this time, the reaction mixture was allowed to cool, and then it was concentrated. The concentrate was dissolved in a minimum volume of EtOH and then pH 7 phosphate buffer (150 mL) was added. The pH of the mixture was adjusted to pH 7 with 1 N aqueous NaOH, and the resulting suspension was stirred for 20 min. After this time, the solids isolated by filtration, washed with water, and then dried by aspiration to afford the title compound as a tan solid.

Intermediate 82

Ethyl 1-(5-bromo-3-(difluoromethoxy)pyridin-2-yl)-2-ethyl-1H-imidazole-4-carboxylate

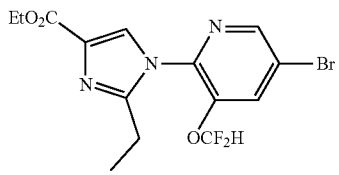

Ethyl 1-(5-bromo-3-hydroxypyridin-2-yl)-2-ethyl-1H-imidazole-4-carboxylate (6.76 g, 19.9 mmol, Intermediate 81), sodium chlorodifluoroacetate (6.57 g, 43.1 mmol), and $Cs_2CO_3$ (19.4 g, 59.6 mmol) were diluted with DMF (40 mL), and the mixture was stirred at 100° C. for 2 h. After this time, an additional portion of sodium chlorodifluoroacetate (0.8 g, 5.3 mmol) was added, and stirring was continued for 1 h. The reaction mixture was then allowed to cool before it was diluted with water (100 mL) and stirred for 20 min. The resulting suspension was filtered, and the solids were washed with water and then dried by aspiration to afford the title compound as a brown solid.

Intermediate 83

Ethyl 1-(5-bromo-3-(difluoromethoxy)pyridin-2-yl)-5-chloro-2-ethyl-1H-imidazole-4-carboxylate

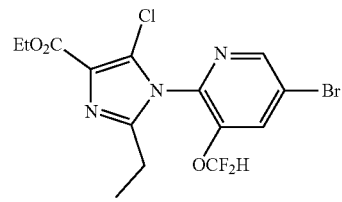

N-Chlorosuccinimide (2.5 g, 19 mmol) was added to a suspension of ethyl 1-(5-bromo-3-(difluoromethoxy)pyridin-2-yl)-2-ethyl-1H-imidazole-4-carboxylate (6.76 g, 17.3 mmol, Intermediate 82) in DMF (35 mL), and the mixture was stirred at 60° C. for 20 h. The resulting solution was then allowed to cool to rt before it was diluted with water (80 mL). The resulting suspension was stirred for 15 min before $Na_2S_2O_3$ (1.4 g, 8.7 mmol) was added. The suspension was stirred for another 5 min and then it was filtered. The solids were washed with water and then dried by aspiration to afford the title compound as a tan solid.

Intermediate 84

Ethyl 5-chloro-1-(3-(difluoromethoxy)-5-(4,4,4-trifluorobutyl)pyridin-2-yl)-2-ethyl-1H-imidazole-4-carboxylate

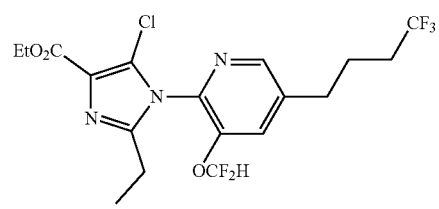

The title compound was prepared as described for the synthesis of Intermediate 71, using ethyl 1-(5-bromo-3-(difluoromethoxy)pyridin-2-yl)-5-chloro-2-ethyl-1H-imidazole-4-carboxylate (Intermediate 83) and 9-(4,4,4-trifluorobutyl)-9-borabicyclo[3.3.1]nonane (Intermediate 66) in place of ethyl 1-(4-bromo-2-methoxyphenyl)-5-cyano-2-ethyl-1H-imidazole-4-carboxylate and 9-(3,3,3-trifluoro-2-methylpropyl)-9-borabicyclo[3.3.1]nonane.

Intermediate 85

Ethyl 5-chloro-1-(3-(difluoromethoxy)-5-(3,3,3-trifluoro-2,2-dimethylpropyl)pyridin-2-yl)-2-ethyl-1H-imidazole-4-carboxylate

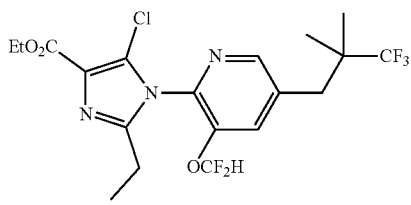

Lithium bromide (2.3 g, 26 mmol) was heated under vacuum at 140° C. for 14 h. The dried salt was allowed to cool before DMI (13 mL) and THF (9.8 mL) were added, and the mixture was stirred at rt until it became homogeneous. In a separate vessel, 1,1,1-trifluoro-3-iodo-2,2-dimethylpropane (2.1 mL, 14 mmol, Intermediate 59) was added to a suspension of Rieke® zinc in THF (17 mL, 0.05 g/mL, 13 mmol) and the mixture was stirred at 65° C. for 30 min. After this time, the LiBr solution and then the organozinc suspension were sequentially added by cannula transfers to a vessel containing ethyl 1-(5-bromo-3-(difluoromethoxy)pyridin-2-yl)-5-chloro-2-ethyl-1H-imidazole-4-carboxylate (3.50 g, 8.24 mmol, Intermediate 83) and PEPPSI-IPr (112 mg, 0.165 mmol), and the resulting mixture was stirred at 65° C. for 20 h. The reaction mixture was then allowed to cool before it was diluted with EtOAc and a saturated aqueous solution of $NH_4Cl$. Water was added to dissolve salts in the aqueous layer, and the mixture was filtered. The layers of the filtrate were mixed and then separated. The organic layer was washed sequentially with water, washed with a saturated aqueous solution of $NH_4Cl$, dried with anhydrous $MgSO_4$, filtered, and then concentrated to afford a yellow oil. This residue was purified by silica gel chromatography (30→50% EtOAc/hexanes) to afford the title compound as a pale yellow solid.

Intermediate 86

5-Bromo-3-methylpyridin-2-amine

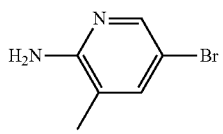

Bromine (0.50 mL, 9.8 mmol) was added dropwise to a 0-5° C. solution of 3-methylpyridin-2-amine (1.0 g, 9.2 mmol) in DCM (30 mL), and the resulting mixture was stirred for 5 h, during which time it was allowed to warm to rt. The mixture was then diluted with water, mixed, and the pH of the aqueous layer was adjusted to pH 9 with 2 N aqueous NaOH. The layers were separated, and the organic layer was washed with a saturated aqueous $NaHCO_3$ solution, washed with a saturated $Na_2SO_3$ solution, washed with brine, dried with anhydrous $Na_2SO_4$, filtered, and then concentrated to afford the title compound as a brown solid.

Intermediate 87

Ethyl 1-(5-bromo-3-methylpyridin-2-yl)-2-ethyl-1H-imidazole-4-carboxylate

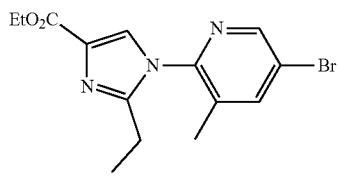

The title compound was prepared as described for the synthesis of Intermediate 79, using 5-bromo-3-methylpyridin-2-amine (Intermediate 86) in place of 5-bromo-3-methoxypyridin-2-amine.

Intermediate 88

Ethyl 5-chloro-2-ethyl-1-(3-methyl-5-(3,3,3-trifluoro-2,2-dimethylpropyl)pyridin-2-yl)-1H-imidazole-4-carboxylate

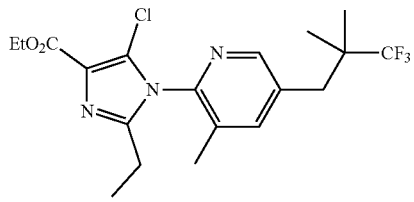 [SMILES: CCOC(=O)c1nc(CC)n(-c2ncc(CC(C)(C)C(F)(F)F)cc2C)c1Cl]

The title compound was prepared as described for the synthesis of Intermediate 85, using ethyl 1-(5-bromo-3-methylpyridin-2-yl)-5-chloro-2-ethyl-1H-imidazole-4-carboxylate (Intermediate 111) in place of ethyl 1-(5-bromo-3-(difluoromethoxy)pyridin-2-yl)-2-ethyl-1H-imidazole-4-carboxylate.

Intermediate 89

Ethyl 1-(3-(difluoromethoxy)-5-(3,3,3-trifluoro-2,2-dimethylpropyl)pyridin-2-yl)-2-ethyl-5-methyl-1H-imidazole-4-carboxylate

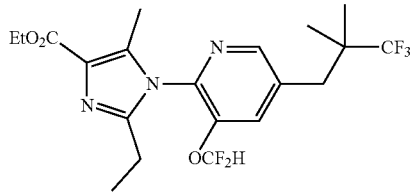

Ethyl 5-chloro-1-(3-(difluoromethoxy)-5-(3,3,3-trifluoro-2,2-dimethylpropyl)pyridin-2-yl)-2-ethyl-1H-imidazole-4-carboxylate (60 mg, 0.13 mmol, Intermediate 85), RuPhos G1 (5 mg, 0.006 mmol), RuPhos (3 mg, 0.006 mmol), and $K_2CO_3$ (71 mg, 0.51 mmol) were combined in a vessel, and the vessel was evacuated and backfilled three times with nitrogen. Dioxane (0.75 mL) and trimethylboroxine (0.050 mL, 0.36 mmol) were successively added, and the resulting mixture was stirred at 90° C. for 2 h. After this time, the mixture was allowed to cool, and then it was diluted with EtOAc and water. The layers were separated, and the aqueous layer was extracted with EtOAc. The combined organic layers were concentrated, and the concentrate was purified by silica gel chromatography (40→70% EtOAc/hexanes) to afford the title compound as a pale yellow film.

Intermediate 90

Ethyl 1-(3-(difluoromethoxy)-5-(4,4,4-trifluorobutyl)pyridin-2-yl)-2-ethyl-5-methyl-1H-imidazole-4-carboxylate

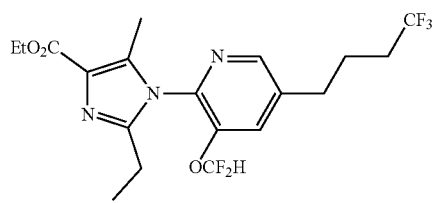

The title compound was prepared as described for the synthesis of Intermediate 89, using ethyl 5-chloro-1-(3-(difluoromethoxy)-5-(4,4,4-trifluorobutyl)pyridin-2-yl)-2-ethyl-1H-imidazole-4-carboxylate (Intermediate 84) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate.

Intermediate 91

4-Bromo-2-(methoxy-d₃)-1-nitrobenzene

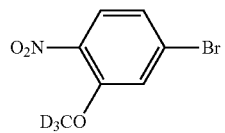

A suspension of 5-bromo-2-nitrophenol, (22.6 g, 103 mmol), CD3I (15.0 g, 103 mmol), and K₂CO₃ (21.5 g, 155 mmol) in DMF (150 mL) was stirred in a sealed tube at 50° C. for 5 h. After this time, the mixture was allowed to cool to rt and then poured into ice water. The resulting yellow precipitate was filtered, washed with cold water, and then dried by aspiration to give the title compound as yellow solid.

Intermediate 92

4-Bromo-2-(methoxy-d₃)aniline

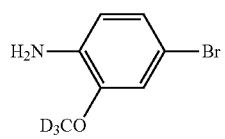

Tin(II) chloride dihydrate (49.1 g, 259 mmol) was added to a solution of 4-bromo-2-(methoxy-d₃)-1-nitrobenzene (15.2 g, 64.7 mmol, Intermediate 91) in EtOAc (500 mL), and the mixture was stirred at reflux temperature until the reaction went to completion. The mixture was then allowed to cool to rt, quenched with water (40 mL), and then neutralized with a saturated aqueous NaHCO₃ solution. The resulting mixture was extracted with twice EtOAc, and the combined organic layers were washed with brine, dried with anhydrous Na₂SO₄, filtered, concentrated, and then purified by silica gel chromatography (10:1 petroleum ether/EtOAc) to afford the title compound as brown solid.

Intermediate 93

Ethyl 1-(4-bromo-2-(methoxy-d₃)phenyl)-2-ethyl-4,5-dihydro-1H-imidazole-4-carboxylate

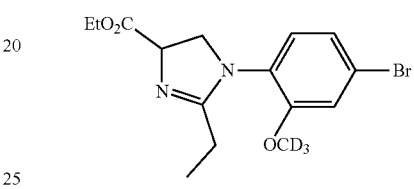

The title compound was prepared as described for the synthesis of Intermediate 68, using N-(4-bromo-2-(methoxy-d₃)phenyl)propionimidamide (Intermediate 98) in place of N-(4-bromo-2-methoxyphenyl)propionimidamide.

Intermediate 94

Ethyl 1-(4-bromo-2-(methoxy-d₃)phenyl)-2-ethyl-1H-imidazole-4-carboxylate

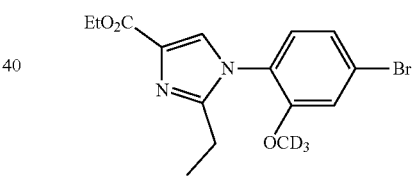

The title compound was prepared as described for the synthesis of Intermediate 79, using ethyl 1-(4-bromo-2-(methoxy-d₃)phenyl)-2-ethyl-4,5-dihydro-1H-imidazole-4-carboxylate (Intermediate 93) in place of ethyl 1-(5-bromo-3-methoxypyridin-2-yl)-2-ethyl-4,5-dihydro-1H-imidazole-4-carboxylate.

Intermediate 95

Ethyl 1-(4-bromo-2-(methoxy-d₃)phenyl)-5-cyano-2-ethyl-1H-imidazole-4-carboxylate

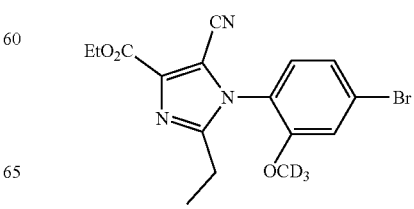

The title compound was prepared as described for the synthesis of Intermediate 70, using ethyl 1-(4-bromo-2-(methoxy-d₃)phenyl)-2-ethyl-1H-imidazole-4-carboxylate (Intermediate 94) in place of ethyl 1-(4-bromo-2-methoxyphenyl)-2-ethyl-1H-imidazole-4-carboxylate.

Intermediate 96

Ethyl 1-(4-bromo-2-methoxyphenyl)-5-chloro-2-ethyl-1H-imidazole-4-carboxylate

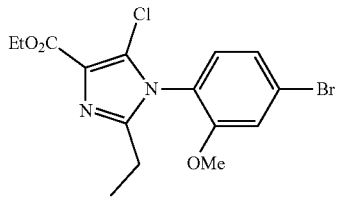

N-Chlorosuccinimide (4.5 g, 33 mmol) was added to a solution of the ethyl 1-(4-bromo-2-methoxyphenyl)-2-ethyl-1H-imidazole-4-carboxylate (12.5 g, 31.9 mmol, Intermediate 69) in DMF (90 mL), and the resulting solution was maintained at rt for 24 h. After this time, an additional portion of NCS was added (0.50 g, 3.7 mmol) and the solution was maintained at rt for another 2 h. After this time, an additional portion of NCS was added (0.50 g, 3.7 mmol), and the solution was maintained at rt for another 6 h. The solution was then diluted with EtOAc and an aqueous Na₂S₂O₃ solution, and the resulting mixture stirred for 1 h. The layers were then separated, and the aqueous layer was extracted with EtOAc. The combined organic layers were dried with anhydrous MgSO₄, filtered, and then concentrated. The concentrate was dissolved in EtOAc, washed twice with 0.5 N aqueous HCl, washed with 1 N aqueous NaOH, washed with brine, dried with anhydrous MgSO₄, filtered, and then concentrated to afford a brown gum. This gum was dissolved in toluene (25 mL) and agitated by rotating for 30 min, after which time crystals had formed. The mixture was cooled to 0-5° C. for 1 h and then filtered. The filter cake was washed with cold toluene and then dried by aspiration to afford colorless crystals. A second crop of crystals was obtained from the concentrate of the combined filtrate and wash, which was crystalized from hot EtOAc. These crystals were washed with a cold EtOAc/hexanes solution (1:1 v/v), dried by aspiration, and then combined with the first crop to afford the title compound as a colorless solid.

Intermediate 97

Ethyl 1-(4-bromo-2-methoxyphenyl)-2-ethyl-5-fluoro-1H-imidazole-4-carboxylate

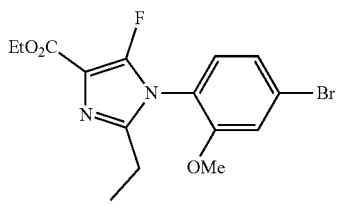 [SMILES: CCOC(=O)c1nc(CC)n(-c2ccc(Br)cc2OC)c1Cl]

A solution of LDA was prepared by adding a solution of n-BuLi in hexane (14.7 mL, 2.5 M, 36.7 mmol) to a −78° C. solution of i-Pr₂NH (5.6 mL, 40 mmol) in THF (80 mL) and stirring for 15 min. After this time, a −78° C. solution of the ethyl 1-(4-bromo-2-methoxyphenyl)-2-ethyl-1H-imidazole-4-carboxylate (10.8 g, 30.6 mmol, Intermediate 69) in THF (40 mL) was added, and stirring was continued at −78° C. for 30 min. A solution of N-fluorobenzenesulfonimide (12.5 g, 39.7 mmol) in THF (40 mL) was then added, and stirring was continued at −78° C. for 1 h before the solution was quenched with a solution of AcOH (3.5 mL, 61 mmol) in THF (3 mL) and allowed to warm to rt. The mixture was then diluted with EtOAc and a saturated aqueous NaHCO₃ solution, and the layers were mixed then separated. The aqueous layer was extracted twice with EtOAc, and the combined organic layers were dried with anhydrous MgSO₄, filtered, and then concentrated. The residue was purified by silica gel chromatography (30→50% EtOAc/hexanes) to afford the title compound as an orange foam.

Intermediate 98

N-(4-Bromo-2-(methoxy-d₃)phenyl)propionimidamide

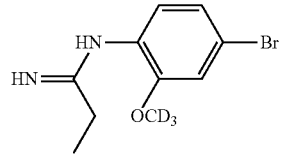

The title compound was prepared as described for the synthesis of Intermediate 67, using 4-bromo-2-(methoxy-d₃)aniline (Intermediate 92) in place of 4-bromo-2-methoxyaniline.

Intermediate 99

Methyl 1-(4-bromo-2-(methoxy-d₃)phenyl)-2-ethyl-5-fluoro-1H-imidazole-4-carboxylate

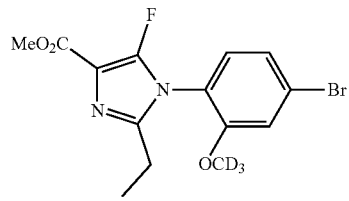

Methyl 2,3-dibromo-3,3-difluoropropanoate (5.05 g, 17.9 mmol, Intermediate 57) was added dropwise to a mixture of N-(4-bromo-2-(methoxy-d₃)phenyl)propionimidamide (4.24 g, 16.3 mmol, Intermediate 98) and Cs₂CO₃ (16.5 g, 50.5 mmol) in DMF (90 mL), and the resulting mixture was stirred for 1 h. After this time, the reaction mixture was filtered, the filter cake was washed with EtOAc, and the filtrate and wash were combined and then concentrated. The concentrate was diluted with EtOAc and water, and the layers were mixed and then separated. The organic layer was washed with water, washed with brine, dried with anhydrous MgSO₄, filtered, and then concentrated to afford a yellow

Intermediate 100

Methyl 2-ethyl-5-fluoro-1-(2-(methoxy-d₃)-4-(3,3,3-trifluoro-2,2-dimethylpropyl)phenyl)-1H-imidazole-4-carboxylate

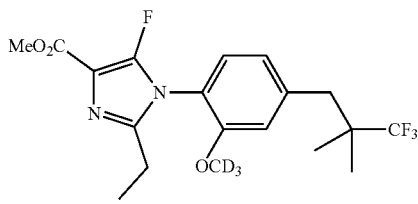

Methyl 1-(4-bromo-2-(methoxy-d₃)phenyl)-2-ethyl-5-fluoro-1H-imidazole-4-carboxylate (273 mg, 0.758 mmol, Intermediate 99) and Pd(t-Bu₃P)₂ (39 mg, 0.076 mmol) were combined in a vessel, and the vessel was evacuated and backfilled with nitrogen three times. A stock suspension of (3,3,3-trifluoro-2,2-dimethylpropyl)zinc(II) iodide (1.6 mL, 0.7 M, 1.1 mmol), which was prepared by reacting equimolar amounts of 1,1,1-trifluoro-3-iodo-2,2-dimethylpropane and Rieke® zinc (5 g/100 mL in THF), was then added, and the resulting mixture were stirred at 65° C. for 4 h. After this time, the mixture was allowed to cool, and then it was diluted with EtOAc and a saturated aqueous NH₄Cl solution. The layers were mixed and then separated, and the aqueous layer was extracted twice with EtOAc. The combined organic layers were dried with anhydrous MgSO₄, filtered, and then concentrated to afford a brown residue. This residue was purified by silica gel chromatography (20→50% EtOAc/hexanes) to afford the title compound as a colorless solid.

Intermediate 101

Ethyl 5-chloro-1-(3-(difluoromethoxy)-5-((S*)-3,3,3-trifluoro-2-methylpropyl)pyridin-2-yl)-2-ethyl-1H-imidazole-4-carboxylate

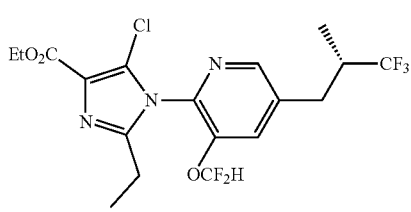

The title compound was prepared as described for the synthesis of Intermediate 100, using ethyl 1-(5-bromo-3-(difluoromethoxy)pyridin-2-yl)-5-chloro-2-ethyl-1H-imidazole-4-carboxylate (Intermediate 83) and (R*)-1,1,1-trifluoro-3-iodo-2-methylpropane (Intermediate 62) in place of methyl 1-(4-bromo-2-(methoxy-d₃)phenyl)-2-ethyl-5-fluoro-1H-imidazole-4-carboxylate and 1,1,1-trifluoro-3-iodo-2,2-dimethylpropane.

Intermediate 102

Ethyl 5-cyano-2-ethyl-1-(2-(methoxy-d₃)-4-(3,3,3-trifluoro-2,2-dimethylpropyl)phenyl)-1H-imidazole-4-carboxylate

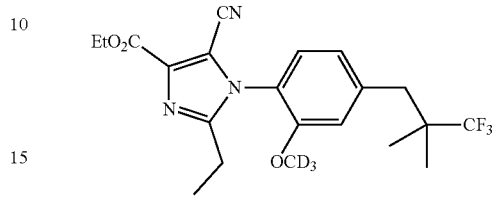

The title compound was prepared as described for the synthesis of Intermediate 100, using ethyl 1-(4-bromo-2-(methoxy-d₃)phenyl)-5-cyano-2-ethyl-1H-imidazole-4-carboxylate (Intermediate 95) in place of methyl 1-(4-bromo-2-(methoxy-d₃)phenyl)-2-ethyl-5-fluoro-1H-imidazole-4-carboxylate.

Intermediate 103

Ethyl 1-(4-bromo-3-methoxyphenyl)-2-ethyl-4,5-dihydro-1H-imidazole-4-carboxylate

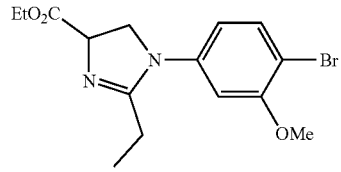 [SMILES: CCOC(=O)C1CN(c2ccc(Br)c(OC)c2)C(CC)=N1]

The title compound was prepared as described for the synthesis of Intermediate 68, using 4-bromo-3-methoxyaniline in place of 4-bromo-2-methoxyaniline.

Intermediate 104

Ethyl 1-(4-bromo-3-methoxyphenyl)-2-ethyl-1H-imidazole-4-carboxylate

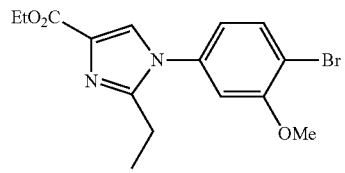 [SMILES: CCOC(=O)c1cn(-c2ccc(Br)c(OC)c2)c(CC)n1]

The title compound was prepared as described for the synthesis of Intermediate 79, using ethyl 1-(4-bromo-3-methoxyphenyl)-2-ethyl-4,5-dihydro-1H-imidazole-4-carboxylate (Intermediate 103) in place of ethyl 1-(5-bromo-3-methoxypyridin-2-yl)-2-ethyl-4,5-dihydro-1H-imidazole-4-carboxylate.

Intermediate 105

Ethyl 1-(4-bromo-3-methoxyphenyl)-5-chloro-2-ethyl-1H-imidazole-4-carboxylate

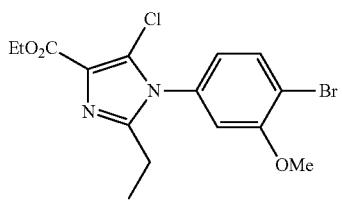 [SMILES: CCOC(=O)c1nc(CC)n(-c2ccc(Br)c(OC)c2)c1Cl]

The title compound was prepared as described for the synthesis of Intermediate 83, using ethyl 1-(4-bromo-3-methoxyphenyl)-2-ethyl-1H-imidazole-4-carboxylate (Intermediate 104) in place of ethyl 1-(5-bromo-3-(difluoromethoxy)pyridin-2-yl)-2-ethyl-1H-imidazole-4-carboxylate.

Intermediate 106

Ethyl 5-chloro-2-ethyl-1-(3-methoxy-4-(3,3,3-trifluoro-2,2-dimethylpropyl)phenyl)-1H-imidazole-4-carboxylate

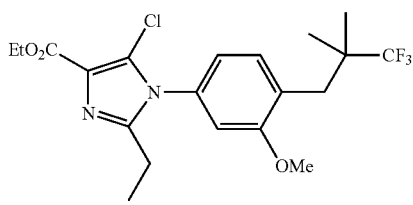 [SMILES: CCOC(=O)c1nc(CC)n(-c2ccc(CC(C)(C)C(F)(F)F)c(OC)c2)c1Cl]

The title compound was prepared as described for the synthesis of Intermediate 100, using ethyl 1-(4-bromo-3-methoxyphenyl)-5-chloro-2-ethyl-1H-imidazole-4-carboxylate (Intermediate 105) in place of methyl 1-(4-bromo-2-(methoxy-d₃)phenyl)-2-ethyl-5-fluoro-1H-imidazole-4-carboxylate.

Intermediate 107

Ethyl 2-ethyl-1-(3-methoxy-4-(3,3,3-trifluoro-2,2-dimethylpropyl)phenyl)-5-methyl-1H-imidazole-4-carboxylate

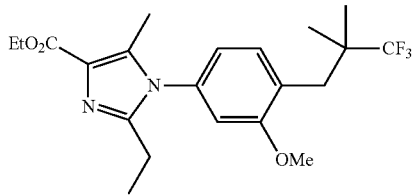 [SMILES: CCOC(=O)c1nc(CC)n(-c2ccc(CC(C)(C)C(F)(F)F)c(OC)c2)c1C]

The title compound was prepared as described for the synthesis of Intermediate 89, using ethyl 5-chloro-2-ethyl-1-(3-methoxy-4-(3,3,3-trifluoro-2,2-dimethylpropyl)phenyl)-1H-imidazole-4-carboxylate (Intermediate 106) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate.

Intermediate 108

Ethyl 1-(4-bromo-2-(difluoromethoxy)phenyl)-2-ethyl-4,5-dihydro-1H-imidazole-4-carboxylate

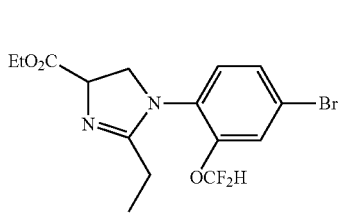

The title compound was prepared as described for the synthesis of Intermediate 68, using N-(4-bromo-2-(difluoromethoxy)phenyl)propionimidamide (Intermediate 75, Step b) in place of N-(4-bromo-2-methoxyphenyl)propionimidamide.

Intermediate 109

Ethyl 1-(4-bromo-2-(difluoromethoxy)phenyl)-2-ethyl-1H-imidazole-4-carboxylate

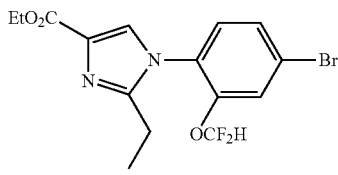

The title compound was prepared as described for the synthesis of Intermediate 79, using ethyl 1-(4-bromo-2-(difluoromethoxy)phenyl)-2-ethyl-4,5-dihydro-1H-imidazole-4-carboxylate (Intermediate 108) in place of ethyl 1-(5-bromo-3-methoxypyridin-2-yl)-2-ethyl-4,5-dihydro-1H-imidazole-4-carboxylate.

Intermediate 110

Ethyl 1-(4-bromo-2-(difluoromethoxy)phenyl)-5-cyano-2-ethyl-1H-imidazole-4-carboxylate

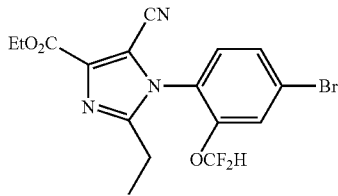

The title compound was prepared as described for the synthesis of Intermediate 70, using ethyl 1-(4-bromo-2-(difluoromethoxy)phenyl)-2-ethyl-1H-imidazole-4-carboxylate (Intermediate 109) in place of ethyl 1-(4-bromo-2-methoxyphenyl)-2-ethyl-1H-imidazole-4-carboxylate.

Intermediate 111

Ethyl 1-(5-bromo-3-methylpyridin-2-yl)-5-chloro-2-ethyl-1H-imidazole-4-carboxylate

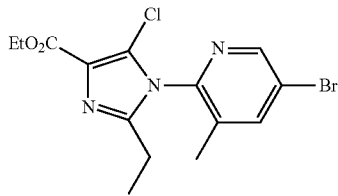 [SMILES: CCOC(=O)c1nc(CC)n(-c2ncc(Br)cc2C)c1Cl]

The title compound was prepared as described for the synthesis of Intermediate 83, using ethyl 1-(5-bromo-3-methylpyridin-2-yl)-2-ethyl-1H-imidazole-4-carboxylate (Intermediate 87) in place of ethyl 1-(5-bromo-3-(difluoromethoxy)pyridin-2-yl)-2-ethyl-1H-imidazole-4-carboxylate.

Intermediate 112

Ethyl 5-cyano-1-(2-(difluoromethoxy)-4-(3,3,3-trifluoro-2,2-dimethylpropyl)phenyl)-2-ethyl-1H-imidazole-4-carboxylate

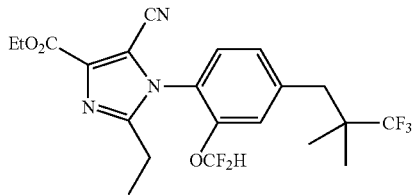

The title compound was prepared as described for the synthesis of Intermediate 100, using ethyl 1-(4-bromo-2-(difluoromethoxy)phenyl)-5-cyano-2-ethyl-1H-imidazole-4-carboxylate (Intermediate 110) in place of methyl 1-(4-bromo-2-(methoxy-$d_3$)phenyl)-2-ethyl-5-fluoro-1H-imidazole-4-carboxylate.

Intermediate 113

Ethyl 5-cyano-1-(2-(difluoromethoxy)-4-(3,3,3-trifluoro-2,2-dimethylpropyl)phenyl)-2-methyl-1H-imidazole-4-carboxylate

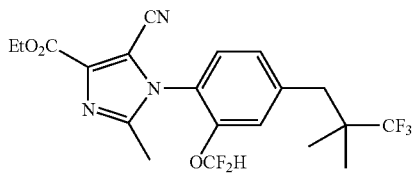

The title compound was prepared as described for the synthesis of Intermediate 112, using acetyl chloride in place of propionyl chloride.

Intermediate 114

Ethyl 1-(4-bromo-2-(difluoromethoxy)phenyl)-2-ethyl-5-fluoro-1H-imidazole-4-carboxylate

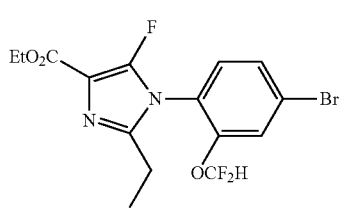

The title compound was prepared as described for the synthesis of Intermediate 99, using N-(4-bromo-2-(difluoromethoxy)phenyl)propionimidamide (Intermediate 75, Step b) in place of N-(4-bromo-2-(methoxy-$d_3$)phenyl)propionimidamide.

Intermediate 115

Ethyl 1-(2-(difluoromethoxy)-4-(3,3,3-trifluoro-2,2-dimethylpropyl)phenyl)-2-ethyl-5-fluoro-1H-imidazole-4-carboxylate

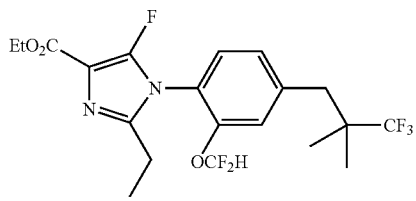

The title compound was prepared as described for the synthesis of Intermediate 100, using ethyl 1-(4-bromo-2-(difluoromethoxy)phenyl)-2-ethyl-5-fluoro-1H-imidazole-4-carboxylate (Intermediate 114) in place of methyl 1-(4-bromo-2-(methoxy-$d_3$)phenyl)-2-ethyl-5-fluoro-1H-imidazole-4-carboxylate.

Intermediate 116

Ethyl 1-(2-(difluoromethoxy)-4-(3,3,3-trifluoro-2,2-dimethylpropyl)phenyl)-2-ethyl-1H-imidazole-4-carboxylate

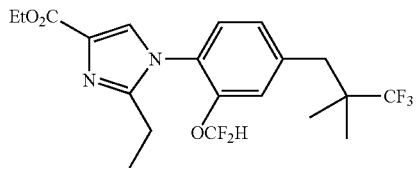

The title compound was prepared as described for the synthesis of Intermediate 100, using ethyl 1-(4-bromo-2-

(difluoromethoxy)phenyl)-2-ethyl-1H-imidazole-4-carboxylate (Intermediate 109) in place of methyl 1-(4-bromo-2-(methoxy-d₃)phenyl)-2-ethyl-5-fluoro-1H-imidazole-4-carboxylate.

Intermediate 117

Ethyl 1-(2-(difluoromethoxy)-4-(3,3,3-trifluoro-2,2-dimethylpropyl)phenyl)-2-ethyl-5-iodo-1H-imidazole-4-carboxylate

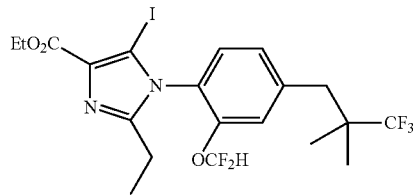

N-Iodosuccinimide (400 mg, 1.78 mmol) was added to a solution of ethyl 1-(2-(difluoromethoxy)-4-(3,3,3-trifluoro-2,2-dimethylpropyl)phenyl)-2-ethyl-1H-imidazole-4-carboxylate (510 mg, 1.2 mmol, Intermediate 116) in AcOH (3.5 mL), and the solution was maintained at 80° C. for 14 h. After this time, the resulting mixture was concentrated and then diluted with EtOAc and a saturated aqueous NaHCO₃ solution. The layers were mixed and then separated, and the organic layer was washed with an aqueous Na₂S₂O₃ solution, washed with water, washed with brine, dried with anhydrous MgSO₄, filtered and then concentrated. The residue was purified by silica gel chromatography (30→60% EtOAc/hexanes) to afford the title compound as a colorless solid.

Intermediate 118

Ethyl 1-(2-(difluoromethoxy)-4-(3,3,3-trifluoro-2,2-dimethylpropyl)phenyl)-2-ethyl-5-((trimethylsilyl)ethynyl)-1H-imidazole-4-carboxylate

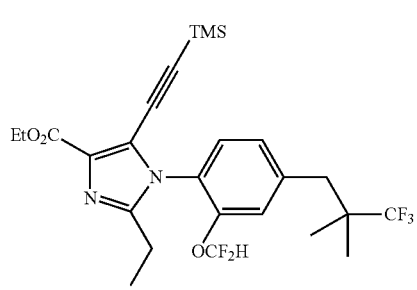

Ethyl 1-(2-(difluoromethoxy)-4-(3,3,3-trifluoro-2,2-dimethylpropyl)phenyl)-2-ethyl-5-iodo-1H-imidazole-4-carboxylate (451 mg, 0.805 mmol, Intermediate 117), CuI (31 mg, 0.16 mmol), and Pd(PPh₃)₄ (93 mg, 0.081 mmol) were combined in a vessel, and the vessel was evacuated and then backfilled with nitrogen three times. Argon-sparged DMF (3 mL), trimethylsilylacetylene (0.171 mL, 1.21 mmol), and then TEA (0.18 mL, 1.3 mmol) were added, and the resulting mixture was stirred at 80° C. for 6 h. After this time, the mixture was allowed to cool and then diluted with EtOAc and water. The layers were mixed and then separated, and the aqueous layer was extracted with EtOAc. The organic layers were combined, washed with twice with water, washed with brine, dried with anhydrous MgSO₄, filtered, and then concentrated to afford a dark residue. This residue was purified by silica gel chromatography (20→50% EtOAc/hexanes) to afford the title compound as a yellow oil.

Intermediate 119

1-(2-(Difluoromethoxy)-4-(3,3,3-trifluoro-2,2-dimethylpropyl)phenyl)-2-ethyl-5-ethynyl-1H-imidazole-4-carboxylic acid

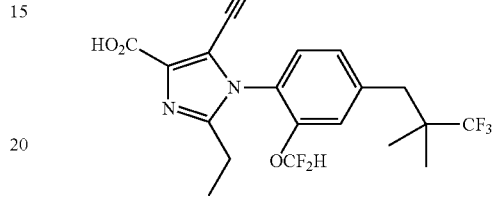

Ethyl 1-(2-(difluoromethoxy)-4-(3,3,3-trifluoro-2,2-dimethylpropyl)phenyl)-2-ethyl-5-((trimethylsilyl)ethynyl)-1H-imidazole-4-carboxylate (220 mg, 0.415 mmol, Intermediate 118) was diluted with 1,4-dioxane (1 mL) and aqueous NaOH (1.0 mL, 1.0 M, 1.0 mmol), and the mixture was stirred at 60° C. for 2 h. After this time, the resulting solution was allowed to cool and then washed with hexanes. The pH of the aqueous layer was adjusted to pH=4 with 1 N aqueous HCl, and then the resulting aqueous mixture was extracted three times with EtOAc. The combined EtOAc layers were dried with anhydrous MgSO₄, filtered, and then concentrated to afford the title compound as a brown film.

Intermediate 120 tert-Butyl 1-(5-bromo-3-(difluoromethoxy)pyridin-2-yl)-5-chloro-2-ethyl-1H-imidazole-4-carboxylate

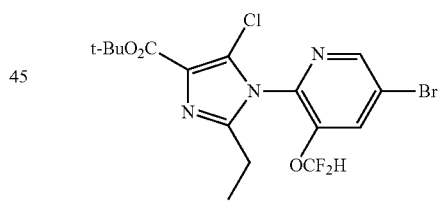

Ethyl 1-(5-bromo-3-(difluoromethoxy)pyridin-2-yl)-5-chloro-2-ethyl-1H-imidazole-4-carboxylate (700 mg, 1.65 mmol, Intermediate 83) was diluted with 1,4-dioxane (5 mL) and aqueous NaOH (5.0 mL, 1.0 M, 5.0 mmol), and the resulting suspension was stirred at 60° C. for 30 min. After this time, the resulting brown solution was allowed to cool, and the pH was adjusted to pH 4 with 1 N aqueous HCl. The supernatant was decanted from a small amount of brown oil that precipitated and then settled at the bottom of the mixture. A few drops of 1 N aqueous NaOH were added to the hazy supernatant to make it homogeneous, and then the pH was adjusted back to pH 4, at which point crystals formed. The mixture was stirred for 5 min and then filtered. The filter cake was washed with water and then dried by aspiration to afford 1-(5-bromo-3-(difluoromethoxy)pyridin-2-yl)-5-chloro-2-ethyl-1H-imidazole-4-carboxylic acid as a colorless solid.

Di-tert-butyl dicarbonate (0.46 mL, 2.14 mmol) was added to a mixture of 1-(5-bromo-3-(difluoromethoxy)pyridin-2-yl)-5-chloro-2-ethyl-1H-imidazole-4-carboxylic acid (424 mg, 1.07 mmol) and DMAP (26 mg, 0.21 mmol) in benzene (2.2 mL), and the resulting mixture was stirred in a sealed tube at 80° C. for 45 h. After this time, the reaction mixture was allowed to cool and then diluted with EtOAc and 1 N aqueous NaOH. The layers were mixed and then separated, and the aqueous layer was extracted twice with EtOAc. The combined organic layers were dried with anhydrous MgSO$_4$, filtered, and then concentrated to afford a pale yellow residue. This residue was purified by silica gel chromatography (20→50% EtOAc/hexanes) to afford the title compound as a colorless solid.

Intermediate 121 tert-Butyl 5-chloro-1-(3-(difluoromethoxy)-5-(3,3,3-trifluoro-2-(trifluoromethyl)propyl)pyridin-2-yl)-2-ethyl-1H-imidazole-4-carboxylate

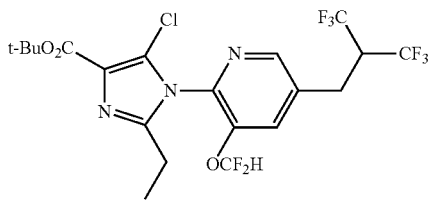

2-(Bromomethyl)-1,1,1,3,3,3-hexafluoropropane (0.77 mL, 5.5 mmol) was added to a 0-5° C. suspension of Rieke® zinc in THF (6.9 mL, 0.05 g/mL, 5.3 mmol), and the mixture was allowed to warm to rt with stirring over 1 h. This black suspension was then cannulated into a vessel containing tert-butyl 1-(5-bromo-3-(difluoromethoxy)pyridin-2-yl)-5-chloro-2-ethyl-1H-imidazole-4-carboxylate (1.19 g, 2.63 mmol, Intermediate 120) and Pd(t-Bu$_3$P)$_2$ (67 mg, 0.13 mmol), and the reaction mixture was stirred at 65° C. for 45 min. After this time, the mixture was allowed to cool to rt and then diluted with EtOAc and a saturated aqueous NH$_4$Cl solution. The mixture was filtered, and the layers of the filtrate were mixed and then separated. The aqueous layer was extracted twice with EtOAc, and the combined organic layers were washed with brine, dried with anhydrous MgSO$_4$, filtered, and then concentrated to afford a yellow residue. This residue was purified by silica gel chromatography (20→50% EtOAc/hexanes) to afford the title compound as a pale yellow foam.

Intermediate 122

5-Chloro-1-(3-(difluoromethoxy)-5-(3,3,3-trifluoro-2-(trifluoromethyl)propyl)pyridin-2-yl)-2-ethyl-1H-imidazole-4-carboxylic acid

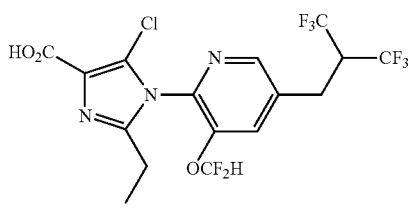

A solution of tert-butyl 5-chloro-1-(3-(difluoromethoxy)-5-(3,3,3-trifluoro-2-(trifluoromethyl)propyl)pyridin-2-yl)-2-ethyl-1H-imidazole-4-carboxylate (144 mg, 0.254 mmol, Intermediate 121) in DCE and TFA (0.64 mL, 1:1 v/v) was maintained at 50° C. for 14 h. After this this time, the reaction mixture was concentrated and then diluted with EtOAc and pH 4 aqueous phosphate buffer. The layers were mixed and then separated, and the aqueous layer was extracted twice with EtOAc. The combined organic layers were dried with anhydrous MgSO$_4$, filtered, and then concentrated to afford the title compound as a yellow film.

Intermediate 123

Ethyl 5-chloro-2-ethyl-1-(2-methoxy-4-(((R)-1,1,1-trifluoropropan-2-yl)amino)phenyl)-1H-imidazole-4-carboxylate

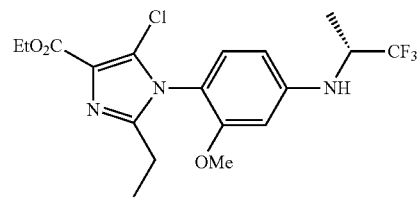 [SMILES: CCOC(=O)c1nc(CC)n(-c2ccc(N[C@H](C)C(F)(F)F)cc2OC)c1Cl]

Ethyl 1-(4-bromo-2-methoxyphenyl)-5-chloro-2-ethyl-1H-imidazole-4-carboxylate (1.0 g, 2.6 mmol, Intermediate 96), RuPhos G1 precatalyst (110 mg, 0.13 mmol, 1:1 MTBE adduct), RuPhos (61 mg, 0.13 mmol), and Cs$_2$CO$_3$ (2.5 g, 7.7 mmol) were combined in a vessel, and the vessel was evacuated and backfilled with nitrogen three times. The mixture was diluted with 1,4-dioxane (5 mL), R-1,1,1-trifluoro-2-propylamine (0.48 mL, 5.2 mmol) was then added, and the resulting mixture was stirred at 110° C. for 5 h. After this time, the mixture was allowed to cool to rt and then diluted with EtOAc and water. The layers were mixed and then separated, and the aqueous layer was extracted twice with EtOAc. The combined organic layers were dried with anhydrous MgSO$_4$, filtered, concentrated, and then purified by silica gel chromatography (40→60% EtOAc/hexanes) to afford the title compound as a pale yellow oil.

Intermediate 124

Methyl 1-(4-bromo-2-methoxyphenyl)-2-ethyl-5-methyl-1H-imidazole-4-carboxylate

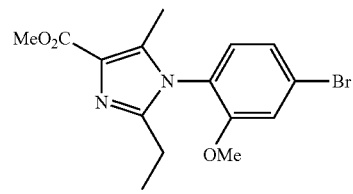 [SMILES: CCc1nc(C(=O)OC)c(C)n1-c1ccc(Br)cc1OC]

Methyl 3-bromo-2-oxobutanoate (4.25 g, 21.8 mmol, Intermediate 55) was added to a mixture of the N-(4-bromo-2-methoxyphenyl)propionimidamide (2.8 g, 11 mmol, Intermediate 67) and NaHCO$_3$ (1.8 g, 22 mmol) in i-PrOH (110 mL), and the resulting mixture was stirred for 80° C. for 16 h. After this time, the mixture was allowed to cool, filtered,

Intermediate 125

Methyl 2-ethyl-1-(2-methoxy-4-(3,3,3-trifluoro-2-methylpropyl)phenyl)-5-methyl-1H-imidazole-4-carboxylate

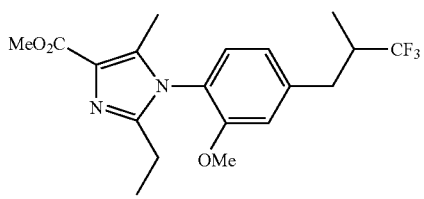 [SMILES: CCc1nc(C(=O)OC)c(C)n1-c1ccc(CC(C)C(F)(F)F)cc1OC]

The title compound was prepared as described for the synthesis of Intermediate 71, using methyl 1-(4-bromo-2-methoxyphenyl)-2-ethyl-5-methyl-1H-imidazole-4-carboxylate (Intermediate 124) in place of ethyl 1-(4-bromo-2-methoxyphenyl)-5-cyano-2-ethyl-1H-imidazole-4-carboxylate.

Intermediate 126

Ethyl 1-(4-bromo-2-methoxyphenyl)-2-isobutyl-1H-imidazole-4-carboxylate

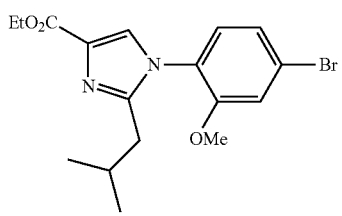 [SMILES: CCOC(=O)c1cn(-c2ccc(Br)cc2OC)c(CC(C)C)n1]

The title compound was prepared as described for the synthesis of Intermediate 124, using 3-methylbutanenitrile and ethyl bromopyruvate in place of propionitrile and methyl 3-bromo-2-oxobutanoate.

Intermediate 127

Ethyl 5-chloro-2-ethyl-1-(2-methoxy-4-(3,3,3-trifluoro-2-methylpropyl)phenyl)-1H-imidazole-4-carboxylate

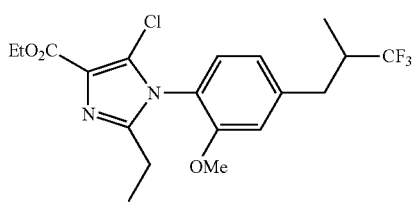 [SMILES: CCOC(=O)c1nc(CC)n(-c2ccc(CC(C)C(F)(F)F)cc2OC)c1Cl]

The title compound was prepared as described for the synthesis of Intermediate 71, using ethyl 1-(4-bromo-2-methoxyphenyl)-5-chloro-2-ethyl-1H-imidazole-4-carboxylate (Intermediate 96) in place of ethyl 1-(4-bromo-2-methoxyphenyl)-5-cyano-2-ethyl-1H-imidazole-4-carboxylate.

Intermediate 128 tert-Butyl (3-methylpyridin-2-yl)carbamate

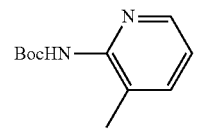

A solution of 3-methylpyridin-2-amine (10.0 g, 92.5 mmol) in EtOAc (10 mL) was added dropwise to a 60° C. solution of Boc$_2$O (32.0 g, 147 mmol) in hexane (50 mL), and the resulting mixture was stirred at 60° C. for 2 h before it was allowed to cool to rt and poured it into water. The aqueous mixture was extracted twice with EtOAc, and the combined organic layers were washed with brine, dried with anhydrous Na$_2$SO$_4$, filtered, and then concentrated. The concentrate was purified by silica gel chromatography (10%→20% EtOAc/petroleum ether) to give the title compound as a colorless solid.

Intermediate 129 tert-Butyl (3-ethylpyridin-2-yl)carbamate

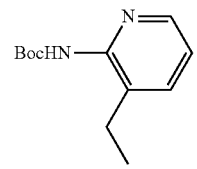 [SMILES: CCc1cccnc1NC(=O)OC(C)(C)C]

n-Butyllithium (33.8 mL, 2.5 M in hexane, 84.5 mmol) was added dropwise to a −40° C. solution of tert-butyl (3-methylpyridin-2-yl)carbamate (8.0 g, 38 mmol, Intermediate 128) in THF (150 mL), and the resulting mixture was stirred and allowed to warm to 0° C. before it was cooled to −70° C. A solution of MeI (2.5 mL, 40 mmol) in THF (50 mL) was then added dropwise, and the resulting mixture was stirred at −70° C. for 30 min before it was poured into ice water. The aqueous mixture was extracted with twice with EtOAc, and the combined organic layers were washed with brine, dried with anhydrous Na$_2$SO$_4$, filtered, and then concentrated to afford the title compound as a colorless oil.

Intermediate 130

3-Ethylpyridin-2-amine

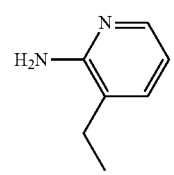

A solution of HCl in 1,4-dioxane (100 mL, 4.0 M, 400 mmol) was added to a 0-5° C. solution of tert-butyl (3-ethylpyridin-2-yl)carbamate (8.5 g, 38 mmol, Intermediate 129) in EtOAc (100 mL), and the resulting mixture was stirred and allowed to warm to rt over 2 h. After this time, the mixture was concentrated and then diluted with water. The resulting solution was made basic (pH=8) with NaHCO₃ and extracted with three times with CH₂Cl₂. The organic layers were combined organic, dried with anhydrous Na₂SO₄, filtered, and then concentrated to afford the title compound as a colorless oil.

Intermediate 131

5-Bromo-3-ethylpyridin-2-amine

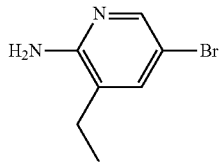

N-Bromosuccinimide (4.08 g, 22.9 mmol) was added in portions to a 0-5° C. solution of 3-ethylpyridine-2-amine (2.8 g, 23 mmol, Intermediate 130) in 1,4-dioxane and water (120 mL, 3:1 v/v), and the resulting mixture was stirred at 0-5° C. for 1.5 h. After this time, the reaction mixture was diluted with water and extracted three times with EtOAc. The organic layers were combined, washed with brine, dried with anhydrous Na₂SO₄, filtered, and then concentrated to afford the title compound as a colorless solid.

Intermediate 132

Ethyl 3-((5-bromo-3-ethylpyridin-2-yl)amino)-2-nitroacrylate

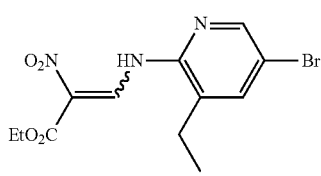 [SMILES: CCOC(=O)C(=CNc1ncc(Br)cc1CC)[N+](=O)[O-]]

A solution of 5-bromo-3-ethylpyridin-2-amine (4.0 g, 20 mmol, Intermediate 131), ethyl 3-ethoxy-2-nitroacrylate (6.0 g, 32 mmol), and AcOH (1.5 mL, 26 mmol) in ethanol (20 mL) was stirred at 80° C. for 1.5 h. After this time, the mixture was allowed to cool to rt, diluted with water, and extracted three times with EtOAc. The organic layers were combined, washed with brine, dried with anhydrous Na₂SO₄, filtered, and then concentrated to afford the title compound as an orange solid.

Intermediate 133

Ethyl 1-(5-bromo-3-ethylpyridin-2-yl)-2-ethyl-1H-imidazole-4-carboxylate

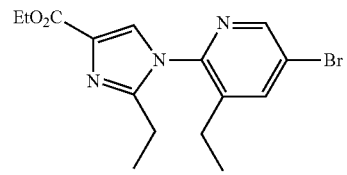 [SMILES: CCOC(=O)c1cn(-c2ncc(Br)cc2CC)c(CC)n1]

A mixture of ethyl 3-((5-bromo-3-ethylpyridin-2-yl)amino)-2-nitroacrylate (7.0 g, 20 mmol, Intermediate 132), triethyl orthopropionate (40 mL), and Pt/C (1.0 g, 5 wt %, 0.26 mmol) was stirred under H₂ (15 psi) at 70° C. for 2 h. After this time, the suspension was filtered through a pad of Celite®, and the pad washed with EtOAc. The filtrate and wash were combined and then concentrated. The concentrate was purified by silica gel chromatography (10→100% EtOAc/petroleum ether) to afford the title compound as an orange solid.

Intermediate 134

Ethyl 5-chloro-1-(3-(difluoromethoxy)-5-((R*)-3,3,3-trifluoro-2-methylpropyl)pyridin-2-yl)-2-ethyl-1H-imidazole-4-carboxylate

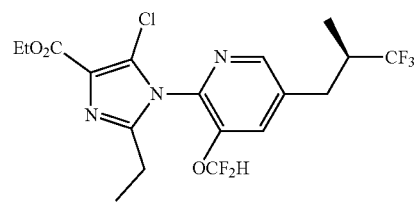

The title compound was prepared as described for the synthesis of Intermediate 100, using ethyl 1-(5-bromo-3-(difluoromethoxy)pyridin-2-yl)-5-chloro-2-ethyl-1H-imidazole-4-carboxylate (Intermediate 83) and (S*)-1,1,1-trifluoro-3-iodo-2-methylpropane (Intermediate 63) in place of methyl 1-(4-bromo-2-(methoxy-d₃)phenyl)-2-ethyl-5-fluoro-1H-imidazole-4-carboxylate and 1,1,1-trifluoro-3-iodo-2,2-dimethylpropane.

Intermediate 135

Ethyl 1-(3-(difluoromethoxy)-5-((R*)-3,3,3-trifluoro-2-methylpropyl)pyridin-2-yl)-2-ethyl-5-methyl-1H-imidazole-4-carboxylate

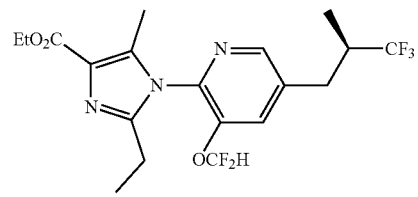

The title compound was prepared as described for the synthesis of Intermediate 89, using ethyl 5-chloro-1-(3-(difluoromethoxy)-5-((R*)-3,3,3-trifluoro-2-methylpropyl)pyridin-2-yl)-2-ethyl-1H-imidazole-4-carboxylate (Intermediate 134) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate.

Intermediate 136 tert-Butyl 1-(3-(difluoromethoxy)-5-(3,3,3-trifluoro-2-(trifluoromethyl)propyl)pyridin-2-yl)-2-ethyl-5-methyl-1H-imidazole-4-carboxylate

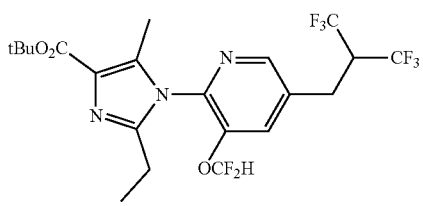

The title compound was prepared as described for the synthesis of Intermediate 89, using tert-butyl 5-chloro-1-(3-(difluoromethoxy)-5-(3,3,3-trifluoro-2-(trifluoromethyl)propyl)pyridin-2-yl)-2-ethyl-1H-imidazole-4-carboxylate (Intermediate 121) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate.

Intermediate 137

1-(3-(Difluoromethoxy)-5-(3,3,3-trifluoro-2-(trifluoromethyl)propyl)pyridin-2-yl)-2-ethyl-5-methyl-1H-imidazole-4-carboxylic acid

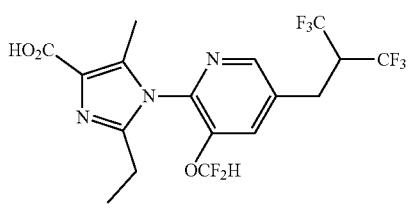

To tert-butyl 1-(3-(difluoromethoxy)-5-(3,3,3-trifluoro-2-(trifluoromethyl)propyl)pyridin-2-yl)-2-ethyl-5-methyl-1H-imidazole-4-carboxylate (200 mg, 0.387 mmol, Intermediate 136) in DCM (1 mL, 15.6 mmol) was added HCl (0.25 mL, 4.0 M in 1,4-dioxane), and the reaction mixture was stirred at rt overnight. Additional HCl (0.2 mL, 4 M in 1,4-dioxane) was then added, and the mixture was heated to 70° C. for 2 h. After this time, the reaction was allowed to cool to rt and then concentrated to afford the title compound.

Intermediate 138

N-(4-Bromo-2,6-difluorophenyl)propionimidamide

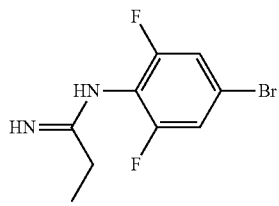

The title compound was prepared as described for the synthesis of Intermediate 67, using 4-bromo-2,6-difluoroaniline in place of 4-bromo-2-methoxyaniline.

Intermediate 139, Step a

Ethyl 1-(4-bromo-2,6-difluorophenyl)-2-ethyl-4,5-dihydro-1H-imidazole-4-carboxylate

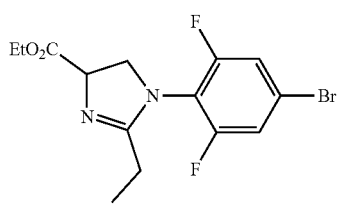 [SMILES: CCOC(=O)C1CN(c2c(F)cc(Br)cc2F)C(CC)=N1]

The title compound was prepared as described for the synthesis of Intermediate 68, using N-(4-bromo-2,6-difluorophenyl)propionimidamide (Intermediate 138) in place of N-(4-bromo-2-methoxyphenyl)propionimidamide.

Intermediate 139, Step b

Ethyl 1-(4-bromo-2,6-difluorophenyl)-2-ethyl-1H-imidazole-4-carboxylate

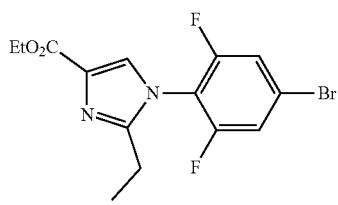 [SMILES: CCOC(=O)c1cn(-c2c(F)cc(Br)cc2F)c(CC)n1]

The title compound was prepared as described for the synthesis of Intermediate 79, using ethyl 1-(4-bromo-2,6-difluorophenyl)-2-ethyl-4,5-dihydro-1H-imidazole-4-carboxylate (Intermediate 139, Step a) in place of ethyl 1-(5-bromo-3-methoxypyridin-2-yl)-2-ethyl-4,5-dihydro-1H-imidazole-4-carboxylate.

Intermediate 140

Ethyl 1-(4-bromo-2,6-difluorophenyl)-5-chloro-2-ethyl-1H-imidazole-4-carboxylate

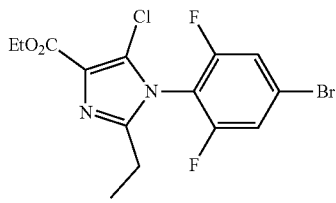 [SMILES: CCc1nc(C(=O)O)c(Cl)n1-c1c(F)cc(Br)cc1F]

The title compound was prepared as described for the synthesis of Intermediate 83, using ethyl 1-(4-bromo-2,6-difluorophenyl)-2-ethyl-1H-imidazole-4-carboxylate (Intermediate 139, Step b) in place of ethyl 1-(5-bromo-3-(difluoromethoxy)pyridin-2-yl)-2-ethyl-1H-imidazole-4-carboxylate.

Intermediate 141

1-(4-Bromo-2,6-difluorophenyl)-5-chloro-2-ethyl-1H-imidazole-4-carboxylic acid

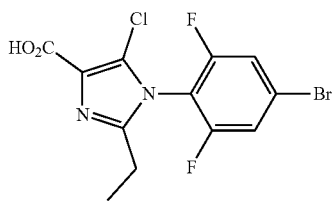

Aqueous NaOH (3.0 mL, 1.0 M, 3.0 mmol) was added to a solution of ethyl 1-(4-bromo-2,6-difluorophenyl)-5-chloro-2-ethyl-1H-imidazole-4-carboxylate (218 mg, 0.554 mmol, Intermediate 140) in 1,4-dioxane (6 mL), and the mixture was stirred at 50° C. for 40 min. After this time, the resulting solution was allowed to cool to rt and diluted with water. The pH of the solution was adjusted to pH 3-4, and then it was diluted with 2-MeTHF (5 mL). The mixture was partitioned between EtOAc and water, the layers were separated, and the aqueous layer was extracted with EtOAc. The organic layers were combined, dried with anhydrous $Na_2SO_4$, filtered, and then concentrated to afford the title compound.

Intermediate 142

5-Chloro-1-(2,6-difluoro-4-(3,3,3-trifluoro-2-hydroxy-2-(trifluoromethyl)propyl)phenyl)-2-ethyl-1H-imidazole-4-carboxylic acid

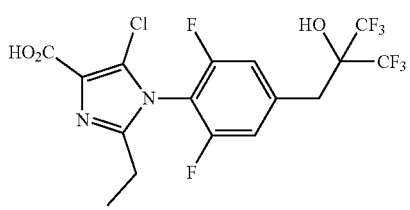 [SMILES: CCc1nc(C(=O)O)c(Cl)n1-c1c(F)cc(CC(O)(C(F)(F)F)C(F)(F)F)cc1F]

A solution of n-BuLi in hexanes (0.94 mL, 1.6 M, 1.5 mmol) was added dropwise to a stirring solution of 1-(4-bromo-2,6-difluorophenyl)-5-chloro-2-ethyl-1H-imidazole-4-carboxylic acid (218 mg, 0.596 mmol, Intermediate 141) in THF (6 mL) at −78° C. After 15 min, 2,2-bis(trifluoromethyl)oxirane (0.36 mL) was added dropwise. After 5 min, the reaction was removed from the cooling bath and allowed to warm to rt over 15 min whereupon a 1 M aqueous solution of NaOH in water (6 mL) was added. After 2 hours, EtOAc was added and the layers were separated. The organic layer was dried over $Na_2SO_4$, filtered and concentrated to afford to titled compound. This material was used in the next step without further purification.

Intermediate 143

Ethyl 1-(2,6-difluoro-4-(3,3,3-trifluoro-2-methylpropyl)phenyl)-2-ethyl-1H-imidazole-4-carboxylate

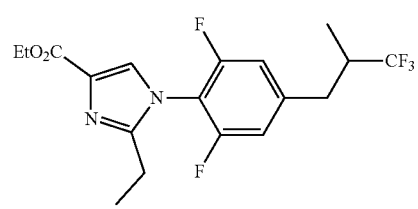 [SMILES: CCOC(=O)c1cn(-c2c(F)cc(CC(C)C(F)(F)F)cc2F)c(CC)n1]

The title compound was prepared as described for the synthesis of Intermediate 71, using ethyl 1-(4-bromo-2,6-difluorophenyl)-2-ethyl-1H-imidazole-4-carboxylate (Intermediate 139, Step b) in place of ethyl 1-(4-bromo-2-methoxyphenyl)-5-cyano-2-ethyl-1H-imidazole-4-carboxylate.

Intermediate 144

Ethyl 5-chloro-1-(2,6-difluoro-4-(3,3,3-trifluoro-2-methylpropyl)phenyl)-2-ethyl-1H-imidazole-4-carboxylate

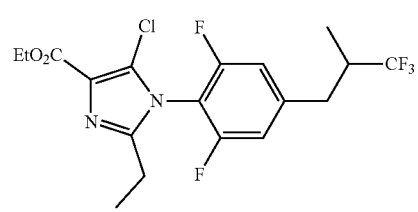 [SMILES: CCOC(=O)c1nc(CC)n(-c2c(F)cc(CC(C)C(F)(F)F)cc2F)c1Cl]

The title compound was prepared as described for the synthesis of Intermediate 71, using ethyl 1-(4-bromo-2,6-difluorophenyl)-5-chloro-2-ethyl-1H-imidazole-4-carboxylate (Intermediate 140) in place of ethyl 1-(4-bromo-2-methoxyphenyl)-5-cyano-2-ethyl-1H-imidazole-4-carboxylate.

Intermediate 145

Ethyl 1-(2,6-difluoro-4-isobutylphenyl)-2-ethyl-1H-imidazole-4-carboxylate

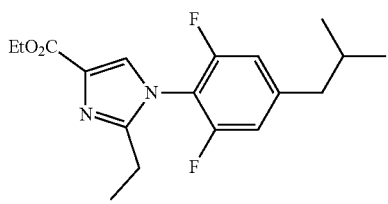 [SMILES: CCOC(=O)c1cn(-c2c(F)cc(CC(C)C)cc2F)c(CC)n1]

The title compound was prepared as described for the synthesis of Intermediate 71, using ethyl 1-(4-bromo-2,6-difluorophenyl)-2-ethyl-1H-imidazole-4-carboxylate (Intermediate 139, Step b) in place of ethyl 1-(4-bromo-2-methoxyphenyl)-5-cyano-2-ethyl-1H-imidazole-4-carboxylate and isobutylboronic acid in place of 9-(3,3,3-trifluoro-2-methylpropyl)-9-borabicyclo[3.3.1]nonane and using toluene as solvent.

Intermediate 146

Ethyl 5-chloro-1-(2,6-difluoro-4-isobutylphenyl)-2-ethyl-1H-imidazole-4-carboxylate

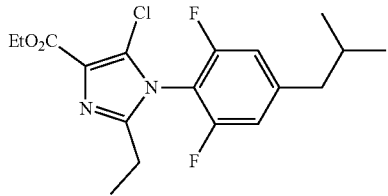 [SMILES: CCOC(=O)c1nc(CC)n(-c2c(F)cc(CC(C)C)cc2F)c1Cl]

The title compound was prepared as described for the synthesis of Intermediate 71, using ethyl 1-(4-bromo-2,6-difluorophenyl)-2-ethyl-1H-imidazole-4-carboxylate (Intermediate 140) in place of ethyl 1-(4-bromo-2-methoxyphenyl)-5-cyano-2-ethyl-1H-imidazole-4-carboxylate and isobutylboronic acid in place of 9-(3,3,3-trifluoro-2-methylpropyl)-9-borabicyclo[3.3.1]nonane and using toluene as solvent.

Intermediate 147

Ethyl 5-chloro-2-ethyl-1-(4-isobutyl-2-methoxyphenyl)-1H-imidazole-4-carboxylate

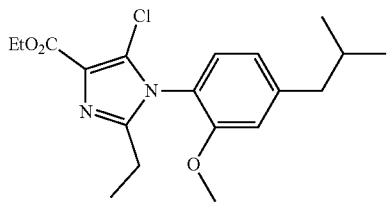 [SMILES: CCOC(=O)c1nc(CC)n(-c2ccc(CC(C)C)cc2OC)c1Cl]

The title compound was prepared as described for the synthesis Intermediate 71, using ethyl 1-(4-bromo-2-methoxyphenyl)-5-chloro-2-ethyl-1H-imidazole-4-carboxylate (Intermediate 96) in place of ethyl 1-(4-bromo-2,6-difluorophenyl)-2-ethyl-1H-imidazole-4-carboxylate and isobutylboronic acid in place of 9-(3,3,3-trifluoro-2-methylpropyl)-9-borabicyclo[3.3.1]nonane and using toluene as solvent.

Intermediate 148

Ethyl 5-cyano-2-ethyl-1-(2-fluoro-4-(3,3,3-trifluoropropyl)phenyl)-1H-imidazole-4-carboxylate

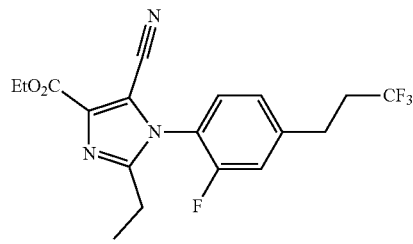 [SMILES: CCOC(=O)c1nc(CC)n(-c2ccc(CCC(F)(F)F)cc2F)c1C#N]

The title compound was prepared as described for the synthesis of Intermediate 71, using ethyl 1-(4-bromo-2-fluorophenyl)-5-cyano-2-ethyl-1H-imidazole-4-carboxylate (Intermediate 163) in place of ethyl 1-(4-bromo-2-methoxyphenyl)-5-cyano-2-ethyl-1H-imidazole-4-carboxylate and 9-(3,3,3-trifluoropropyl)-9-borabicyclo[3.3.1]nonane (Intermediate 65) in place of 9-(3,3,3-trifluoro-2-methylpropyl)-9-borabicyclo[3.3.1]nonane.

Intermediate 149

N-(4-Bromo-2-fluorophenyl)propionimidamide

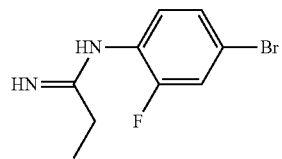

The title compound was prepared as described for the synthesis of Intermediate 67, using 4-bromo-2-fluoroaniline in place of 4-bromo-2-methoxyaniline.

Intermediate 150

Ethyl 1-(4-bromo-2-fluorophenyl)-2-ethyl-4,5-dihydro-1H-imidazole-4-carboxylate

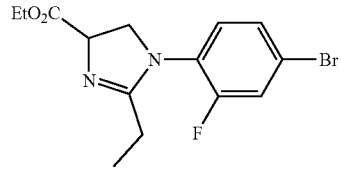 [SMILES: CCOC(=O)C1CN(c2ccc(Br)cc2F)C(CC)=N1]

The title compound was prepared as described for the synthesis of Intermediate 68, using N-(4-bromo-2-fluorophenyl)propionimidamide (Intermediate 149) in place of N-(4-bromo-2-methoxyphenyl)propionimidamide.

Intermediate 151

Ethyl 1-(4-bromo-2-fluorophenyl)-2-ethyl-1H-imidazole-4-carboxylate

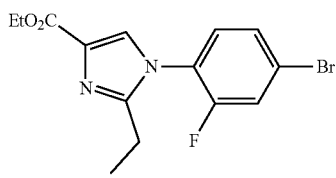 [SMILES: CCOC(=O)c1cn(-c2ccc(Br)cc2F)c(CC)n1]

A solution of bromotrichloromethane (34.5 g, 174 mmol) in DCM (50 mL) was added to a stirring mixture of DBU (44.1 g, 290 mmol) and ethyl 1-(4-bromo-2-fluorophenyl)-2-ethyl-4,5-dihydro-1H-imidazole-4-carboxylate (19.9 g, 58 mmol, Intermediate 150) in DCM (150 mL) at 0° C. The reaction was allowed to warm to rt. After 6 h, water was added and the mixture was extracted with DCM. The organic layers were combined, washed with water, dried over $Na_2SO_4$, filtered, and then concentrated. Purification by silica gel chromatography (EtOAc-petroleum ether) afforded the title compound.

Intermediate 152

Ethyl 1-(4-bromo-2-fluorophenyl)-5-chloro-2-ethyl-1H-imidazole-4-carboxylate

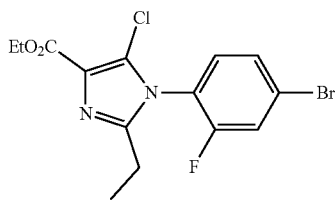 [SMILES: CCOC(=O)c1nc(CC)n(-c2ccc(Br)cc2F)c1Cl]

The title compound was prepared as described for the synthesis of Intermediate 83, using ethyl 1-(4-bromo-2-fluorophenyl)-2-ethyl-1H-imidazole-4-carboxylate (Intermediate 151) in place of ethyl 1-(5-bromo-3-(difluoromethoxy)pyridin-2-yl)-2-ethyl-1H-imidazole-4-carboxylate and MeCN in place of DMF as solvent.

Intermediate 153

Ethyl 5-chloro-2-ethyl-1-(2-fluoro-4-(4,4,4-trifluorobutyl)phenyl)-1H-imidazole-4-carboxylate

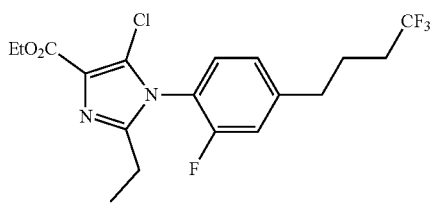 [SMILES: CCOC(=O)c1nc(CC)n(-c2ccc(CCCC(F)(F)F)cc2F)c1Cl]

The title compound was prepared as described for the synthesis of Intermediate 71, using ethyl 1-(4-bromo-2-fluorophenyl)-5-chloro-2-ethyl-1H-imidazole-4-carboxylate (Intermediate 152) in place of ethyl 1-(4-bromo-2-methoxyphenyl)-5-cyano-2-ethyl-1H-imidazole-4-carboxylate and 9-(4,4,4-trifluorobutyl)-9-borabicyclo[3.3.1]nonane (Intermediate 66) in place of 9-(3,3,3-trifluoro-2-methylpropyl)-9-borabicyclo[3.3.1]nonane.

Intermediate 154

Ethyl 5-chloro-2-ethyl-1-(2-fluoro-4-(3,3,3-trifluoro-2,2-dimethylpropyl)phenyl)-1H-imidazole-4-carboxylate

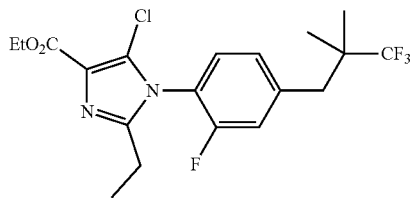 [SMILES: CCOC(=O)c1nc(CC)n(-c2ccc(CC(C)(C)C(F)(F)F)cc2F)c1Cl]

A mixture containing (3,3,3-trifluoro-2,2-dimethylpropyl)zinc(II) iodide (1.6 mL, 0.73 M solution in THF), which was prepared by reacting equimolar amounts of 1,1,1-trifluoro-3-iodo-2,2-dimethylpropane and Rieke® zinc (5 g/100 mL in THF) was combined with ethyl 1-(4-bromo-2-fluorophenyl)-5-chloro-2-ethyl-1H-imidazole-4-carboxylate (302 mg, 0.804 mmol, Intermediate 152) and $Pd(t-Bu_3P)_2$ (47 mg, 0.092 mmol), and the resulting mixture was warmed to 65° C. After 2 h, the mixture was cooled to rt, EtOAc was added, and then the solution was absorbed onto Celite®. Purification by silica gel chromatography (EtOAc-DCM) provided the title compound.

Intermediate 155

N-(4-Bromo-3-fluorophenyl)propionimidamide

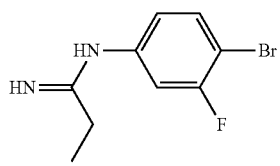

The title compound was prepared as described for the synthesis of Intermediate 67, using 4-bromo-3-fluoroaniline in place of 4-bromo-2-methoxyaniline.

Intermediate 156

Ethyl 1-(4-bromo-3-fluorophenyl)-2-ethyl-4,5-dihydro-1H-imidazole-4-carboxylate

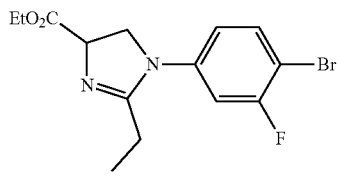 [SMILES: CCOC(=O)C1CN(c2ccc(Br)c(F)c2)C(CC)=N1]

The title compound was prepared as described for the synthesis of Intermediate 68, using N-(4-bromo-3-fluorophenyl)propionimidamide (Intermediate 155) in place of N-(4-bromo-2-methoxyphenyl)propionimidamide.

Intermediate 157

Ethyl 1-(4-bromo-3-fluorophenyl)-2-ethyl-1H-imidazole-4-carboxylate

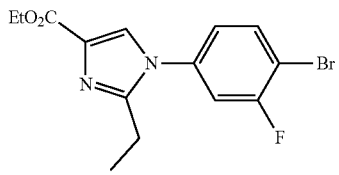 [SMILES: CCOC(=O)c1cn(-c2ccc(Br)c(F)c2)c(CC)n1]

The title compound was prepared as described for the synthesis of Intermediate 79, using ethyl 1-(4-bromo-3-fluorophenyl)-2-ethyl-4,5-dihydro-1H-imidazole-4-carboxylate (Intermediate 156) in place of ethyl 1-(5-bromo-3-methoxypyridin-2-yl)-2-ethyl-4,5-dihydro-1H-imidazole-4-carboxylate.

Intermediate 158

Ethyl 1-(4-bromo-3-fluorophenyl)-5-chloro-2-ethyl-1H-imidazole-4-carboxylate

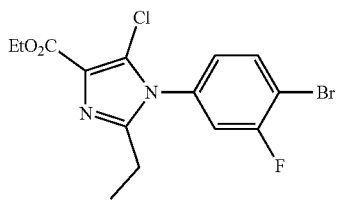 [SMILES: CCOC(=O)c1nc(CC)n(-c2ccc(Br)c(F)c2)c1Cl]

A mixture containing ethyl 1-(4-bromo-3-fluorophenyl)-2-ethyl-1H-imidazole-4-carboxylate (1.64 g, 4.81 mmol, Intermediate 157), NCS (708 mg, 5.30 mmol) and DMF (15 mL) was stirred at 55° C. After 3 h, the mixture was cooled to rt, EtOAc was added and the mixture washed with half-saturated aqueous sodium chloride solution. The organic layer was dried with anhydrous Na$_2$SO$_4$, filtered, and then absorbed onto Celite®. Purification by silica gel chromatography afforded the title compound as a colorless solid.

Intermediate 159

Ethyl 5-chloro-2-ethyl-1-(3-fluoro-4-(3,3,3-trifluoro-2,2-dimethylpropyl)phenyl)-1H-imidazole-4-carboxylate

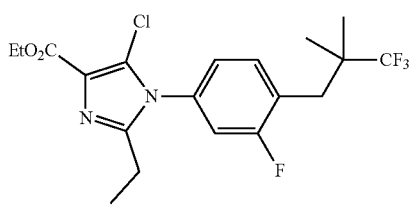 [SMILES: CCOC(=O)c1nc(CC)n(-c2ccc(CC(C)(C)C(F)(F)F)c(F)c2)c1Cl]

The title compound was prepared as described for the synthesis of Intermediate 154, using ethyl 1-(4-bromo-3-fluorophenyl)-5-chloro-2-ethyl-1H-imidazole-4-carboxylate (Intermediate 158) in place of ethyl 1-(4-bromo-2-fluorophenyl)-5-chloro-2-ethyl-1H-imidazole-4-carboxylate.

Intermediate 160

Ethyl 5-chloro-1-(3-(difluoromethoxy)-5-(4,4,4-trifluoro-2,2-dimethylbutyl)pyridin-2-yl)-2-ethyl-1H-imidazole-4-carboxylate

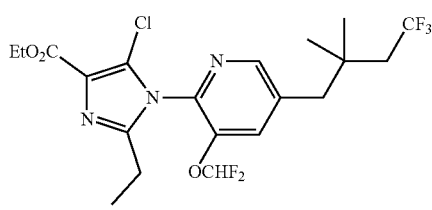 [SMILES: CCOC(=O)c1nc(CC)n(-c2ncc(CC(C)(C)CC(F)(F)F)cc2OC(F)F)c1Cl]

The title compound was prepared as described for the synthesis of Intermediate 85, using 1,1,1-trifluoro-4-iodo-3,3-dimethylbutane in place of 1,1,1-trifluoro-3-iodo-2,2-dimethylpropane.

Intermediate 161

1-(4-Bromo-3-fluorophenyl)-5-chloro-2-ethyl-N-(((1s,4s)-1-hydroxy-4-(methylsulfonyl)cyclohexyl)methyl)-1H-imidazole-4-carboxamide

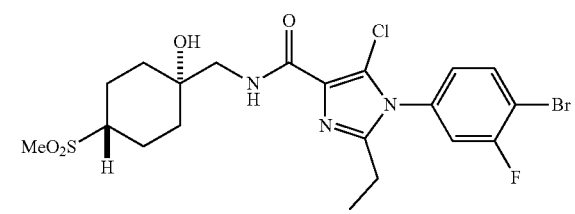 [SMILES: CCc1nc(C(=O)NC[C@]2(O)CC[C@@H](S(C)(=O)=O)CC2)c(Cl)n1-c1ccc(Br)c(F)c1]

The title compound was prepared as described for the synthesis of Example 2, using ethyl 1-(4-bromo-3-fluorophenyl)-5-chloro-2-ethyl-1H-imidazole-4-carboxylate (Intermediate 158) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate, (1s,4s)-1-(aminomethyl)-4-(methylsulfonyl)cyclohexanol hydrochloride (Intermediate 9) in place of ((1r,4r)-4-(methylsulfonyl)cyclohexyl)methanamine hydrochloride, and DCM in place of MeCN as solvent.

Intermediate 162, Step a

N-(4-Bromo-2-(trifluoromethoxy)phenyl)propionimidamide

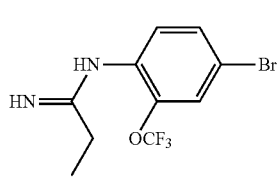 [SMILES: CCC(=N)Nc1ccc(Br)cc1OC(F)(F)F]

Trimethylaluminum (30 mL, 2 M in toluene, 60 mmol) was added dropwise to a 0° C. solution of 4-bromo-2-(trifluoromethoxy)aniline (15.04 g, 58.745 mmol) and propionitrile (4.5 mL, 63 mmol) under a nitrogen atmosphere. The reaction was then heated to 100° C. under a reflux condenser and stirred overnight. After this time, the solution was allowed to cool to rt, then cooled to 0° C. in an ice bath and diluted with 50 mL of THF. Water (4.3 mL), 15% aqueous NaOH (4.3 mL), and then more water (13 mL) were slowly added, and the resulting mixture was allowed to warm to rt with stirring. The mixture was then filtered through Celite® and concentrated. The concentrate was diluted with enough 1 N aqueous HCl to give a solution with pH 1-2, and the solution was washed with EtOAc. The organic layer was then separated and discarded. The aqueous layer was adjusted to pH 13-14 with 1 M NaOH, and resulting mixture was extracted with EtOAc. The organic layer was washed with brine, dried with anhydrous MgSO$_4$, filtered, and then concentrated to afford the title compound as a colorless oil, which was used in the next step without further purification.

Intermediate 162, Step b

Ethyl 1-(4-bromo-2-(trifluoromethoxy)phenyl)-2-ethyl-4,5-dihydro-1H-imidazole-4-carboxylate

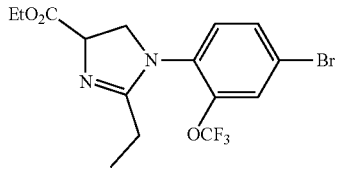

A solution of ethyl 2-bromoacrylate (10.5 g, 58.6 mmol, Intermediate 56) in EtOH (20 mL) was added to a mixture of N-(4-bromo-2-(trifluoromethoxy)phenyl)propionimidamide (15.395 g, 47.011 mmol, Intermediate 162, Step a) and NaHCO$_3$ (5.972 g, 71.09 mmol) in EtOH (220 mL). The resulting mixture was heated to 70° C. under a reflux condenser stirred for 19 hours under nitrogen. After this time, the mixture was allowed to cool to rt and then concentrated. The concentrate was diluted with EtOAc and water, and the aqueous layer was acidified with 1M HCl to pH ~1. The mixture was shaken, the layers were separated, and the organic layer was discarded. The pH of the aqueous layer was adjusted to pH 13-14, and extracted with EtOAc. The organic layer was dried with anhydrous MgSO$_4$, filtered, and then concentrated to afford the title compound as an orange oil, which was used in the next step without further purification.

Intermediate 162, Step c

Ethyl 1-(4-bromo-2-(trifluoromethoxy)phenyl)-2-ethyl-1H-imidazole-4-carboxylate

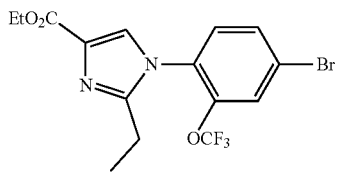 [SMILES: CCOC(=O)c1cn(-c2ccc(Br)cc2OC(F)(F)F)c(CC)n1]

1,8-Diazabicyclo[5.4.0]undec-7-ene (1.6 mL, 10.7 mmol) was added to a solution of ethyl 1-(4-bromo-2-(trifluoromethoxy)phenyl)-2-ethyl-4,5-dihydro-1H-imidazole-4-carboxylate (1.089 g, 2.395 mmol, Intermediate 162, Step b), CCl$_4$ (8 mL, 83 mmol), pyridine (8 mL), and MeCN (16 mL). The reaction was stirred at rt overnight. After this time, the solution was diluted with EtOAc, then washed with 1 N HCl and brine. The organic layer was dried with anhydrous MgSO$_4$, filtered, and then concentrated to afford the title compound as an orange solid, which was used in the next step without further purification.

Intermediate 162, Step d

Ethyl 1-(4-bromo-2-(trifluoromethoxy)phenyl)-5-cyano-2-ethyl-1H-imidazole-4-carboxylate

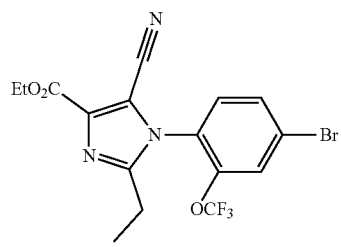 [SMILES: CCOC(=O)c1nc(CC)n(-c2ccc(Br)cc2OC(F)(F)F)c1C#N]

A solution of TMPMgCl.LiCl (7.5 mL, 1.0 M in THF/toluene, 7.5 mmol) was added drop-wise to a solution of ethyl 1-(4-bromo-2-(trifluoromethoxy)phenyl)-2-ethyl-1H-imidazole-4-carboxylate (2.014 g, 4.945 mmol, Intermediate 162, Step c) in THF (16 mL) cooled in an ice bath under a nitrogen atmosphere. The resulting solution was stirred for 4 hours, then p-Toluenesulfonyl cyanide (1.157 g, 6.386 mmol) was added and the mixture was allowed to warm to rt and stir overnight. The reaction was diluted with saturated aqueous ammonium chloride and EtOAc. The layers were separated and the organic layer was dried over anhydrous magnesium sulfate, filtered, and concentrated. The residue was purified by silica gel chromatography (20→50% EtOAc/hexanes) to provide the title compound.

Intermediate 163

Ethyl 1-(4-bromo-2-fluorophenyl)-5-cyano-2-ethyl-1H-imidazole-4-carboxylate

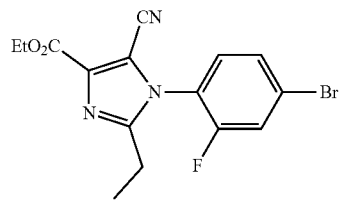 [SMILES: CCOC(=O)c1nc(CC)n(-c2ccc(Br)cc2F)c1C#N]

The title compound was prepared as described for the synthesis of Intermediate 162, Step d, using ethyl 1-(4-bromo-2-fluorophenyl)-2-ethyl-1H-imidazole-4-carboxylate (Intermediate 151) in place of ethyl 1-(4-bromo-2-(trifluoromethoxy)phenyl)-2-ethyl-1H-imidazole-4-carboxylate.

Intermediate 164

Ethyl 5-cyano-2-ethyl-1-(4-(3,3,3-trifluoro-2,2-dimethylpropyl)-2-(trifluoromethoxy)phenyl)-1H-imidazole-4-carboxylate

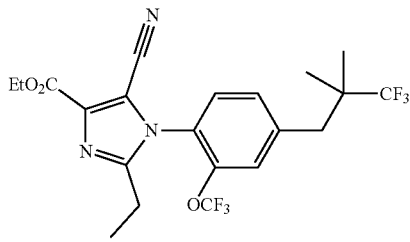 [SMILES: CCc1nc(C(=O)O)c(C#N)n1-c1ccc(CC(C)(C)C(F)(F)F)cc1OC(F)(F)F]

Ethyl 1-(4-bromo-2-(trifluoromethoxy)phenyl)-5-cyano-2-ethyl-1H-imidazole-4-carboxylate (544 mg, 1.26 mmol, Intermediate 162, Step d) and Pd(t-Bu₃P)₂ (70.2 mg, 0.137 mmol) were combined in a vessel, and the vessel was evacuated and backfilled with nitrogen three times. A stock suspension of (3,3,3-trifluoro-2,2-dimethylpropyl)zinc(II) iodide (3.4 mL, 0.73 M, 2.5 mmol), which was prepared by reacting equimolar amounts of 1,1,1-trifluoro-3-iodo-2,2-dimethylpropane Intermediate 59) and Rieke® zinc (5 g/100 mL in THF), was then added, and the resulting mixture were stirred at 65° C. for 3 hours. After this time, the mixture was allowed to cool to rt, and then it was diluted with EtOAc and water. The layers were mixed and then separated, and the aqueous layer was extracted with EtOAc. The combined organic layers were dried with anhydrous sodium sulfate, filtered, and then concentrated. The residue was purified by silica gel chromatography (0→40% EtOAc/hexanes) and then preparative HPLC (XBridge C18, 5→99% MeCN/water, 20 mM NH₄OH) to afford the title compound.

Intermediate 165

5-Cyano-2-ethyl-1-(4-(3,3,3-trifluoro-2,2-dimethylpropyl)-2-(trifluoromethoxy)phenyl)-1H-imidazole-4-carboxylic acid

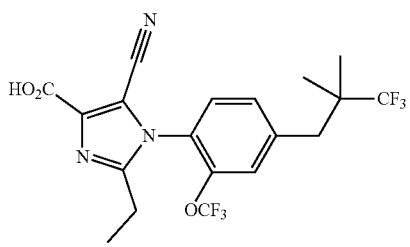

Aqueous NaOH (1.1 mL, 1.0 M, 1.1 mmol) was added to a solution of ethyl 5-cyano-2-ethyl-1-(4-(3,3,3-trifluoro-2,2-dimethylpropyl)-2-(trifluoromethoxy)phenyl)-1H-imidazole-4-carboxylate (174.6 mg, 0.366 mmol, Intermediate 164) in 1,4-dioxane (2 mL) and the mixture was stirred at 60° C. overnight. After this time, 1 N HCl was added to adjust the mixture to pH 2. Dichloromethane was added, the layers were separated, and the aqueous layer was extracted with DCM. The combined organic layers were dried with anhydrous sodium sulfate, filtered, and concentrated to provide the title compound as an off-white solid, which was used in the next step without further purification.

Intermediate 166

Ethyl 5-cyano-2-ethyl-1-(2-(trifluoromethoxy)-4-(3,3,3-trifluoropropyl)phenyl)-1H-imidazole-4-carboxylate

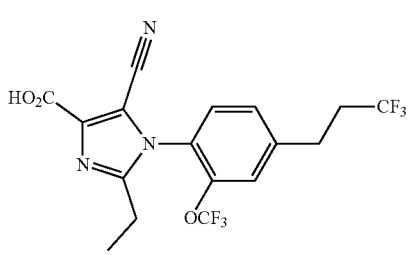 [SMILES: CCc1nc(C(=O)O)c(C#N)n1-c1ccc(CCC(F)(F)F)cc1OC(F)(F)F]

Ethyl 1-(4-bromo-2-(trifluoromethoxy)phenyl)-5-cyano-2-ethyl-1H-imidazole-4-carboxylate (504.8 mg, 1.168 mmol, Intermediate 162, Step d), potassium carbonate (355 mg, 2.57 mmol), and Pd(dppf)Cl₂·CH₂Cl₂ were combined in a vessel, and the vessel was evacuated and backfilled with nitrogen three times. A stock solution of 9-(3,3,3-trifluoropropyl)-9-borabicyclo[3.3.1]nonane (4 mL, 0.5 M in THF, 2 mmol, Intermediate 65) and DMF (3 mL) were then added, and the resulting mixture were stirred at 65° C. overnight. After this time, the mixture was allowed to cool to rt, and then it was diluted with EtOAc and water. The layers were mixed and then separated, and the aqueous layer was extracted with EtOAc. The combined organic layers were dried with anhydrous sodium sulfate, filtered, and then concentrated to afford a brown oil. The residue was purified by silica gel chromatography (0→40% EtOAc/hexanes) to provide the title compound.

Intermediate 167

5-Cyano-2-ethyl-1-(2-(trifluoromethoxy)-4-(3,3,3-trifluoropropyl)phenyl)-1H-imidazole-4-carboxylic acid

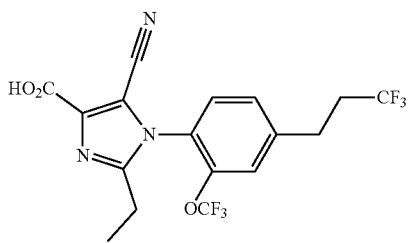 [SMILES: CCc1nc(C(=O)O)c(C#N)n1-c1ccc(CCC(F)(F)F)cc1OC(F)(F)F]

The title compound was prepared as described for the synthesis of Intermediate 165, using ethyl 5-cyano-2-ethyl-1-(2-(trifluoromethoxy)-4-(3,3,3-trifluoropropyl)phenyl)-1H-imidazole-4-carboxylate (Intermediate 166) in place of ethyl 5-cyano-2-ethyl-1-(4-(3,3,3-trifluoro-2,2-dimethylpropyl)-2-(trifluoromethoxy)phenyl)-1H-imidazole-4-carboxylate.

Intermediate 168

N-(6-Chloro-4-methoxypyridin-3-yl)propionimidamide

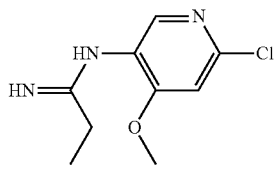

Trimethylaluminum (7.6 mL, 2.0 M in toluene, 15 mmol) was added slowly to a 0° C. mixture of 6-chloro-4-methoxypyridin-3-amine (2.4 g, 15 mmol) and propionitrile (1.16 mL, 16.1 mmol). The flask was removed from the ice bath, allowed to warm to rt over 5 min, then was stirred at 105° C. for 17 hours. The mixture was cooled to 0° C. and THF (15 mL) was added very slowly followed by water (1 mL), 15 wt % aqueous NaOH (1 mL) and water (3 mL), stirring for 10 min after each addition. The resulting mixture was allowed to warm to rt over 30 min with stirring, then Celite® was added, and the mixture stirred an additional 30 min. The mixture was then filtered through Celite® with THF and concentrated. The residue was diluted with water and the pH adjusted to pH 1-2 by the addition of 1 N aqueous HCl. The solution was then washed twice with EtOAc and the aqueous layer pH adjusted to pH 10-11 by the addition of 1 N aqueous NaOH. The aqueous solution was then extracted four times with DCM, the organic layers combined, dried with anhydrous $Na_2SO_4$, filtered and concentrated to provide the title compound, which was used without further purification.

Intermediate 169

Ethyl 1-(6-chloro-4-methoxypyridin-3-yl)-2-ethyl-4,5-dihydro-1H-imidazole-4-carboxylate

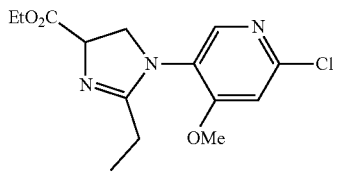

The title compound was prepared as described in Intermediate 68, using N-(6-chloro-4-methoxypyridin-3-yl)propionimidamide (Intermediate 168) in place of N-(4-bromo-2-methoxyphenyl)propionimidamide.

Intermediate 170

Ethyl 1-(6-chloro-4-methoxypyridin-3-yl)-2-ethyl-1H-imidazole-4-carboxylate

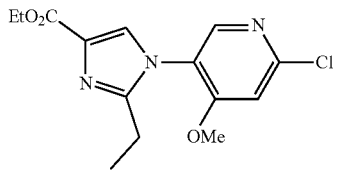 [SMILES: CCOC(=O)c1cn(-c2cnc(Cl)cc2OC)c(CC)n1]

Ethyl 1-(6-bromo-4-methoxypyridin-3-yl)-2-ethyl-4,5-dihydro-1H-imidazole-4-carboxylate (1.0 g, 3.2 mmol, Intermediate 169) was sequentially diluted with MeCN (9.8 mL), pyridine (4.9 mL, 61 mmol), $CCl_4$ (0.90 mL, 9.6 mmol) and 1,8-diazabicyclo[5.4.0]undec-7-ene (1.9 mL, 13 mmol), and the resulting solution was stirred at rt for 3.5 hours. The reaction mixture was concentrated and purified by silica gel chromatography (0-7.5% 2 M methanolic $NH_3$/DCM). The fractions enriched in the title compound were concentrated, dissolved in DCM, and washed with a saturated aqueous $Na_2CO_3$ solution. The aqueous layer was further extracted with DCM, then the organic layers were combined, dried with anhydrous $Na_2SO_4$, filtered and concentrated to provide the title compound as a light-yellow amorphous solid.

Intermediate 171

Ethyl 2-ethyl-1-(4-methoxy-6-(3,3,3-trifluoropropyl)pyridin-3-yl)-1H-imidazole-4-carboxylate

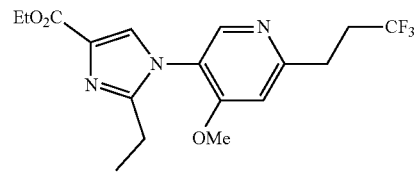

Ethyl 1-(6-chloro-4-methoxypyridin-3-yl)-2-ethyl-1H-imidazole-4-carboxylate (415 mg, 1.34 mmol, Intermediate 170), $K_2CO_3$ (370 mg, 2.68 mmol), and Pd(dppf)$Cl_2$.DCM (55 mg, 67 mmol) were combined in a vessel, and the vessel was evacuated and backfilled with nitrogen three times. A THF solution of 9-(3,3,3-trifluoropropyl)-9-borabicyclo[3.3.1]nonane (5.4 mL, 0.5 M, 2.7 mmol, Intermediate 65) and DMF (3.3 mL) were then added, and the resulting mixture was stirred at 65° C. for 3 h. An additional aliquot of Pd(dppf)$Cl_2$.DCM (55 mg, 67 mmol) was added and the mixture stirred at 65° C. for 2 hours. An additional aliquot of 9-(3,3,3-trifluoropropyl)-9-borabicyclo[3.3.1]nonane (2.7 mL, 0.5 M in THF, 0.8 mmol) was added and the mixture stirred at 65° C. for 3 days. After this time, the mixture was allowed to cool to rt and then it was partitioned between EtOAc and water. The layers were separated, and the aqueous layer was further extracted with EtOAc. The organic layers were combined, washed with water and brine, dried with anhydrous $Na_2SO_4$, filtered and concentrated. The residue was purified by silica gel chromatography (0→5% MeOH/DCM) to afford the title compound as a yellow oil.

Intermediate 172

2-Ethyl-1-(4-methoxy-6-(3,3,3-trifluoropropyl)pyridin-3-yl)-1H-imidazole-4-carboxylic acid

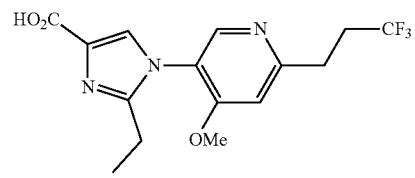 [SMILES: CCc1nc(C(=O)O)cn1-c1cnc(CCC(F)(F)F)cc1OC]

Aqueous NaOH (1.13 mL, 1.0 N, 1.13 mmol) was added to a solution of ethyl 2-ethyl-1-(4-methoxy-6-(3,3,3-trifluoropropyl)pyridin-3-yl)-1H-imidazole-4-carboxylate (80 mg, 0.22 mmol, Intermediate 171) in 1,4-dioxane (1.13 mL), and the mixture was stirred at 50° C. for 3 h. After this time, the resulting solution was allowed to cool to rt, water was added and the pH was adjusted to pH 4.5 with 1 N aqueous HCl. The aqueous was then extracted four times with DCM, the organic layers combined, dried with anhydrous Na₂SO₄, filtered and concentrated to provide the title compound as a cream-colored solid.

Intermediate 173

Ethyl 5-cyano-2-ethyl-1-(4-methoxy-6-(3,3,3-trifluoropropyl)pyridin-3-yl)-1H-imidazole-4-carboxylate

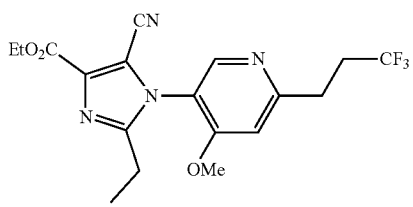 [SMILES: CCc1nc(C(=O)O)c(C#N)n1-c1cnc(CCC(F)(F)F)cc1OC]

The title compound was prepared as described for Intermediate 70, using ethyl 2-ethyl-1-(4-methoxy-6-(3,3,3-trifluoropropyl)pyridin-3-yl)-1H-imidazole-4-carboxylate (Intermediate 171) in place of ethyl 1-(4-bromo-2-methoxyphenyl)-2-ethyl-1H-imidazole-4-carboxylate.

Intermediate 174

5-Cyano-2-ethyl-1-(4-methoxy-6-(3,3,3-trifluoropropyl)pyridin-3-yl)-1H-imidazole-4-carboxylic acid

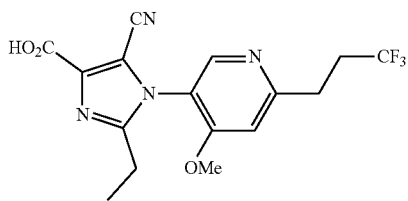

The title compound was prepared as described for Intermediate 172, using ethyl 5-cyano-2-ethyl-1-(4-methoxy-6-(3,3,3-trifluoropropyl)pyridin-3-yl)-1H-imidazole-4-carboxylate (Intermediate 173) in place of ethyl 2-ethyl-1-(4-methoxy-6-(3,3,3-trifluoropropyl)pyridin-3-yl)-1H-imidazole-4-carboxylate.

Intermediate 175

Ethyl 1-(5-bromo-3-methoxypyridin-2-yl)-5-cyano-2-ethyl-1H-imidazole-4-carboxylate

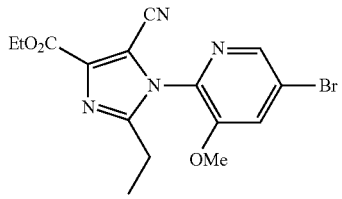

The title compound was prepared as described for Intermediate 70, using ethyl 1-(5-bromo-3-methoxypyridin-2-yl)-2-ethyl-1H-imidazole-4-carboxylate (Intermediate 79) in place of ethyl 1-(4-bromo-2-methoxyphenyl)-2-ethyl-1H-imidazole-4-carboxylate.

Intermediate 176

Ethyl 5-cyano-2-ethyl-1-(3-methoxy-5-(3,3,3-trifluoropropyl)pyridin-2-yl)-1H-imidazole-4-carboxylate

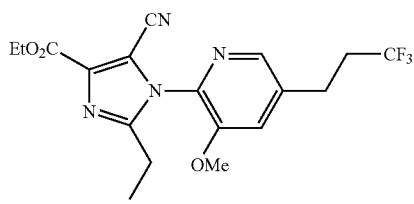 [SMILES: CCc1nc(C(=O)O)c(C#N)n1-c1ncc(CCC(F)(F)F)cc1OC]

The title compound was prepared as described for Intermediate 171, using ethyl 1-(5-bromo-3-methoxypyridin-2-yl)-5-cyano-2-ethyl-1H-imidazole-4-carboxylate (Intermediate 175) in place of ethyl 1-(6-chloro-4-methoxypyridin-3-yl)-2-ethyl-1H-imidazole-4-carboxylate.

Intermediate 177

5-Cyano-2-ethyl-1-(3-methoxy-5-(3,3,3-trifluoropropyl)pyridin-2-yl)-1H-imidazole-4-carboxylic acid

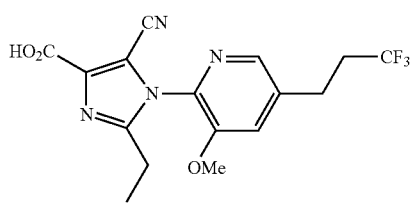

The title compound was prepared as described for Intermediate 172, using ethyl 5-cyano-2-ethyl-1-(3-methoxy-5-(3,3,3-trifluoropropyl)pyridin-2-yl)-1H-imidazole-4-carboxylate (Intermediate 176) in place of ethyl 2-ethyl-1-(4-methoxy-6-(3,3,3-trifluoropropyl)pyridin-3-yl)-1H-imidazole-4-carboxylate.

Intermediate 178

Ethyl 5-cyano-2-ethyl-1-(3-methoxy-5-(3,3,3-trifluoro-2,2-dimethylpropyl)pyridin-2-yl)-1H-imidazole-4-carboxylate

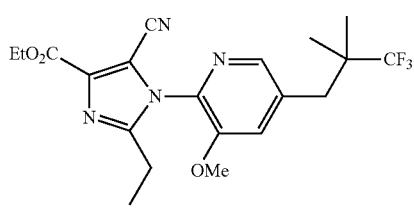

1,1,1-Trifluoro-3-iodo-2,2-dimethylpropane (0.22 mL, 1.48 mmol, Intermediate 59) was added to a suspension of Rieke® zinc (1.8 mL, 0.05 g/mL, 1.3 mmol), and the resulting suspension was stirred at 60° C. for 1 h. Ethyl 1-(5-bromo-3-methoxypyridin-2-yl)-5-cyano-2-ethyl-1H-imidazole-4-carboxylate (0.26 g, 0.67 mmol, Intermediate 175) and Pd(t-Bu₃P)₂ (34 mg, 0.070 mmol) were combined in a separate vessel, and the vessel was evacuated and backfilled with nitrogen three times. The organozinc suspension was then added to the vessel containing the aryl bromide by cannula transfer, and the resulting suspension was stirred at 65° C. for 6 hours, before it was allowed to cool to rt. The mixture was then diluted with water and the mixture stirred at rt for 20 min followed by filtration through a pad of Celite®. The pad was washed with EtOAc and then combined with brine and the layers were separated. The aqueous layer was extracted with EtOAc, and then the combined organic layers were combined, dried with anhydrous Na₂SO₄, filtered, and concentrated. The residue was purified by silica gel chromatography (0→15% MeOH/DCM) to provide the title compound.

Intermediate 179

5-Cyano-2-ethyl-1-(3-methoxy-5-(3,3,3-trifluoro-2,2-dimethylpropyl)pyridin-2-yl)-1H-imidazole-4-carboxylic acid

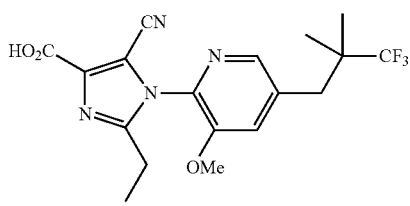

The title compound was prepared as described for Intermediate 172, using ethyl 5-cyano-2-ethyl-1-(3-methoxy-5-(3,3,3-trifluoro-2,2-dimethylpropyl)pyridin-2-yl)-1H-imidazole-4-carboxylate (Intermediate 178) in place of ethyl 2-ethyl-1-(4-methoxy-6-(3,3,3-trifluoropropyl)pyridin-3-yl)-1H-imidazole-4-carboxylate.

Intermediate 180

1-(5-Bromo-3-methoxypyridin-2-yl)-5-cyano-2-ethyl-1H-imidazole-4-carboxylic acid

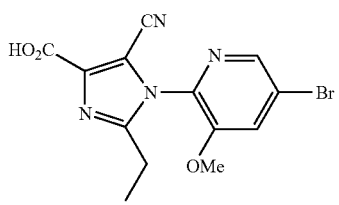

The title compound was prepared as described for Intermediate 172, using ethyl 1-(5-bromo-3-methoxypyridin-2-yl)-5-cyano-2-ethyl-1H-imidazole-4-carboxylate (Intermediate 175) in place of ethyl 2-ethyl-1-(4-methoxy-6-(3,3,3-trifluoropropyl)pyridin-3-yl)-1H-imidazole-4-carboxylate.

Intermediate 181

Ethyl 1-(5-bromo-3-methoxypyridin-2-yl)-5-chloro-2-ethyl-1H-imidazole-4-carboxylate

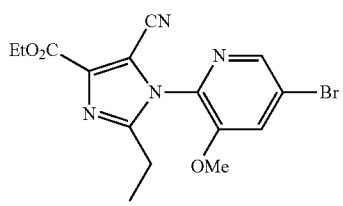 [SMILES: CCc1nc(C(=O)O)c(C#N)n1-c1ncc(Br)cc1OC]

The title compound was prepared as described for Intermediate 83, using ethyl 1-(5-bromo-3-methoxypyridin-2-yl)-2-ethyl-1H-imidazole-4-carboxylate (Intermediate 79) in place of ethyl 1-(5-bromo-3-(difluoromethoxy)pyridin-2-yl)-2-ethyl-1H-imidazole-4-carboxylate.

Intermediate 182

Ethyl 5-chloro-2-ethyl-1-(3-methoxy-5-(3,3,3-trifluoro-2,2-dimethylpropyl)pyridin-2-yl)-1H-imidazole-4-carboxylate

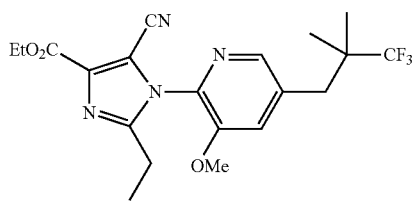

The title compound was prepared as described for Intermediate 178, using ethyl 1-(5-bromo-3-methoxypyridin-2-yl)-5-chloro-2-ethyl-1H-imidazole-4-carboxylate (Intermediate 181) in place of ethyl 1-(5-bromo-3-methoxypyridin-2-yl)-5-cyano-2-ethyl-1H-imidazole-4-carboxylate.

Intermediate 183

5-Chloro-2-ethyl-1-(3-methoxy-5-(3,3,3-trifluoro-2,2-dimethylpropyl)pyridin-2-yl)-1H-imidazole-4-carboxylic acid

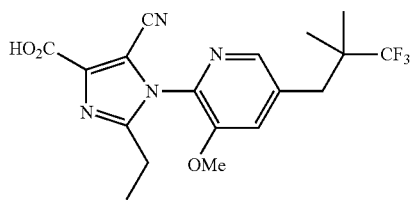 [SMILES: CCc1nc(C(=O)O)c(C#N)n1-c1ncc(CC(C)(C)C(F)(F)F)cc1OC]

The title compound was prepared as described for Intermediate 172, using ethyl 5-chloro-2-ethyl-1-(3-methoxy-5-(3,3,3-trifluoro-2,2-dimethylpropyl)pyridin-2-yl)-1H-imidazole-4-carboxylate (Intermediate 182) in place of ethyl 2-ethyl-1-(4-methoxy-6-(3,3,3-trifluoropropyl)pyridin-3-yl)-1H-imidazole-4-carboxylate.

Intermediate 184

Ethyl 2-ethyl-1-(3-methoxy-5-(3,3,3-trifluoro-2,2-dimethylpropyl)pyridin-2-yl)-5-methyl-1H-imidazole-4-carboxylate

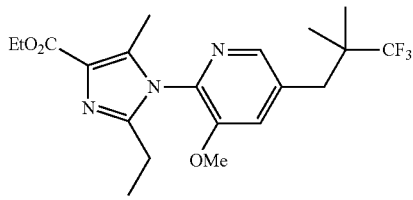 [SMILES: CCc1nc(C(=O)O)c(C)n1-c1ncc(CC(C)(C)C(F)(F)F)cc1OC]

The title compound was prepared as described for Intermediate 89, using ethyl 5-chloro-2-ethyl-1-(3-methoxy-5-(3,3,3-trifluoro-2,2-dimethylpropyl)pyridin-2-yl)-1H-imidazole-4-carboxylate (Intermediate 182) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate.

Intermediate 185

2-Ethyl-1-(3-methoxy-5-(3,3,3-trifluoro-2,2-dimethylpropyl)pyridin-2-yl)-5-methyl-1H-imidazole-4-carboxylic acid

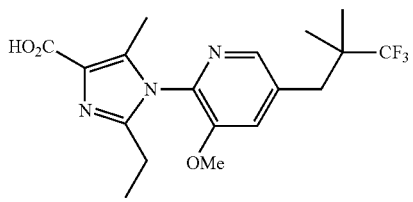

The title compound was prepared as described for Intermediate 172, using ethyl 2-ethyl-1-(3-methoxy-5-(3,3,3-trifluoro-2,2-dimethylpropyl)pyridin-2-yl)-5-methyl-1H-imidazole-4-carboxylate (Intermediate 184) in place of ethyl 2-ethyl-1-(4-methoxy-6-(3,3,3-trifluoropropyl)pyridin-3-yl)-1H-imidazole-4-carboxylate.

Intermediate 186

1-(4-Bromo-2-fluorophenyl)-5-chloro-2-ethyl-N-(((1r,4r)-4-(methylsulfonyl)cyclohexyl)methyl)-1H-imidazole-4-carboxamide

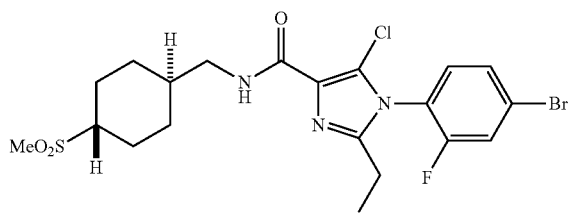 [SMILES: CCc1nc(C(=O)NC[C@H]2CC[C@H](S(C)(=O)=O)CC2)c(Cl)n1-c1ccc(Br)cc1F]

The title compound was prepared as described for the synthesis of Example 2, using ethyl 1-(4-bromo-2-fluorophenyl)-5-chloro-2-ethyl-1H-imidazole-4-carboxylate (Intermediate 152) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate and DCM in place of MeCN as solvent.

Intermediate 187

1-(4-Bromo-2-fluorophenyl)-5-chloro-2-ethyl-N-(((1s,4s)-1-hydroxy-4-(methylsulfonyl)cyclohexyl)methyl)-1H-imidazole-4-carboxamide

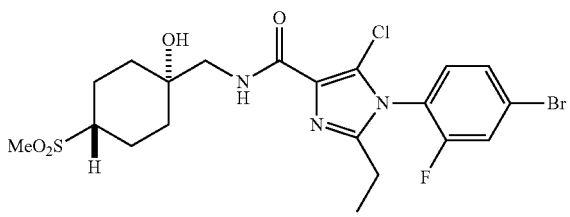 [SMILES: CCc1nc(C(=O)NC[C@]2(O)CC[C@@H](S(C)(=O)=O)CC2)c(Cl)n1-c1ccc(Br)cc1F]

The title compound was prepared as described for the synthesis of Example 2, using ethyl 1-(4-bromo-2-fluorophenyl)-5-chloro-2-ethyl-1H-imidazole-4-carboxylate (Intermediate 152) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate, (1s,4s)-1-(aminomethyl)-4-(methylsulfonyl)cyclohexanol hydrochloride (Intermediate 9) in place of ((1r,4r)-4-(methylsulfonyl)cyclohexyl)methanamine hydrochloride, and DCM in place of MeCN as solvent.

Intermediate 188

5-Chloro-2-ethyl-1-(2-methoxy-4-(((R)-1,1,1-trifluoropropan-2-yl)amino)phenyl)-N-((4-(methylsulfonyl)cyclohexyl)methyl)-1H-imidazole-4-carboxamide

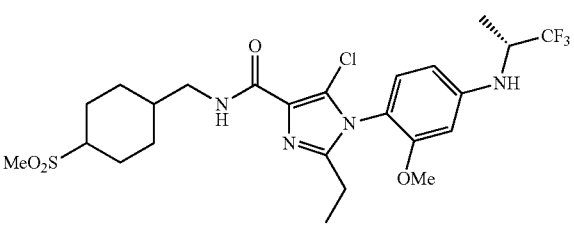 [SMILES: CCc1nc(C(=O)NCC2CCC(S(C)(=O)=O)CC2)c(Cl)n1-c1ccc(N[C@H](C)C(F)(F)F)cc1OC]

The title compound was prepared as described for the synthesis of Example 1, using ethyl 5-chloro-2-ethyl-1-(2-methoxy-4-(((R)-1,1,1-trifluoropropan-2-yl)amino)phenyl)-1H-imidazole-4-carboxylate (Intermediate 123) and (4-(methylsulfonyl)cyclohexyl)methanamine (Intermediate 52) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride.

Intermediate 189

5-Chloro-2-ethyl-1-(2-methoxy-4-(3,3,3-trifluoro-2-methylpropyl)phenyl)-N-((4-(methylsulfonyl)cyclohexyl)methyl)-1H-imidazole-4-carboxamide

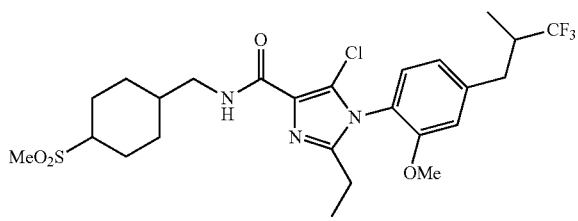 [SMILES: CCc1nc(C(=O)NCC2CCC(S(C)(=O)=O)CC2)c(Cl)n1-c1ccc(CC(C)C(F)(F)F)cc1OC]

The title compound was prepared as described for the synthesis of Example 1, using ethyl 5-chloro-2-ethyl-1-(2-methoxy-4-(3,3,3-trifluoro-2-methylpropyl)phenyl)-1H-imidazole-4-carboxylate (Intermediate 127) and (4-(methylsulfonyl)cyclohexyl)methanamine (Intermediate 52) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methyl sulfonyl)cyclohexanol hydrochloride.

Intermediate 190

2-Ethyl-1-(2-methoxy-4-(3,3,3-trifluoro-2-methylpropyl)phenyl)-5-methyl-N-(((1r,4r)-4-(methylsulfonyl)cyclohexyl)methyl)-1H-imidazole-4-carboxamide

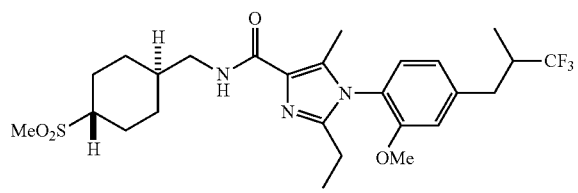 [SMILES: CCc1nc(C(=O)NC[C@H]2CC[C@H](S(C)(=O)=O)CC2)c(C)n1-c1ccc(CC(C)C(F)(F)F)cc1OC]

The title compound was prepared as described for the synthesis of Example 1, using methyl 2-ethyl-1-(2-methoxy-4-(3,3,3-trifluoro-2-methylpropyl)phenyl)-5-methyl-1H-imidazole-4-carboxylate (Intermediate 125) and ((1r,4r)-4-(methylsulfonyl)cyclohexyl)methanamine hydrochloride (Intermediate 13) in place of 5-cyano-2-ethyl-1-(2-methoxy-4-(3,3,3-trifluoro-2-methylpropyl)phenyl)-1H-imidazole-4-carboxylic acid and (1s,4s)-1-(aminomethyl)-4-(methylsulfonyl)cyclohexanol hydrochloride.

Intermediate 191

5-Chloro-1-(3-(difluoromethoxy)-5-(3,3,3-trifluoro-2,2-dimethylpropyl)pyridin-2-yl)-2-ethyl-N-(((1RS,2SR,4SR)-2-hydroxy-4-(methylsulfonyl)cyclohexyl)methyl)-1H-imidazole-4-carboxamide

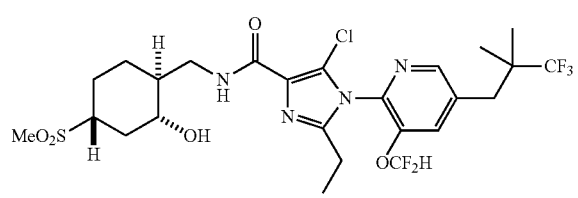

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (Intermediate 85) and (1RS,2SR,5RS)-2-(aminomethyl)-5-(methylsulfonyl)cyclohexan-1-ol hydrochloride (Intermediate 54) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methyl sulfonyl)cyclohexanol hydrochloride.

Intermediate 192

5-Chloro-1-(3-(difluoromethoxy)-5-(3,3,3-trifluoro-2-(trifluoromethyl)propyl)pyridin-2-yl)-2-ethyl-N-(((1RS,2SR,4SR)-2-hydroxy-4-(methylsulfonyl)cyclohexyl)methyl)-1H-imidazole-4-carboxamide

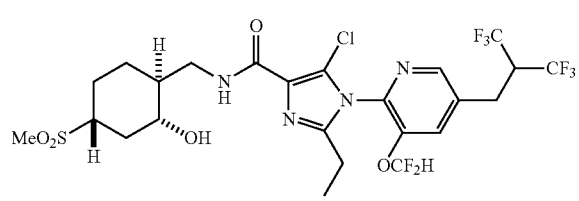

The title compound was prepared as described for the synthesis of Example 1, using 5-chloro-1-(3-(difluoromethoxy)-5-(3,3,3-trifluoro-2-(trifluoromethyl)propyl)pyridin-2-yl)-2-ethyl-1H-imidazole-4-carboxylic acid (Intermediate 122) and (1RS,2SR,5RS)-2-(aminomethyl)-5-(methylsulfonyl)cyclohexan-1-ol hydrochloride (Intermediate 54) in place of 5-cyano-2-ethyl-1-(2-methoxy-4-(3,3,3-trifluoro-2-methylpropyl)phenyl)-1H-imidazole-4-carboxylic acid and (1s,4s)-1-(aminomethyl)-4-(methylsulfonyl)cyclohexanol hydrochloride.

Intermediate 193

Ethyl-3-((4-bromo-2-methoxyphenyl)amino)-2-nitroacrylate

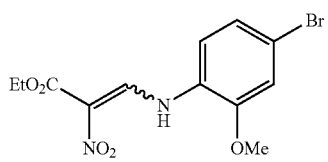 [SMILES: CCOC(=O)C(=CNc1ccc(Br)cc1OC)[N+](=O)[O-]]

4-Bromo-2-methoxyaniline (5.07 g, 25.1 mmol), triethyl orthoformate (5.5 mL, 33 mmol), ethyl nitroacetate (4.08 g, 30.7 mmol) and AcOH (1.0 mL, 18 mmol) were combined and heated at 125° C. under a nitrogen atmosphere for 3 h. The contents were allowed to cool to rt and then cooled to 0° C. in an ice bath. The resulting mixture was filtered, and the solids were rinsed with cold EtOH and dried by aspiration to afford the title compound.

Intermediate 194

Ethyl-2-amino-3-((4-bromo-2-methoxyphenyl)amino)acrylate

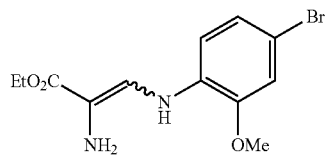 [SMILES: CCOC(=O)C(N)=CNc1ccc(Br)cc1OC]

Zinc metal (12.4 g, 190 mmol) was added in three equal portions over 3 min to a mixture of ethyl-3-((4-bromo-2-methoxyphenyl)amino)-2-nitroacrylate (5.02 g, 14.5 mmol, Intermediate 193), NH$_4$Cl (14 g, 200 mmol), acetone (150 mL), and water (30 mL). The resulting mixture was stirred at rt for 20 min then filtered through a pad of Celite® with EtOAc washing. The filtrate was dried with anhydrous MgSO$_4$, filtered, and concentrated to afford the title compound.

Intermediate 195

Ethyl 1-(4-bromo-2-methoxyphenyl)-2-methyl-1H-imidazole-4-carboxylate

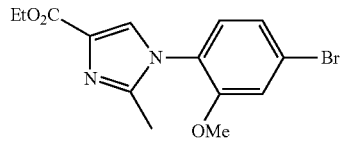

Ethyl-2-amino-3-((4-bromo-2-methoxyphenyl)amino)acrylate (5.2 g, 13.2 mmol, Intermediate 194), triethyl orthoacetate (100 mL, 545.5 mmol) and TsOH (230 mg, 1.33 mmol) were combined and heated to reflux temperature overnight. The reaction mixture was allowed to cool to rt and then concentrated. The crude material was taken up into EtOAc and washed with a saturated aqueous NH$_4$Cl solution. The layers were separated, and the aqueous layer was extracted with EtOAc. The organic layers were combined, dried with anhydrous MgSO$_4$, filtered, and concentrated. The residue was purified by silica gel chromatography (0→100% EtOAc/hexanes) to afford the title compound.

Intermediate 196

Ethyl 1-(2-methoxy-4-(3,3,3-trifluoro-2,2-dimethylpropyl)phenyl)-2-methyl-1H-imidazole-4-carboxylate

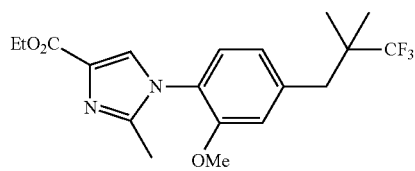 [SMILES: CCOC(=O)c1cn(-c2ccc(CC(C)(C)C(F)(F)F)cc2OC)c(C)n1]

The title compound was prepared as described for the synthesis of Intermediate 100, using ethyl 1-(4-bromo-2-methoxyphenyl)-2-methyl-1H-imidazole-4-carboxylate (Intermediate 195) in place of methyl 1-(4-bromo-2-(methoxy-d$_3$)phenyl)-2-ethyl-5-fluoro-1H-imidazole-4-carboxylate.

Intermediate 197

Ethyl 3,3-diethoxy-2-nitropropanoate

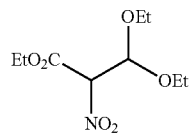

Ethyl nitroacetate (10.0 g, 75.3 mmol), triethyl orthoformate (12.6 mL, 75.8 mmol) and toluene (50 mL) were combined, and the mixture was heated at reflux temperature for 23 h in a vessel equipped with a with a Dean-Stark trap. After this time, the mixture was allowed to cool to rt then concentrated to afford the title compound.

Intermediate 198

Ethyl-3-((4-bromo-2-(difluoromethoxy)phenyl)amino)-2-nitroacrylate

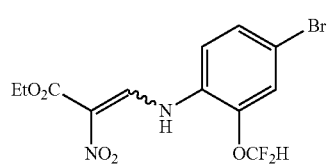

Ethyl 3,3-diethoxy-2-nitropropanoate (3.53 g, 18.7 mmol, Intermediate 197), 4-bromo-2-(difluoromethoxy)aniline (5.03 g, 21.1 mmol) and EtOH (50 mL) were combined under a nitrogen atmosphere and stirred at rt for 3 days. The reaction solution was then concentrated to afford the title compound.

Intermediate 199

Ethyl 1-(4-bromo-2-(difluoromethoxy)phenyl)-2-methyl-1H-imidazole-4-carboxylate

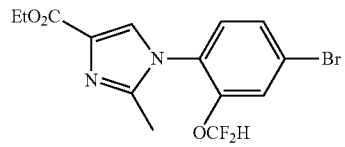

Ethyl-3-((4-bromo-2-(difluoromethoxy)phenyl)amino)-2-nitroacrylate (7.11 g, 18.7 mmol, Intermediate 198), AcOH (75 mL), triethyl orthoacetate (18 mL, 98.2 mmol) and iron (10.58 g, 189.4 mmol) were combined and heated to 100° C. under a nitrogen atmosphere. The mixture was allowed to cool and then filtered through Celite® with EtOAc rinsing. The filtrate was washed with a saturated aqueous NaHCO₃ solution and then with brine. The organic layer was then dried with anhydrous MgSO₄, filtered, and concentrated. The residue was purified by silica gel chromatography (0→100% EtOAc/hexanes) to afford the title compound.

Intermediate 200

Ethyl 1-(2-(difluoromethoxy)-4-(3,3,3-trifluoro-2,2-dimethylpropyl)phenyl)-2-methyl-1H-imidazole-4-carboxylate

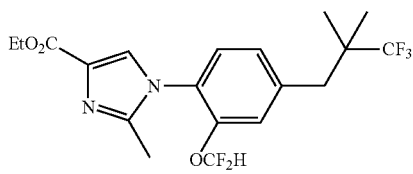

The title compound was prepared as described for the synthesis of Intermediate 100, using ethyl 1-(4-bromo-2-(difluoromethoxy)phenyl)-2-methyl-1H-imidazole-4-carboxylate (Intermediate 199) in place of methyl 1-(4-bromo-2-(methoxy-d₃)phenyl)-2-ethyl-5-fluoro-1H-imidazole-4-carboxylate.

Intermediate 201

Ethyl-3-((5-bromo-3-(difluoromethoxy)pyridin-2-yl)amino)-2-nitroacrylate

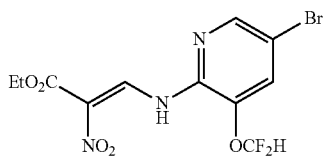

The title compound was prepared as described for the synthesis of Intermediate 198, using 5-bromo-3-(difluoromethoxy)pyridin-2-amine in place of 4-bromo-2-(difluoromethoxy)aniline.

Intermediate 202

Ethyl 1-(5-bromo-3-(difluoromethoxy)pyridin-2-yl)-2-methyl-1H-imidazole-4-carboxylate

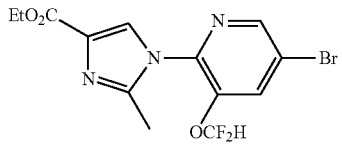

The title compound was prepared as described for the synthesis of Intermediate 199, using ethyl-3-((5-bromo-3-(difluoromethoxy)pyridin-2-yl)amino)-2-nitroacrylate (Intermediate 201) in place of ethyl-3-((4-bromo-2-(difluoromethoxy)phenyl)amino)-2-nitroacrylate.

Intermediate 203

Ethyl 1-(5-bromo-3-(difluoromethoxy)pyridin-2-yl)-5-chloro-2-methyl-1H-imidazole-4-carboxylate

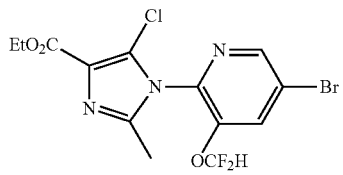

The title compound was prepared as described for the synthesis of Intermediate 158, using ethyl 1-(5-bromo-3-(difluoromethoxy)pyridin-2-yl)-2-methyl-1H-imidazole-4-carboxylate (Intermediate 202) in place of 1-(4-bromo-3-fluorophenyl)-2-ethyl-1H-imidazole-4-carboxylate.

Intermediate 204

Ethyl 5-chloro-1-(3-(difluoromethoxy)-5-(3,3,3-trifluoro-2,2-dimethylpropyl)pyridin-2-yl)-2-methyl-1H-imidazole-4-carboxylate

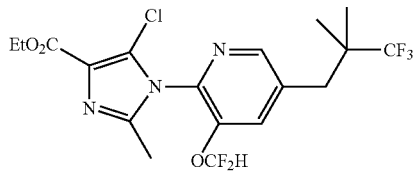

The title compound was prepared as described for the synthesis of Intermediate 100, using ethyl 1-(5-bromo-3-(difluoromethoxy)pyridin-2-yl)-5-chloro-2-methyl-1H-imidazole-4-carboxylate (Intermediate 203) in place of methyl 1-(4-bromo-2-(methoxy-d₃)phenyl)-2-ethyl-5-fluoro-1H-imidazole-4-carboxylate.

Example 1, Step a

5-Cyano-2-ethyl-1-(2-methoxy-4-(3,3,3-trifluoro-2-methylpropyl)phenyl)-1H-imidazole-4-carboxylic acid

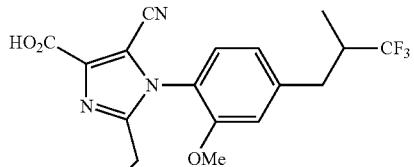

Aqueous NaOH (0.48 mL, 1.0 N, 0.48 mmol) was added to a solution of the ethyl 5-cyano-2-ethyl-1-(2-methoxy-4-(3,3,3-trifluoro-2-methylpropyl)phenyl)-1H-imidazole-4-carboxylate (50 mg, 0.12 mmol, Intermediate 71) in 1,4-dioxane (0.48 mL), and the mixture was stirred at 45° C. for 2 h. After this time, the resulting solution was allowed to cool, and the pH was adjusted to pH 4 with 1 N aqueous HCl, at which point a precipitate formed. The solids were collected by filtration, washed with water, and then dried by aspiration to afford the title compound as a colorless solid.

Example 1, Step b

5-Cyano-2-ethyl-N-(((1s,4s)-1-hydroxy-4-(methylsulfonyl)cyclohexyl)methyl)-1-(2-methoxy-4-(3,3,3-trifluoro-2-methylpropyl)phenyl)-1H-imidazole-4-carboxamide

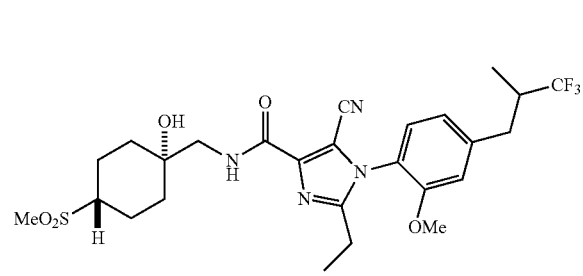 [SMILES: CCc1nc(C(=O)NC[C@]2(O)CC[C@@H](S(C)(=O)=O)CC2)c(C#N)n1-c1ccc(CC(C)C(F)(F)F)cc1OC]

HATU (28 mg, 0.073 mmol) was added to a suspension of 5-cyano-2-ethyl-1-(2-methoxy-4-(3,3,3-trifluoro-2-methylpropyl)phenyl)-1H-imidazole-4-carboxylic acid (28 mg, 0.073 mmol, Example 1, Step a), (1s,4s)-1-(aminomethyl)-4-(methyl sulfonyl)cyclohexanol hydrochloride (18 mg, 0.073 mmol, Intermediate 9), and DIPEA (0.026 mL, 0.15 mmol) in DMF (0.3 mL), and the mixture was stirred at 50° C. for 1 h. The resulting solution was diluted with MeOH, filtered, and then purified by preparative HPLC (XBridge C18, 10→100% of MeCN/water, 0.05% TFA) to afford the title compound. $^1$H NMR (500 MHz, CDCl$_3$) δ 7.66 (t, J=6.4 Hz, 1H), 7.21-7.17 (m, 1H), 6.96-6.92 (m, 1H), 6.90 (s, 1H), 3.85 (s, 3H), 3.54-3.45 (m, 2H), 3.17 (dd, J=13.3, 3.6 Hz, 1H), 3.09 (br s, OH), 2.87-2.78 (m, 1H), 2.84 (s, 3H), 2.61-2.46 (m, 4H), 2.16-2.09 (m, 2H), 2.03-1.92 (m, 4H), 1.45 (td, J=13.7, 3.7 Hz, 2H), 1.21 (t, J=7.5 Hz, 3H), 1.10 (d, J=6.5 Hz, 3H). MS (ESI) m/z: [M+H]$^+$ Found 571.2.

Example 2, Step a

5-Chloro-1-(3-(difluoromethoxy)-5-(3,3,3-trifluoro-2,2-dimethylpropyl)pyridin-2-yl)-2-ethyl-1H-imidazole-4-carboxylic acid

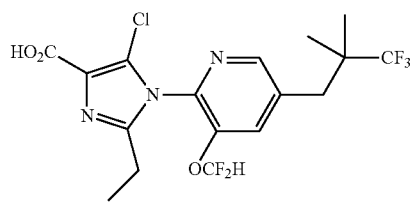

The title compound was prepared as described for the synthesis of Example 1, Step a, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (2.84 g, 6.05 mmol, Intermediate 85) instead of ethyl 5-cyano-2-ethyl-1-(2-methoxy-4-(3,3,3-trifluoro-2-methylpropyl)phenyl)-1H-imidazole-4-carboxylate.

Example 2, Step b

5-Chloro-1-(3-(difluoromethoxy)-5-(3,3,3-trifluoro-2,2-dimethylpropyl)pyridin-2-yl)-2-ethyl-N-((4-(methylsulfonyl)cyclohexyl)methyl)-1H-imidazole-4-carboxamide

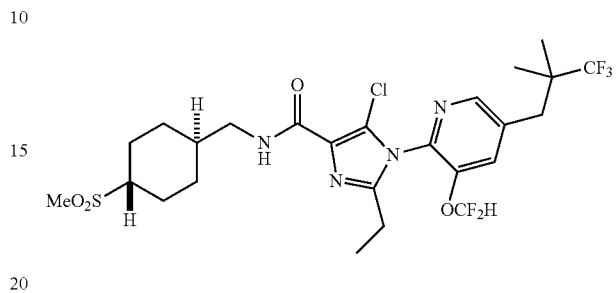

A mixture of 5-chloro-1-(3-(difluoromethoxy)-5-(3,3,3-trifluoro-2,2-dimethylpropyl)pyridin-2-yl)-2-ethyl-1H-imidazole-4-carboxylic acid (300 mg, 0.679 mmol, Example 2, Step a), EDCI (130 mg, 0.679 mmol), and HOBt (92 mg, 0.68 mmol) were dissolved in MeCN (1.5 mL) before DIPEA (0.24 mL, 1.4 mmol) and then ((1r,4r)-4-(methylsulfonyl)cyclohexyl)methanamine hydrochloride (155 mg, 0.679 mmol, Intermediate 13) were added, and the mixture was stirred for 3.5 h at 50° C. After this time, the reaction mixture was allowed to cool, diluted with water, and then the MeCN was removed by rotary evaporation. The resulting mixture was extracted with EtOAc. The layers were separated, and the organic layer was washed with brine, dried with anhydrous MgSO$_4$, filtered, and then concentrated to afford a yellow foam. This residue was combined with a second batch prepared in a similar way and then purified by silica gel chromatography (70→100% EtOAc/hexanes) to afford the title compound as a colorless foam. $^1$H NMR (500 MHz, CDCl$_3$) δ 8.33 (d, J=2.0 Hz, 1H), 7.65 (s, 1H), 7.29-7.23 (m, 1H), 6.48 (dd, J=71.7, 70.3 Hz, 1H), 3.37-3.27 (m, 2H), 2.93 (s, 2H), 2.86-2.79 (m, 1H), 2.82 (s, 3H), 2.57-2.42 (m, 2H), 2.31-2.24 (m, 2H), 2.11-2.04 (m, 2H), 1.73-1.64 (m, 1H), 1.64-1.54 (m, 2H), 1.23-1.08 (m, 11H). MS (ESI) m/z: [M+H]$^+$ Found 615.1.

Example 3

5-Chloro-2-ethyl-1-(2-methoxy-4-(((R)-1,1,1-trifluoropropan-2-yl)amino)phenyl)-N-(((1r,4R)-4-(methylsulfonyl)cyclohexyl)methyl)-1H-imidazole-4-carboxamide

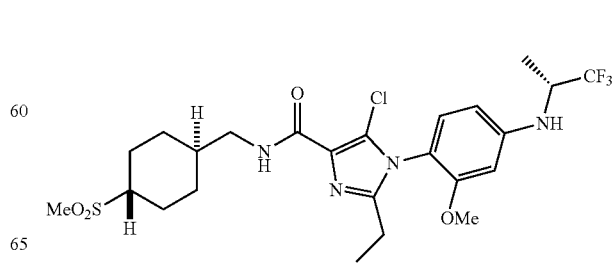

Example 4

5-Chloro-2-ethyl-1-(2-methoxy-4-(((R)-1,1,1-trifluoropropan-2-yl)amino)phenyl)-N-(((1s,4S)-4-(methylsulfonyl)cyclohexyl)methyl)-1H-imidazole-4-carboxamide

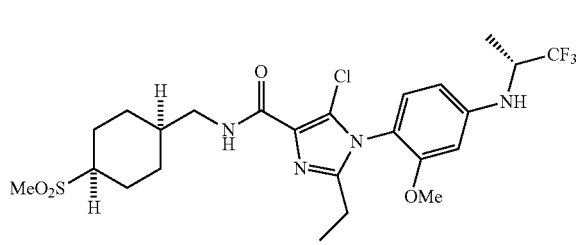 [SMILES: CCc1nc(C(=O)NC[C@H]2CC[C@@H](S(C)(=O)=O)CC2)c(Cl)n1-c1ccc(N[C@H](C)C(F)(F)F)cc1OC]

Intermediate 188 was purified by preparative HPLC (RP YMC Triart C18, 9:11 MeCN/water, 0.5% NH₄Ac) to give a pair of diastereomers. The first-eluting isomer was Example 3, and the second-eluting isomer was Example 4. Example 3: ¹H NMR (400 MHz, DMSO-d₆) δ 7.86 (t, J=6.3 Hz, 1H), 6.98 (d, J=8.5 Hz, 1H), 6.51 (t, J=2.1 Hz, 1H), 6.44 (d, J=8.9 Hz, 1H), 6.37 (dd, J=8.6, 2.2 Hz, 1H), 4.51-4.40 (m, 1H), 3.64 (s, 3H), 3.04 (t, J=6.5 Hz, 2H), 2.94 (tt, J=12.3, 3.5 Hz, 1H), 2.83 (s, 3H), 2.32 (q, J=7.5 Hz, 2H), 2.09-1.99 (m, 2H), 1.83-1.73 (m, 2H), 1.54-1.41 (m, 1H), 1.37-1.23 (m, 2H), 1.27 (d, J=6.8 Hz, 3H), 1.00-0.89 (m, 2H), 0.99 (td, J=7.5, 1.6 Hz, 3H). MS (ESI) m/z: [M+H]⁺ Found 565.2. Example 4: ¹H NMR (400 MHz, CDCl₃, mixture of rotamers) δ 7.23 (t, J=6.6 Hz, 1H), 6.98-6.93 (m, 1H), 6.35-6.30 (m, 1H), 6.30-6.28 (m, 1H), 4.12-4.02 (m, 1H), 3.91 (d, J=8.9 Hz, 1H), 3.74 (s, 3H of one rotamer), 3.73 (s, 3H of one rotamer), 3.44 (t, J=7.1 Hz, 2H), 2.92-2.82 (m, 1H), 2.84 (s, 3H), 2.48-2.39 (m, 2H), 2.08-1.99 (m, 3H), 1.99-1.86 (m, 4H), 1.67-1.59 (m, 2H), 1.47 (d, J=6.7 Hz, 3H), 1.15 (t, J=7.5 Hz, 3H). MS (ESI) m/z: [M+H]⁺ Found 565.2.

Example 6

5-Chloro-2-ethyl-1-(((1S*)-2-methoxy-4-(3,3,3-trifluoro-2-methylpropyl)phenyl)-N-(((1r,4S)-4-(methylsulfonyl)cyclohexyl)methyl)-1H-imidazole-4-carboxamide

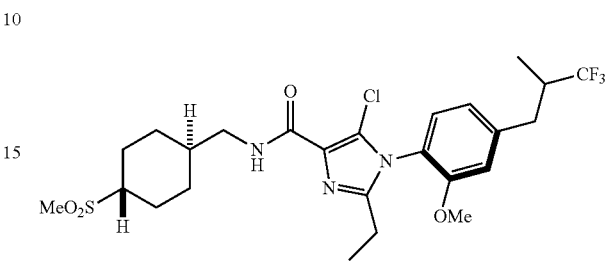

Intermediate 189 was purified by SFC using a chiral stationary phase (Chiralpak IC, 60% CO₂, 40% EtOH) to give a pair of atropisomers. The first-eluting isomer was Example 5, and the second-eluting isomer was Example 6. The isomers derived from the cis-cyclohexane diastereomer were not isolated. Example 5: ¹H NMR (400 MHz, CDCl₃) δ 7.25 (t, J=6.8 Hz, 1H), 7.13-7.09 (m, 1H), 6.92-6.88 (m, 1H), 6.87-6.85 (m, 1H), 3.79 (s, 3H), 3.32 (t, J=6.6 Hz, 2H), 3.21-3.14 (m, 1H), 2.88-2.77 (m, 1H), 2.82 (s, 3H), 2.61-2.47 (m, 2H), 2.47-2.39 (m, 2H), 2.32-2.22 (m, 2H), 2.13-2.03 (m, 2H), 1.73-1.62 (m, 1H), 1.64-1.52 (m, 2H), 1.20-1.07 (m, 8H). MS (ESI) m/z: [M+H]⁺ Found 564.0. Example 6: ¹H NMR (400 MHz, CDCl₃) δ 7.25 (t, J=6.8 Hz, 1H), 7.13-7.09 (m, 1H), 6.92-6.88 (m, 1H), 6.87-6.85 (m, 1H), 3.79 (s, 3H), 3.32 (t, J=6.6 Hz, 2H), 3.21-3.14 (m, 1H), 2.88-2.77 (m, 1H), 2.82 (s, 3H), 2.61-2.47 (m, 2H), 2.47-2.39 (m, 2H), 2.32-2.22 (m, 2H), 2.13-2.03 (m, 2H), 1.73-1.62 (m, 1H), 1.64-1.52 (m, 2H), 1.20-1.07 (m, 8H). MS (ESI) m/z: [M+H]⁺ Found 564.0.

Example 5

5-Chloro-2-ethyl-1-(((1R*)-2-methoxy-4-(3,3,3-trifluoro-2-methylpropyl)phenyl)-N-(((1r,4R)-4-(methylsulfonyl)cyclohexyl)methyl)-1H-imidazole-4-carboxamide

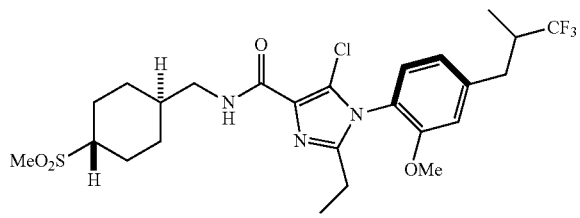

Example 7

2-Ethyl-1-(((1R)-2-methoxy-4-(3,3,3-trifluoro-2-methylpropyl)phenyl)-5-methyl-N-(((1r,4S)-4-(methylsulfonyl)cyclohexyl)methyl)-1H-imidazole-4-carboxamide

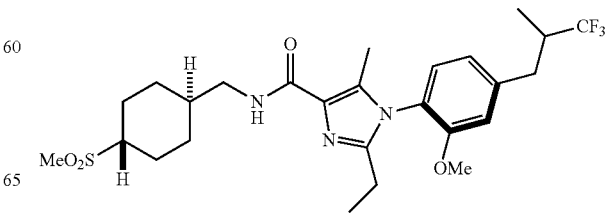

Example 8

2-Ethyl-1-((1S)-2-methoxy-4-(3,3,3-trifluoro-2-methylpropyl)phenyl)-5-methyl-N-(((1r,4R)-4-(methylsulfonyl)cyclohexyl)methyl)-1H-imidazole-4-carboxamide

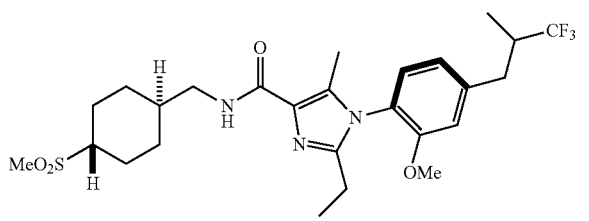

Intermediate 190 was purified by SFC using a chiral stationary phase ((S,S) Whelk O 2, 75% CO$_2$, 25% i-PrOH) to give a pair of atropisomers. The first-eluting isomer was Example 7, and the second-eluting isomer was Example 8. Example 7: $^1$H NMR (500 MHz, CDCl$_3$) δ 7.32 (t, J=6.6 Hz, 1H), 7.06 (d, J=7.8 Hz, 1H), 6.90-6.87 (m, 1H), 6.86-6.83 (m, 1H), 3.78 (s, 3H), 3.30 (t, J=6.6 Hz, 2H), 3.16 (dd, J=12.9, 3.3 Hz, 1H), 2.86-2.78 (m, 1H), 2.82 (s, 3H), 2.60-2.45 (m, 2H), 2.40 (q, J=7.5 Hz, 2H), 2.31-2.23 (m, 5H), 2.14-2.06 (m, 2H), 1.72-1.63 (m, 1H), 1.63-1.51 (m, 2H), 1.19-1.07 (m, 8H). MS (ESI) m/z: [M+H]$^+$ Found 544.3. Example 8: $^1$H NMR (500 MHz, CDCl$_3$) δ 7.32 (t, J=6.6 Hz, 1H), 7.06 (d, J=7.8 Hz, 1H), 6.90-6.87 (m, 1H), 6.86-6.83 (m, 1H), 3.78 (s, 3H), 3.30 (t, J=6.6 Hz, 2H), 3.16 (dd, J=12.9, 3.3 Hz, 1H), 2.86-2.78 (m, 1H), 2.82 (s, 3H), 2.60-2.45 (m, 2H), 2.40 (q, J=7.5 Hz, 2H), 2.31-2.23 (m, 5H), 2.14-2.06 (m, 2H), 1.72-1.63 (m, 1H), 1.63-1.51 (m, 2H), 1.19-1.07 (m, 8H). MS (ESI) m/z: [M+H]$^+$ Found 544.3.

Example 9

5-Chloro-2-isobutyl-1-(2-methoxy-4-(((R)-1,1,1-trifluoropropan-2-yl)amino)phenyl)-N-(((1r,4R)-4-(methylsulfonyl)cyclohexyl)methyl)-1H-imidazole-4-carboxamide

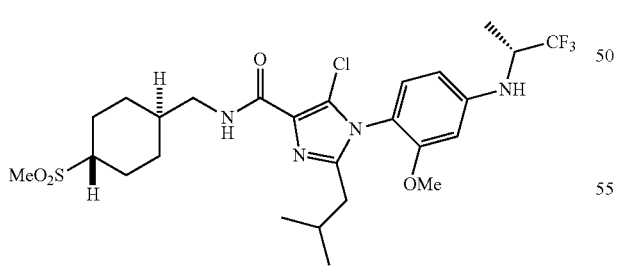

The title compound was prepared as described for the synthesis of Intermediate 188, using ethyl 1-(4-bromo-2-methoxyphenyl)-2-isobutyl-1H-imidazole-4-carboxylate (Intermediate 126) and ((1r,4r)-4-(methylsulfonyl)cyclohexyl)methanamine hydrochloride (Intermediate 13) in place of ethyl 1-(4-bromo-2-methoxyphenyl)-2-ethyl-1H-imidazole-4-carboxylate and (4-(methylsulfonyl)cyclohexyl)methanamine. $^1$H NMR (400 MHz, CDCl$_3$, mixture of rotamers) δ 7.23 (t, J=6.4 Hz, 1H), 6.95-6.91 (m, 1H), 6.34-6.30 (m, 1H), 6.30-6.27 (m, 1H), 4.12-4.02 (m, 1H), 3.94 (d, J=8.9 Hz, 1H), 3.723 (s, 3H of one rotamer), 3.719 (s, 3H of one rotamer), 3.31 (t, J=6.6 Hz, 2H), 2.87-2.78 (m, 1H), 2.82 (s, 3H), 2.36-2.21 (m, 4H), 2.12-2.03 (m, 2H), 2.02-1.90 (m, 1H), 1.73-1.63 (m, 1H), 1.58 (qd, J=13.1, 3.5 Hz, 2H), 1.47 (d, J=6.7 Hz, 3H), 1.12 (qd, J=13.1, 3.5 Hz, 2H), 0.85 (d, J=6.6, 6H of one rotamer), 0.84 (d, J=6.6, 6H of one rotamer). MS (ESI) m/z: [M+H]$^+$ Found 593.3.

Example 10

2-(tert-Butyl)-5-chloro-1-(2-methoxy-4-(((R)-1,1,1-trifluoropropan-2-yl)amino)phenyl)-N-(((1r,4R)-4-(methylsulfonyl)cyclohexyl)methyl)-1H-imidazole-4-carboxamide

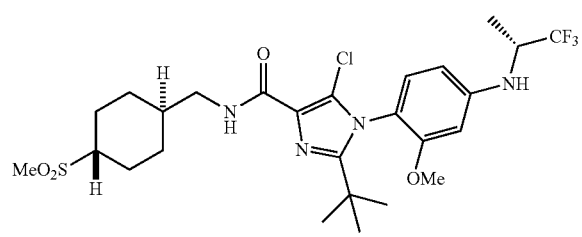 [SMILES: COc1cc(N[C@H](C)C(F)(F)F)ccc1-n1c(C(C)(C)C)nc(C(=O)NC[C@H]2CC[C@H](S(C)(=O)=O)CC2)c1Cl]

The title compound was prepared as described for the synthesis of Intermediate 188, using N-(4-bromo-2-methoxyphenyl)pivalimidamide (Intermediate 76) in place of N-(4-bromo-2-methoxyphenyl)propionimidamide and ((1r,4r)-4-(methylsulfonyl)cyclohexyl)methanamine hydrochloride (Intermediate 13) in place of (4-(methylsulfonyl)cyclohexyl)methanamine. $^1$H NMR (600 MHz, CDCl$_3$, mixture of rotamers) δ 8.32 (t, J=6.1 Hz, 1H), 7.01-6.98 (m, 1H), 6.37-6.34 (m, 1H), 6.30-6.28 (m, 1H), 4.38 (br s, 1H), 4.13-4.05 (m, 1H), 3.76 (s, 3H of one rotamer), 3.76 (s, 3H of one rotamer), 3.35-3.27 (m, 2H), 2.85-2.78 (m, 1H), 2.81 (s, 3H), 2.29-2.24 (m, 2H), 2.08-2.02 (m, 2H), 1.72-1.63 (m, 1H), 1.57 (qd, J=12.9, 3.5 Hz, 2H), 1.48 (d, J=6.7 Hz, 3H), 1.29 (s, 9H), 1.11 (qd, J=13.0, 3.4 Hz, 2H). MS (ESI) m/z: [M+H]$^+$ Found 593.0.

Example 11

5-Chloro-1-(2-methoxy-4-(((R)-1,1,1-trifluoropropan-2-yl)amino)phenyl)-N-(((1r,4R)-4-(methylsulfonyl)cyclohexyl)methyl)-2-propyl-1H-imidazole-4-carboxamide

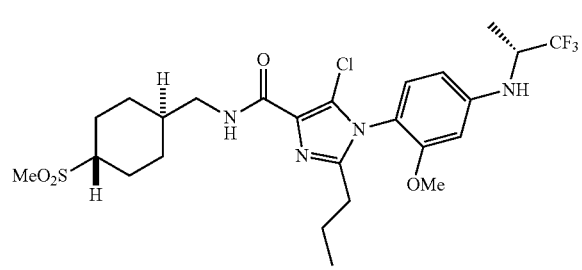 [SMILES: CCCc1nc(C(=O)NC[C@H]2CC[C@H](S(C)(=O)=O)CC2)c(Cl)n1-c1ccc(N[C@H](C)C(F)(F)F)cc1OC]

The title compound was prepared as described for the synthesis of Intermediate 188, using butyronitrile in place of propionitrile and ((1r,4r)-4-(methylsulfonyl)cyclohexyl)methanamine hydrochloride (Intermediate 13) in place of (4-(methylsulfonyl)cyclohexyl)methanamine. ¹H NMR (400 MHz, CDCl₃, mixture of rotamers) δ 8.21 (t, J=5.8 Hz, 1H), 6.99-6.94 (m, 1H), 6.38-6.33 (m, 1H), 6.32-6.30 (m, 1H), 4.14-4.03 (m, 1H), 3.79 (br s, 1H), 3.766 (s, 3H of one rotamer), 3.762 (s, 3H of one rotamer), 3.32 (t, J=6.3 Hz, 2H), 2.86-2.77 (m, 1H), 2.81 (s, 3H), 2.73-2.55 (m, 2H), 2.31-2.22 (m, 2H), 2.11-2.02 (m, 2H), 1.75-1.64 (m, 1H), 1.66-1.51 (m, 4H), 1.48 (d, J=6.5 Hz, 3H), 1.12 (qd, J=13.2, 3.5 Hz, 2H), 0.88 (t, J=7.4 Hz, 3H). MS (ESI) m/z: [M+H]⁺ Found 579.2.

Example 12

2-Ethyl-5-fluoro-1-(2-methoxy-4-(((R)-1,1,1-trifluoropropan-2-yl)amino)phenyl)-N-(((1r,4R)-4-(methylsulfonyl)cyclohexyl)methyl)-1H-imidazole-4-carboxamide

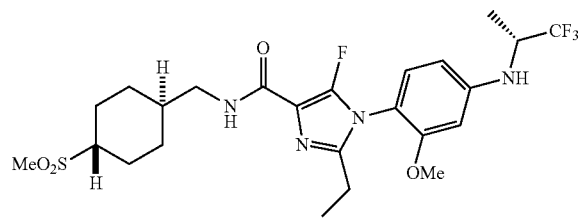 [SMILES: CCc1nc(C(=O)NC[C@H]2CC[C@H](S(C)(=O)=O)CC2)c(F)n1-c1ccc(N[C@H](C)C(F)(F)F)cc1OC]

The title compound was prepared as described for the synthesis of Intermediate 188, using ethyl 1-(4-bromo-2-methoxyphenyl)-2-ethyl-5-fluoro-1H-imidazole-4-carboxylate (Intermediate 97) and ((1r,4r)-4-(methylsulfonyl)cyclohexyl)methanamine hydrochloride (Intermediate 13) in place of ethyl 1-(4-bromo-2-methoxyphenyl)-5-chloro-2-ethyl-1H-imidazole-4-carboxylate and (4-(methylsulfonyl)cyclohexyl)methanamine. ¹H NMR (500 MHz, CDCl₃, mixture of rotamers) δ 8.25 (t, J=5.8 Hz, 1H), 7.06-7.01 (m, 1H), 6.38-6.33 (m, 1H), 6.33-6.29 (m, 1H), 4.13-4.05 (m, 1H), 3.97 (br s, 1H), 3.795 (s, 3H of one rotamer), 3.790 (s, 3H of one rotamer), 3.31 (t, J=6.3 Hz, 2H), 2.86-2.77 (m, 1H), 2.82 (s, 3H), 2.77-2.63 (m, 2H), 2.30-2.23 (m, 2H), 2.08-2.02 (m, 2H), 1.73-1.63 (m, 1H), 1.57 (qd, J=13.0, 3.7 Hz, 2H), 1.48 (d, J=6.6 Hz, 3H), 1.20 (t, J=7.6 Hz, 3H), 1.12 (qd, J=13.0, 3.5 Hz, 2H). MS (ESI) m/z: [M+H]⁺ Found 549.2.

Example 13

2-Ethyl-5-fluoro-1-(2-methoxy-4-(3,3,3-trifluoropropyl)phenyl)-N-(((1r,4r)-4-(methylsulfonyl)cyclohexyl)methyl)-1H-imidazole-4-carboxamide

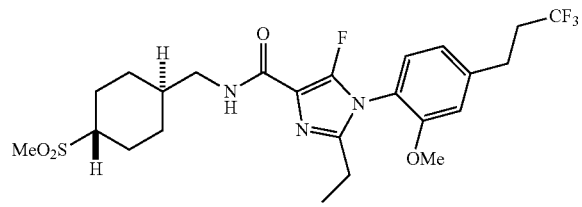 [SMILES: CCc1nc(C(=O)NC[C@H]2CC[C@H](S(C)(=O)=O)CC2)c(F)n1-c1ccc(CCC(F)(F)F)cc1OC]

The title compound was prepared as described for the synthesis of Example 1, using ethyl 1-(4-bromo-2-methoxyphenyl)-2-ethyl-5-fluoro-1H-imidazole-4-carboxylate (Intermediate 97), 9-(3,3,3-trifluoropropyl)-9-borabicyclo[3.3.1]nonane (Intermediate 65), and ((1r,4r)-4-(methylsulfonyl)cyclohexyl)methanamine hydrochloride (Intermediate 13) in place of ethyl 1-(4-bromo-2-methoxyphenyl)-5-cyano-2-ethyl-1H-imidazole-4-carboxylate, 9-(3,3,3-trifluoro-2-methylpropyl)-9-borabicyclo[3.3.1]nonane, and (1s,4s)-1-(aminomethyl)-4-(methylsulfonyl)cyclohexanol hydrochloride. ¹H NMR (500 MHz, CDCl₃) δ 7.95 (t, J=6.1 Hz, 1H), 7.20 (d, J=8.0 Hz, 1H), 6.98 (dd, J=8.0, 1.7 Hz, 1H), 6.95 (d, J=1.7 Hz, 1H), 3.85 (s, 3H), 3.32 (t, J=6.4 Hz, 2H), 3.01-2.95 (m, 2H), 2.86-2.78 (m, 1H), 2.82 (s, 3H), 2.70-2.55 (m, J=7.5 Hz, 2H), 2.53-2.42 (m, 2H), 2.31-2.23 (m, 2H), 2.09-2.02 (m, 2H), 1.73-1.62 (m, 1H), 1.58 (qd, J=13.0, 3.6 Hz, 2H), 1.17 (t, J=7.6 Hz, 3H), 1.15-1.06 (qd, J=12.6, 3.4 Hz, 2H). MS (ESI) m/z: [M+H]⁺ Found 534.0.

Example 14

2-Ethyl-5-fluoro-N-(((1s,4s)-1-hydroxy-4-(methylsulfonyl)cyclohexyl)methyl)-1-(2-methoxy-4-(3,3,3-trifluoropropyl)phenyl)-1H-imidazole-4-carboxamide

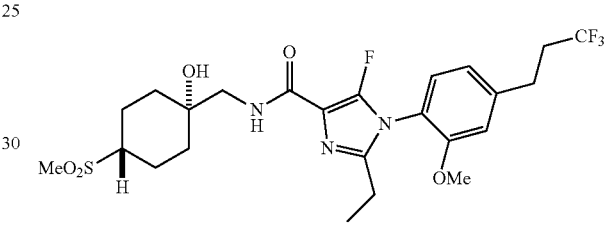

The title compound was prepared as described for the synthesis of Example 1, using ethyl 1-(4-bromo-2-methoxyphenyl)-2-ethyl-5-fluoro-1H-imidazole-4-carboxylate (Intermediate 97) and 9-(3,3,3-trifluoropropyl)-9-borabicyclo[3.3.1]nonane (Intermediate 65) in place of ethyl 1-(4-bromo-2-methoxyphenyl)-5-cyano-2-ethyl-1H-imidazole-4-carboxylate and 9-(3,3,3-trifluoro-2-methylpropyl)-9-borabicyclo[3.3.1]nonane. ¹H NMR (500 MHz, CDCl₃) δ 8.10 (t, J=6.1 Hz, 1H), 7.20 (d, J=8.0 Hz, 1H), 6.98 (dd, J=8.0, 1.7 Hz, 1H), 6.94 (d, J=1.7 Hz, 1H), 4.35 (br s, 1H), 3.85 (s, 3H), 3.51-3.42 (m, 2H), 3.01-2.96 (m, 2H), 2.85-2.75 (m, 1H), 2.83 (s, 3H), 2.65-2.53 (m, 2H), 2.53-2.43 (m, 2H), 2.15-2.08 (m, 2H), 2.03-1.92 (m, 4H), 1.41 (td, J=13.9, 3.8 Hz, 2H), 1.17 (t, J=7.6 Hz, 3H). MS (ESI) m/z: [M+H]⁺ Found 550.2.

Example 15

2-Ethyl-5-fluoro-1-(2-methoxy-4-(3,3,3-trifluoro-2-methylpropyl)phenyl)-N-(((1r,4r)-4-(methylsulfonyl)cyclohexyl)methyl)-1H-imidazole-4-carboxamide

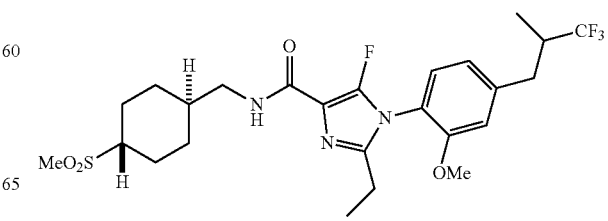

The title compound was prepared as described for the synthesis of Example 1, using ethyl 1-(4-bromo-2-methoxyphenyl)-2-ethyl-5-fluoro-1H-imidazole-4-carboxylate (Intermediate 97) and ((1r,4r)-4-(methylsulfonyl)cyclohexyl)methanamine hydrochloride (Intermediate 13) in place of ethyl 1-(4-bromo-2-methoxyphenyl)-5-cyano-2-ethyl-1H-imidazole-4-carboxylate and (1s,4s)-1-(aminomethyl)-4-(methylsulfonyl)cyclohexanol hydrochloride. $^1$H NMR (500 MHz, CDCl$_3$) δ 7.64 (t, J=6.2 Hz, 1H), 7.20-7.16 (m, 1H), 6.95-6.92 (m, 1H), 6.90-6.87 (m, 1H), 3.84 (s, 3H), 3.32 (t, J=6.5 Hz, 2H), 3.17 (dd, J=13.4, 3.7 Hz, 1H), 2.86-2.78 (m, 1H), 2.82 (s, 3H), 2.62-2.48 (m, 4H), 2.31-2.23 (m, 2H), 2.10-2.02 (m, 2H), 1.73-1.63 (m, 1H), 1.58 (qd, J=12.9, 3.5 Hz, 2H), 1.19-1.07 (m, 8H). MS (ESI) m/z: [M+H]$^+$ Found 547.9.

Example 16

5-Cyano-2-ethyl-1-(2-methoxy-4-(3,3,3-trifluoro-2-methylpropyl)phenyl)-N-(((1r,4r)-4-(methylsulfonyl)cyclohexyl)methyl)-1H-imidazole-4-carboxamide

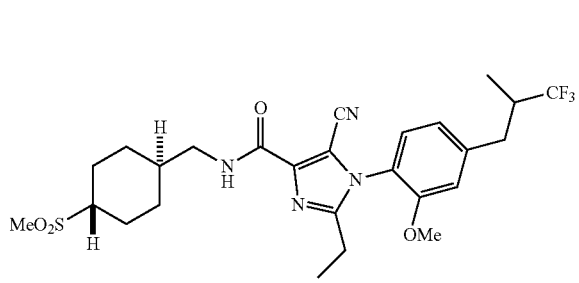 [SMILES: CCc1nc(C(=O)NC[C@H]2CC[C@H](S(C)(=O)=O)CC2)c(C#N)n1-c1ccc(CC(C)C(F)(F)F)cc1OC]

The title compound was prepared as described for the synthesis of Example 1, using ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. $^1$H NMR (500 MHz, CDCl$_3$) δ 7.30 (t, J=6.5 Hz, 1H), 7.21-7.16 (m, 1H), 6.95-6.90 (m, 1H), 6.89 (s, 1H), 3.84 (s, 3H), 3.36 (t, J=6.6 Hz, 2H), 3.17 (dd, J=13.2, 3.5 Hz, 1H), 2.88-2.79 (m, 1H), 2.83 (s, 3H), 2.61-2.44 (m, 4H), 2.32-2.25 (m, 2H), 2.10-2.04 (m, 2H), 1.75-1.64 (m, 1H), 1.59 (qd, J=13.0, 3.6 Hz, 2H), 1.22 (t, J=7.5 Hz, 3H), 1.15 (qd, J=12.9, 3.5 Hz, 2H), 1.10 (d, J=6.5 Hz, 3H). MS (ESI) m/z: [M+H]$^+$ Found 555.2.

Example 17

2-Ethyl-N-(((1s,4S)-1-hydroxy-4-(methylsulfonyl)cyclohexyl)methyl)-1-(2-methoxy-4-((R*)-3,3,3-trifluoro-2-methylpropyl)phenyl)-1H-imidazole-4-carboxamide

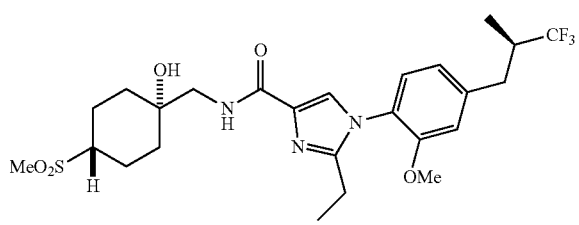 [SMILES: CCc1nc(C(=O)NC[C@]2(O)CC[C@@H](S(C)(=O)=O)CC2)cn1-c1ccc(C[C@@H](C)C(F)(F)F)cc1OC]

The title compound was prepared as described for the synthesis of Example 1, using ethyl (R*)-2-ethyl-1-(2-methoxy-4-(3,3,3-trifluoro-2-methylpropyl)phenyl)-1H-imidazole-4-carboxylate (Intermediate 73) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 9.14 (t, J=5.8 Hz, 1H), 7.64 (s, 1H), 7.23 (d, J=7.9 Hz, 1H), 6.98 (dd, J=8.0, 1.7 Hz, 1H), 6.93 (d, J=1.7 Hz, 1H), 3.87 (s, 3H), 3.13 (br s, 1H), 3.50 (d, J=5.7 Hz, 2H), 3.17 (dd, J=13.7, 4.3 Hz, 1H), 2.86-2.75 (m, 6H), 2.63 (dd, J=13.7, 9.9 Hz, 1H), 2.59-2.48 (m, 1H), 2.14-2.08 (m, 2H), 2.04-1.93 (m, 4H), 1.42 (td, J=13.8, 3.2 Hz, 2H), 1.27 (t, J=7.6 Hz, 3H), 1.13 (d, J=6.8 Hz, 3H). MS (ESI) m/z: [M+H]$^+$ Found 546.3.

Example 18

2-Ethyl-1-(2-methoxy-4-((R*)-3,3,3-trifluoro-2-methylpropyl)phenyl)-N-(((1r,4R)-4-(methylsulfonyl)cyclohexyl)methyl)-1H-imidazole-4-carboxamide

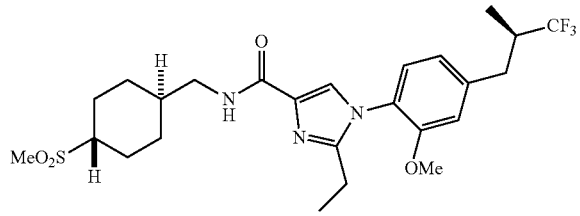 [SMILES: CCc1nc(C(=O)NC[C@H]2CC[C@H](S(C)(=O)=O)CC2)cn1-c1ccc(C[C@@H](C)C(F)(F)F)cc1OC]

The title compound was prepared as described for the synthesis of Example 1, using ethyl (R*)-2-ethyl-1-(2-methoxy-4-(3,3,3-trifluoro-2-methylpropyl)phenyl)-1H-imidazole-4-carboxylate (Intermediate 73) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$) δ 8.83 (t, J=5.8 Hz, 1H), 7.61 (s, 1H), 7.22 (d, J=7.9 Hz, 1H), 6.97 (dd, J=8.0, 1.7 Hz, 1H), 6.92 (d, J=1.6 Hz, 1H), 3.86 (s, 3H), 3.34 (t, J=6.2 Hz, 2H), 3.17 (dd, J=13.6, 4.2 Hz, 1H), 2.83 (d, J=6.9 Hz, 6H), 2.62 (dd, J=13.6, 10.0 Hz, 1H), 2.58-2.47 (m, 1H), 2.30-2.23 (m, 2H), 2.10-2.02 (m, 2H), 1.75-1.65 (m, 1H), 1.57 (qd, J=12.9, 3.6 Hz, 2H), 1.26 (t, J=7.6 Hz, 3H), 1.18-1.07 (m, 5H). MS (ESI) m/z: [M+H]$^+$ Found 530.2.

Example 19

2-Ethyl-N-(((1s,4R)-1-hydroxy-4-(methylsulfonyl)cyclohexyl)methyl)-1-(2-methoxy-4-((S*)-3,3,3-trifluoro-2-methylpropyl)phenyl)-1H-imidazole-4-carboxamide

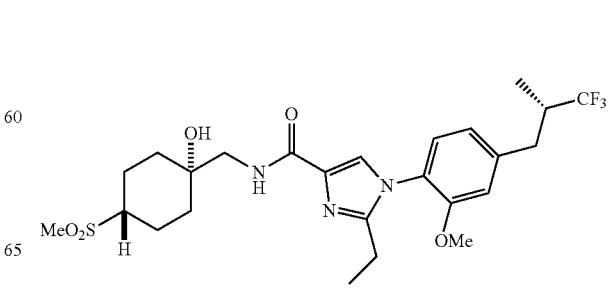

The title compound was prepared as described for the synthesis of Example 1, using ethyl (S*)-2-ethyl-1-(2-methoxy-4-(3,3,3-trifluoro-2-methylpropyl)phenyl)-1H-imidazole-4-carboxylate (Intermediate 74) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 9.14 (t, J=5.8 Hz, 1H), 7.64 (s, 1H), 7.23 (d, J=7.9 Hz, 1H), 6.98 (dd, J=8.0, 1.7 Hz, 1H), 6.93 (d, J=1.7 Hz, 1H), 3.87 (s, 3H), 3.81 (br s, 1H), 3.50 (d, J=5.7 Hz, 2H), 3.17 (dd, J=13.7, 4.3 Hz, 1H), 2.86-2.75 (m, 6H), 2.63 (dd, J=13.7, 9.9 Hz, 1H), 2.59-2.48 (m, 1H), 2.14-2.08 (m, 2H), 2.04-1.93 (m, 4H), 1.42 (td, J=13.8, 3.2 Hz, 2H), 1.27 (t, J=7.6 Hz, 3H), 1.13 (d, J=6.8 Hz, 3H). MS (ESI) m/z: [M+H]$^+$ Found 546.2.

Example 20

2-Ethyl-1-(2-methoxy-4-((S*)-3,3,3-trifluoro-2-methylpropyl)phenyl)-N-(((1r,4S)-4-(methylsulfonyl)cyclohexyl)methyl)-1H-imidazole-4-carboxamide

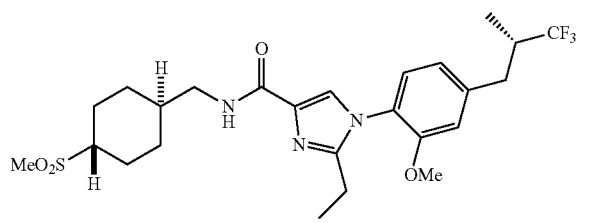 [SMILES: CCc1nc(C(=O)NC[C@H]2CC[C@H](S(C)(=O)=O)CC2)cn1-c1ccc(C[C@H](C)C(F)(F)F)cc1OC]

The title compound was prepared as described for the synthesis of Example 1, using ethyl (S*)-2-ethyl-1-(2-methoxy-4-(3,3,3-trifluoro-2-methylpropyl)phenyl)-1H-imidazole-4-carboxylate (Intermediate 74) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$) δ 8.83 (t, J=5.8 Hz, 1H), 7.61 (s, 1H), 7.22 (d, J=7.9 Hz, 1H), 6.97 (dd, J=8.0, 1.7 Hz, 1H), 6.92 (d, J=1.6 Hz, 1H), 3.86 (s, 3H), 3.34 (t, J=6.2 Hz, 2H), 3.17 (dd, J=13.6, 4.2 Hz, 1H), 2.83 (d, J=6.9 Hz, 6H), 2.62 (dd, J=13.6, 10.0 Hz, 1H), 2.58-2.47 (m, 1H), 2.30-2.23 (m, 2H), 2.10-2.02 (m, 2H), 1.75-1.65 (m, 1H), 1.57 (qd, J=12.9, 3.6 Hz, 2H), 1.26 (t, J=7.6 Hz, 3H), 1.18-1.07 (m, 5H). MS (ESI) m/z: [M+H]$^+$ Found 530.3.

Example 21

5-Cyano-2-ethyl-1-(2-methoxy-4-(3,3,3-trifluoropropyl)phenyl)-N-(((1r,4r)-4-(methylsulfonyl)cyclohexyl)methyl)-1H-imidazole-4-carboxamide

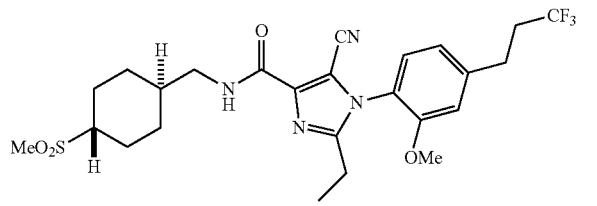 [SMILES: CCc1nc(C(=O)NC[C@H]2CC[C@H](S(C)(=O)=O)CC2)c(C#N)n1-c1ccc(CCC(F)(F)F)cc1OC]

The title compound was prepared as described for the synthesis of Example 1, using 9-(3,3,3-trifluoropropyl)-9-borabicyclo[3.3.1]nonane (Intermediate 65) and ((1r,4r)-4-(methylsulfonyl)cyclohexyl)methanamine hydrochloride (Intermediate 13) in place of 9-(3,3,3-trifluoro-2-methylpropyl)-9-borabicyclo[3.3.1]nonane and (1s,4s)-1-(aminomethyl)-4-(methylsulfonyl)cyclohexanol hydrochloride. $^1$H NMR (500 MHz, CDCl$_3$) δ 7.41 (t, J=6.4 Hz, 1H), 7.19 (d, J=7.9 Hz, 1H), 6.96 (dd, J=7.9, 1.7 Hz, 1H), 6.93 (d, J=1.7 Hz, 1H), 3.84 (s, 3H), 3.36 (t, J=6.6 Hz, 2H), 3.00-2.93 (m, 2H), 2.88-2.80 (m, 1H), 2.84 (s, 3H), 2.60-2.42 (m, 4H), 2.32-2.25 (m, 2H), 2.10-2.02 (m, 2H), 1.75-1.65 (m, 1H), 1.59 (qd, J=13.0, 3.6 Hz, 2H), 1.21 (t, J=7.6 Hz, 3H), 1.14 (qd, J=13.2, 3.6 Hz, 2H). MS (ESI) m/z: [M+H]$^+$ Found 541.2.

Example 22

5-Chloro-2-ethyl-1-(2-fluoro-4-(3,3,3-trifluoropropyl)phenyl)-N-(((1r,4r)-4-(methylsulfonyl)cyclohexyl)methyl)-1H-imidazole-4-carboxamide

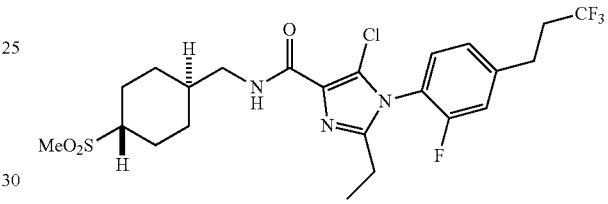

The title compound was prepared as described for the synthesis of Example 1, using ethyl 1-(4-bromo-2-fluorophenyl)-5-chloro-2-ethyl-1H-imidazole-4-carboxylate (Intermediate 152), 9-(3,3,3-trifluoropropyl)-9-borabicyclo[3.3.1]nonane (Intermediate 65), and ((1r,4r)-4-(methylsulfonyl)cyclohexyl)methanamine hydrochloride (Intermediate 13) in place of ethyl 1-(4-bromo-2-methoxyphenyl)-5-cyano-2-ethyl-1H-imidazole-4-carboxylate, 9-(3,3,3-trifluoro-2-methylpropyl)-9-borabicyclo[3.3.1]nonane, and (1s,4s)-1-(aminomethyl)-4-(methylsulfonyl)cyclohexanol hydrochloride. $^1$H NMR (500 MHz, CDCl$_3$) δ 7.38-7.30 (br m, 1H), 7.25-7.15 (m, 3H), 3.33 (t, J=6.6 Hz, 2H), 3.03-2.96 (m, 2H), 2.87-2.79 (m, 1H), 2.82 (s, 3H), 2.57-2.43 (m, 4H), 2.32-2.24 (m, 2H), 2.11-2.03 (m, 2H), 1.74-1.63 (m, 1H), 1.59 (qd, J=12.9, 3.5 Hz, 2H), 1.19 (t, J=7.5 Hz, 3H), 1.18-1.08 (m, 2H). MS (ESI) m/z: [M+H]$^+$ Found 537.9.

Example 23

5-Chloro-2-ethyl-1-(2-fluoro-4-(3,3,3-trifluoropropyl)phenyl)-N-(((1s,4s)-1-hydroxy-4-(methylsulfonyl)cyclohexyl)methyl)-1H-imidazole-4-carboxamide

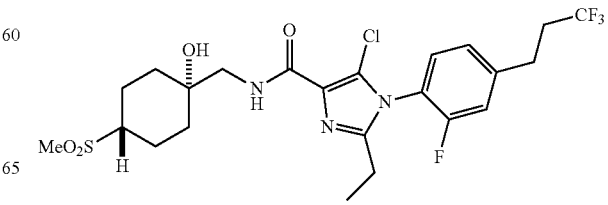

The title compound was prepared as described for the synthesis of Example 1, using ethyl 1-(4-bromo-2-fluorophenyl)-5-chloro-2-ethyl-1H-imidazole-4-carboxylate (Intermediate 152) and 9-(3,3,3-trifluoropropyl)-9-borabicyclo[3.3.1]nonane (Intermediate 65) in place of ethyl 1-(4-bromo-2-methoxyphenyl)-5-cyano-2-ethyl-1H-imidazole-4-carboxylate and 9-(3,3,3-trifluoro-2-methylpropyl)-9-borabicyclo[3.3.1]nonane. $^1$H NMR (500 MHz, CDCl$_3$) δ 7.56 (t, J=6.2 Hz, 1H), 7.25-7.16 (m, 3H), 3.45 (d, J=6.3 Hz, 2H), 3.03-2.96 (m, 2H), 2.85-2.75 (m, 1H), 2.83 (s, 3H), 2.56-2.42 (m, 4H), 2.17-2.09 (m, 2H), 1.99 (dd, J=14.8, 10.6 Hz, 4H), 1.79 (br s, 1H), 1.41 (td, J=13.8, 3.9 Hz, 2H), 1.20 (t, J=7.5 Hz, 3H). MS (ESI) m/z: [M+H]$^+$ Found 553.9.

Example 24

5-Cyano-1-(2-(difluoromethoxy)-4-(3,3,3-trifluoro-2,2-dimethylpropyl)phenyl)-2-ethyl-N-(((1s,4s)-1-hydroxy-4-(methylsulfonyl)cyclohexyl)methyl)-1H-imidazole-4-carboxamide

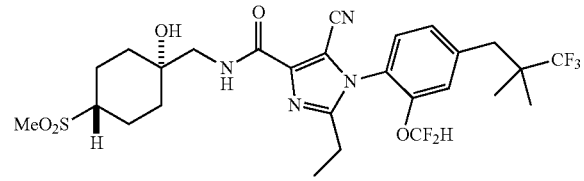

The title compound was prepared as described for the synthesis of Example 1, using ethyl 5-cyano-1-(2-(difluoromethoxy)-4-(3,3,3-trifluoro-2,2-dimethylpropyl)phenyl)-2-ethyl-1H-imidazole-4-carboxylate (Intermediate 112) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 7.51 (t, J=6.5 Hz, 1H), 7.30 (d, J=8.0 Hz, 1H), 7.25-7.21 (m, 2H), 6.47 (dd, J=73.1, 70.4 Hz, 1H), 3.53-3.45 (m, 2H), 2.89 (s, 2H), 2.85-2.78 (m, 1H), 2.84 (s, 3H), 2.60-2.45 (m, 2H), 2.17-2.10 (m, 2H), 2.03-1.93 (m, 4H), 1.89 (br s, 1H), 1.45 (td, J=13.9, 3.8 Hz, 2H), 1.26 (t, J=7.5 Hz, 3H), 1.13 (s, 6H). MS (ESI) m/z: [M+H]$^+$ Found 621.3.

Example 25

5-Cyano-1-(2-(difluoromethoxy)-4-(3,3,3-trifluoropropyl)phenyl)-2-ethyl-N-(((1s,4s)-1-hydroxy-4-(methylsulfonyl)cyclohexyl)methyl)-1H-imidazole-4-carboxamide

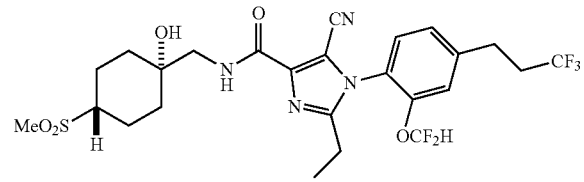

The title compound was prepared as described for the synthesis of Example 1, using ethyl 1-(4-bromo-2-(difluoromethoxy)phenyl)-5-cyano-2-ethyl-1H-imidazole-4-carboxylate (Intermediate 110) and 9-(3,3,3-trifluoropropyl)-9-borabicyclo[3.3.1]nonane (Intermediate 65) in place of ethyl 1-(4-bromo-2-methoxyphenyl)-5-cyano-2-ethyl-1H-imidazole-4-carboxylate and 9-(3,3,3-trifluoro-2-methylpropyl)-9-borabicyclo[3.3.1]nonane. $^1$H NMR (500 MHz, CDCl$_3$) δ 7.56 (t, J=6.3 Hz, 1H), 7.35-7.31 (m, 1H), 7.29-7.26 (m, 2H), 6.49 (dd, J=73.2, 70.3 Hz, 1H), 3.54-3.44 (m, 2H), 3.04-2.97 (m, 2H), 2.87-2.78 (m, 1H), 2.84 (s, 3H), 2.70 (br s, 1H), 2.60-2.43 (m, 4H), 2.16-2.09 (m, 2H), 2.03-1.92 (m, 4H), 1.52-1.41 (m, 2H), 1.25 (t, J=7.5 Hz, 3H). MS (ESI) m/z: [M+H]$^+$ Found 593.2.

Example 26

5-Cyano-1-(2-(difluoromethoxy)-4-(3,3,3-trifluoropropyl)phenyl)-2-ethyl-N-(((1r,4r)-4-(methylsulfonyl)cyclohexyl)methyl)-1H-imidazole-4-carboxamide

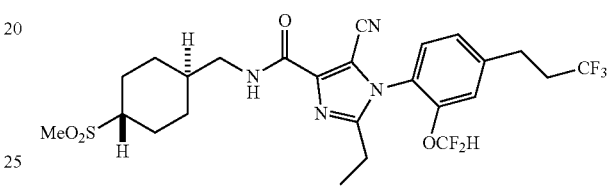

The title compound was prepared as described for the synthesis of Example 1, using ethyl 1-(4-bromo-2-(difluoromethoxy)phenyl)-5-cyano-2-ethyl-1H-imidazole-4-carboxylate (Intermediate 110), 9-(3,3,3-trifluoropropyl)-9-borabicyclo[3.3.1]nonane (Intermediate 65), and ((1r,4r)-4-(methylsulfonyl)cyclohexyl)methanamine hydrochloride (Intermediate 13) in place of ethyl 1-(4-bromo-2-methoxyphenyl)-5-cyano-2-ethyl-1H-imidazole-4-carboxylate, 9-(3,3,3-trifluoro-2-methylpropyl)-9-borabicyclo[3.3.1]nonane, and (1s,4s)-1-(aminomethyl)-4-(methylsulfonyl)cyclohexanol hydrochloride. $^1$H NMR (500 MHz, CDCl$_3$) δ 7.33 (d, J=8.5 Hz, 1H), 7.31-7.25 (m, 3H), 6.48 (dd, J=73.4, 70.2 Hz, 1H), 3.36 (t, J=6.6 Hz, 2H), 3.03-2.97 (m, 2H), 2.88-2.80 (m, 1H), 2.83 (s, 3H), 2.60-2.43 (m, 4H), 2.32-2.25 (m, 2H), 2.11-2.03 (m, 2H), 1.75-1.66 (m, 1H), 1.65-1.54 (m, 2H), 1.25 (t, J=7.5 Hz, 3H), 1.15 (qd, J=13.1, 3.5 Hz, 2H). MS (ESI) m/z: [M+H]$^+$ Found 577.2.

Example 27

5-Cyano-2-ethyl-1-(2-(methoxy-d$_3$)-4-(3,3,3-trifluoro-2,2-dimethylpropyl)phenyl)-N-(((1r,4r)-4-(methylsulfonyl)cyclohexyl)methyl)-1H-imidazole-4-carboxamide

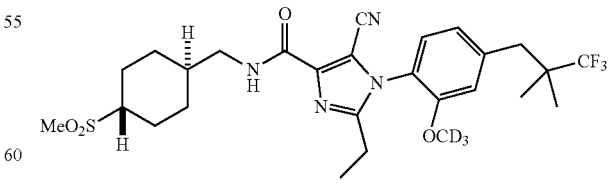

The title compound was prepared as described for the synthesis of Example 1, using ethyl 5-cyano-2-ethyl-1-(2-(methoxy-d$_3$)-4-(3,3,3-trifluoro-2,2-dimethylpropyl)phenyl)-1H-imidazole-4-carboxylate (Intermediate 102) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$, mixture of rotamers) δ 7.44 (t, J=6.5 Hz, 1H), 7.18 (d, J=8.0 Hz, 1H), 6.92 (dd, J=8.0, 1.7 Hz, 1H), 6.88 (d, J=1.7 Hz, 1H), 3.39-3.32 (m, 2H), 2.86 (s, 2H), 2.86-2.80 (m, 1H), 2.84 (s, 3H), 2.61-2.49 (m, 2H), 2.31-2.25 (m, 2H), 2.10-2.03 (m, 2H), 1.76-1.65 (m, 1H), 1.59 (qd, J=13.0, 3.6 Hz, 2H), 1.21 (t, J=7.5 Hz, 3H), 1.19-1.09 (m, 2H), 1.131 (s, 6H of one rotamer), 1.127 (s, 6H of one rotamer). MS (ESI) m/z: [M+H]$^+$ Found 572.2.

Example 28

5-Cyano-2-ethyl-N-(((1s,4s)-1-hydroxy-4-(methylsulfonyl)cyclohexyl)methyl)-1-(2-(methoxy-d$_3$)-4-(3,3,3-trifluoro-2,2-dimethylpropyl)phenyl)-1H-imidazole-4-carboxamide

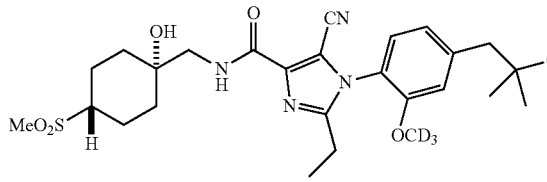

The title compound was prepared as described for the synthesis of Example 1, using ethyl 5-cyano-2-ethyl-1-(2-(methoxy-d$_3$)-4-(3,3,3-trifluoro-2,2-dimethylpropyl)phenyl)-1H-imidazole-4-carboxylate (Intermediate 102) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 7.68 (br s, 1H), 7.18 (d, J=7.9 Hz, 1H), 6.92 (dd, J=7.9, 1.7 Hz, 1H), 6.88 (d, J=1.7 Hz, 1H), 3.55-3.45 (m, 2H), 3.17 (br s, 1H), 2.87 (s, 2H), 2.86-2.78 (m, 1H), 2.84 (s, 3H), 2.61-2.48 (m, 2H), 2.17-2.08 (m, 2H), 2.04-1.92 (m, 4H), 1.46 (dt, J=14.7, 7.0 Hz, 2H), 1.22 (t, J=7.2 Hz, 3H), 1.133 (s, 6H of one rotamer), 1.129 (s, 6H of one rotamer). MS (ESI) m/z: [M+H]$^+$ Found 588.3.

Example 29

5-Cyano-2-ethyl-1-(2-(methoxy-d$_3$)-4-(3,3,3-trifluoropropyl)phenyl)-N-(((1r,4r)-4-(methylsulfonyl)cyclohexyl)methyl)-1H-imidazole-4-carboxamide

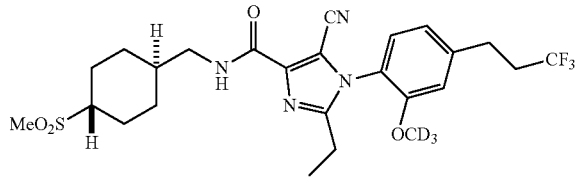

The title compound was prepared as described for the synthesis of Example 1, using ethyl 1-(4-bromo-2-(methoxy-d$_3$)phenyl)-5-cyano-2-ethyl-1H-imidazole-4-carboxylate (Intermediate 95), 9-(3,3,3-trifluoropropyl)-9-borabicyclo[3.3.1]nonane (Intermediate 65), and ((1r,4r)-4-(methylsulfonyl)cyclohexyl)methanamine hydrochloride (Intermediate 13) in place of ethyl 1-(4-bromo-2-methoxyphenyl)-5-cyano-2-ethyl-1H-imidazole-4-carboxylate, 9-(3,3,3-trifluoro-2-methylpropyl)-9-borabicyclo[3.3.1]nonane, and (1s,4s)-1-(aminomethyl)-4-(methylsulfonyl)cyclohexanol hydrochloride. $^1$H NMR (500 MHz, CDCl$_3$) δ 7.41 (t, J=6.4 Hz, 1H), 7.19 (d, J=7.9 Hz, 1H), 6.95 (dd, J=8.0, 1.8 Hz, 1H), 6.92 (d, J=1.7 Hz, 1H), 3.40-3.31 (m, 2H), 2.99-2.93 (m, 2H), 2.88-2.80 (m, 1H), 2.84 (s, 3H), 2.59-2.41 (m, 4H), 2.31-2.25 (m, 2H), 2.10-2.03 (m, 2H), 1.75-1.65 (m, 1H), 1.59 (qd, J=13.0, 3.6 Hz, 2H), 1.21 (t, J=7.5 Hz, 3H), 1.14 (qd, J=13.3, 3.6 Hz, 2H). MS (ESI) m/z: [M+H]$^+$ Found 544.2.

Example 30

5-Cyano-2-ethyl-N-(((1s,4s)-1-hydroxy-4-(methylsulfonyl)cyclohexyl)methyl)-1-(2-(methoxy-d$_3$)-4-(3,3,3-trifluoropropyl)phenyl)-1H-imidazole-4-carboxamide

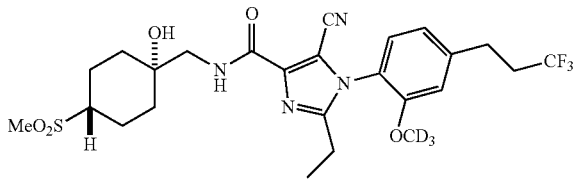

The title compound was prepared as described for the synthesis of Example 1, using ethyl 1-(4-bromo-2-(methoxy-d$_3$)phenyl)-5-cyano-2-ethyl-1H-imidazole-4-carboxylate (Intermediate 95) and 9-(3,3,3-trifluoropropyl)-9-borabicyclo[3.3.1]nonane (Intermediate 65) in place of ethyl 1-(4-bromo-2-methoxyphenyl)-5-cyano-2-ethyl-1H-imidazole-4-carboxylate and 9-(3,3,3-trifluoro-2-methylpropyl)-9-borabicyclo[3.3.1]nonane. $^1$H NMR (500 MHz, CDCl$_3$) δ 7.79 (br s, 1H), 7.20 (d, J=8.0 Hz, 1H), 6.97 (dd, J=8.0, 1.7 Hz, 1H), 6.94 (d, J=1.7 Hz, 1H), 5.49 (br s, 1H), 3.55-3.46 (m, 2H), 3.00-2.94 (m, 2H), 2.88-2.80 (m, 1H), 2.85 (s, 3H), 2.62-2.41 (m, 4H), 2.16-2.09 (m, 2H), 2.03-1.92 (m, 4H), 1.46 (td, J=14.1, 4.1 Hz, 2H), 1.20 (t, J=7.4 Hz, 3H). MS (ESI) m/z: [M+H]$^+$ Found 560.2.

Example 31

N-(((1s*,4s*)-1-Cyano-4-(methylsulfonyl)cyclohexyl)methyl)-2-ethyl-5-fluoro-1-(2-(methoxy-d$_3$)-4-(3,3,3-trifluoro-2,2-dimethylpropyl)phenyl)-1H-imidazole-4-carboxamide

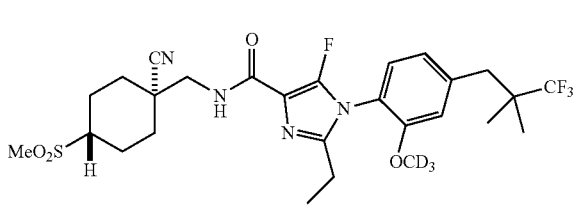

The title compound was prepared as described for the synthesis of Example 1, using methyl 2-ethyl-5-fluoro-1-(2-(methoxy-d$_3$)-4-(3,3,3-trifluoro-2,2-dimethylpropyl)phenyl)-1H-imidazole-4-carboxylate (Intermediate 100) and (1s*,4s*)-1-(aminomethyl)-4-(methylsulfonyl)cyclohexane-1-carbonitrile hydrochloride (Intermediate 51) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 8.38 (t, J=6.6 Hz, 1H), 7.20 (d, J=8.0 Hz, 1H), 6.96 (dd, J=8.0, 1.7 Hz, 1H), 6.90 (d, J=1.7 Hz, 1H), 3.68 (appar d, J=6.6 Hz, 2H), 2.89 (s, 2H), 2.86 (s, 3H), 2.85-2.78 (m, 1H), 2.73-2.59 (m, J=7.7 Hz, 2H), 2.38-2.31 (m, 2H), 2.31-2.24 (m, 2H), 1.91 (qd, J=13.3, 3.4 Hz, 2H), 1.54 (td, J=13.7, 3.5 Hz, 2H), 1.18 (t, J=7.6 Hz, 3H), 1.16 (s, 6H of one rotamer), 1.15 (s, 6H of one rotamer). MS (ESI) m/z: [M+H]⁺ Found 590.2.

Example 32

2-Ethyl-5-fluoro-N-(((1s,4s)-1-hydroxy-4-(methylsulfonyl)cyclohexyl)methyl)-1-(2-(methoxy-d₃)-4-(3,3,3-trifluoro-2,2-dimethylpropyl)phenyl)-1H-imidazole-4-carboxamide

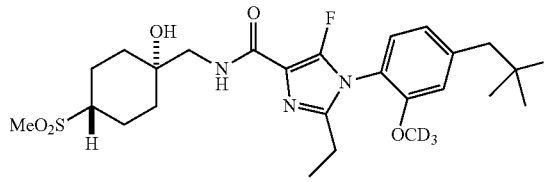

The title compound was prepared as described for the synthesis of Example 1, using methyl 2-ethyl-5-fluoro-1-(2-(methoxy-d₃)-4-(3,3,3-trifluoro-2,2-dimethylpropyl)phenyl)-1H-imidazole-4-carboxylate (Intermediate 100) in place of ethyl 5-cyano-2-ethyl-1-(2-methoxy-4-(3,3,3-trifluoro-2-methylpropyl)phenyl)-1H-imidazole-4-carboxylate. ¹H NMR (500 MHz, CDCl₃) δ 8.40 (t, J=6.0 Hz, 1H), 7.21 (d, J=8.0 Hz, 1H), 6.97 (dd, J=8.0, 1.7 Hz, 1H), 6.91 (d, J=1.7 Hz, 1H), 5.32 (br s, 1H), 3.48 (appar d, J=6.0 Hz, 2H), 2.89 (s, 2H), 2.83 (s, 3H), 2.84-2.76 (m, 1H), 2.73-2.61 (m, J=7.7 Hz, 2H), 2.15-2.08 (m, 2H), 2.03-1.92 (m, 4H), 1.43 (td, J=14.0, 3.8 Hz, 2H), 1.19 (t, J=7.6 Hz, 3H), 1.16 (s, 6H of one rotamer), 1.15 (s, 6H of one rotamer). MS (ESI) m/z: [M+H]⁺ Found 581.3.

Example 33

2-Ethyl-5-fluoro-1-(2-(methoxy-d₃)-4-(3,3,3-trifluoro-2,2-dimethylpropyl)phenyl)-N-(((1r,4r)-4-(methylsulfonyl)cyclohexyl)methyl)-1H-imidazole-4-carboxamide

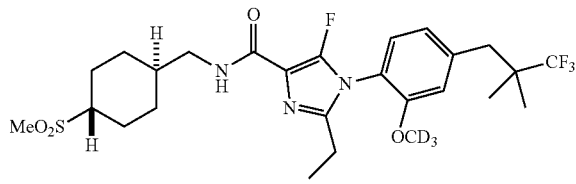

The title compound was prepared as described for the synthesis of Example 1, using methyl 2-ethyl-5-fluoro-1-(2-(methoxy-d₃)-4-(3,3,3-trifluoro-2,2-dimethylpropyl)phenyl)-1H-imidazole-4-carboxylate (Intermediate 100) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 8.10 (t, J=5.9 Hz, 1H), 7.19 (d, J=7.9 Hz, 1H), 6.96 (dd, J=8.0, 1.7 Hz, 1H), 6.90 (d, J=1.7 Hz, 1H), 3.32 (t, J=6.4 Hz, 2H), 2.88 (s, 2H), 2.86-2.79 (m, 1H), 2.83 (s, 3H), 2.74-2.60 (m, J=7.7 Hz, 2H), 2.31-2.24 (m, 2H), 2.08-2.02 (m, 2H), 1.74-1.63 (m, 1H), 1.58 (qd, J=13.0, 3.6 Hz, 2H), 1.18 (t, J=7.6 Hz, 3H), 1.153 (s, 6H of one rotamer), 1.149 (s, 6H of one rotamer), 1.16-1.07 (m, 2H). MS (ESI) m/z: [M+H]⁺ Found 565.3.

Example 34

1-(2-(Difluoromethoxy)-4-(3,3,3-trifluoro-2,2-dimethylpropyl)phenyl)-2-ethyl-5-fluoro-N-(((1r,4r)-4-(methylsulfonyl)cyclohexyl)methyl)-1H-imidazole-4-carboxamide

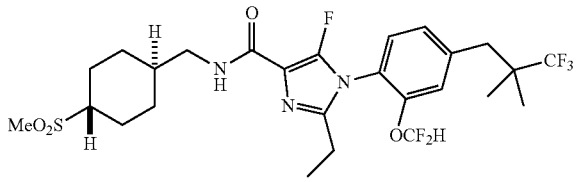

The title compound was prepared as described for the synthesis of Example 1, using ethyl 1-(2-(difluoromethoxy)-4-(3,3,3-trifluoro-2,2-dimethylpropyl)phenyl)-2-ethyl-5-fluoro-1H-imidazole-4-carboxylate (Intermediate 115) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 7.77 (t, J=6.1 Hz, 1H), 7.31 (d, J=8.1 Hz, 1H), 7.28 (s, 1H), 7.25 (dd, J=8.1, 1.8 Hz, 1H), 6.49 (appar t, J=71.5 Hz, 1H), 3.37-3.29 (m, 2H), 2.90 (s, 2H), 2.87-2.79 (m, 1H), 2.83 (s, 3H), 2.66-2.52 (m, 2H), 2.31-2.24 (m, 2H), 2.09-2.01 (m, 2H), 1.73-1.64 (m, 1H), 1.58 (qd, J=12.8, 3.5 Hz, 2H), 1.22-1.08 (m, 11H). MS (ESI) m/z: [M+H]⁺ Found 598.2.

Example 35

1-(2-(Difluoromethoxy)-4-(3,3,3-trifluoro-2,2-dimethylpropyl)phenyl)-2-ethyl-5-fluoro-N-(((1s,4s)-1-hydroxy-4-(methylsulfonyl)cyclohexyl)methyl)-1H-imidazole-4-carboxamide

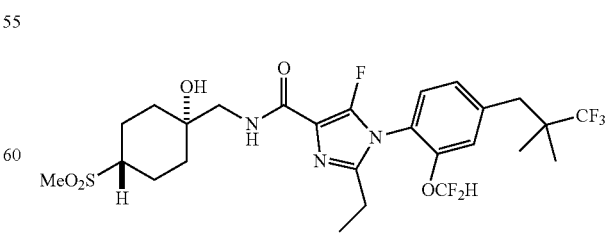

The title compound was prepared as described for the synthesis of Example 1, using ethyl 1-(2-(difluoromethoxy)-4-(3,3,3-trifluoro-2,2-dimethylpropyl)phenyl)-2-ethyl-5- fluoro-1H-imidazole-4-carboxylate (Intermediate 115) in place of ethyl 5-cyano-2-ethyl-1-(2-methoxy-4-(3,3,3-trifluoro-2-methylpropyl)phenyl)-1H-imidazole-4-carboxylate. ¹H NMR (500 MHz, CDCl₃) δ 8.05 (t, J=6.2 Hz, 1H), 7.32 (d, J=8.1 Hz, 1H), 7.29 (s, 1H), 7.27-7.24 (m, 1H), 6.51 (br s, 1H), 6.47 (appat t, J=71 Hz, 1H), 3.52-3.43 (m, 2H), 2.91 (s, 2H), 2.87-2.77 (m, 1H), 2.84 (s, 3H), 2.68-2.53 (m, 2H), 2.16-2.08 (m, 2H), 2.02-1.91 (m, 4H), 1.44 (td, J=14.2, 4.2 Hz, 2H), 1.20 (t, J=7.6 Hz, 3H), 1.15 (s, 6H). MS (ESI) m/z: [M+H]⁺ Found 614.2.

Example 36

5-Cyano-1-(2-(difluoromethoxy)-4-(3,3,3-trifluoro-2,2-dimethylpropyl)phenyl)-2-ethyl-N-(((1r,4r)-4-(methylsulfonyl)cyclohexyl)methyl)-1H-imidazole-4-carboxamide

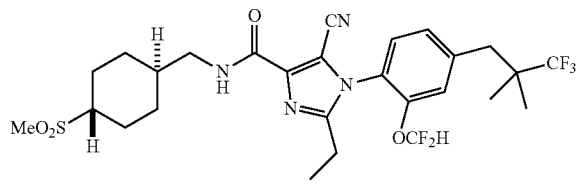

The title compound was prepared as described for the synthesis of Example 1, using ethyl 5-cyano-1-(2-(difluoromethoxy)-4-(3,3,3-trifluoro-2,2-dimethylpropyl)phenyl)-2-ethyl-1H-imidazole-4-carboxylate (Intermediate 112) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 7.30 (d, J=8.3 Hz, 1H), 7.25-7.20 (d, J=7.1 Hz, 3H), 6.46 (dd, J=73.3, 70.4 Hz, 1H), 3.36 (t, J=6.6 Hz, 2H), 2.89 (s, 2H), 2.87-2.80 (m, 1H), 2.83 (s, 3H), 2.60-2.45 (m, 2H), 2.32-2.25 (m, 2H), 2.11-2.04 (m, 2H), 1.75-1.65 (m, 1H), 1.65-1.55 (m, 2H), 1.26 (t, J=7.5 Hz, 3H), 1.19-1.09 (m, 2H), 1.13 (s, 6H). MS (ESI) m/z: [M+H]⁺ Found 605.2.

Example 37

5-Cyano-N-(((1s*,4s*)-1-cyano-4-(methylsulfonyl)cyclohexyl)methyl)-1-(2-(difluoromethoxy)-4-(3,3,3-trifluoro-2,2-dimethylpropyl)phenyl)-2-ethyl-1H-imidazole-4-carboxamide

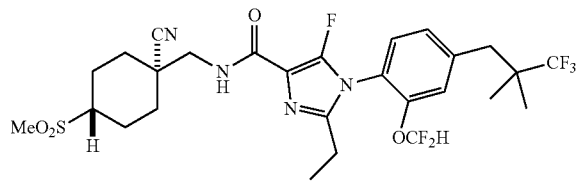

The title compound was prepared as described for the synthesis of Example 1, using ethyl 5-cyano-1-(2-(difluoromethoxy)-4-(3,3,3-trifluoro-2,2-dimethylpropyl)phenyl)-2-ethyl-1H-imidazole-4-carboxylate (Intermediate 112) and (1s*,4s*)-1-(aminomethyl)-4-(methylsulfonyl)cyclohexane-1-carbonitrile hydrochloride (Intermediate 51) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 7.60 (t, J=6.9 Hz, 1H), 7.31 (d, J=7.9 Hz, 1H), 7.25-7.22 (m, 2H), 6.48 (appar dd, J=73.0, 70.4 Hz, 1H), 3.74-3.63 (m, 2H), 2.90 (s, 2H), 2.88-2.80 (m, 1H), 2.87 (s, 3H), 2.60-2.46 (m, 2H), 2.40-2.23 (m, 4H), 1.98-1.86 (m, 2H), 1.63-1.54 (m, 2H), 1.27 (t, J=7.5 Hz, 3H), 1.14 (s, 6H). MS (ESI) m/z: [M+H]⁺ Found 630.3.

Example 38

N-(((1s*,4s*)-1-Cyano-4-(methylsulfonyl)cyclohexyl)methyl)-1-(2-(difluoromethoxy)-4-(3,3,3-trifluoro-2,2-dimethylpropyl)phenyl)-2-ethyl-5-fluoro-1H-imidazole-4-carboxamide

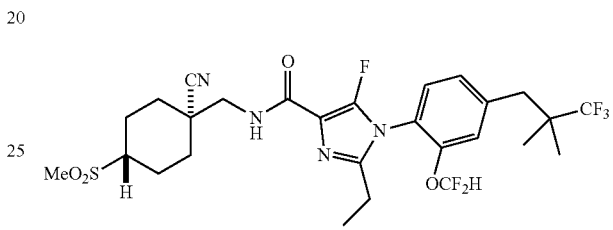

The title compound was prepared as described for the synthesis of Example 1, using ethyl 1-(2-(difluoromethoxy)-4-(3,3,3-trifluoro-2,2-dimethylpropyl)phenyl)-2-ethyl-5-fluoro-1H-imidazole-4-carboxylate (Intermediate 115) and (1s*,4s*)-1-(aminomethyl)-4-(methylsulfonyl)cyclohexane-1-carbonitrile hydrochloride (Intermediate 51) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 7.66 (t, J=6.8 Hz, 1H), 7.28 (d, J=8.1 Hz, 1H), 7.27-7.24 (m, 1H), 7.22 (dd, J=8.1, 1.8 Hz, 1H), 6.47 (appar dd, J=72.2, 71.0 Hz, 1H), 3.71-3.61 (m, 2H), 2.89 (s, 2H), 2.88-2.78 (m, 1H), 2.86 (s, 3H), 2.55-2.42 (m, J=7.8 Hz, 2H), 2.39-2.31 (m, 2H), 2.31-2.23 (m, 2H), 1.91 (qd, J=13.3, 3.5 Hz, 2H), 1.56 (td, J=13.7, 3.5 Hz, 2H), 1.19 (t, J=7.5 Hz, 3H), 1.14 (s, 6H). MS (ESI) m/z: [M+H]⁺ Found 623.2.

Example 39

N-(((1s*,4s*)-1-Cyano-4-(methylsulfonyl)cyclohexyl)methyl)-1-(2-(difluoromethoxy)-4-(3,3,3-trifluoro-2,2-dimethylpropyl)phenyl)-2-ethyl-5-ethynyl-1H-imidazole-4-carboxamide

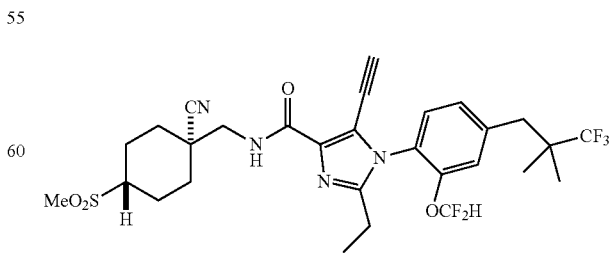

The title compound was prepared as described for the synthesis of Example 1, using 1-(2-(difluoromethoxy)-4-(3, 3,3-trifluoro-2,2-dimethylpropyl)phenyl)-2-ethyl-5-ethynyl-1H-imidazole-4-carboxylic acid (Intermediate 119) and (1s*,4s*)-1-(aminomethyl)-4-(methylsulfonyl)cyclohexane-1-carbonitrile hydrochloride (Intermediate 51) in place of 5-cyano-2-ethyl-1-(2-methoxy-4-(3,3,3-trifluoro-2-methylpropyl)phenyl)-1H-imidazole-4-carboxylic acid and (1s,4s)-1-(aminomethyl)-4-(methyl sulfonyl)cyclohexanol hydrochloride. $^1$H NMR (500 MHz, CDCl$_3$) δ 7.57 (t, J=7.0 Hz, 1H), 7.26 (d, J=8.0 Hz, 1H), 7.21 (s, 1H), 7.18 (dd, J=8.1, 1.8 Hz, 1H), 6.39 (dd, J=73.7, 70.8 Hz, 1H), 3.72-3.63 (m, 2H), 3.42 (s, 1H), 2.88 (s, 2H), 2.87-2.77 (m, 1H), 2.85 (s, 3H), 2.56-2.39 (m, 2H), 2.38-2.31 (m, 2H), 2.31-2.24 (m, 2H), 1.96-1.84 (m, 2H), 1.63-1.54 (m, 2H), 1.23 (t, J=7.5 Hz, 3H), 1.13 (s, 6H). MS (ESI) m/z: [M+H]$^+$ Found 628.9.

Example 40

1-(2-(Difluoromethoxy)-4-(3,3,3-trifluoro-2,2-dimethylpropyl)phenyl)-2-ethyl-5-ethynyl-N-(((1s,4s)-1-hydroxy-4-(methylsulfonyl)cyclohexyl)methyl)-1H-imidazole-4-carboxamide

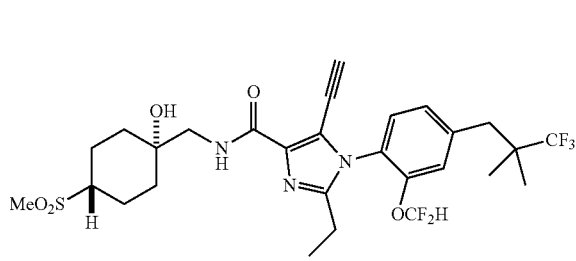

The title compound was prepared as described for the synthesis of Example 1, using 1-(2-(difluoromethoxy)-4-(3,3,3-trifluoro-2,2-dimethylpropyl)phenyl)-2-ethyl-5-ethynyl-1H-imidazole-4-carboxylic acid (Intermediate 119) in place of 5-cyano-2-ethyl-1-(2-methoxy-4-(3,3,3-trifluoro-2-methylpropyl)phenyl)-1H-imidazole-4-carboxylic acid. $^1$H NMR (500 MHz, CDCl$_3$) δ 8.14 (t, J=6.1 Hz, 1H), 7.29 (d, J=8.0 Hz, 1H), 7.26 (s, 1H), 7.23 (dd, J=8.1, 1.8 Hz, 1H), 6.45 (dd, J=72.7, 70.7 Hz, 1H), 4.88 (br s, 1H), 3.54-3.45 (m, 2H), 3.47 (s, 1H), 2.91 (s, 2H), 2.85-2.76 (m, 1H), 2.83 (s, 3H), 2.74-2.55 (m, 2H), 2.16-2.08 (m, 2H), 2.03-1.92 (m, 4H), 1.44 (td, J=14.1, 4.0 Hz, 2H), 1.23 (t, J=7.6 Hz, 3H), 1.15 (s, 6H). MS (ESI) m/z: [M+H]$^+$ Found 619.9.

Example 41

1-(2-(Difluoromethoxy)-4-(3,3,3-trifluoro-2,2-dimethylpropyl)phenyl)-2-ethyl-5-ethynyl-N-(((1r,4r)-4-(methylsulfonyl)cyclohexyl)methyl)-1H-imidazole-4-carboxamide

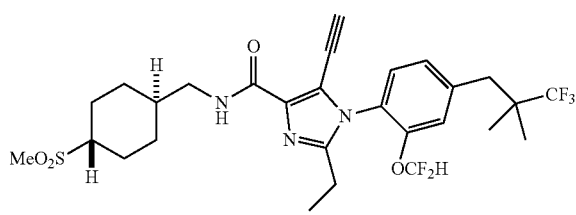

The title compound was prepared as described for the synthesis of Example 1, using 1-(2-(difluoromethoxy)-4-(3,3,3-trifluoro-2,2-dimethylpropyl)phenyl)-2-ethyl-5-ethynyl-1H-imidazole-4-carboxylic acid (Intermediate 119) and ((1r,4r)-4-(methylsulfonyl)cyclohexyl)methanamine hydrochloride (Intermediate 13) in place of 5-cyano-2-ethyl-1-(2-methoxy-4-(3,3,3-trifluoro-2-methylpropyl)phenyl)-1H-imidazole-4-carboxylic acid and (1s,4s)-1-(aminomethyl)-4-(methylsulfonyl)cyclohexanol hydrochloride. $^1$H NMR (500 MHz, CDCl$_3$) δ 7.97 (t, J=6.1 Hz, 1H), 7.30 (d, J=8.1 Hz, 1H), 7.27 (s, 1H), 7.23 (dd, J=8.0, 1.8 Hz, 1H), 6.45 (dd, J=72.7, 70.7 Hz, 1H), 3.45 (s, 1H), 3.38-3.32 (m, 2H), 2.91 (s, 2H), 2.86-2.78 (m, 1H), 2.83 (s, 3H), 2.76-2.58 (m, 2H), 2.31-2.23 (m, 2H), 2.09-2.02 (m, 2H), 1.75-1.65 (m, 1H), 1.63-1.52 (m, 2H), 1.23 (t, J=7.6 Hz, 3H), 1.18-1.07 (m, 2H), 1.15 (s, 6H). MS (ESI) m/z: [M+H]$^+$ Found 603.9.

Example 42

5-Chloro-2-ethyl-1-(3-methoxy-4-(3,3,3-trifluoro-2,2-dimethylpropyl)phenyl)-N-(((1r,4r)-4-(methylsulfonyl)cyclohexyl)methyl)-1H-imidazole-4-carboxamide

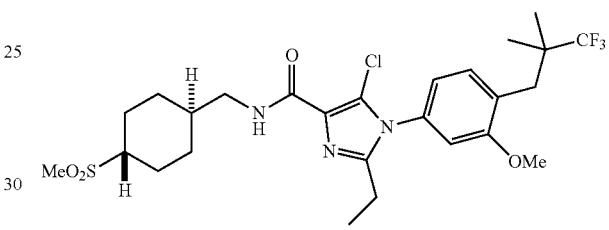

The title compound was prepared as described for the synthesis of Example 1, using ethyl 5-chloro-2-ethyl-1-(3-methoxy-4-(3,3,3-trifluoro-2,2-dimethylpropyl)phenyl)-1H-imidazole-4-carboxylate (Intermediate 106) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$) δ 7.87 (t, J=6.1 Hz, 1H), 7.31 (d, J=7.9 Hz, 1H), 6.81 (dd, J=7.9, 2.0 Hz, 1H), 6.71 (d, J=2.0 Hz, 1H), 3.83 (s, 3H), 3.33 (t, J=6.4 Hz, 2H), 2.94 (s, 2H), 2.86-2.78 (m, 1H), 2.83 (s, 3H), 2.71 (q, J=7.5 Hz, 2H), 2.31-2.24 (m, 2H), 2.09-2.02 (m, 2H), 1.74-1.64 (m, 1H), 1.58 (qd, J=13.0, 3.6 Hz, 2H), 1.22 (t, J=7.5 Hz, 3H), 1.18-1.06 (m, 8H). MS (ESI) m/z: [M+H]$^+$ Found 577.9.

Example 43

5-Chloro-2-ethyl-N-(((1s,4s)-1-hydroxy-4-(methylsulfonyl)cyclohexyl)methyl)-1-(3-methoxy-4-(3,3,3-trifluoro-2,2-dimethylpropyl)phenyl)-1H-imidazole-4-carboxamide

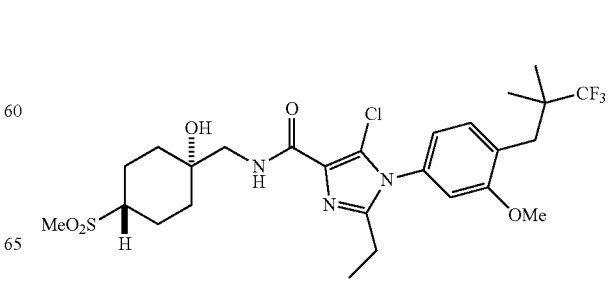

The title compound was prepared as described for the synthesis of Example 1, using ethyl 5-chloro-2-ethyl-1-(3-methoxy-4-(3,3,3-trifluoro-2,2-dimethylpropyl)phenyl)-1H-imidazole-4-carboxylate (Intermediate 106) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 8.23 (t, J=6.2 Hz, 1H), 7.34 (d, J=7.9 Hz, 1H), 6.83 (d, J=8.0 Hz, 1H), 6.73 (s, 1H), 5.13 (br s, 1H), 3.84 (s, 3H), 3.49 (d, J=6.0 Hz, 2H), 2.95 (br s, 2H), 2.84 (s, 3H), 2.84-2.70 (m, 3H), 2.16-2.06 (m, 2H), 2.02-1.90 (m, 4H), 1.44 (td, J=14.3, 4.1 Hz, 2H), 1.23 (t, J=7.5 Hz, 3H), 1.10 (s, 6H). MS (ESI) m/z: [M+H]$^+$ Found 593.9.

Example 44

2-Ethyl-1-(3-methoxy-4-(3,3,3-trifluoro-2,2-dimethylpropyl)phenyl)-5-methyl-N-(((1r,4r)-4-(methylsulfonyl)cyclohexyl)methyl)-1H-imidazole-4-carboxamide

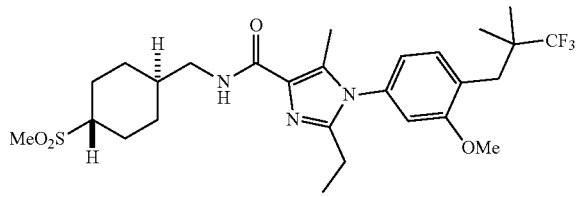 [SMILES: CCc1nc(C(=O)NC[C@H]2CC[C@H](S(C)(=O)=O)CC2)c(C)n1-c1ccc(CC(C)(C)C(F)(F)F)c(OC)c1]

The title compound was prepared as described for the synthesis of Example 1, using ethyl 2-ethyl-1-(3-methoxy-4-(3,3,3-trifluoro-2,2-dimethylpropyl)phenyl)-5-methyl-1H-imidazole-4-carboxylate (Intermediate 107) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$) δ 8.62 (t, J=5.7 Hz, 1H), 7.37 (d, J=7.9 Hz, 1H), 6.81 (dd, J=7.9, 2.1 Hz, 1H), 6.70 (d, J=2.1 Hz, 1H), 3.85 (s, 3H), 3.32 (t, J=6.2 Hz, 2H), 3.01-2.91 (m, 2H), 2.91-2.77 (m, 3H), 2.82 (s, 3H), 2.41 (s, 3H), 2.30-2.23 (m, 2H), 2.09-2.01 (m, 2H), 1.74-1.64 (m, 1H), 1.57 (qd, J=13.0, 3.6 Hz, 2H), 1.26 (t, J=7.6 Hz, 3H), 1.17-1.06 (m, 2H), 1.11 (s, 6H). MS (ESI) m/z: [M+H]$^+$ Found 558.0.

Example 45

2-Ethyl-N-(((1s,4s)-1-hydroxy-4-(methylsulfonyl)cyclohexyl)methyl)-1-(3-methoxy-4-(3,3,3-trifluoro-2,2-dimethylpropyl)phenyl)-5-methyl-1H-imidazole-4-carboxamide

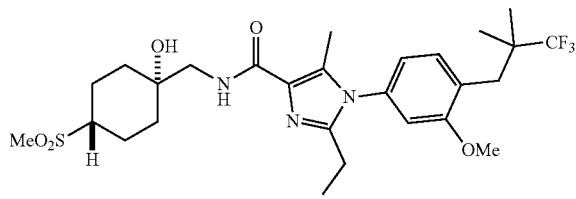

The title compound was prepared as described for the synthesis of Example 1, using ethyl 2-ethyl-1-(3-methoxy-4-(3,3,3-trifluoro-2,2-dimethylpropyl)phenyl)-5-methyl-1H-imidazole-4-carboxylate (Intermediate 106) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 8.87 (t, J=5.8 Hz, 1H), 7.38 (d, J=7.9 Hz, 1H), 6.82 (d, J=7.7 Hz, 1H), 6.71 (s, 1H), 5.88 (br s, 1H), 3.85 (s, 3H), 3.54-3.43 (m, 2H), 3.00-2.91 (m, 2H), 2.91-2.74 (m, 3H), 2.82 (s, 3H), 2.41 (s, 3H), 2.13-2.06 (m, 2H), 2.03-1.91 (m, 4H), 1.42 (td, J=13.8, 3.7 Hz, 2H), 1.26 (t, J=7.6 Hz, 3H), 1.11 (s, 6H). MS (ESI) m/z: [M+H]$^+$ Found 574.0.

Example 46

5-Chloro-1-(3-(difluoromethoxy)-5-(3,3,3-trifluoro-2,2-dimethylpropyl)pyridin-2-yl)-2-ethyl-N-(((1s,4s)-1-hydroxy-4-(methylsulfonyl)cyclohexyl)methyl)-1H-imidazole-4-carboxamide

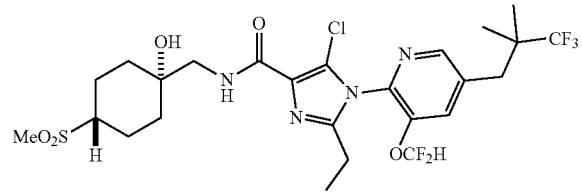

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (Intermediate 85) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 8.35 (d, J=1.9 Hz, 1H), 7.89 (t, J=6.2 Hz, 1H), 7.70 (s, 1H), 6.53 (t, J=70.6 Hz, 1H), 4.17 (br s, 1H), 3.54-3.41 (m, 2H), 2.95 (s, 2H), 2.85-2.77 (m, 1H), 2.83 (s, 3H), 2.65-2.52 (m, 2H), 2.16-2.09 (m, 2H), 2.03-1.92 (m, 4H), 1.48-1.38 (m, 2H), 1.24-1.15 (m, 9H). MS (ESI) m/z: [M+H]$^+$ Found 631.2.

Example 47

5-Chloro-1-(3-(difluoromethoxy)-5-(4,4,4-trifluorobutyl)pyridin-2-yl)-2-ethyl-N-(((1s,4s)-1-hydroxy-4-(methylsulfonyl)cyclohexyl)methyl)-1H-imidazole-4-carboxamide

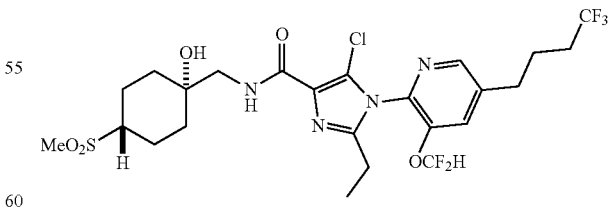

The title compound was prepared as described for the synthesis of Example 1, using ethyl 5-chloro-1-(3-(difluoromethoxy)-5-(4,4,4-trifluorobutyl)pyridin-2-yl)-2-ethyl-1H-imidazole-4-carboxylate (Intermediate 84) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl₃) δ 8.39 (d, J=1.9 Hz, 1H), 7.85 (t, J=6.3 Hz, 1H), 7.70 (s, 1H), 6.53 (appar t, J=71 Hz, 1H), 4.65 (br s, 1H), 3.54-3.40 (m, 2H), 2.91-2.85 (m, 2H), 2.85-2.76 (m, 1H), 2.83 (s, 3H), 2.63-2.52 (m, 2H), 2.29-2.18 (m, 2H), 2.16-2.08 (m, 2H), 2.07-1.92 (m, 6H), 1.48-1.38 (m, 2H), 1.21 (t, J=7.6 Hz, 3H). MS (ESI) m/z: [M+H]⁺ Found 616.6.

Example 48

5-Chloro-1-(3-(difluoromethoxy)-5-(4,4,4-trifluorobutyl)pyridin-2-yl)-2-ethyl-N-(((1r,4r)-4-(methylsulfonyl)cyclohexyl)methyl)-1H-imidazole-4-carboxamide

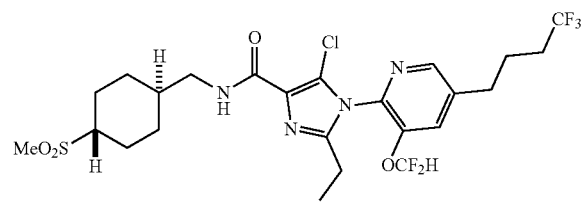

The title compound was prepared as described for the synthesis of Example 1, using ethyl 5-chloro-1-(3-(difluoromethoxy)-5-(4,4,4-trifluorobutyl)pyridin-2-yl)-2-ethyl-1H-imidazole-4-carboxylate (Intermediate 84) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 8.38 (d, J=1.9 Hz, 1H), 7.69 (s, 1H), 7.63 (t, J=6.3 Hz, 1H), 6.52 (appar t, J=71 Hz, 1H), 3.33 (t, J=6.5 Hz, 2H), 2.91-2.85 (m, 2H), 2.85-2.79 (m, 1H), 2.83 (s, 3H), 2.65-2.52 (m, 2H), 2.32-2.17 (m, 4H), 2.11-1.98 (m, 4H), 1.74-1.64 (m, 1H), 1.58 (qd, J=13.0, 3.6 Hz, 2H), 1.20 (t, J=7.6 Hz, 3H), 1.13 (qd, J=13.1, 3.5 Hz, 2H). MS (ESI) m/z: [M+H]⁺ Found 600.5.

Example 49

1-(3-(Difluoromethoxy)-5-(3,3,3-trifluoro-2,2-dimethylpropyl)pyridin-2-yl)-2-ethyl-5-methyl-N-(((1r,4r)-4-(methylsulfonyl)cyclohexyl)methyl)-1H-imidazole-4-carboxamide

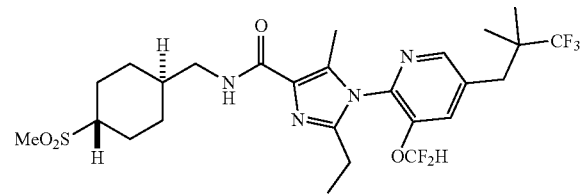

The title compound was prepared as described for the synthesis of Example 1, using ethyl 1-(3-(difluoromethoxy)-5-(3,3,3-trifluoro-2,2-dimethylpropyl)pyridin-2-yl)-2-ethyl-5-methyl-1H-imidazole-4-carboxylate (Intermediate 89) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methyl sulfonyl)cyclohexanol hydrochloride. ¹H NMR (600 MHz, CDCl₃) δ 8.33 (d, J=2.0 Hz, 1H), 7.64 (s, 1H), 7.33 (t, J=6.5 Hz, 1H), 6.43 (t, J=71.0 Hz, 1H), 3.35-3.26 (m, 2H), 2.92 (s, 2H), 2.86-2.80 (m, 1H), 2.83 (s, 3H), 2.50-2.42 (m, 2H), 2.34 (s, 3H), 2.30-2.25 (m, 2H), 2.12-2.06 (m, 2H), 1.71-1.63 (m, 1H), 1.63-1.55 (m, 2H), 1.19-1.09 (m, 11H). MS (ESI) m/z: [M+H]⁺ Found 594.7.

Example 50

1-(3-(Difluoromethoxy)-5-(3,3,3-trifluoro-2,2-dimethylpropyl)pyridin-2-yl)-2-ethyl-N-(((1s,4s)-1-hydroxy-4-(methylsulfonyl)cyclohexyl)methyl)-5-methyl-1H-imidazole-4-carboxamide

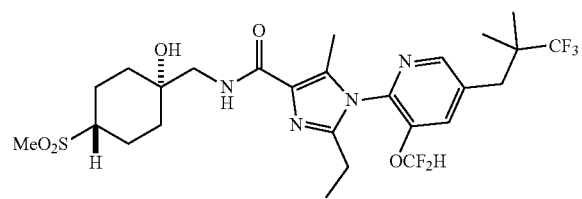

The title compound was prepared as described for the synthesis of Example 1, using ethyl 1-(3-(difluoromethoxy)-5-(3,3,3-trifluoro-2,2-dimethylpropyl)pyridin-2-yl)-2-ethyl-5-methyl-1H-imidazole-4-carboxylate (Intermediate 89) in place of ethyl 5-cyano-2-ethyl-1-(2-methoxy-4-(3,3,3-trifluoro-2-methylpropyl)phenyl)-1H-imidazole-4-carboxylate. ¹H NMR (600 MHz, CDCl₃) δ 8.33 (d, J=2.0 Hz, 1H), 7.64 (s, 1H), 7.33 (t, J=6.5 Hz, 1H), 6.43 (t, J=71.0 Hz, 1H), 3.35-3.26 (m, 2H), 2.92 (s, 2H), 2.86-2.80 (m, 1H), 2.83 (s, 3H), 2.50-2.42 (m, 2H), 2.34 (s, 3H), 2.30-2.25 (m, 2H), 2.12-2.06 (m, 2H), 1.71-1.63 (m, 1H), 1.63-1.55 (m, 2H), 1.19-1.09 (m, 11H). MS (ESI) m/z: [M+H]⁺ Found 610.6.

Example 51

1-(3-(Difluoromethoxy)-5-(4,4,4-trifluorobutyl)pyridin-2-yl)-2-ethyl-5-methyl-N-(((1r,4r)-4-(methylsulfonyl)cyclohexyl)methyl)-1H-imidazole-4-carboxamide

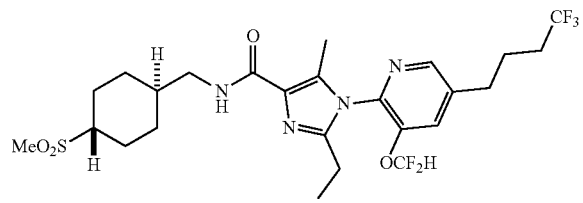

The title compound was prepared as described for the synthesis of Example 1, using ethyl 1-(3-(difluoromethoxy)-5-(4,4,4-trifluorobutyl)pyridin-2-yl)-2-ethyl-5-methyl-1H-imidazole-4-carboxylate (Intermediate 90) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 8.36 (d, J=2.0 Hz, 1H), 7.64 (s, 1H), 7.33 (t, J=6.5 Hz, 1H), 6.43 (t, J=71.2 Hz, 1H), 3.35-3.26 (m, 2H), 2.88-2.79 (m, 6H), 2.51-2.39 (m, 2H), 2.34 (s, 3H), 2.31-2.26 (m, 2H), 2.26-2.17 (m, 2H), 2.12-2.06 (m, 2H), 2.05-1.97 (m, 2H), 1.72-1.63 (m, 1H), 1.63-1.53 (m, 2H), 1.18 (t, J=7.5 Hz, 3H), 1.17-1.08 (m, 2H). MS (ESI) m/z: [M+H]$^+$ Found 581.3.

Example 52

1-(3-(Difluoromethoxy)-5-(4,4,4-trifluorobutyl)pyridin-2-yl)-2-ethyl-N-(((1s,4s)-1-hydroxy-4-(methylsulfonyl)cyclohexyl)methyl)-5-methyl-1H-imidazole-4-carboxamide

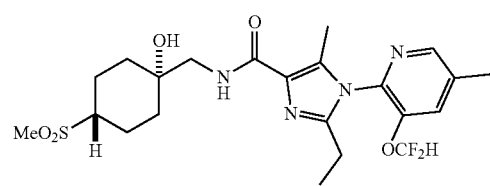

The title compound was prepared as described for the synthesis of Example 1, using ethyl 1-(3-(difluoromethoxy)-5-(4,4,4-trifluorobutyl)pyridin-2-yl)-2-ethyl-5-methyl-1H-imidazole-4-carboxylate (Intermediate 90) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 8.37 (d, J=2.0 Hz, 1H), 7.65 (s, 1H), 7.57 (t, J=6.3 Hz, 1H), 6.45 (t, J=71.0 Hz, 1H), 4.15 (s, 1H), 3.42 (qd, J=14.2, 6.4 Hz, 2H), 2.88-2.83 (m, 2H), 2.82 (s, 3H), 2.81-2.75 (m, 1H), 2.50-2.39 (m, 2H), 2.32 (s, 3H), 2.28-2.17 (m, 2H), 2.16-2.08 (m, 2H), 2.06-1.93 (m, 6H), 1.38 (tt, J=14.3, 4.3 Hz, 2H), 1.18 (t, J=7.5 Hz, 3H). MS (ESI) m/z: [M+H]$^+$ Found 597.2.

Example 53

5-Cyano-1-(2-(difluoromethoxy)-4-(3,3,3-trifluoro-2,2-dimethylpropyl)phenyl)-2-methyl-N-(((1r,4r)-4-(methylsulfonyl)cyclohexyl)methyl)-1H-imidazole-4-carboxamide

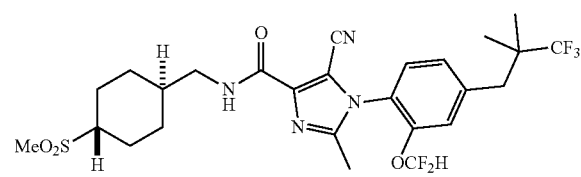

The title compound was prepared as described for the synthesis of Example 1, using ethyl 5-cyano-1-(2-(difluoromethoxy)-4-(3,3,3-trifluoro-2,2-dimethylpropyl)phenyl)-2-methyl-1H-imidazole-4-carboxylate (Intermediate 90) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (400 MHz, CDCl$_3$) δ 7.41 (t, J=6.4 Hz, 1H), 7.32 (d, J=8.6 Hz, 1H), 7.27-7.23 (m, 2H), 6.48 (dd, J=73.0, 70.5 Hz, 1H), 3.36 (t, J=6.6 Hz, 2H), 2.90 (s, 3H), 2.89-2.80 (m, 1H), 2.84 (s, 3H), 2.33-2.24 (m, 2H), 2.31 (s, 3H), 2.10-2.01 (m, 2H), 1.75-1.53 (m, 3H), 1.20-1.07 (m, 2H), 1.14 (s, 6H). MS (ESI) m/z: [M+H]$^+$ Found 590.7.

Example 54

5-Cyano-1-(2-(difluoromethoxy)-4-(3,3,3-trifluoro-2,2-dimethylpropyl)phenyl)-N-(((1s,4s)-1-hydroxy-4-(methylsulfonyl)cyclohexyl)methyl)-2-methyl-1H-imidazole-4-carboxamide

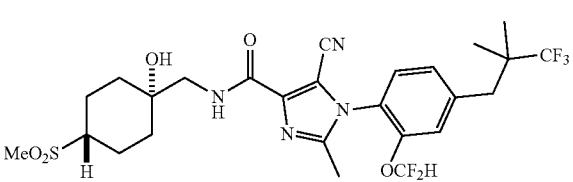

The title compound was prepared as described for the synthesis of Example 1, using ethyl 5-cyano-1-(2-(difluoromethoxy)-4-(3,3,3-trifluoro-2,2-dimethylpropyl)phenyl)-2-methyl-1H-imidazole-4-carboxylate (Intermediate 90) in place of ethyl 5-cyano-2-ethyl-1-(2-methoxy-4-(3,3,3-trifluoro-2-methylpropyl)phenyl)-1H-imidazole-4-carboxylate. $^1$H NMR (400 MHz, CDCl$_3$) δ 7.63 (t, J=6.4 Hz, 1H), 7.32 (d, J=8.4 Hz, 1H), 7.28-7.23 (m, 2H), 6.48 (dd, J=72.8, 70.5 Hz, 1H), 3.55-3.44 (m, 2H), 3.23 (br s, 1H), 2.90 (s, 2H), 2.88-2.78 (m, 1H), 2.85 (s, 3H), 2.30 (s, 3H), 2.18-2.09 (m, 2H), 2.04-1.90 (m, 4H), 1.46 (td, J=14.0, 3.8 Hz, 2H), 1.14 (s, 6H). MS (ESI) m/z: [M+H]$^+$ Found 606.7.

Example 55

5-Cyano-1-(2-(difluoromethoxy)-4-(3,3,3-trifluoro-2,2-dimethylpropyl)phenyl)-N-(((1RS,2SR,4SR)-2-hydroxy-4-(methylsulfonyl)cyclohexyl)methyl)-2-methyl-1H-imidazole-4-carboxamide

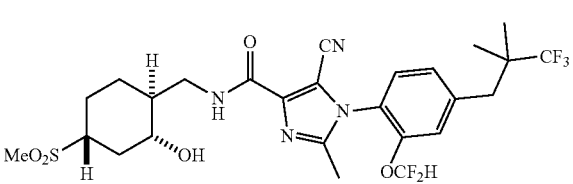

The title compound was prepared as described for the synthesis of Example 1, using ethyl 5-cyano-1-(2-(difluoromethoxy)-4-(3,3,3-trifluoro-2,2-dimethylpropyl)phenyl)-2-methyl-1H-imidazole-4-carboxylate (Intermediate 90) and (1RS,2SR,5RS)-2-(aminomethyl)-5-(methylsulfonyl)cyclohexan-1-ol hydrochloride (Intermediate 54) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methyl sulfonyl)cyclohexanol hydrochloride. $^1$H NMR (500 MHz, CDCl$_3$, mixture of rotamers) δ 7.45-7.39 (m, 1H), 7.33-7.30 (m, 1H), 7.26-7.23 (m, 2H), 6.65-6.31 (m, 1H), 4.50-4.39 (m, 1H), 4.22-4.15 (m, 1H), 3.44-3.33 (m, 1H), 3.13-3.07 (m, 1H), 2.95-2.84 (m, 1H), 2.90 (s, 3H), 2.84 (s, 3H of one rotamer), 2.83 (s, 3H of one rotamer), 2.51-2.45 (m, 1H), 2.30-2.23 (m, 1H), 2.28 (s, 3H), 1.98-1.91 (m, 1H), 1.73-1.54 (m, 2H), 1.41-1.29 (m, 1H), 1.14 (s, 6H). MS (ESI) m/z: [M+H]$^+$ Found 606.7.

Example 56

5-Cyano-1-(2-(difluoromethoxy)-4-(3,3,3-trifluoro-2,2-dimethylpropyl)phenyl)-N-(((1R*,2S*,4S*)-2-hydroxy-4-(methylsulfonyl)cyclohexyl)methyl)-2-methyl-1H-imidazole-4-carboxamide

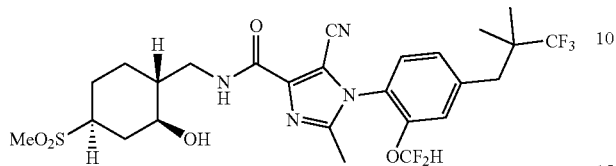

Example 57

5-Cyano-1-(2-(difluoromethoxy)-4-(3,3,3-trifluoro-2,2-dimethylpropyl)phenyl)-N-(((1S*,2R*,4R*)-2-hydroxy-4-(methylsulfonyl)cyclohexyl)methyl)-2-methyl-1H-imidazole-4-carboxamide

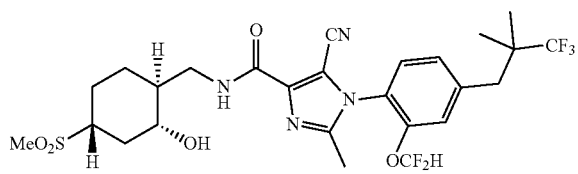

Example 55 was purified by SFC using a chiral stationary phase (Chiralpak IC, 70% CO$_2$, 30% EtOH) to give a pair of enantiomers. The first-eluting isomer was Example 56, and the second-eluting isomer was Example 57. Example 7: $^1$H NMR (500 MHz, CDCl$_3$, mixture of rotamers) δ 7.45-7.39 (m, 1H), 7.33-7.30 (m, 1H), 7.26-7.23 (m, 2H), 6.65-6.31 (m, 1H), 4.50-4.39 (m, 1H), 4.22-4.15 (m, 1H), 3.44-3.33 (m, 1H), 3.13-3.07 (m, 1H), 2.95-2.84 (m, 1H), 2.90 (s, 3H), 2.84 (s, 3H of one rotamer), 2.83 (s, 3H of one rotamer), 2.51-2.45 (m, 1H), 2.30-2.23 (m, 1H), 2.28 (s, 3H), 1.98-1.91 (m, 1H), 1.73-1.54 (m, 2H), 1.41-1.29 (m, 1H), 1.14 (s, 6H). MS (ESI) m/z: [M+H]$^+$ Found 606.7. Example 57: $^1$H NMR (500 MHz, CDCl$_3$, mixture of rotamers) δ 7.45-7.39 (m, 1H), 7.33-7.30 (m, 1H), 7.26-7.23 (m, 2H), 6.65-6.31 (m, 1H), 4.50-4.39 (m, 1H), 4.22-4.15 (m, 1H), 3.44-3.33 (m, 1H), 3.13-3.07 (m, 1H), 2.95-2.84 (m, 1H), 2.90 (s, 3H), 2.84 (s, 3H of one rotamer), 2.83 (s, 3H of one rotamer), 2.51-2.45 (m, 1H), 2.30-2.23 (m, 1H), 2.28 (s, 3H), 1.98-1.91 (m, 1H), 1.73-1.54 (m, 2H), 1.41-1.29 (m, 1H), 1.14 (s, 6H). MS (ESI) m/z: [M+H]$^+$ Found 606.7.

Example 58

5-Chloro-1-(3-(difluoromethoxy)-5-(3,3,3-trifluoro-2,2-dimethylpropyl)pyridin-2-yl)-2-ethyl-N-(((1R*,2S*,4S*)-2-hydroxy-4-(methylsulfonyl)cyclohexyl)methyl)-1H-imidazole-4-carboxamide

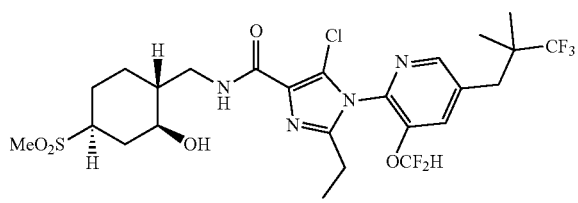

Example 59

5-Chloro-1-(3-(difluoromethoxy)-5-(3,3,3-trifluoro-2,2-dimethylpropyl)pyridin-2-yl)-2-ethyl-N-(((1S*,2R*,4R*)-2-hydroxy-4-(methylsulfonyl)cyclohexyl)methyl)-1H-imidazole-4-carboxamide

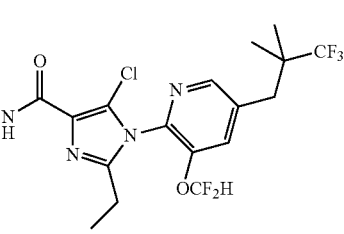

Intermediate 191 was purified by SFC using a chiral stationary phase (Lux Cellulose 2, 75% CO$_2$, 25% MeOH) to give a pair of enantiomers. The first-eluting isomer was Example 58, and the second-eluting isomer was Example 59. Example 58: $^1$H NMR (500 MHz, CDCl$_3$, mixture of rotamers) δ 8.34 (d, J=1.9 Hz, 1H), 7.66 (s, 1H), 7.47-7.41 (m, 1H), 6.67-6.32 (m, 1H), 5.06 (dd, J=8.1, 4.0 Hz, 1H), 4.25-4.18 (m, 1H), 3.42-3.32 (m, 1H), 3.06-2.99 (m, 1H), 2.93 (s, 2H), 2.92-2.86 (m, 1H), 2.83 (s, 3H of one rotamer), 2.82 (s, 3H of one rotamer), 2.57-2.41 (m, 3H), 2.30-2.23 (m, 1H), 1.96-1.89 (m, 1H), 1.72-1.50 (m, 3H), 1.46-1.32 (m, 1H), 1.22-1.16 (m, 9H). MS (ESI) m/z: [M+H]$^+$ Found 631.2. Example 59: $^1$H NMR (500 MHz, CDCl$_3$, mixture of rotamers) δ 8.34 (d, J=1.9 Hz, 1H), 7.66 (s, 1H), 7.47-7.41 (m, 1H), 6.67-6.32 (m, 1H), 5.06 (dd, J=8.1, 4.0 Hz, 1H), 4.25-4.18 (m, 1H), 3.42-3.32 (m, 1H), 3.06-2.99 (m, 1H), 2.93 (s, 2H), 2.92-2.86 (m, 1H), 2.83 (s, 3H of one rotamer), 2.82 (s, 3H of one rotamer), 2.57-2.41 (m, 3H), 2.30-2.23 (m, 1H), 1.96-1.89 (m, 1H), 1.72-1.50 (m, 3H), 1.46-1.32 (m, 1H), 1.22-1.16 (m, 9H). MS (ESI) m/z: [M+H]$^+$ Found 631.2.

Example 60

5-Chloro-1-(3-(difluoromethoxy)-5-(3,3,3-trifluoro-2,2-dimethylpropyl)pyridin-2-yl)-N-(((1R*,2R*,4R*)-1,2-dihydroxy-4-(methylsulfonyl)cyclohexyl)methyl)-2-ethyl-1H-imidazole-4-carboxamide

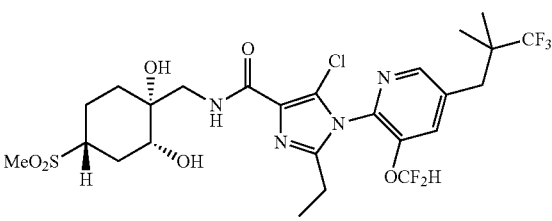

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (Intermediate 85) and (1R*,2R*,4R*)-1-(aminomethyl)-4-(methylsulfonyl)cyclohexane-1,2-diol hydrochloride (Intermediate 23) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$) δ 8.35 (s, 1H), 7.89 (appar q, J=6.9 Hz, 1H), 7.70 (s, 1H), 6.55 (td, J=70.7, 15.3 Hz, 1H), 4.45 (br s, 2H), 3.86-3.78 (m, 1H), 3.65-3.58 (m, 1H), 3.23-3.16 (m, 1H), 2.95 (s, 2H), 2.90-2.81 (m, 1H), 2.84 (s, 3H of one rotamer), 2.83 (s, 3H of one rotamer), 2.63-2.52 (m, 2H), 2.30-2.26 (m, 1H), 2.07-1.88 (m, 4H), 1.59-1.49 (m, 1H), 1.22-1.16 (m, 9H). MS (ESI) m/z: [M+H]+ Found 646.5.

Example 61

5-Chloro-1-(3-(difluoromethoxy)-5-(3,3,3-trifluoro-2,2-dimethylpropyl)pyridin-2-yl)-N-(((1S*,2S*,4S*)-1,2-dihydroxy-4-(methylsulfonyl)cyclohexyl)methyl)-2-ethyl-1H-imidazole-4-carboxamide

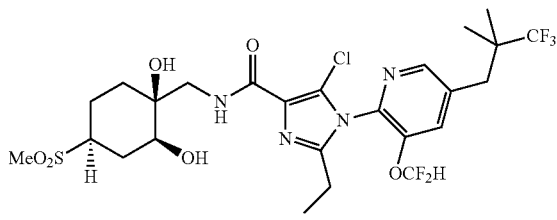

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (Intermediate 85) and (1S*,2S*,4S*)-1-(aminomethyl)-4-(methyl sulfonyl)cyclohexane-1,2-diol hydrochloride (Intermediate 23) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. 1H NMR (500 MHz, CDCl3) δ 8.35 (d, J=1.8 Hz, 1H), 7.74 (q, J=6.1 Hz, 1H), 7.69 (s, 1H), 6.69-6.35 (m, 1H), 3.87-3.80 (m, 1H), 3.59 (td, J=11.3, 4.7 Hz, 1H), 3.12 (dt, J=14.2, 6.2 Hz, 1H), 2.96 (br s, 2H), 2.95 (s, 2H), 2.88-2.81 (m, 1H), 2.83 (s, 3H of one rotamer), 2.82 (s, 3H of one rotamer), 2.58-2.49 (m, 2H), 2.31-2.23 (m, 1H), 2.09-2.02 (m, 1H), 2.01-1.88 (m, 3H), 1.55 (qd, J=14.8, 14.2, 4.5 Hz, 1H), 1.22-1.17 (m, 9H). MS (ESI) m/z: [M+H]+ Found 646.5.

Example 62

5-Chloro-1-(3-(difluoromethoxy)-5-(3,3,3-trifluoro-2-(trifluoromethyl)propyl)pyridin-2-yl)-2-ethyl-N-(((1s,4s)-1-hydroxy-4-(methylsulfonyl)cyclohexyl)methyl)-1H-imidazole-4-carboxamide

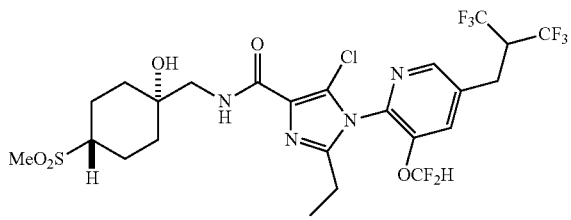

The title compound was prepared as described for the synthesis of Example 1, using 5-chloro-1-(3-(difluoromethoxy)-5-(3,3,3-trifluoro-2-(trifluoromethyl)propyl)pyridin-2-yl)-2-ethyl-1H-imidazole-4-carboxylic acid (Intermediate 122) in place of 5-cyano-2-ethyl-1-(2-methoxy-4-(3,3,3-trifluoro-2-methylpropyl)phenyl)-1H-imidazole-4-carboxylic acid. 1H NMR (500 MHz, CDCl3) δ 8.43 (d, J=2.0 Hz, 1H), 7.73 (s, 1H), 7.52 (t, J=6.4 Hz, 1H), 6.66-6.36 (m, 1H), 3.50-3.39 (m, 2H), 3.49 (s, 1H), 3.36-3.25 (m, 3H), 2.84-2.75 (m, 1H), 2.83 (s, 3H), 2.56-2.40 (m, 2H), 2.16-2.09 (m, 2H), 2.04-1.93 (m, 4H), 1.46-1.36 (m, 2H), 1.19 (t, J=7.5 Hz, 3H). MS (ESI) m/z: [M+H]+ Found 670.7.

Example 63

5-Chloro-1-(3-(difluoromethoxy)-5-(3,3,3-trifluoro-2-(trifluoromethyl)propyl)pyridin-2-yl)-2-ethyl-N-(((1r,4r)-4-(methylsulfonyl)cyclohexyl)methyl)-1H-imidazole-4-carboxamide

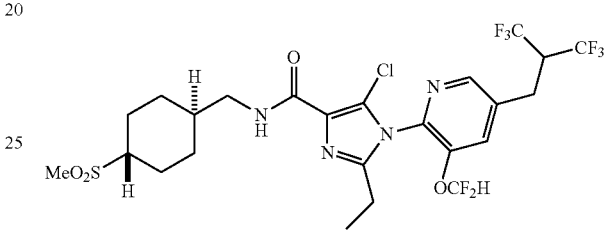

The title compound was prepared as described for the synthesis of Example 1, using 5-chloro-1-(3-(difluoromethoxy)-5-(3,3,3-trifluoro-2-(trifluoromethyl)propyl)pyridin-2-yl)-2-ethyl-1H-imidazole-4-carboxylic acid (Intermediate 122) and ((1r,4r)-4-(methylsulfonyl)cyclohexyl)methanamine hydrochloride (Intermediate 13) in place of 5-cyano-2-ethyl-1-(2-methoxy-4-(3,3,3-trifluoro-2-methylpropyl)phenyl)-1H-imidazole-4-carboxylic acid and (1s,4s)-1-(aminomethyl)-4-(methylsulfonyl)cyclohexanol hydrochloride. 1H NMR (500 MHz, CDCl3) δ 8.43 (d, J=2.0 Hz, 1H), 7.72 (s, 1H), 7.31 (t, J=6.5 Hz, 1H), 6.65-6.35 (m, 1H), 3.36-3.25 (m, 5H), 2.87-2.79 (m, 1H), 2.82 (s, 3H), 2.57-2.42 (m, 2H), 2.31-2.24 (m, 2H), 2.11-2.04 (m, 2H), 1.76-1.65 (m, 1H), 1.59 (qd, J=12.8, 3.6 Hz, 2H), 1.20 (t, J=7.5 Hz, 3H), 1.18-1.09 (m, 2H). MS (ESI) m/z: [M+H]+ Found 655.1.

Example 64

5-Chloro-1-(3-(difluoromethoxy)-5-(3,3,3-trifluoro-2-(trifluoromethyl)propyl)pyridin-2-yl)-2-ethyl-N-(((1R*,2S*,4S*)-2-hydroxy-4-(methylsulfonyl)cyclohexyl)methyl)-H-imidazole-4-carboxamide

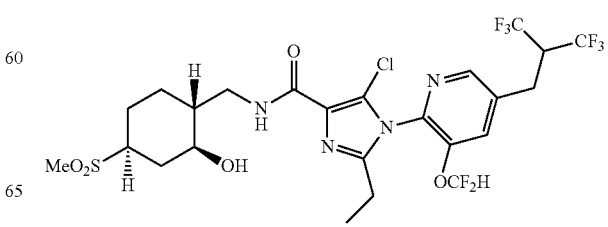

Example 65

5-Chloro-1-(3-(difluoromethoxy)-5-(3,3,3-trifluoro-2-(trifluoromethyl)propyl)pyridin-2-yl)-2-ethyl-N-(((1S*,2R*,4R*)-2-hydroxy-4-(methylsulfonyl)cyclohexyl)methyl)-1H-imidazole-4-carboxamide

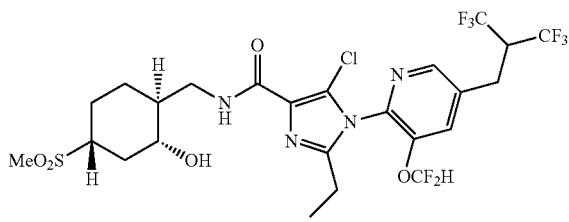

Intermediate 192 was purified by SFC using a chiral stationary phase (Lux Cellulose 2, 80% CO₂, 20% MeOH) to give a pair of enantiomers. The first-eluting isomer was Example 64, and the second-eluting isomer was Example 65. Example 64: ¹H NMR (400 MHz, CDCl₃, mixture of rotamers) δ 8.43 (d, J=2.0 Hz, 1H), 7.73 (s, 1H), 7.48-7.41 (m, 1H), 6.72-6.30 (m, 1H), 5.03 (dd, J=7.8, 4.0 Hz, 1H), 4.26-4.16 (m, 1H), 3.42-3.25 (m, 4H), 3.07-2.99 (m, 1H), 2.95-2.86 (m, 1H), 2.83 (s, 3H of one rotamer), 2.82 (s, 3H of one rotamer), 2.55-2.41 (m, 3H), 2.31-2.23 (m, 1H), 1.97-1.88 (m, 1H), 1.73-1.49 (m, 3H), 1.46-1.31 (m, 1H), 1.23-1.16 (m, 3H). MS (ESI) m/z: [M+H]⁺ Found 671.0. Example 65: ¹H NMR (400 MHz, CDCl₃, mixture of rotamers) δ 8.43 (d, J=2.0 Hz, 1H), 7.73 (s, 1H), 7.48-7.41 (m, 1H), 6.72-6.30 (m, 1H), 5.03 (dd, J=7.8, 4.0 Hz, 1H), 4.26-4.16 (m, 1H), 3.42-3.25 (m, 4H), 3.07-2.99 (m, 1H), 2.95-2.86 (m, 1H), 2.83 (s, 3H of one rotamer), 2.82 (s, 3H of one rotamer), 2.55-2.41 (m, 3H), 2.31-2.23 (m, 1H), 1.97-1.88 (m, 1H), 1.73-1.49 (m, 3H), 1.46-1.31 (m, 1H), 1.23-1.16 (m, 3H). MS (ESI) m/z: [M+H]⁺ Found 671.0.

Example 66

5-Chloro-1-(3-(difluoromethoxy)-5-(3,3,3-trifluoro-2-(trifluoromethyl)propyl)pyridin-2-yl)-N-(((1S*,2S*,4S*)-1,2-dihydroxy-4-(methylsulfonyl)cyclohexyl)methyl)-2-ethyl-1H-imidazole-4-carboxamide

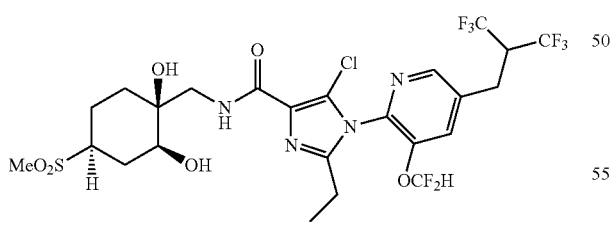

The title compound was prepared as described for the synthesis of Example 1, using 5-chloro-1-(3-(difluoromethoxy)-5-(3,3,3-trifluoro-2-(trifluoromethyl)propyl)pyridin-2-yl)-2-ethyl-1H-imidazole-4-carboxylic acid (Intermediate 122) and (1S*,2S*,4S*)-1-(aminomethyl)-4-(methylsulfonyl)cyclohexane-1,2-diol hydrochloride (Intermediate 23) in place of 5-cyano-2-ethyl-1-(2-methoxy-4-(3,3,3-trifluoro-2-methylpropyl)phenyl)-1H-imidazole-4-carboxylic acid and (1s,4s)-1-(aminomethyl)-4-(methylsulfonyl)cyclohexanol hydrochloride. ¹H NMR (500 MHz, CDCl₃) δ 8.44 (s, 1H), 7.74 (s, 1H), 7.66-7.61 (m, 1H), 6.70-6.36 (m, 1H), 3.88-3.81 (m, 1H), 3.59 (td, J=11.4, 4.7 Hz, 1H), 3.36-3.26 (m, 3H), 3.10 (dt, J=14.1, 6.2 Hz, 1H), 2.88-2.80 (m, 1H), 2.83 (s, 3H of one rotamer), 2.82 (3H of one rotamer), 2.66 (br s, 2H), 2.58-2.44 (m, 2H), 2.31-2.23 (m, 1H), 2.08-2.03 (m, 1H), 2.01-1.87 (m, 3H), 1.55 (qd, J=13.9, 4.8 Hz, 1H), 1.19 (td, J=7.5, 1.8 Hz, 3H). MS (ESI) m/z: [M+H]⁺ Found 687.1.

Example 67

5-Chloro-1-(3-(difluoromethoxy)-5-(3,3,3-trifluoro-2-(trifluoromethyl)propyl)pyridin-2-yl)-N-(((1R*,2R*,4R*)-1,2-dihydroxy-4-(methylsulfonyl)cyclohexyl)methyl)-2-ethyl-1H-imidazole-4-carboxamide

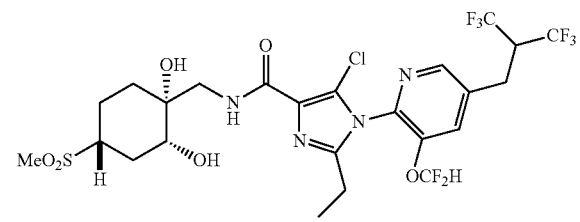

The title compound was prepared as described for the synthesis of Example 1, using 5-chloro-1-(3-(difluoromethoxy)-5-(3,3,3-trifluoro-2-(trifluoromethyl)propyl)pyridin-2-yl)-2-ethyl-1H-imidazole-4-carboxylic acid (Intermediate 122) and (1R*,2R*,4R*)-1-(aminomethyl)-4-(methylsulfonyl)cyclohexane-1,2-diol hydrochloride (Intermediate 23) in place of 5-cyano-2-ethyl-1-(2-methoxy-4-(3,3,3-trifluoro-2-methylpropyl)phenyl)-1H-imidazole-4-carboxylic acid and (1s,4s)-1-(aminomethyl)-4-(methylsulfonyl)cyclohexanol hydrochloride. ¹H NMR (500 MHz, CDCl₃) δ 8.44 (s, 1H), 7.74 (s, 1H), 7.66-7.61 (m, 1H), 6.70-6.36 (m, 1H), 3.88-3.81 (m, 1H), 3.59 (td, J=11.4, 4.7 Hz, 1H), 3.36-3.26 (m, 3H), 3.10 (dt, J=14.1, 6.2 Hz, 1H), 2.88-2.80 (m, 1H), 2.83 (s, 3H of one rotamer), 2.82 (s, 3H of one rotamer), 2.58-2.44 (m, 2H), 2.31-2.23 (m, 1H), 2.28 (br s, 20H), 2.08-2.03 (m, 1H), 2.01-1.87 (m, 3H), 1.55 (qd, J=13.9, 4.8 Hz, 1H), 1.19 (td, J=7.5, 1.8 Hz, 3H). MS (ESI) m/z: [M+H]⁺ Found 687.1.

Example 68

5-Chloro-1-(3-(difluoromethoxy)-5-(3,3,3-trifluoro-2,2-dimethylpropyl)pyridin-2-yl)-2-ethyl-N-(((1r,4r)-4-(N-methylsulfamoyl)cyclohexyl)methyl)-1H-imidazole-4-carboxamide

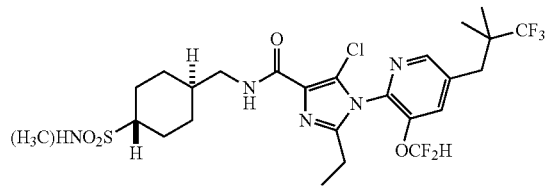

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (Intermediate 85) and (1r,4r)-4-(aminomethyl)-N-methylcyclohexane-1-sulfonamide (Intermediate 39) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 8.35 (d, J=1.9 Hz, 1H), 7.70 (s, 1H), 7.68 (t, J=7.6 Hz, 1H), 6.67-6.37 (m, 1H), 4.05 (br s, 1H), 3.37-3.27 (m, 2H), 2.96-2.87 (m, 1H), 2.95 (s, 2H), 2.82 (s, 3H), 2.66-2.53 (m, 2H), 2.26-2.19 (m, 2H), 2.05-1.98 (m, 2H), 1.72-1.64 (m, 1H), 1.59 (qd, J=13.0, 3.6 Hz, 2H), 1.22-1.16 (m, 9H), 1.10 (qd, J=13.2, 3.6 Hz, 2H). MS (ESI) m/z: [M+H]⁺ Found 630.3.

Example 69

5-Chloro-1-(3-(difluoromethoxy)-5-(3,3,3-trifluoro-2,2-dimethylpropyl)pyridin-2-yl)-2-ethyl-N-(((1r,4r)-4-sulfamoylcyclohexyl)methyl)-1H-imidazole-4-carboxamide

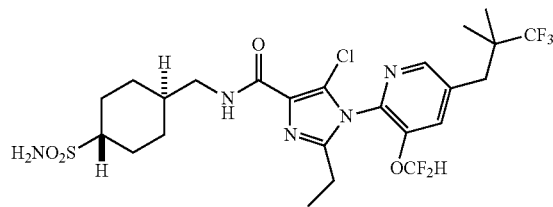

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (Intermediate 85) and (1r,4r)-4-(aminomethyl)cyclohexane-1-sulfonamide hydrochloride (Intermediate 43) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (500 MHz, CDCl₃) δ 8.35 (d, J=1.9 Hz, 1H), 7.69 (s, 1H), 7.64 (t, J=6.3 Hz, 1H), 6.67-6.36 (m, 1H), 4.43 (s, 2H), 3.37-3.28 (m, 2H), 2.97-2.89 (m, 3H), 2.65-2.52 (m, 2H), 2.35-2.28 (m, 2H), 2.07-2.00 (m, 2H), 1.73-1.63 (m, 1H), 1.59 (qd, J=12.9, 3.7 Hz, 2H), 1.22-1.07 (m, 11H). MS (ESI) m/z: [M+H]⁺ Found 616.2.

Example 70

5-Chloro-1-(3-(difluoromethoxy)-5-(3,3,3-trifluoro-2,2-dimethylpropyl)pyridin-2-yl)-N-(((1r,4r)-4-(N,N-dimethylsulfamoyl)cyclohexyl)methyl)-2-ethyl-1H-imidazole-4-carboxamide

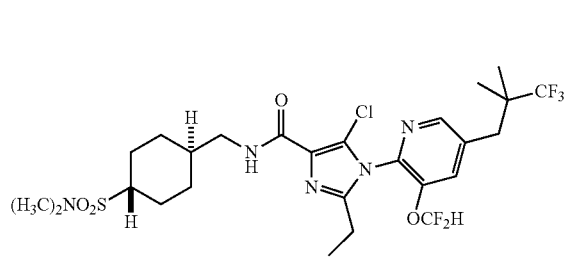

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-ethyl-1H-imidazole-4-carboxylate (Intermediate 85) and (1r,4r)-4-(aminomethyl)-N,N-dimethylcyclohexane-1-sulfonamide (Intermediate 36) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (400 MHz, CDCl₃) δ 8.34 (d, J=2.0 Hz, 1H), 7.69 (s, 1H), 7.60 (t, J=6.3 Hz, 1H), 6.72-6.31 (m, 1H), 3.37-3.26 (m, 2H), 3.01-2.90 (m, 9H), 2.66-2.50 (m, 2H), 2.22-2.11 (m, 2H), 2.05-1.95 (m, 2H), 1.72-1.54 (m, 3H), 1.25-1.01 (m, 11H). MS (ESI) m/z: [M+H]⁺ Found 644.2.

Example 71

5-Chloro-1-(3-(difluoromethoxy)-5-((S*)-3,3,3-trifluoro-2-methylpropyl)pyridin-2-yl)-2-ethyl-N-(((1s,4R)-1-hydroxy-4-(methylsulfonyl)cyclohexyl)methyl)-1H-imidazole-4-carboxamide

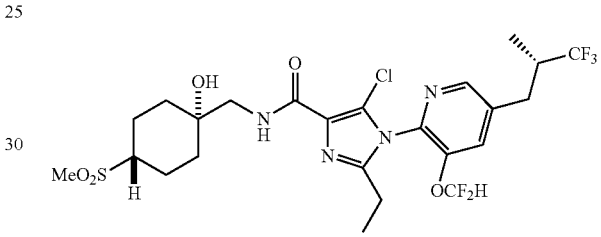

The title compound was prepared as described for the synthesis of Example 1, using ethyl 5-chloro-1-(3-(difluoromethoxy)-5-((S*)-3,3,3-trifluoro-2-methylpropyl)pyridin-2-yl)-2-ethyl-1H-imidazole-4-carboxylate (Intermediate 101) in place of ethyl 5-cyano-2-ethyl-1-(2-methoxy-4-(3,3,3-trifluoro-2-methylpropyl)phenyl)-1H-imidazole-4-carboxylate. ¹H NMR (400 MHz, CDCl₃) δ 8.37 (t, J=2.3 Hz, 1H), 7.80 (t, J=6.3 Hz, 1H), 7.69 (s, 1H), 6.72-6.34 (m, 1H), 4.19 (s, 1H), 3.46 (qd, J=14.1, 6.3 Hz, 2H), 3.18 (dd, J=14.2, 5.0 Hz, 1H), 2.86-2.71 (m, 5H), 2.63-2.51 (m, 3H), 2.16-2.07 (m, 2H), 2.03-1.90 (m, 4H), 1.48-1.36 (m, 2H), 1.23-1.14 (m, 6H). MS (ESI) m/z: [M+H]⁺ Found 617.0.

Example 72

5-Chloro-1-(3-(difluoromethoxy)-5-((S*)-3,3,3-trifluoro-2-methylpropyl)pyridin-2-yl)-2-ethyl-N-(((1r,4S)-4-(methylsulfonyl)cyclohexyl)methyl)-1H-imidazole-4-carboxamide

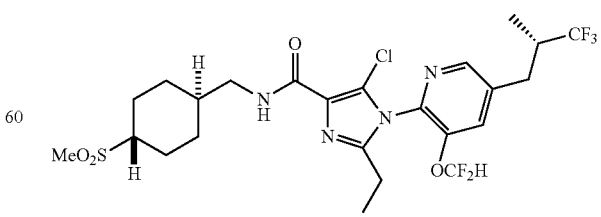

The title compound was prepared as described for the synthesis of Example 1, using ethyl 5-chloro-1-(3-(difluoromethoxy)-5-((S*)-3,3,3-trifluoro-2-methylpropyl)pyridin- 2-yl)-2-ethyl-1H-imidazole-4-carboxylate (Intermediate 101) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (400 MHz, CDCl$_3$) δ 8.37 (t, J=2.4 Hz, 1H), 7.68 (s, 1H), 7.53 (t, J=6.3 Hz, 1H), 6.70-6.32 (m, 1H), 3.32 (t, J=6.5 Hz, 2H), 3.18 (ddd, J=14.3, 5.0, 1.7 Hz, 1H), 2.87-2.78 (m, 1H), 2.82 (s, 3H), 2.75 (dd, J=14.1, 9.3 Hz, 1H), 2.62-2.50 (m, 3H), 2.31-2.23 (m, 2H), 2.11-2.02 (m, 2H), 1.74-1.64 (m, 1H), 1.58 (qd, J=13.2, 3.7 Hz, 2H), 1.23-1.06 (m, 8H). MS (ESI) m/z: [M+H]$^+$ Found 601.2.

Example 73

1-(3-(Difluoromethoxy)-5-((S*)-3,3,3-trifluoro-2-methylpropyl)pyridin-2-yl)-2-ethyl-5-methyl-N-(((1r,4S)-4-(methylsulfonyl)cyclohexyl)methyl)-1H-imidazole-4-carboxamide

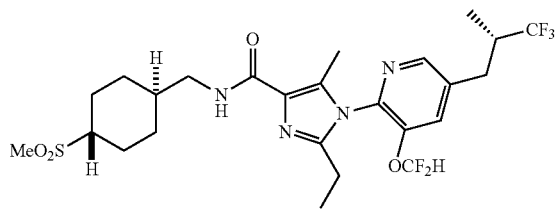

The title compound was prepared as described for the synthesis of Intermediate 89, using 5-chloro-1-(3-(difluoromethoxy)-5-((S*)-3,3,3-trifluoro-2-methylpropyl)pyridin-2-yl)-2-ethyl-N-(((1 r,4S)-4-(methylsulfonyl)cyclohexyl)methyl)-1H-imidazole-4-carboxamide (Example 72) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate. $^1$H NMR (500 MHz, CDCl$_3$) δ 8.36 (s, 1H), 7.65 (s, 1H), 7.33 (s, 1H), 6.44 (t, J=71.0 Hz, 1H), 3.34-3.27 (m, 2H), 3.17 (dd, J=14.2, 5.0 Hz, 1H), 2.87-2.79 (m, 1H), 2.82 (s, 3H), 2.73 (dd, J=14.2, 9.3 Hz, 1H), 2.61-2.39 (m, 3H), 2.34 (s, 3H), 2.31-2.24 (m, 2H), 2.13-2.05 (m, 2H), 1.73-1.52 (m, 3H), 1.22-1.08 (m, 8H). MS (ESI) m/z: [M+H]$^+$ Found 581.2.

Example 74

5-Chloro-2-ethyl-1-(3-methyl-5-(3,3,3-trifluoro-2,2-dimethylpropyl)pyridin-2-yl)-N-(((1r,4r)-4-(methylsulfonyl)cyclohexyl)methyl)-1H-imidazole-4-carboxamide

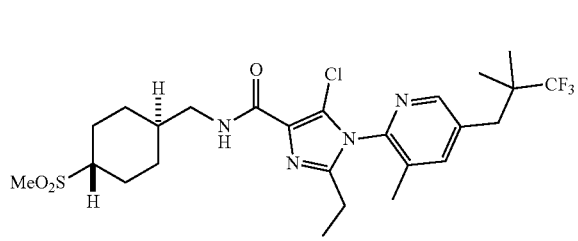 [SMILES: CCc1cc(CC(C)(C)C(F)(F)F)cnc1-n1c(CC)nc(C(=O)NC[C@H]2CC[C@H](S(C)(=O)=O)CC2)c1Cl]

The title compound was prepared as described for the synthesis of Example 1, using ethyl 5-chloro-2-ethyl-1-(3-methyl-5-(3,3,3-trifluoro-2,2-dimethylpropyl)pyridin-2-yl)-1H-imidazole-4-carboxylate (Intermediate 88) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$) δ 8.33 (d, J=1.5 Hz, 1H), 7.76 (t, J=6.2 Hz, 1H), 7.63 (d, J=1.5 Hz, 1H), 3.38-3.28 (m, 2H), 2.91-2.87 (m, 2H), 2.87-2.79 (m, 1H), 2.83 (s, 3H), 2.65-2.52 (m, J=7.7 Hz, 2H), 2.31-2.24 (m, 2H), 2.14 (s, 3H), 2.10-2.03 (m, 2H), 1.74-1.64 (m, 1H), 1.58 (qd, J=12.9, 3.6 Hz, 2H), 1.19-1.08 (m, 11H). MS (ESI) m/z: [M+H]$^+$ Found 563.2.

Example 75

5-Chloro-2-ethyl-1-(3-ethyl-5-(3,3,3-trifluoro-2,2-dimethylpropyl)pyridin-2-yl)-N-(((1r,4r)-4-(methylsulfonyl)cyclohexyl)methyl)-1H-imidazole-4-carboxamide

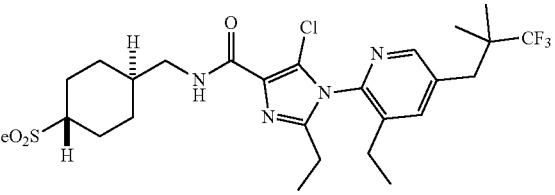

The title compound was prepared as described for the synthesis of Example 74, using ethyl 1-(5-bromo-3-ethylpyridin-2-yl)-2-ethyl-1H-imidazole-4-carboxylate (Intermediate 133) in place of ethyl 1-(5-bromo-3-methylpyridin-2-yl)-2-ethyl-1H-imidazole-4-carboxylate. $^1$H NMR (500 MHz, CDCl$_3$) δ 8.33 (d, J=2.2 Hz, 1H), 7.73 (t, J=6.2 Hz, 1H), 7.66 (d, J=2.2 Hz, 1H), 3.38-3.28 (m, 2H), 2.90 (s, 2H), 2.86-2.79 (m, 1H), 2.82 (s, 3H), 2.62-2.47 (m, 2H), 2.47-2.32 (m, 2H), 2.31-2.24 (m, 2H), 2.10-2.03 (m, 2H), 1.74-1.64 (m, 1H), 1.58 (qd, J=13.0, 3.6 Hz, 2H), 1.21-1.08 (m, 14H). MS (ESI) m/z: [M+H]$^+$ Found 577.2.

Example 76

1-(3-(Difluoromethoxy)-5-(3,3,3-trifluoro-2-(trifluoromethyl)propyl)pyridin-2-yl)-2-ethyl-N-(((1s,4s)-1-hydroxy-4-(methylsulfonyl)cyclohexyl)methyl)-5-methyl-1H-imidazole-4-carboxamide

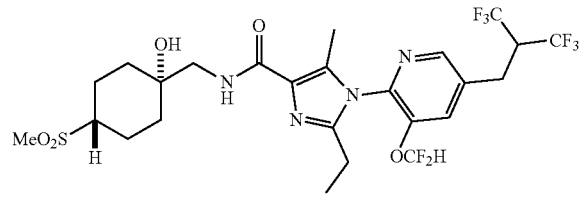

The title compound was prepared as described for the synthesis of Example 2, using 1-(3-(difluoromethoxy)-5-(3,3,3-trifluoro-2-(trifluoromethyl)propyl)pyridin-2-yl)-2-ethyl-5-methyl-1H-imidazole-4-carboxylic acid (Intermediate 137) and (1s,4s)-1-(aminomethyl)-4-(methylsulfonyl)

cyclohexanol hydrochloride (Intermediate 9) in place of of 5-chloro-1-(3-(difluoromethoxy)-5-(3,3,3-trifluoro-2,2-dimethylpropyl)pyridin-2-yl)-2-ethyl-1H-imidazole-4-carboxylic acid and ((1r,4r)-4-(methyl sulfonyl)cyclohexyl) methanamine hydrochloride. ¹H NMR (400 MHz, CDCl₃) δ 8.45-8.40 (m, 1H), 7.76-7.68 (m, 1H), 7.60-7.53 (m, 1H), 6.66-6.25 (m, 1H), 4.07 (s, 1H), 3.51-3.34 (m, 2H), 3.32-3.24 (m, 3H), 2.82 (s, 3H), 2.81-2.73 (m, 1H), 2.49-2.39 (m, 2H), 2.32 (s, 3H), 2.18-2.08 (m, 2H), 2.04-1.91 (m, 4H), 1.44-1.30 (m, 2H), 1.17 (t, J=7.5 Hz, 3H). MS (ESI) m/z: [M+H]⁺ Found 650.8.

Example 77

1-(3-(Difluoromethoxy)-5-(3,3,3-trifluoro-2-(trifluoromethyl)propyl)pyridin-2-yl)-2-ethyl-5-methyl-N-(((1r,4r)-4-(methylsulfonyl)cyclohexyl)methyl)-1H-imidazole-4-carboxamide

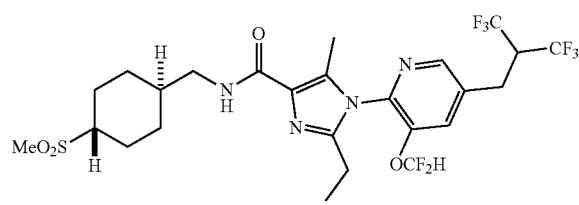

The title compound was prepared as described for the synthesis of Example 2, using 1-(3-(difluoromethoxy)-5-(3,3,3-trifluoro-2-(trifluoromethyl)propyl)pyridin-2-yl)-2-ethyl-5-methyl-1H-imidazole-4-carboxylic acid (Intermediate 137) in place of of 5-chloro-1-(3-(difluoromethoxy)-5-(3,3,3-trifluoro-2,2-dimethylpropyl)pyridin-2-yl)-1H-imidazole-4-carboxylic acid. ¹H NMR (400 MHz, CDCl₃) δ 8.45-8.39 (m, 1H), 7.70 (s, 1H), 7.36-7.29 (m, 1H), 6.65-6.23 (m, 1H), 3.36-3.23 (m, 5H), 2.88-2.76 (m, 4H), 2.51-2.39 (m, 2H), 2.33 (s, 3H), 2.31-2.22 (m, 2H), 2.15-2.06 (m, 2H), 1.74-1.64 (m, 1H), 1.64-1.57 (m, 2H), 1.21-1.06 (m, 5H). MS (ESI) m/z: [M+H]⁺ Found 634.8.

Example 78

5-Chloro-1-(3-(difluoromethoxy)-5-((R*)-3,3,3-trifluoro-2-methylpropyl)pyridin-2-yl)-2-ethyl-N-(((1r,4R)-4-(methylsulfonyl)cyclohexyl)methyl)-1H-imidazole-4-carboxamide

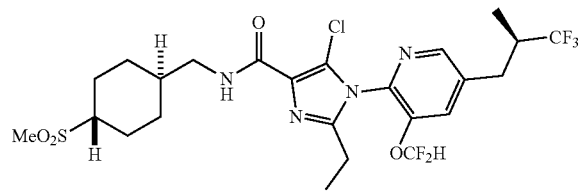

The title compound was prepared as described for the synthesis of Example 1, using ethyl 5-chloro-1-(3-(difluoromethoxy)-5-((R*)-3,3,3-trifluoro-2-methylpropyl)pyridin-2-yl)-2-ethyl-1H-imidazole-4-carboxylate (Intermediate 134) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (400 MHz, CDCl₃) δ 8.37 (t, J=2.3 Hz, 1H), 7.68 (s, 1H), 7.60-7.53 (m, 1H), 6.73-6.32 (m, 1H), 3.33 (t, J=6.5 Hz, 2H), 3.22-3.14 (m, 1H), 2.89-2.71 (m, 5H), 2.61-2.50 (m, 3H), 2.33-2.23 (m, 2H), 2.13-2.01 (m, 2H), 1.77-1.52 (m, 3H), 1.24-1.06 (m, 8H). MS (ESI) m/z: [M+H]⁺ Found 601.2.

Example 79

5-Chloro-1-(3-(difluoromethoxy)-5-((R*)-3,3,3-trifluoro-2-methylpropyl)pyridin-2-yl)-2-ethyl-N-(((1s,4S)-1-hydroxy-4-(methylsulfonyl)cyclohexyl)methyl)-1H-imidazole-4-carboxamide

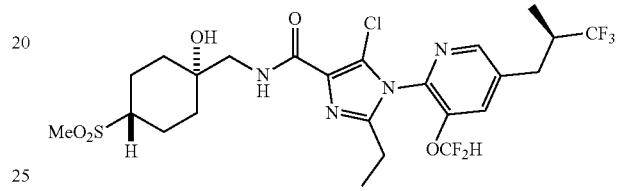

The title compound was prepared as described for the synthesis of Example 1, using ethyl 5-chloro-1-(3-(difluoromethoxy)-5-((R*)-3,3,3-trifluoro-2-methylpropyl)pyridin-2-yl)-2-ethyl-1H-imidazole-4-carboxylate (Intermediate 134) in place of ethyl 5-cyano-2-ethyl-1-(2-methoxy-4-(3,3,3-trifluoro-2-methylpropyl)phenyl)-1H-imidazole-4-carboxylate. ¹H NMR (400 MHz, CDCl₃) δ 8.38 (t, J=2.3 Hz, 1H), 7.85-7.75 (m, 1H), 7.72-7.66 (m, 1H), 6.74-6.31 (m, 1H), 4.54 (brs, 1H), 3.56-3.38 (m, 2H), 3.25-3.13 (m, 1H), 2.88-2.70 (m, 5H), 2.64-2.50 (m, 3H), 2.18-2.06 (m, 2H), 2.05-1.89 (m, 4H), 1.49-1.35 (m, 2H), 1.25-1.11 (m, 6H). MS (ESI) m/z: [M+H]⁺ Found 617.2.

Example 80

1-(3-(Difluoromethoxy)-5-((R*)-3,3,3-trifluoro-2-methylpropyl)pyridin-2-yl)-2-ethyl-5-methyl-N-(((1r,4R)-4-(methylsulfonyl)cyclohexyl)methyl)-1H-imidazole-4-carboxamide

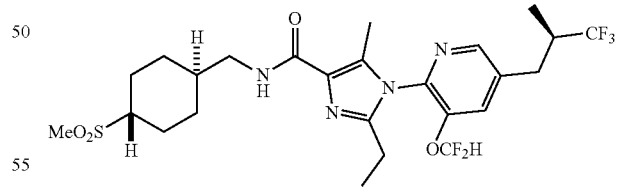

The title compound was prepared as described for the synthesis of Example 1, using ethyl 1-(3-(difluoromethoxy)-5-((R*)-3,3,3-trifluoro-2-methylpropyl)pyridin-2-yl)-2-ethyl-5-methyl-1H-imidazole-4-carboxylate (Intermediate 135) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. ¹H NMR (400 MHz, CDCl₃) δ 8.62 (t, J=5.7 Hz, 1H), 8.46-8.40 (m, 1H), 7.80-7.74 (m, 1H), 6.77-6.37 (m, 1H), 3.32 (t, J=6.2 Hz, 2H), 3.24-3.14 (m, 1H), 2.97-2.76 (m, 6H), 2.75-2.52 (m, 2H), 2.42-2.36 (m, 3H), 2.33-2.23 (m, 2H), 2.11-2.02 (m, 2H), 1.77-1.64 (m, 1H), 1.64-1.50 (m, 2H), 1.28-1.18 (m, 6H), 1.18-1.05 (m, 2H). MS (ESI) m/z: [M+H]⁺ Found 581.3.

Example 81

1-(2,6-Difluoro-4-isobutylphenyl)-2-ethyl-N-(((1s,4s)-1-hydroxy-4-(methylsulfonyl)cyclohexyl)methyl)-1H-imidazole-4-carboxamide

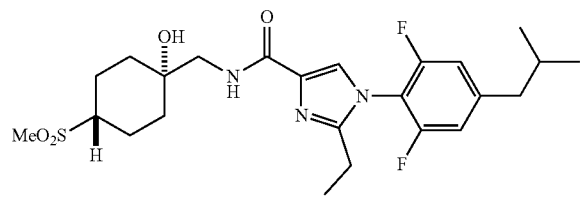 [SMILES: CCc1nc(C(=O)NC[C@]2(O)CC[C@@H](S(C)(=O)=O)CC2)cn1-c1c(F)cc(CC(C)C)cc1F]

The title compound was prepared as described for the synthesis of Example 1, using ethyl 1-(2,6-difluoro-4-isobutylphenyl)-2-ethyl-1H-imidazole-4-carboxylate (Intermediate 145) in place of ethyl 5-cyano-2-ethyl-1-(2-methoxy-4-(3,3,3-trifluoro-2-methylpropyl)phenyl)-1H-imidazole-4-carboxylate. ¹H NMR (400 MHz, CDCl₃) δ 8.02-7.93 (m, 1H), 7.58 (s, 1H), 6.97-6.89 (m, 2H), 3.47 (d, J=6.2 Hz, 2H), 2.85-2.74 (m, 4H), 2.67-2.59 (m, 2H), 2.56 (d, J=7.3 Hz, 2H), 2.05-1.88 (m, 6H), 1.47-1.35 (m, 2H), 1.28-1.22 (m, 3H), 0.97 (d, J=6.6 Hz, 6H); MS (ESI) m/z: [M+H]⁺ Found 498.0.

Example 82

1-(2,6-Difluoro-4-isobutylphenyl)-2-ethyl-N-(((1r,4r)-4-(methylsulfonyl)cyclohexyl)methyl)-1H-imidazole-4-carboxamide

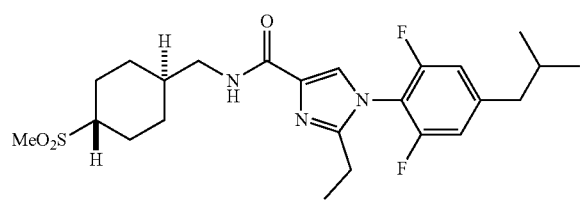 [SMILES: CCc1nc(C(=O)NC[C@H]2CC[C@H](S(C)(=O)=O)CC2)cn1-c1c(F)cc(CC(C)C)cc1F]

The title compound was prepared as described for the synthesis of Example 1, using ethyl 1-(2,6-difluoro-4-isobutylphenyl)-2-ethyl-1H-imidazole-4-carboxylate (Intermediate 145) in place of ethyl 5-cyano-2-ethyl-1-(2-methoxy-4-(3,3,3-trifluoro-2-methylpropyl)phenyl)-1H-imidazole-4-carboxylate and ((1r,4r)-4-(methylsulfonyl)cyclohexyl)methanamine hydrochloride (Intermediate 13) in place of (1s,4s)-1-(aminomethyl)-4-(methyl sulfonyl)cyclohexanol hydrochloride. ¹H NMR (400 MHz, CDCl₃) δ 7.66-7.58 (m, 1H), 7.55 (s, 1H), 6.95-6.89 (m, 2H), 3.38-3.30 (m, 2H), 2.88-2.78 (m, 4H), 2.65-2.57 (m, 2H), 2.55 (d, J=7.2 Hz, 2H), 2.33-2.24 (m, 2H), 2.13-2.02 (m, 2H), 1.99-1.87 (m, 1H), 1.76-1.51 (m, 3H), 1.29-1.21 (m, 3H), 1.21-1.05 (m, 2H), 0.96 (d, J=6.6 Hz, 6H); MS (ESI) m/z: [M+H]⁺ Found 482.0.

Example 83

5-Chloro-1-(2,6-difluoro-4-isobutylphenyl)-2-ethyl-N-(((1s,4s)-1-hydroxy-4-(methylsulfonyl)cyclohexyl)methyl)-1H-imidazole-4-carboxamide

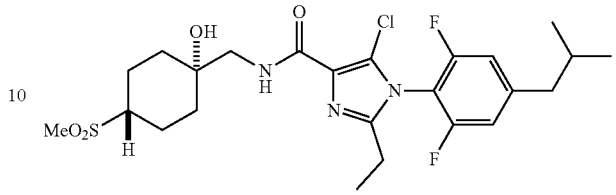

The title compound was prepared as described for the synthesis of Example 1, using ethyl 5-chloro-1-(2,6-difluoro-4-isobutylphenyl)-2-ethyl-1H-imidazole-4-carboxylate (Intermediate 146) in place of ethyl 5-cyano-2-ethyl-1-(2-methoxy-4-(3,3,3-trifluoro-2-methylpropyl)phenyl)-1H-imidazole-4-carboxylate. ¹H NMR (500 MHz, CDCl₃) δ 7.63-7.57 (m, 1H), 6.94 (d, J=9.3 Hz, 2H), 3.45 (d, J=6.4 Hz, 2H), 2.84-2.76 (m, 4H), 2.57 (d, J=7.6 Hz, 2H), 2.54-2.47 (m, 2H), 2.16-1.91 (m, 8H, with water), 1.47-1.37 (m, 2H), 1.24-1.18 (m, 3H), 0.97 (d, J=6.5 Hz, 6H); MS (ESI) m/z: [M+H]⁺ Found 532.0.

Example 84

1-(2,6-Difluoro-4-(3,3,3-trifluoro-2-methylpropyl)phenyl)-2-ethyl-N-(((1s,4s)-1-hydroxy-4-(methylsulfonyl)cyclohexyl)methyl)-1H-imidazole-4-carboxamide

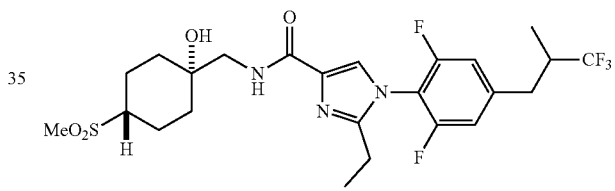

The title compound was prepared as described for the synthesis of Example 1, using ethyl 1-(2,6-difluoro-4-(3,3,3-trifluoro-2-methylpropyl)phenyl)-2-ethyl-1H-imidazole-4-carboxylate (Intermediate 143) in place of ethyl 5-cyano-2-ethyl-1-(2-methoxy-4-(3,3,3-trifluoro-2-methylpropyl)phenyl)-1H-imidazole-4-carboxylate. ¹H NMR (500 MHz, CDCl₃) δ 7.59-7.48 (m, 2H), 7.01-6.93 (m, 2H), 3.78-3.71 (m, 1H), 3.50-3.43 (m, 2H), 3.19-3.10 (m, 1H), 2.87-2.75 (m, 4H), 2.65-2.47 (m, 4H), 2.13 (d, J=10.7 Hz, 2H), 1.98 (d, J=12.0 Hz, 4H), 1.46-1.35 (m, 2H), 1.30-1.21 (m, 3H), 1.18-1.11 (m, 3H); MS (ESI) m/z: [M+H]⁺ Found 552.0.

Example 85

5-Chloro-1-(2,6-difluoro-4-(3,3,3-trifluoro-2-methylpropyl)phenyl)-2-ethyl-N-(((1r,4r)-4-(methylsulfonyl)cyclohexyl)methyl)-1H-imidazole-4-carboxamide

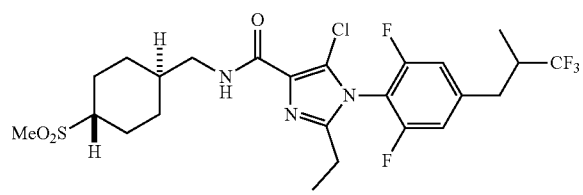 [SMILES: CCc1nc(C(=O)NC[C@H]2CC[C@H](S(C)(=O)=O)CC2)c(Cl)n1-c1c(F)cc(CC(C)C(F)(F)F)cc1F]

The title compound was prepared as described for the synthesis of Example 1, using ethyl 5-chloro-1-(2,6-difluoro-4-(3,3,3-trifluoro-2-methylpropyl)phenyl)-2-ethyl-1H-imidazole-4-carboxylate (Intermediate 144) in place of ethyl 5-cyano-2-ethyl-1-(2-methoxy-4-(3,3,3-trifluoro-2-methylpropyl)phenyl)-1H-imidazole-4-carboxylate and ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. ¹H NMR (400 MHz, CDCl₃) δ 7.26-7.21 (m, 1H coincident with CHCl₃), 6.98 (d, J=8.4 Hz, 2H), 3.37-3.28 (m, 2H), 3.19-3.10 (m, 1H), 2.89-2.78 (m, 4H), 2.66-2.43 (m, 4H), 2.33-2.24 (m, 2H), 2.14-2.02 (m, 2H), 1.75-1.51 (m, 3H coincident with water), 1.25-1.09 (m, 8H); MS (ESI) m/z: [M+H]⁺ Found 569.8.

Example 86

5-Chloro-1-(2,6-difluoro-4-((S*)-3,3,3-trifluoro-2-methylpropyl)phenyl)-2-ethyl-N-(((1r,4S)-4-(methylsulfonyl)cyclohexyl)methyl)-1H-imidazole-4-carboxamide

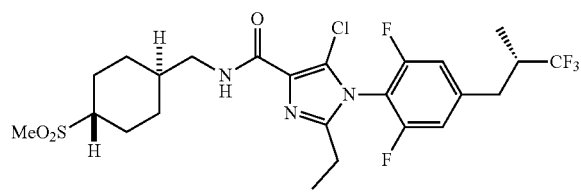 [SMILES: CCc1nc(C(=O)NC[C@H]2CC[C@H](S(C)(=O)=O)CC2)c(Cl)n1-c1c(F)cc(C[C@H](C)C(F)(F)F)cc1F]

Example 87

5-Chloro-1-(2,6-difluoro-4-((R*)-3,3,3-trifluoro-2-methylpropyl)phenyl)-2-ethyl-N-(((1r,4R)-4-(methylsulfonyl)cyclohexyl)methyl)-1H-imidazole-4-carboxamide

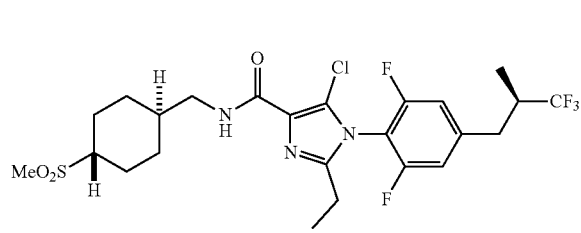 [SMILES: CCc1nc(C(=O)NC[C@H]2CC[C@H](S(C)(=O)=O)CC2)c(Cl)n1-c1c(F)cc(C[C@@H](C)C(F)(F)F)cc1F]

Example 86 was purified by SFC using a chiral stationary phase (Chiralpak AD-H, 80% CO₂, 20% i-PrOH) to afford two enantiomers. The first eluting enantiomer was Example 86, and the second eluting enantiomer was Example 87. Example 86: ¹H NMR (400 MHz, CDCl₃) δ 7.26-7.20 (m, 1H coincident with CHCl₃), 7.04-6.93 (m, 2H), 3.33 (t, J=6.6 Hz, 2H), 3.19-3.11 (m, 1H), 2.88-2.78 (m, 4H), 2.66-2.58 (m, 1H), 2.58-2.42 (m, 3H), 2.28 (d, J=12.8 Hz, 2H), 2.13-2.02 (m, 2H), 1.76-1.52 (m, 3H coincident with water), 1.27-1.08 (m, 8H); MS (ESI) m/z: [M+H]⁺ Found 570.0. Example 87: ¹H NMR (400 MHz, CDCl₃) δ 7.26-7.21 (m, 1H coincident with CHCl₃), 7.02-6.95 (m, 2H), 3.37-3.30 (m, 2H), 3.20-3.10 (m, 1H), 2.89-2.78 (m, 4H), 2.68-2.44 (m, 4H), 2.33-2.23 (m, 2H), 2.14-2.03 (m, 2H), 1.76-1.55 (m, 3H coincident with water) 1.28-1.08 (m, 8H); MS (ESI) m/z: [M+H]⁺ Found 570.0.

Example 88

5-Chloro-1-(2,6-difluoro-4-(3,3,3-trifluoro-2-methylpropyl)phenyl)-2-ethyl-N-(((1s,4s)-1-hydroxy-4-(methylsulfonyl)cyclohexyl)methyl)-1H-imidazole-4-carboxamide

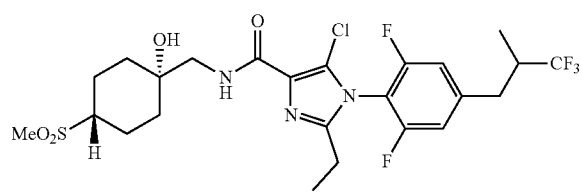 [SMILES: CCc1nc(C(=O)NC[C@]2(O)CC[C@@H](S(C)(=O)=O)CC2)c(Cl)n1-c1c(F)cc(CC(C)C(F)(F)F)cc1F]

The title compound was prepared as described for the synthesis of Example 1, using ethyl 5-chloro-1-(2,6-difluoro-4-(3,3,3-trifluoro-2-methylpropyl)phenyl)-2-ethyl-1H-imidazole-4-carboxylate (Intermediate 144) in place of ethyl 5-cyano-2-ethyl-1-(2-methoxy-4-(3,3,3-trifluoro-2-methylpropyl)phenyl)-1H-imidazole-4-carboxylate. ¹H NMR (500 MHz, CDCl₃) δ 7.57-7.47 (m, 1H), 7.04-6.95 (m, 2H), 3.49-3.42 (m, 3H), 3.20-3.11 (m, 1H), 2.88-2.74 (m, 4H), 2.66-2.59 (m, 1H), 2.58-2.44 (m, 3H), 2.18-2.09 (m, 2H), 2.04-1.93 (m, 4H), 1.46-1.37 (m, 2H), 1.25-1.19 (m, 3H), 1.14 (d, J=6.7 Hz, 3H); MS (ESI) m/z: [M+H]⁺ Found 585.9.

Example 89

5-Chloro-2-ethyl-1-(4-isobutyl-2-methoxyphenyl)-N-(((1r,4r)-4-(methylsulfonyl)cyclohexyl)methyl)-1H-imidazole-4-carboxamide

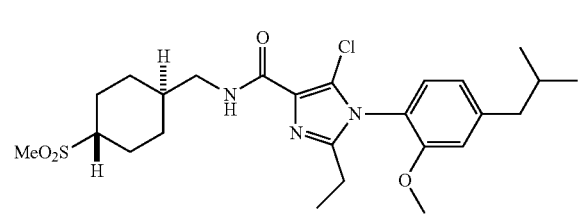

The title compound was prepared as described for the synthesis of Example 1, using ethyl 5-chloro-2-ethyl-1-(4-isobutyl-2-methoxyphenyl)-1H-imidazole-4-carboxylate (Intermediate 147) in place of ethyl 5-cyano-2-ethyl-1-(2-methoxy-4-(3,3,3-trifluoro-2-methylpropyl)phenyl)-1H-imidazole-4-carboxylate and ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. ¹H NMR (500 MHz, CDCl₃) δ 7.26-7.21 (m, 1H), 7.07-7.03 (m, 1H), 6.88-6.84 (m, 1H), 6.84-6.82 (m, 1H), 3.83-3.71 (m, 3H), 3.36-3.28 (m, 2H), 2.87-2.78 (m, 4H), 2.59-2.52 (m, 2H), 2.50-2.37 (m, 2H), 2.32-2.24 (m, 2H), 2.13-2.04 (m, 2H), 1.99-1.89 (m, 1H), 1.74-1.63 (m, 1H), 1.63-1.53 (m, 2H coincident with water), 1.20-1.08 (m, 5H), 1.01-0.93 (m, 6H); MS (ESI) m/z: [M+H]⁺ Found 510.3.

Example 90

5-Chloro-2-ethyl-N-(((1s,4s)-1-hydroxy-4-(methylsulfonyl)cyclohexyl)methyl)-1-(4-isobutyl-2-methoxyphenyl)-1H-imidazole-4-carboxamide

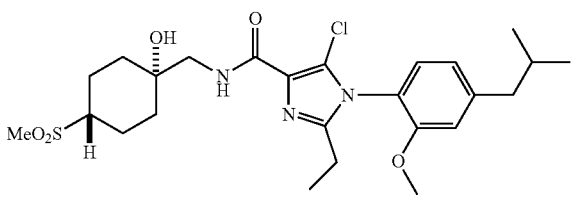 [SMILES: CCc1nc(C(=O)NC[C@]2(O)CC[C@@H](S(C)(=O)=O)CC2)c(Cl)n1-c1ccc(CC(C)C)cc1OC]

The title compound was prepared as described for the synthesis of Example 1, using ethyl 5-chloro-2-ethyl-1-(4-isobutyl-2-methoxyphenyl)-1H-imidazole-4-carboxylate (Intermediate 147) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 7.54-7.48 (m, 1H), 7.06-7.02 (m, 1H), 6.88-6.85 (m, 1H), 6.85-6.82 (m, 1H), 3.77 (s, 3H), 3.74 (s, 1H), 3.48-3.39 (m, 2H), 2.84-2.81 (m, 3H), 2.81-2.74 (m, 1H), 2.58-2.52 (m, 2H), 2.47-2.39 (m, 2H), 2.16-2.08 (m, 2H), 2.04-1.89 (m, 5H), 1.43-1.34 (m, 2H), 1.18-1.12 (m, 3H), 0.98-0.94 (m, 6H); MS (ESI) m/z: [M+H]$^+$ Found 526.2.

Example 91

5-Chloro-2-ethyl-N-(((1s,4S)-1-hydroxy-4-(methylsulfonyl)cyclohexyl)methyl)-1-((S*)-4-isobutyl-2-methoxyphenyl)-1H-imidazole-4-carboxamide

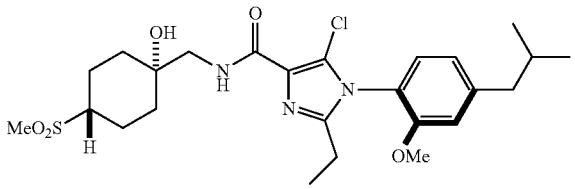

Example 92

5-Chloro-2-ethyl-N-(((1s,4S)-1-hydroxy-4-(methylsulfonyl)cyclohexyl)methyl)-1-((R*)-4-isobutyl-2-methoxyphenyl)-1H-imidazole-4-carboxamide

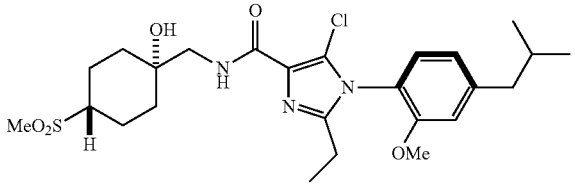

Example 90 was purified by SFC using a chiral stationary phase (Lux 5 m Cellulose-4, 50% MeOH, 50% CO$_2$) to give a pair of atropisomers. The first-eluting isomer was Example 91, and the second-eluting isomer was Example 92. Example 91: $^1$H NMR (500 MHz, CDCl$_3$) δ 7.54-7.48 (m, 1H), 7.04 (d, J=7.8 Hz, 1H), 6.86 (dd, J=7.9, 1.6 Hz, 1H), 6.84 (d, J=1.6 Hz, 1H), 3.78 (s, 3H), 3.74 (s, 1H), 3.48-3.39 (m, 2H), 2.84-2.75 (m, 4H), 2.55 (d, J=7.2 Hz, 2H), 2.47-2.41 (m, 2H), 2.16-2.09 (m, 2H), 2.03-1.89 (m, 5H), 1.44-1.35 (m, 2H), 1.16 (t, J=7.5 Hz, 3H), 0.96 (d, J=6.6 Hz, 6H). MS (ESI) m/z: [M+H]$^+$ Found 526.1. Example 92: $^1$H NMR (500 MHz, CDCl$_3$) δ 7.53-7.49 (m, 1H), 7.04 (d, J=7.8 Hz, 1H), 6.86 (dd, J=7.9, 1.6 Hz, 1H), 6.84 (d, J=1.6 Hz, 1H), 3.78 (s, 3H), 3.74 (s, 1H), 3.48-3.39 (m, 2H), 2.85-2.74 (m, 4H), 2.55 (d, J=7.3 Hz, 2H), 2.47-2.40 (m, 2H), 2.16-2.09 (m, 2H), 2.04-1.90 (m, 5H), 1.44-1.35 (m, 2H), 1.18-1.14 (m, 3H), 0.96 (d, J=6.6 Hz, 6H). MS (ESI) m/z: [M+H]$^+$ Found 526.2.

Example 93

5-Cyano-2-ethyl-1-(2-fluoro-4-(3,3,3-trifluoropropyl)phenyl)-N-(((1r,4r)-4-(methylsulfonyl)cyclohexyl)methyl)-1H-imidazole-4-carboxamide

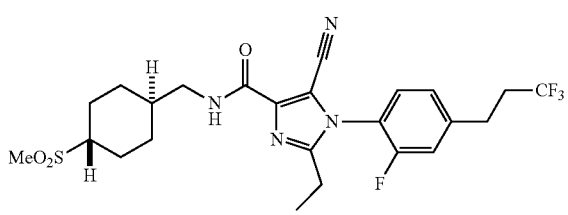 [SMILES: CCc1nc(C(=O)NC[C@H]2CC[C@H](S(C)(=O)=O)CC2)c(C#N)n1-c1ccc(CCC(F)(F)F)cc1F]

The title compound was prepared as described for the synthesis of Example 1, using ethyl 5-cyano-2-ethyl-1-(2-fluoro-4-(3,3,3-trifluoropropyl)phenyl)-1H-imidazole-4-carboxylate (Intermediate 148) in place of ethyl 5-cyano-2-ethyl-1-(2-methoxy-4-(3,3,3-trifluoro-2-methylpropyl)phenyl)-1H-imidazole-4-carboxylate and ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. $^1$H NMR (500 MHz, CDCl$_3$) δ 7.34-7.30 (m, 1H), 7.24-7.17 (m, 3H), 3.43-3.28 (m, 2H), 3.03-2.95 (m, 2H), 2.88-2.79 (m, 4H), 2.64-2.42 (m, 4H), 2.33-2.25 (m, 2H), 2.11-2.03 (m, 2H), 1.75-1.65 (m, 1H), 1.65-1.54 (m, 2H coincident with water), 1.28-1.23 (m, 3H), 1.20-1.09 (m, 2H); MS (ESI) m/z: [M+H]$^+$ Found 529.0.

Example 94

2-Ethyl-1-(2-fluoro-4-(3,3,3-trifluoropropyl)phenyl)-N$^4$-(((1r,4r)-4-(methylsulfonyl)cyclohexyl)methyl)-1H-imidazole-4,5-dicarboxamide

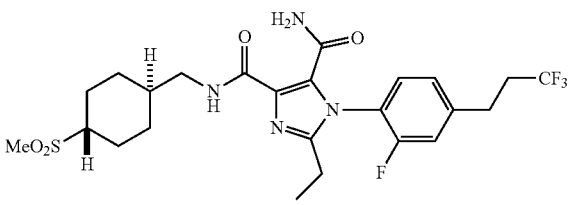 [SMILES: CCc1nc(C(=O)NC[C@H]2CC[C@H](S(C)(=O)=O)CC2)c(C(N)=O)n1-c1ccc(CCC(F)(F)F)cc1F]

This product was isolated from the same reaction mixture that gave Example 93. $^1$H NMR (500 MHz, CDCl$_3$) δ 10.93 (s, 1H), 7.95 (t, J=6.4 Hz, 1H), 7.19-7.14 (m, 1H), 7.11-7.06 (m, 2H), 5.42 (s, 1H), 3.41-3.30 (m, 2H), 2.98-2.92 (m, 2H), 2.88-2.80 (m, 4H), 2.51-2.39 (m, 4H), 2.34-2.27 (m, 2H), 2.13-2.05 (m, 2H), 1.77-1.67 (m, 1H), 1.67-1.57 (m, 2H), 1.23-1.10 (m, 5H); MS (ESI) m/z: [M+H]$^+$ Found 547.2.

Example 95

5-Cyano-2-ethyl-1-(2-fluoro-4-(3,3,3-trifluoropropyl)phenyl)-N-(((1s,4s)-1-hydroxy-4-(methylsulfonyl)cyclohexyl)methyl)-1H-imidazole-4-carboxamide

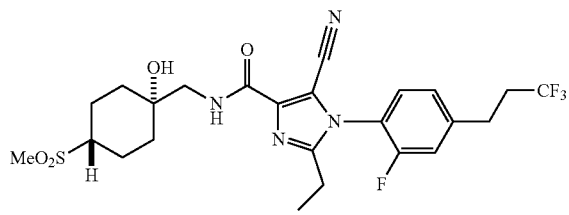 [SMILES: CCc1nc(C(=O)NC[C@]2(O)CC[C@@H](S(C)(=O)=O)CC2)c(C#N)n1-c1ccc(CCC(F)(F)F)cc1F]

The title compound was prepared as described for the synthesis of Example 1, using ethyl 5-cyano-2-ethyl-1-(2-fluoro-4-(3,3,3-trifluoropropyl)phenyl)-1H-imidazole-4-carboxylate (Intermediate 148) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 7.51-7.47 (m, 1H), 7.35-7.29 (m, 1H), 7.24-7.19 (m, 2H), 3.49 (d, J=6.4 Hz, 2H), 3.03-2.96 (m, 2H), 2.85-2.77 (m, 4H), 2.64-2.42 (m, 4H), 2.17-2.10 (m, 2H), 2.02-1.92 (m, 4H), 1.49-1.41 (m, 2H), 1.29-1.24 (m, 3H); MS (ESI) m/z: [M+H]$^+$ Found 545.1.

Example 96

2-Ethyl-1-(2-fluoro-4-(3,3,3-trifluoropropyl)phenyl)-N-(((1s,4s)-1-hydroxy-4-(methylsulfonyl)cyclohexyl)methyl)-1H-imidazole-4,5-dicarboxamide

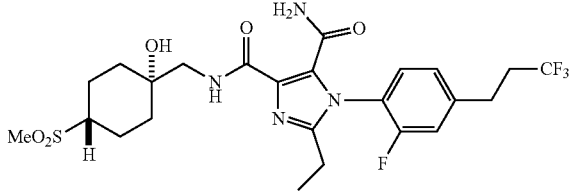 [SMILES: CCc1nc(C(=O)NC[C@]2(O)CC[C@@H](S(C)(=O)=O)CC2)c(C(N)=O)n1-c1ccc(CCC(F)(F)F)cc1F]

This product was isolated from the same reaction mixture that gave Example 95. $^1$H NMR (500 MHz, CDCl$_3$) δ 10.83 (s, 1H), 8.23-8.17 (m, 1H), 7.19-7.13 (m, 1H), 7.11-7.06 (m, 2H), 5.82 (s, 1H), 3.49 (d, J=6.5 Hz, 2H), 2.99-2.92 (m, 2H), 2.87-2.78 (m, 4H), 2.52-2.41 (m, 4H), 2.19-1.93 (m, 6H coincident with water), 1.51-1.42 (m, 2H), 1.20 (t, J=7.5 Hz, 3H); MS (ESI) m/z: [M+H]$^+$ Found 563.1.

Example 97

5-Chloro-2-ethyl-1-(2-fluoro-4-(4,4,4-trifluorobutyl)phenyl)-N-(((1r,4r)-4-(methylsulfonyl)cyclohexyl)methyl)-1H-imidazole-4-carboxamide

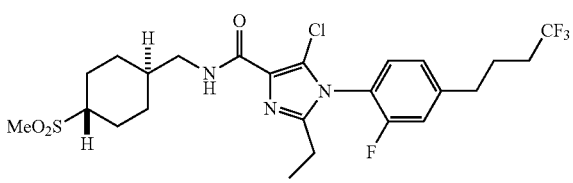 [SMILES: CCc1nc(C(=O)NC[C@H]2CC[C@H](S(C)(=O)=O)CC2)c(Cl)n1-c1ccc(CCCC(F)(F)F)cc1F]

The title compound was prepared as described for the synthesis of Example 1, using ethyl 5-chloro-2-ethyl-1-(2-fluoro-4-(4,4,4-trifluorobutyl)phenyl)-1H-imidazole-4-carboxylate (Intermediate 153) in place of ethyl 5-cyano-2-ethyl-1-(2-methoxy-4-(3,3,3-trifluoro-2-methylpropyl)phenyl)-1H-imidazole-4-carboxylate and ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. $^1$H NMR (500 MHz, CDCl$_3$) δ 7.26-7.18 (m, 2H), 7.16-7.12 (m, 2H), 3.37-3.28 (m, 2H), 2.86-2.77 (m, 6H), 2.55-2.42 (m, 2H), 2.31-2.25 (m, 2H), 2.22-2.12 (m, 2H), 2.08 (dd, J=14.2, 3.6 Hz, 2H), 2.01-1.93 (m, 2H), 1.73-1.64 (m, 1H), 1.64-1.54 (m, 2H coincident with water), 1.22-1.09 (m, 5H); MS (ESI) m/z: [M+H]$^+$ Found 552.1.

Example 98

5-Chloro-2-ethyl-1-(2-fluoro-4-(4,4,4-trifluorobutyl)phenyl)-N-(((1s,4s)-1-hydroxy-4-(methylsulfonyl)cyclohexyl)methyl)-1H-imidazole-4-carboxamide

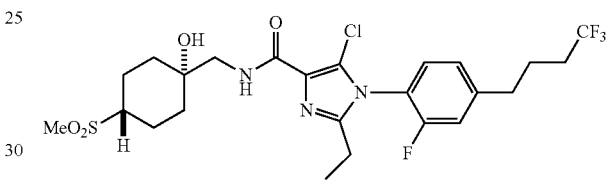

The title compound was prepared as described for the synthesis of Example 1, using ethyl 5-chloro-2-ethyl-1-(2-fluoro-4-(4,4,4-trifluorobutyl)phenyl)-1H-imidazole-4-carboxylate (Intermediate 153) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 7.51 (t, J=6.4 Hz, 1H), 7.22-7.18 (m, 1H), 7.17-7.13 (m, 2H), 3.52 (s, 1H), 3.45 (d, J=6.4 Hz, 2H), 2.84-2.75 (m, 6H), 2.55-2.42 (m, 2H), 2.22-2.09 (m, 4H), 2.03-1.94 (m, 6H), 1.45-1.37 (m, 2H), 1.20 (t, J=7.5 Hz, 3H); MS (ESI) m/z: [M+H]$^+$ Found 568.0.

Example 99

5-Chloro-2-ethyl-1-(2-fluoro-4-(3,3,3-trifluoro-2-(trifluoromethyl)propyl)phenyl)-N-(((1r,4r)-4-(methylsulfonyl)cyclohexyl)methyl)-1H-imidazole-4-carboxamide

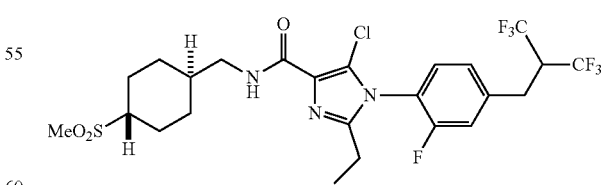

A Rieke® zinc in THF suspension (1 mL, 0.05 g/mL, 0.765 mmol) was added to a stirring solution of 2-(bromomethyl)-1,1,1,3,3,3-hexafluropropane (0.11 mL) in THF (0.8 mL) at 0° C. After 45 min, a solution of 1-(4-bromo-2-fluorophenyl)-5-chloro-2-ethyl-N-(((1r,4r)-4-(methylsulfonyl)cyclohexyl)methyl)-1H-imidazole-4-carboxamide (75 mg, 0.14 mmol, Intermediate 186) was added followed by Pd(t-Bu₃P)₂ (17 mg, 0.033 mmol). The mixture was warmed to 60° C. After 3 h, the mixture was cooled to rt and partitioned between aqueous sodium chloride solution and EtOAc; the layers were separated. The organic layer was dried with anhydrous Na₂SO₄, filtered, and then absorbed onto Celite®. Purification by silica gel chromatography provided the title compound after lyophilization as a colorless powder. ¹H NMR (500 MHz, CDCl₃) δ 7.28-7.19 (m, 4H coincident with residual CHCl₃), 3.36-3.20 (m, 5H), 2.87-2.79 (m, 4H), 2.54-2.42 (m, 2H), 2.31-2.24 (m, 2H), 2.11-2.04 (m, 2H), 1.73-1.63 (m, 1H), 1.63-1.53 (m, 2H coincident with water), 1.22-1.09 (m, 5H); MS (ESI) m/z: [M+H]⁺ Found 606.0.

Example 100

5-Chloro-2-ethyl-1-(2-fluoro-4-(3,3,3-trifluoro-2-(trifluoromethyl)propyl)phenyl)-N-(((1s,4s)-1-hydroxy-4-(methylsulfonyl)cyclohexyl)methyl)-1H-imidazole-4-carboxamide

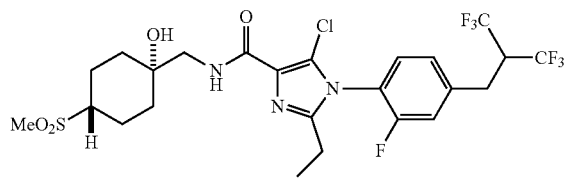 [SMILES: CCc1nc(C(=O)NC[C@]2(O)CC[C@@H](S(C)(=O)=O)CC2)c(Cl)n1-c1ccc(CC(C(F)(F)F)C(F)(F)F)cc1F]

The title compound was prepared as described for the synthesis of Example 99, using 1-(4-bromo-2-fluorophenyl)-5-chloro-2-ethyl-N-(((1s,4s)-1-hydroxy-4-(methylsulfonyl)cyclohexyl)methyl)-1H-imidazole-4-carboxamide (Intermediate 187) in place of 1-(4-bromo-2-fluorophenyl)-5-chloro-2-ethyl-N-(((1 r,4r)-4-(methylsulfonyl)cyclohexyl)methyl)-1H-imidazole-4-carboxamide. ¹H NMR (500 MHz, CDCl₃) δ 7.54-7.48 (t, J=6.2 Hz, 1H), 7.26-7.19 (m, 3H), 3.48-3.42 (m, 3H), 3.31-3.20 (m, 3H), 2.83-2.75 (m, 4H), 2.54-2.41 (m, 2H), 2.16-2.09 (m, 2H), 2.04-1.93 (m, 4H), 1.46-1.36 (m, 2H), 1.23-1.17 (t, J=7.5 Hz, 3H); MS (ESI) m/z: [M+H]⁺ Found 622.0.

Example 101

5-Chloro-2-ethyl-1-(2-fluoro-4-(3,3,3-trifluoro-2,2-dimethylpropyl)phenyl)-N-(((1r,4r)-4-(methylsulfonyl)cyclohexyl)methyl)-1H-imidazole-4-carboxamide

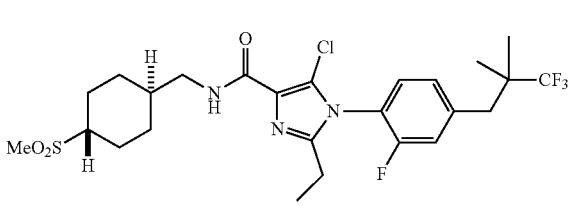 [SMILES: CCc1nc(C(=O)NC[C@H]2CC[C@H](S(C)(=O)=O)CC2)c(Cl)n1-c1ccc(CC(C)(C)C(F)(F)F)cc1F]

The title compound was prepared as described for the synthesis of Example 2, using ethyl 5-chloro-2-ethyl-1-(2-fluoro-4-(3,3,3-trifluoro-2,2-dimethylpropyl)phenyl)-1H-imidazole-4-carboxylate (Intermediate 154) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate and DCM in place of MeCN as solvent. ¹H NMR (500 MHz, CDCl₃) δ 7.26-7.22 (m, 1H), 7.20 (t, J=7.7 Hz, 1H), 7.13 (d, J=8.9 Hz, 2H), 3.36-3.29 (m, 2H), 2.89-2.80 (m, 6H), 2.55-2.43 (m, 2H), 2.28 (d, J=12.6 Hz, 2H), 2.08 (d, J=13.1 Hz, 2H), 1.73-1.65 (m, 1H), 1.65-1.55 (m, 2H coincident with water), 1.19 (t, J=7.5 Hz, 3H), 1.18-1.09 (m, 8H); MS (ESI) m/z: [M+H]⁺ Found 566.2.

Example 102

5-Chloro-2-ethyl-1-(2-fluoro-4-(3,3,3-trifluoro-2,2-dimethylpropyl)phenyl)-N-(((1s,4s)-1-hydroxy-4-(methylsulfonyl)cyclohexyl)methyl)-1H-imidazole-4-carboxamide

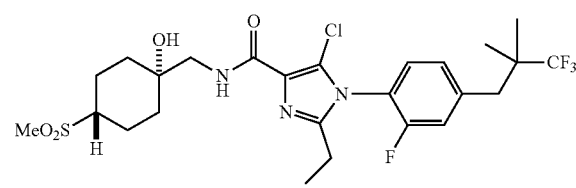 [SMILES: CCc1nc(C(=O)NC[C@]2(O)CC[C@@H](S(C)(=O)=O)CC2)c(Cl)n1-c1ccc(CC(C)(C)C(F)(F)F)cc1F]

The title compound was prepared as described for the synthesis of Example 2, using ethyl 5-chloro-2-ethyl-1-(2-fluoro-4-(3,3,3-trifluoro-2,2-dimethylpropyl)phenyl)-1H-imidazole-4-carboxylate (Intermediate 154) in place of 5-chloro-1-(3-(difluoromethoxy)-5-(3,3,3-trifluoro-2,2-dimethylpropyl)pyridin-2-yl)-2-ethyl-1H-imidazole-4-carboxylic acid, (1s,4s)-1-(aminomethyl)-4-(methyl sulfonyl)cyclohexanol hydrochloride (Intermediate 9) in place of ((1r,4r)-4-(methylsulfonyl)cyclohexyl)methanamine hydrochloride, and DCM in place of MeCN as solvent. ¹H NMR (500 MHz, CDCl₃) δ 7.54-7.50 (m, 1H), 7.22-7.18 (m, 1H), 7.15-7.12 (m, 2H), 3.52 (s, 1H), 3.45 (d, J=6.3 Hz, 2H), 2.88 (s, 2H), 2.84-2.76 (m, 4H), 2.54-2.43 (m, 2H), 2.13 (d, J=10.9 Hz, 2H), 2.03-1.93 (m, 4H), 1.46-1.37 (m, 2H), 1.22-1.18 (m, 3H), 1.14 (s, 6H); MS (ESI) m/z: [M+H]⁺ Found 582.2.

Example 103

5-Chloro-2-ethyl-1-(3-fluoro-4-(3,3,3-trifluoro-2,2-dimethylpropyl)phenyl)-N-(((1r,4r)-4-(methylsulfonyl)cyclohexyl)methyl)-1H-imidazole-4-carboxamide

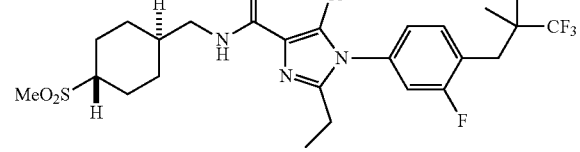

The title compound was prepared as described for the synthesis of Example 2, using ethyl 5-chloro-2-ethyl-1-(3-fluoro-4-(3,3,3-trifluoro-2,2-dimethylpropyl)phenyl)-1H-imidazole-4-carboxylate (Intermediate 159) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate and DCM in place of MeCN as solvent. ¹H NMR (500 MHz, CDCl$_3$) δ 7.39-7.33 (m, 1H), 7.25-7.21 (m, 1H), 7.03-6.97 (m, 2H), 3.35-3.30 (t, J=6.6 Hz, 2H), 2.96-2.91 (s, 2H), 2.86-2.79 (m, 4H), 2.56-2.50 (q, J=7.5 Hz, 2H), 2.31-2.24 (m, 2H), 2.11-2.04 (m, 2H), 1.73-1.64 (m, 1H), 1.64-1.53 (m, 2H), 1.23-1.09 (m, 11H); MS (ESI) m/z: [M+H]$^+$ Found 566.1.

Example 104

5-Chloro-2-ethyl-1-(3-fluoro-4-(3,3,3-trifluoro-2,2-dimethylpropyl)phenyl)-N-(((1s,4s)-1-hydroxy-4-(methylsulfonyl)cyclohexyl)methyl)-1H-imidazole-4-carboxamide

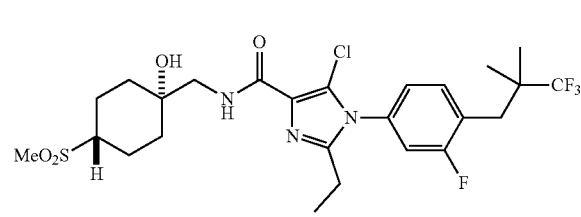 [SMILES: CCc1nc(C(=O)NC[C@]2(O)CC[C@@H](S(C)(=O)=O)CC2)c(Cl)n1-c1ccc(CC(C)(C)C(F)(F)F)c(F)c1]

The title compound was prepared as described for the synthesis of Example 2, using ethyl 5-chloro-2-ethyl-1-(3-fluoro-4-(3,3,3-trifluoro-2,2-dimethylpropyl)phenyl)-1H-imidazole-4-carboxylate (Intermediate 159) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate, (1 s,4s)-1-(aminomethyl)-4-(methylsulfonyl)cyclohexanol hydrochloride (Intermediate 9) in place of ((1r,4r)-4-(methylsulfonyl)cyclohexyl)methanamine hydrochloride, and DCM in place of MeCN as solvent. $^1$H NMR (500 MHz, CDCl$_3$) δ 7.53-7.48 (m, 1H), 7.40-7.34 (m, 1H), 7.03-6.98 (m, 2H), 3.48-3.42 (m, 3H), 2.96-2.92 (s, 2H), 2.84-2.75 (m, 4H), 2.56-2.50 (m, 2H), 2.16-2.09 (m, 2H), 2.03-1.92 (m, 4H), 1.46-1.36 (m, 2H), 1.23-1.17 (m, 3H), 1.16-1.13 (s, 6H); MS (ESI) m/z: [M+H]$^+$ Found 582.2.

Example 105

5-Chloro-2-ethyl-1-(3-fluoro-4-(3,3,3-trifluoro-2-(trifluoromethyl)propyl)phenyl)-N-(((1s,4s)-1-hydroxy-4-(methylsulfonyl)cyclohexyl)methyl)-1H-imidazole-4-carboxamide

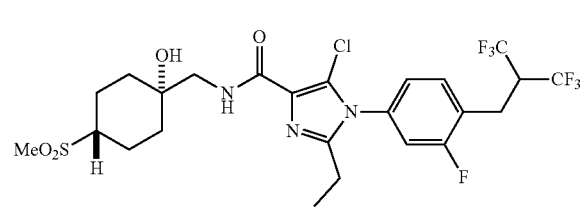 [SMILES: CCc1nc(C(=O)NC[C@]2(O)CC[C@@H](S(C)(=O)=O)CC2)c(Cl)n1-c1ccc(CC(C(F)(F)F)C(F)(F)F)c(F)c1]

The title compound was prepared as described for the synthesis of Example 99, using 1-(4-bromo-3-fluorophenyl)-5-chloro-2-ethyl-N-(((1s,4s)-1-hydroxy-4-(methylsulfonyl)cyclohexyl)methyl)-1H-imidazole-4-carboxamide (Intermediate 161) in place of 1-(4-bromo-2-fluorophenyl)-5-chloro-2-ethyl-N-(((1 r,4r)-4-(methylsulfonyl)cyclohexyl)methyl)-1H-imidazole-4-carboxamide. $^1$H NMR (500 MHz, DMSO-d$_6$) δ 7.79-7.74 (m, 1H), 7.72-7.67 (m, 1H), 7.61-7.56 (m, 1H), 7.39-7.35 (m, 1H), 4.69-4.63 (s, 1H), 4.59-4.44 (m, 1H), 3.31-3.27 (m, 2H), 3.27-3.23 (d, J=6.2 Hz, 2H), 3.04-2.95 (m, 1H), 2.92-2.87 (s, 3H), 2.52-2.47 (m, 2H), 1.90-1.82 (m, 2H), 1.80-1.63 (m, 4H), 1.40-1.30 (m, 2H), 1.11-1.05 (m, 3H); MS (ESI) m/z: [M+H]$^+$ Found 622.0.

Example 106

2-Ethyl-1-(3-fluoro-4-(3,3,3-trifluoro-2-(trifluoromethyl)propyl)phenyl)-N-(((1s,4s)-1-hydroxy-4-(methylsulfonyl)cyclohexyl)methyl)-5-methyl-1H-imidazole-4-carboxamide

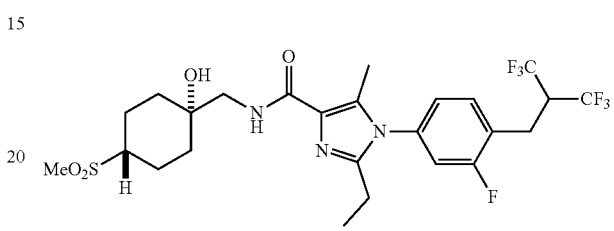

The title compound was prepared as described for the synthesis of Intermediate 89, using 5-chloro-2-ethyl-1-(3-fluoro-4-(3,3,3-trifluoro-2-(trifluoromethyl)propyl)phenyl)-N-(((1 s,4s)-1-hydroxy-4-(methylsulfonyl)cyclohexyl)methyl)-1H-imidazole-4-carboxamide (Example 105) in place of ethyl 5-chloro-1-(3-(difluoromethoxy)-5-(3,3,3-trifluoro-2,2-dimethylpropyl)pyridin-2-yl)-2-ethyl-1H-imidazole-4-carboxylate. $^1$H NMR (400 MHz, CDCl$_3$) δ 7.78-7.60 (br s, 1H), 7.47-7.41 (m, 1H), 7.04-6.96 (m, 2H), 4.09-3.95 (br s, 1H), 3.47-3.30 (m, 3H), 3.29-3.24 (d, J=6.7 Hz, 2H), 2.85-2.73 (m, 4H), 2.55-2.47 (m, 2H), 2.37-2.30 (s, 3H), 2.17-2.08 (m, 2H), 2.06-1.91 (m, 4H), 1.44-1.32 (m, 2H), 1.22-1.16 (m, 3H); MS (ESI) m/z: [M+H]$^+$ Found 602.1.

Example 107

5-Chloro-1-(3-(difluoromethoxy)-5-(4,4,4-trifluoro-2,2-dimethylbutyl)pyridin-2-yl)-2-ethyl-N-(((1s,4s)-1-hydroxy-4-(methylsulfonyl)cyclohexyl)methyl)-1H-imidazole-4-carboxamide

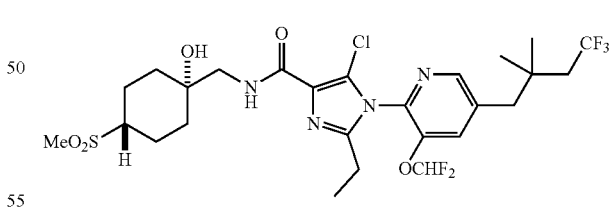

The title compound was prepared as described for the synthesis of Example 2, using ethyl 5-chloro-1-(3-(difluoromethoxy)-5-(4,4,4-trifluoro-2,2-dimethylbutyl)pyridin-2-yl)-2-ethyl-1H-imidazole-4-carboxylate (Intermediate 160) in place of 5-chloro-1-(3-(difluoromethoxy)-5-(3,3,3-trifluoro-2,2-dimethylpropyl)pyridin-2-yl)-2-ethyl-1H-imidazole-4-carboxylic acid, (1s,4s)-1-(aminomethyl)-4-(methylsulfonyl)cyclohexanol hydrochloride (Intermediate 9) in place of ((1r,4r)-4-(methylsulfonyl)cyclohexyl)methanamine hydrochloride, and DCM in place of MeCN as solvent. $^1$H NMR (400 MHz, CDCl$_3$) δ 8.33-8.30 (d, J=1.9

Hz, 1H), 7.66-7.62 (s, 1H), 7.55-7.49 (m, 1H), 6.70-6.27 (m, 1H), 3.54-3.51 (s, 1H), 3.51-3.37 (m, 2H), 2.85-2.73 (m, 6H), 2.59-2.40 (m, 2H), 2.16-2.06 (m, 4H), 2.05-1.91 (m, 4H), 1.47-1.34 (m, 2H), 1.24-1.17 (m, 3H), 1.16-1.09 (s, 6H); MS (ESI) m/z: [M+H]+ Found 645.2.

Example 108

5-Chloro-1-(2,6-difluoro-4-(3,3,3-trifluoro-2-hydroxy-2-(trifluoromethyl)propyl)phenyl)-2-ethyl-N-(((1s,4s)-1-hydroxy-4-(methylsulfonyl)cyclohexyl)methyl)-1H-imidazole-4-carboxamide

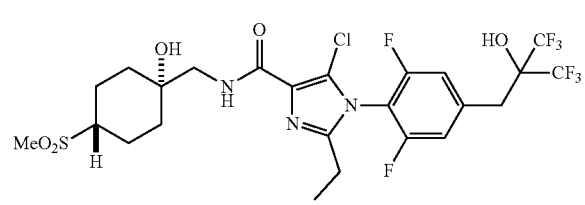 [SMILES: CCc1nc(C(=O)NC[C@]2(O)CC[C@@H](S(C)(=O)=O)CC2)c(Cl)n1-c1c(F)cc(CC(O)(C(F)(F)F)C(F)(F)F)cc1F]

The title compound was prepared as described for the synthesis of Example 1, using 5-chloro-1-(2,6-difluoro-4-(3,3,3-trifluoro-2-hydroxy-2-(trifluoromethyl)propyl)phenyl)-2-ethyl-1H-imidazole-4-carboxylic acid (Intermediate 142) in place of 5-cyano-2-ethyl-1-(2-methoxy-4-(3,3,3-trifluoro-2-methylpropyl)phenyl)-1H-imidazole-4-carboxylic acid. $^1$H NMR (500 MHz, DMSO-d6) δ 8.37 (s, 1H), 7.86-7.78 (m, 2H), 7.56-7.50 (m, 1H), 3.82 (s, 1H, OH proton coincident with water), 3.37 (s, 2H), 3.25 (d, J=6.3 Hz, 2H), 3.06-2.96 (m, 1H), 2.89 (s, 3H), 2.48-2.42 (m, 2H), 1.86 (d, J=11.9 Hz, 2H), 1.79-1.64 (m, 4H), 1.41-1.31 (m, 2H), 1.13-1.06 (m, 3H); MS (ESI) m/z: [M+H]+ Found 656.0.

Example 109

2-Ethyl-1-(2-fluoro-4-(3,3,3-trifluoro-2-(trifluoromethyl)propyl)phenyl)-N-(((1s,4s)-1-hydroxy-4-(methylsulfonyl)cyclohexyl)methyl)-5-methyl-1H-imidazole-4-carboxamide

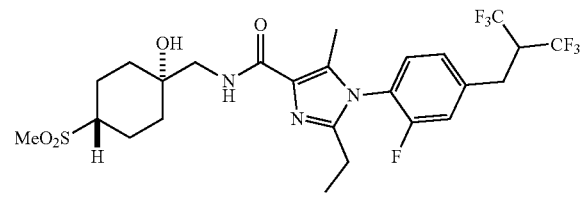 [SMILES: CCc1nc(C(=O)NC[C@]2(O)CC[C@@H](S(C)(=O)=O)CC2)c(C)n1-c1ccc(CC(C(F)(F)F)C(F)(F)F)cc1F]

RuPhos G1 (2.8 mg, 0.0034 mmol), RuPhos (1.5 mg, 0.0032 mmol), and K$_2$CO$_3$ (29.9 mg, 0.216 mmol) were combined in a vessel, and the vessel was evacuated and backfilled three times with nitrogen. A solution of 5-chloro-2-ethyl-1-(2-fluoro-4-(3,3,3-trifluoro-2-(trifluoromethyl)propyl)phenyl)-N-(((1s,4s)-1-hydroxy-4-(methylsulfonyl)cyclohexyl)methyl)-1H-imidazole-4-carboxamide (32.6 mg, 0.0524 mmol, Example 100) in 1,4-dioxane (0.5 mL) and trimethylboroxine (0.02 mL, 0.14 mmol) were sequentially added, and the resulting mixture was stirred at 110° C. for 1 hour and 15 min. After this time, the mixture was allowed to cool to rt, and then it was diluted with EtOAc and water. The layers were separated, and the aqueous layer was extracted with EtOAc. The combined organic layers were dried with anhydrous MgSO$_4$, filtered, and concentrated. The residue was purified by preparative HPLC (XBridge C18, 5→99% MeCN/water, 20 mM NH$_4$OH) to afford the title compound. $^1$H NMR (500 MHz, CDCl$_3$) δ 7.56 (t, J=6.3 Hz, 1H), 7.22-7.18 (m, 3H), 4.06 (s, 1H), 3.42 (d, J=6.3 Hz, 2H), 3.31-3.20 (m, 3H), 2.83-2.75 (m, 4H), 2.44 (qd, J=7.6, 1.4 Hz, 2H), 2.31 (s, 3H), 2.15-2.09 (m, 2H), 2.04-1.94 (m, 4H), 1.42-1.34 (m, 2H), 1.17 (t, J=7.5 Hz, 3H). MS (ESI) m/z: [M+H]+ Found 601.9.

Example 110

2-Ethyl-1-(2-fluoro-4-(3,3,3-trifluoro-2-(trifluoromethyl)propyl)phenyl)-5-methyl-N-(((r,4r)-4-(methylsulfonyl)cyclohexyl)methyl)-1H-imidazole-4-carboxamide

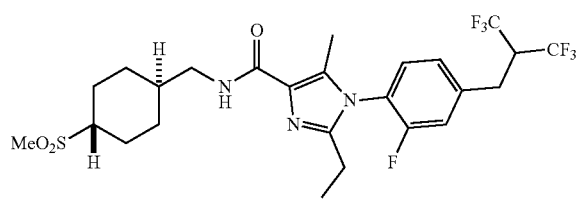 [SMILES: CCc1nc(C(=O)NC[C@H]2CC[C@H](S(C)(=O)=O)CC2)c(C)n1-c1ccc(CC(C(F)(F)F)C(F)(F)F)cc1F]

The title compound was prepared as described for the synthesis of Example 109, using 5-chloro-2-ethyl-1-(2-fluoro-4-(3,3,3-trifluoro-2-(trifluoromethyl)propyl)phenyl)-N-(((1 r,4r)-4-(methylsulfonyl)cyclohexyl)methyl)-1H-imidazole-4-carboxamide (Example 99) in place of 5-chloro-2-ethyl-1-(2-fluoro-4-(3,3,3-trifluoro-2-(trifluoromethyl)propyl)phenyl)-N-(((1 s,4s)-1-hydroxy-4-(methylsulfonyl)cyclohexyl)methyl)-1H-imidazole-4-carboxamide. $^1$H NMR (500 MHz, CDCl$_3$) δ 7.32 (t, J=6.4 Hz, 1H), 7.24-7.18 (m, 3H), 3.31 (t, J=6.7 Hz, 2H), 3.28-3.20 (m, 3H), 2.86-2.79 (m, 4H), 2.45 (qd, J=7.6, 1.6 Hz, 2H), 2.32 (s, 3H), 2.27 (d, J=12.8 Hz, 2H), 2.12-2.05 (m, 2H), 1.71-1.64 (m, 1H), 1.63-1.54 (m, 2H), 1.19-1.08 (m, 5H). MS (ESI) m/z: [M+H]+ Found 586.1.

Example 111

5-Cyano-2-ethyl-N-(((1s,4s)-1-hydroxy-4-(methylsulfonyl)cyclohexyl)methyl)-1-(4-(3,3,3-trifluoro-2,2-dimethylpropyl)-2-(trifluoromethoxy)phenyl)-1H-imidazole-4-carboxamide

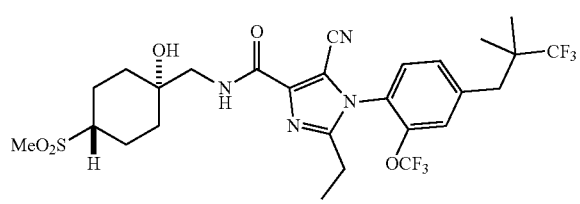 [SMILES: CCc1nc(C(=O)NC[C@]2(O)CC[C@@H](S(C)(=O)=O)CC2)c(C#N)n1-c1ccc(CC(C)(C)C(F)(F)F)cc1OC(F)(F)F]

HATU (36 mg, 0.096 mmol) was added to a 0° C. solution of 5-cyano-2-ethyl-1-(4-(3,3,3-trifluoro-2,2-dimethylpropyl)-2-(trifluoromethoxy)phenyl)-1H-imidazole-4-carboxylic acid (36 mg, 0.081 mmol, Intermediate 165) in DMF (0.9 mL). (1s,4s)-1-(Aminomethyl)-4-(methylsulfonyl)cyclohexan-1-ol hydrochloride (25 mg, 0.10 mmol, Intermediate 9) and then DIPEA (0.04 mL, 0.2 mmol) were added, and the resulting mixture was stirred and allowed to warm to rt over 16 h. After this time, the reaction mixture was diluted with water and EtOAc. The layers were separated, and the aqueous layer was extracted with EtOAc. The organic layers were combined, dried with anhydrous Na$_2$SO$_4$, filtered, and then concentrated. The residue was purified by silica gel chromatography (50→100% EtOAc/hexanes) and then by preparative HPLC (XBridge C18, 10→100% of MeCN/water, 0.05% TFA) to afford the title compound. $^1$H NMR (500 MHz, CDCl$_3$) δ 7.51-7.46 (m, 1H), 7.36-7.31 (m, 3H), 3.56-3.42 (m, 2H), 2.91 (s, 2H), 2.86-2.78 (m, 5H), 2.60-2.43 (m, 2H), 2.17-2.10 (m, 2H), 2.03-1.93 (m, 4H), 1.50-1.42 (m, 2H), 1.28 (t, J=7.5 Hz, 3H), 1.14 (s, 6H). MS (ESI) m/z: [M+H]$^+$ Found 639.0.

Example 112

2-Ethyl-N$^4$-(((1s,4s)-1-hydroxy-4-(methylsulfonyl)cyclohexyl)methyl)-1-(4-(3,3,3-trifluoro-2,2-dimethylpropyl)-2-(trifluoromethoxy)phenyl)-1H-imidazole-4,5-dicarboxamide

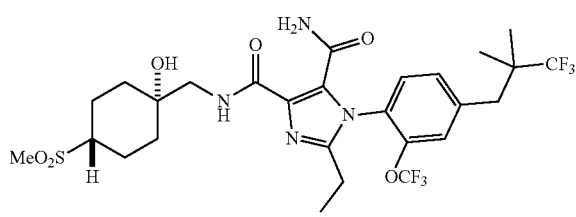 [SMILES: CCc1nc(C(=O)NC[C@]2(O)CC[C@@H](S(C)(=O)=O)CC2)c(C(N)=O)n1-c1ccc(CC(C)(C)C(F)(F)F)cc1OC(F)(F)F]

The title compound was a side product from the synthesis of Example 111. MS (ESI) m/z: [M+H]$^+$ Found 657.2.

Example 113

5-Cyano-2-ethyl-N-(((1r,4r)-4-(methylsulfonyl)cyclohexyl)methyl)-1-(4-(3,3,3-trifluoro-2,2-dimethylpropyl)-2-(trifluoromethoxy)phenyl)-1H-imidazole-4-carboxamide

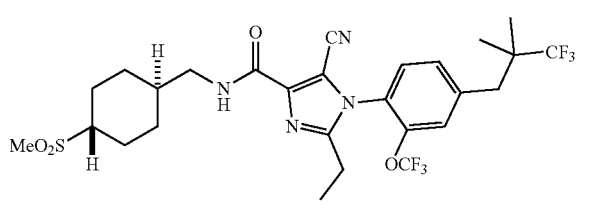 [SMILES: CCc1nc(C(=O)NC[C@H]2CC[C@H](S(C)(=O)=O)CC2)c(C#N)n1-c1ccc(CC(C)(C)C(F)(F)F)cc1OC(F)(F)F]

The title compound was prepared as described for the synthesis of Example 111, using ((1r,4r)-4-(methylsulfonyl)cyclohexyl)methanamine hydrochloride (Intermediate 13) in place of (1s,4s)-1-(aminomethyl)-4-(methylsulfonyl)cyclohexan-1-ol hydrochloride. $^1$H NMR (500 MHz, CDCl$_3$) δ 7.38-7.29 (m, 3H), 7.23-7.19 (m, 1H), 3.41-3.31 (m, 2H), 2.91 (s, 2H), 2.88-2.79 (m, 4H), 2.59-2.42 (m, 2H), 2.29 (d, J=12.0 Hz, 2H), 2.08 (d, J=12.6 Hz, 2H), 1.77-1.66 (m, 1H), 1.66-1.57 (m, 2H), 1.30-1.22 (m, 3H), 1.20-1.10 (m, 8H). MS (ESI) m/z: [M+H]$^+$ Found 623.2.

Example 114

5-Cyano-2-ethyl-N-(((1s,4s)-1-hydroxy-4-(methylsulfonyl)cyclohexyl)methyl)-1-(2-(trifluoromethoxy)-4-(3,3,3-trifluoropropyl)phenyl)-1H-imidazole-4-carboxamide

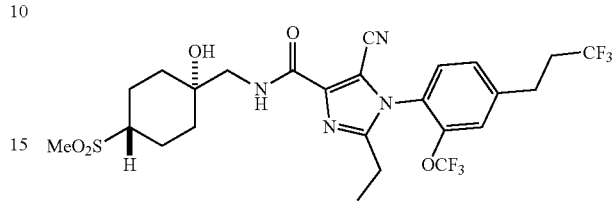

The title compound was prepared as described for the synthesis of Example 111, using 5-cyano-2-ethyl-1-(2-(trifluoromethoxy)-4-(3,3,3-trifluoropropyl)phenyl)-1H-imidazole-4-carboxylic acid (Intermediate 167) in place of 5-cyano-2-ethyl-1-(4-(3,3,3-trifluoro-2,2-dimethylpropyl)-2-(trifluoromethoxy)phenyl)-1H-imidazole-4-carboxylic acid. $^1$H NMR (500 MHz, CDCl$_3$) δ 7.51-7.46 (m, 1H), 7.38-7.35 (m, 3H), 3.55-3.43 (m, 2H), 3.06-3.00 (m, 2H), 2.86-2.78 (m, 5H), 2.59-2.41 (m, 4H), 2.17-2.10 (m, 2H), 2.04-1.93 (m, 4H), 1.50-1.42 (m, 2H), 1.27 (t, J=7.5 Hz, 3H). MS (ESI) m/z: [M+H]$^+$ Found 610.9.

Example 115

5-Cyano-2-ethyl-N-(((1r,4r)-4-(methylsulfonyl)cyclohexyl)methyl)-1-(2-(trifluoromethoxy)-4-(3,3,3-trifluoropropyl)phenyl)-1H-imidazole-4-carboxamide

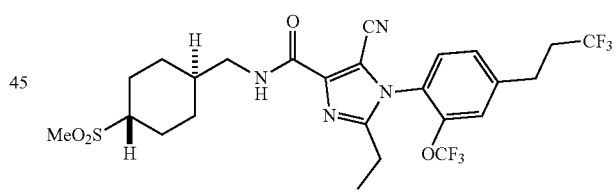

The title compound was prepared as described for the synthesis of Example 111, using 5-cyano-2-ethyl-1-(2-(trifluoromethoxy)-4-(3,3,3-trifluoropropyl)phenyl)-1H-imidazole-4-carboxylic acid (Intermediate 167) in place of 5-cyano-2-ethyl-1-(4-(3,3,3-trifluoro-2,2-dimethylpropyl)-2-(trifluoromethoxy)phenyl)-1H-imidazole-4-carboxylic acid and ((1r,4r)-4-(methylsulfonyl)cyclohexyl)methanamine hydrochloride (Intermediate 13) in place of (1s,4s)-1-(aminomethyl)-4-(methyl sulfonyl)cyclohexan-1-ol hydrochloride. $^1$H NMR (500 MHz, CDCl$_3$) δ 7.38-7.34 (m, 3H), 7.21 (t, J=6.5 Hz, 1H), 3.43-3.29 (m, 2H), 3.06-3.00 (m, 2H), 2.88-2.81 (m, 4H), 2.59-2.41 (m, 4H), 2.33-2.26 (m, 2H), 2.11-2.04 (m, 2H), 1.76-1.66 (m, 1H), 1.66-1.58 (m, 2H), 1.27 (t, J=7.5 Hz, 3H), 1.20-1.10 (m, 2H). MS (ESI) m/z: [M+H]$^+$ Found 595.0.

Example 116

2-Ethyl-1-(4-methoxy-6-(3,3,3-trifluoropropyl)pyridin-3-yl)-N-(((1r,4r)-4-(methylsulfonyl)cyclohexyl)methyl)-1H-imidazole-4-carboxamide

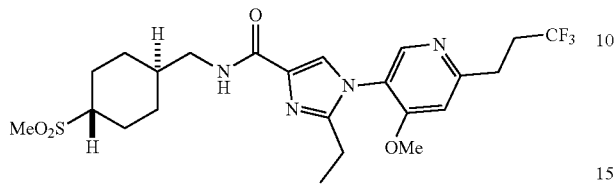

The title compound was prepared as described for Example 1, using 2-ethyl-1-(4-methoxy-6-(3,3,3-trifluoropropyl)pyridin-3-yl)-1H-imidazole-4-carboxylic acid (Intermediate 172) in place of 5-cyano-2-ethyl-1-(2-methoxy-4-(3,3,3-trifluoro-2-methylpropyl)phenyl)-1H-imidazole-4-carboxylic acid and ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. The purified product was free-based by partitioning between DCM and saturated aqueous NaHCO$_3$. The aqueous layer was further extracted with DCM, then the organic layers were combined, dried with anhydrous Na$_2$SO$_4$, filtered and concentrated to provide the title compound as a colorless oil. $^1$H NMR (500 MHz, CDCl$_3$) δ 8.28 (s, 1H), 7.47 (s, 1H), 7.24-7.21 (m, 1H), 6.87 (s, 1H), 3.87 (s, 3H), 3.35-3.30 (m, 2H), 3.11-3.07 (m, 2H), 2.86-2.78 (m, 4H), 2.71-2.62 (m, 2H), 2.48 (q, J=7.5 Hz, 2H), 2.30-2.24 (m, 2H), 2.10-2.05 (m, 2H), 1.69-1.64 (m, 1H), 1.62-1.53 (m, 2H), 1.20 (t, J=7.5 Hz, 3H), 1.17-1.08 (m, 2H). MS (ESI) m/z: [M+H]$^+$ Found 517.2.

Example 117

5-Cyano-2-ethyl-1-(4-methoxy-6-(3,3,3-trifluoropropyl)pyridin-3-yl)-N-(((1r,4r)-4-(methylsulfonyl)cyclohexyl)methyl)-1H-imidazole-4-carboxamide

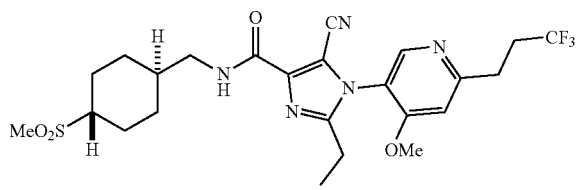 [SMILES: CCc1nc(C(=O)NC[C@H]2CC[C@H](S(C)(=O)=O)CC2)c(C#N)n1-c1cnc(CCC(F)(F)F)cc1OC]

The title compound was prepared as described for Example 1, using 5-cyano-2-ethyl-1-(4-methoxy-6-(3,3,3-trifluoropropyl)pyridin-3-yl)-1H-imidazole-4-carboxylic acid (Intermediate 174) in place of 5-cyano-2-ethyl-1-(2-methoxy-4-(3,3,3-trifluoro-2-methylpropyl)phenyl)-1H-imidazole-4-carboxylic acid and ((1r,4r)-4-(methylsulfonyl)cyclohexyl)methanamine hydrochloride (Intermediate 9) in place of (1s,4s)-1-(aminomethyl)-4-(methylsulfonyl)cyclohexanol hydrochloride. The purified product was free-based by partitioning between DCM and saturated aqueous NaHCO$_3$. The aqueous layer was further extracted with DCM, then the organic layers were combined, dried with anhydrous Na$_2$SO$_4$, filtered and concentrated to provide the title compound as a colorless oil. $^1$H NMR (500 MHz, CDCl$_3$) δ 8.32 (s, 1H), 7.23-7.17 (m, 1H), 6.93 (s, 1H), 3.92 (s, 3H), 3.38-3.33 (m, 2H), 3.15-3.09 (m, 2H), 2.87-2.80 (m, 4H), 2.77-2.62 (m, 2H), 2.55-2.48 (m, 2H), 2.32-2.25 (m, 2H), 2.10-2.04 (m, 2H), 1.74-1.66 (m, 1H), 1.63-1.55 (m, 2H), 1.26-1.22 (m, 3H), 1.18-1.09 (m, 2H). MS (ESI) m/z: [M+H]$^+$ Found 542.2.

Example 118

5-Cyano-2-ethyl-N-(((1s,4s)-1-hydroxy-4-(methylsulfonyl)cyclohexyl)methyl)-1-(4-methoxy-6-(3,3,3-trifluoropropyl)pyridin-3-yl)-1H-imidazole-4-carboxamide

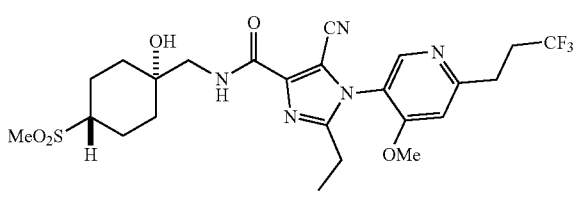 [SMILES: CCc1nc(C(=O)NC[C@]2(O)CC[C@@H](S(C)(=O)=O)CC2)c(C#N)n1-c1cnc(CCC(F)(F)F)cc1OC]

The title compound was prepared as described for Example 1, using 5-cyano-2-ethyl-1-(4-methoxy-6-(3,3,3-trifluoropropyl)pyridin-3-yl)-1H-imidazole-4-carboxylic acid (Intermediate 174) in place of 5-cyano-2-ethyl-1-(2-methoxy-4-(3,3,3-trifluoro-2-methylpropyl)phenyl)-1H-imidazole-4-carboxylic acid. The purified product was free-based by partitioning between DCM and saturated aqueous NaHCO$_3$. The aqueous layer was further extracted with DCM, then the organic layers were combined, dried with anhydrous Na$_2$SO$_4$, filtered and concentrated to provide the title compound as a colorless oil. $^1$H NMR (500 MHz, CDCl$_3$) δ 8.32 (s, 1H), 7.51-7.46 (m, 1H), 6.93 (s, 1H), 3.93 (s, 3H), 3.53-3.44 (m, 2H), 3.14-3.09 (m, 2H), 2.94 (s, 1H), 2.84 (s, 3H), 2.83-2.77 (m, 1H), 2.75-2.62 (m, 2H), 2.56-2.48 (m, 2H), 2.16-2.09 (m, 2H), 2.02-1.94 (m, 4H), 1.49-1.41 (m, 2H), 1.26-1.23 (m, 3H). MS (ESI) m/z: [M+H]$^+$ Found 558.2.

Example 119

5-Cyano-2-ethyl-1-(3-methoxy-5-(3,3,3-trifluoropropyl)pyridin-2-yl)-N-(((1r,4r)-4-(methylsulfonyl)cyclohexyl)methyl)-1H-imidazole-4-carboxamide

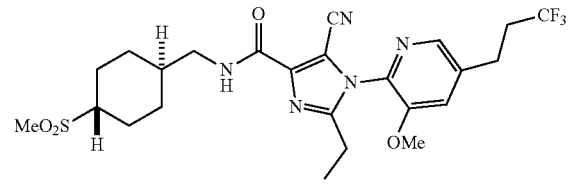 [SMILES: CCc1nc(C(=O)NC[C@H]2CC[C@H](S(C)(=O)=O)CC2)c(C#N)n1-c1ncc(CCC(F)(F)F)cc1OC]

The title compound was prepared as described for Example 1, using 5-cyano-2-ethyl-1-(3-methoxy-5-(3,3,3-trifluoropropyl)pyridin-2-yl)-1H-imidazole-4-carboxylic acid (Intermediate 177) in place of 5-cyano-2-ethyl-1-(2-methoxy-4-(3,3,3-trifluoro-2-methylpropyl)phenyl)-1H-imidazole-4-carboxylic acid and ((1r,4r)-4-(methylsulfonyl)cyclohexyl)methanamine hydrochloride (Intermediate 13)

in place of (1s,4s)-1-(aminomethyl)-4-(methylsulfonyl)cyclohexanol hydrochloride. The product was purified by preparative HPLC (XBridge C18, MeCN/H$_2$O, 0.4% NH$_4$OH) to provide the title compound as a colorless solid. $^1$H NMR (500 MHz, CDCl$_3$) δ 8.09 (d, J=1.8 Hz, 1H), 7.31 (d, J=1.8 Hz, 1H), 7.24-7.20 (m, 1H), 3.92 (s, 3H), 3.37-3.32 (m, 2H), 3.04-2.98 (m, 2H), 2.87-2.80 (m, 4H), 2.55-2.46 (m, 2H), 2.31-2.25 (m, 2H), 2.10-2.03 (m, 2H), 1.74-1.66 (m, 1H), 1.64 (s, 2H), 1.62-1.54 (m, 2H), 1.25-1.20 (m, 3H), 1.19-1.09 (m, 2H). MS (ESI) m/z: [M+H]$^+$ Found 542.1.

Example 120

5-Cyano-2-ethyl-N-(((1s,4s)-1-hydroxy-4-(methylsulfonyl)cyclohexyl)methyl)-1-(3-methoxy-5-(3,3,3-trifluoropropyl)pyridin-2-yl)-1H-imidazole-4-carboxamide

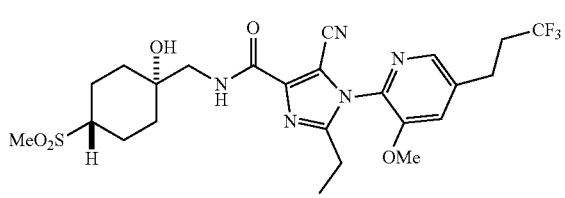 [SMILES: CCc1nc(C(=O)NC[C@]2(O)CC[C@@H](S(C)(=O)=O)CC2)c(C#N)n1-c1ncc(CCC(F)(F)F)cc1OC]

The title compound was prepared as described for Example 1, using 5-cyano-2-ethyl-1-(3-methoxy-5-(3,3,3-trifluoropropyl)pyridin-2-yl)-1H-imidazole-4-carboxylic acid (Intermediate 177) in place of 5-cyano-2-ethyl-1-(2-methoxy-4-(3,3,3-trifluoro-2-methylpropyl)phenyl)-1H-imidazole-4-carboxylic acid. The product was purified by preparative HPLC (XBridge C18, MeCN/H$_2$O, 0.4% NH$_4$OH) to provide the title compound as a clear colorless oil. $^1$H NMR (400 MHz, CDCl$_3$) δ 8.09 (d, J=1.8 Hz, 1H), 7.54-7.47 (m, 1H), 7.31 (d, J=1.8 Hz, 1H), 3.92 (s, 3H), 3.53-3.43 (m, 2H), 3.04-2.99 (m, 2H), 2.84 (s, 3H), 2.83-2.76 (m, 1H), 2.67-2.57 (m, 2H), 2.55-2.46 (m, 2H), 2.16-2.10 (m, 2H), 2.01-1.92 (m, 4H), 1.75-1.61 (m, 1H), 1.49-1.39 (m, 2H), 1.23 (t, J=7.5 Hz, 3H). MS (ESI) m/z: [M+H]$^+$ Found 558.1.

Example 121

5-Cyano-N-(((1s*,4s*)-1-cyano-4-(methylsulfonyl)cyclohexyl)methyl)-2-ethyl-1-(3-methoxy-5-(3,3,3-trifluoropropyl)pyridin-2-yl)-1H-imidazole-4-carboxamide

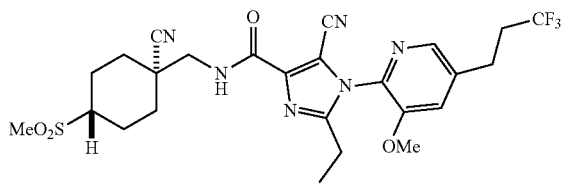 [SMILES: CCc1nc(C(=O)NC[C@]2(C#N)CC[C@@H](S(C)(=O)=O)CC2)c(C#N)n1-c1ncc(CCC(F)(F)F)cc1OC]

The title compound was prepared as described for Example 1, using 5-cyano-2-ethyl-1-(3-methoxy-5-(3,3,3-trifluoropropyl)pyridin-2-yl)-1H-imidazole-4-carboxylic acid (Intermediate 177) in place of 5-cyano-2-ethyl-1-(2-methoxy-4-(3,3,3-trifluoro-2-methylpropyl)phenyl)-1H-imidazole-4-carboxylic acid and (1s*,4s*)-1-(aminomethyl)-4-(methyl sulfonyl)cyclohexane-1-carbonitrile hydrochloride (Intermediate 51) in place of (1s,4s)-1-(aminomethyl)-4-(methylsulfonyl)cyclohexanol hydrochloride. The product was purified by preparative HPLC (XBridge C18, MeCN/H$_2$O, 0.4% NH$_4$OH) to provide the title compound as a colorless solid. $^1$H NMR (500 MHz, CDCl$_3$) δ 8.10 (d, J=1.8 Hz, 1H), 7.59-7.53 (m, 1H), 7.32 (d, J=1.8 Hz, 1H), 3.93 (s, 3H), 3.68 (s, 2H), 3.05-2.99 (m, 2H), 2.87 (s, 3H), 2.85-2.79 (m, 1H), 2.55-2.47 (m, 2H), 2.39-2.32 (m, 2H), 2.30-2.23 (m, 2H), 1.97-1.87 (m, 2H), 1.62-1.55 (m, 4H), 1.24 (t, J=7.5 Hz, 3H). MS (ESI) m/z: [M+H]$^+$ Found 567.0.

Example 122

5-Cyano-2-ethyl-1-(3-methoxy-5-(3,3,3-trifluoro-2,2-dimethylpropyl)pyridin-2-yl)-N-(((1r,4r)-4-(methylsulfonyl)cyclohexyl)methyl)-1H-imidazole-4-carboxamide

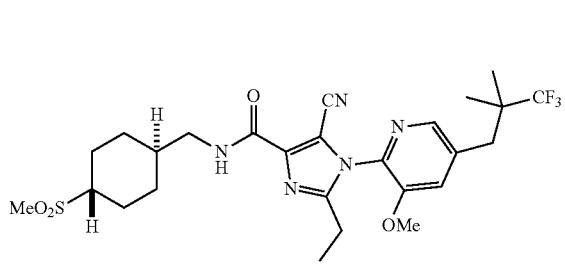 [SMILES: CCc1nc(C(=O)NC[C@H]2CC[C@H](S(C)(=O)=O)CC2)c(C#N)n1-c1ncc(CC(C)(C)C(F)(F)F)cc1OC]

The title compound was prepared as described for Example 1, using 5-cyano-2-ethyl-1-(3-methoxy-5-(3,3,3-trifluoro-2,2-dimethylpropyl)pyridin-2-yl)-1H-imidazole-4-carboxylic acid (Intermediate 179) in place of 5-cyano-2-ethyl-1-(2-methoxy-4-(3,3,3-trifluoro-2-methylpropyl)phenyl)-1H-imidazole-4-carboxylic acid and ((1r,4r)-4-(methylsulfonyl)cyclohexyl)methanamine hydrochloride (Intermediate 13) in place of (1s,4s)-1-(aminomethyl)-4-(methyl sulfonyl)cyclohexanol hydrochloride. The product was purified by preparative HPLC (XBridge C18, MeCN/H$_2$O, 0.4% NH$_4$OH) to provide the title compound as a colorless solid. $^1$H NMR (500 MHz, CDCl$_3$) δ 8.03 (d, J=1.8 Hz, 1H), 7.26-7.25 (m, 1H), 7.25-7.20 (m, 1H), 3.91 (s, 3H), 3.39-3.31 (m, 2H), 2.90 (s, 2H), 2.86-2.80 (m, 4H), 2.32-2.25 (m, 2H), 2.10-2.04 (m, 2H), 1.75-1.66 (m, 1H), 1.61-1.58 (m, 4H), 1.23 (t, J=7.5 Hz, 3H), 1.19-1.17 (m, 1H), 1.16 (s, 6H), 1.14-1.10 (m, 1H). MS (ESI) m/z: [M+H]$^+$ Found 570.1.

Example 123

5-Cyano-2-ethyl-N-(((1s,4s)-1-hydroxy-4-(methylsulfonyl)cyclohexyl)methyl)-1-(3-methoxy-5-(3,3,3-trifluoro-2,2-dimethylpropyl)pyridin-2-yl)-1H-imidazole-4-carboxamide

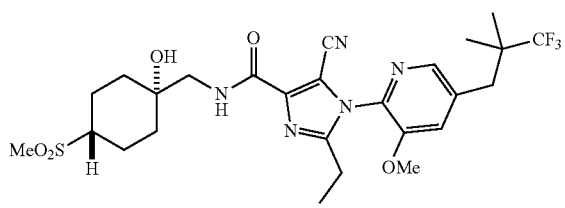

The title compound was prepared as described for Example 1, using 5-cyano-2-ethyl-1-(3-methoxy-5-(3,3,3-trifluoro-2,2-dimethylpropyl)pyridin-2-yl)-1H-imidazole-4-carboxylic acid (Intermediate 179) in place of 5-cyano-2-ethyl-1-(2-methoxy-4-(3,3,3-trifluoro-2-methylpropyl)phenyl)-1H-imidazole-4-carboxylic acid. The product was purified by preparative HPLC (XBridge C18, MeCN/H$_2$O, 0.4% NH$_4$OH) to provide the title compound as a colorless solid. $^1$H NMR (400 MHz, CDCl$_3$) δ 8.04 (d, J=1.8 Hz, 1H), 7.54-7.48 (m, 1H), 7.28-7.26 (m, 1H), 3.91 (s, 3H), 3.48 (br s, 2H), 3.05 (s, 1H), 2.90 (s, 2H), 2.84 (s, 3H), 2.82-2.77 (m, 1H), 2.63 (br s, 2H), 2.16-2.09 (m, 2H), 2.03-1.93 (m, 4H), 1.49-1.40 (m, 2H), 1.25-1.21 (m, 3H), 1.17 (s, 6H). MS (ESI) m/z: [M+H]$^+$ Found 586.1.

Example 124

5-Cyano-N-(((1s*,4s*)-1-cyano-4-(methylsulfonyl)cyclohexyl)methyl)-2-ethyl-1-(3-methoxy-5-(3,3,3-trifluoro-2,2-dimethylpropyl)pyridin-2-yl)-1H-imidazole-4-carboxamide

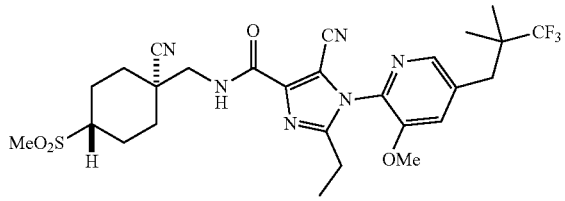 [SMILES: CCc1nc(C(=O)NC[C@]2(C#N)CC[C@@H](S(C)(=O)=O)CC2)c(C#N)n1-c1ncc(CC(C)(C)C(F)(F)F)cc1OC]

The title compound was prepared as described for Example 1, using 5-cyano-2-ethyl-1-(3-methoxy-5-(3,3,3-trifluoro-2,2-dimethylpropyl)pyridin-2-yl)-1H-imidazole-4-carboxylic acid (Intermediate 179) in place of 5-cyano-2-ethyl-1-(2-methoxy-4-(3,3,3-trifluoro-2-methylpropyl)phenyl)-1H-imidazole-4-carboxylic acid and (1s*,4s*)-1-(aminomethyl)-4-(methylsulfonyl)cyclohexane-1-carbonitrile hydrochloride (Intermediate 51) in place of (1s,4s)-1-(aminomethyl)-4-(methyl sulfonyl)cyclohexanol hydrochloride. The product was purified by preparative HPLC (XBridge C18, MeCN/H$_2$O, 0.4% NH$_4$OH) to provide the title compound as a colorless solid. $^1$H NMR (500 MHz, CDCl$_3$) δ 8.04 (d, J=1.8 Hz, 1H), 7.59-7.53 (m, 1H), 7.28-7.27 (m, 1H), 3.91 (s, 3H), 3.68 (s, 2H), 2.90 (s, 2H), 2.87 (s, 3H), 2.84-2.79 (m, 1H), 2.39-2.24 (m, 4H), 1.97-1.86 (m, 2H), 1.61-1.55 (m, 4H), 1.26-1.22 (m, 3H), 1.17 (s, 6H). MS (ESI) m/z: [M+H]$^+$ Found 595.1.

Example 125

5-Chloro-2-ethyl-1-(3-methoxy-5-(3,3,3-trifluoro-2,2-dimethylpropyl)pyridin-2-yl)-N-(((1r,4r)-4-(methylsulfonyl)cyclohexyl)methyl)-1H-imidazole-4-carboxamide

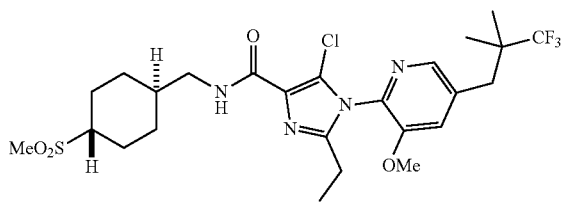 [SMILES: CCc1nc(C(=O)NC[C@H]2CC[C@H](S(C)(=O)=O)CC2)c(Cl)n1-c1ncc(CC(C)(C)C(F)(F)F)cc1OC]

The title compound was prepared as described for Example 1, using 5-chloro-2-ethyl-1-(3-methoxy-5-(3,3,3-trifluoro-2,2-dimethylpropyl)pyridin-2-yl)-1H-imidazole-4-carboxylic acid (Intermediate 183) in place of 5-cyano-2-ethyl-1-(2-methoxy-4-(3,3,3-trifluoro-2-methylpropyl)phenyl)-1H-imidazole-4-carboxylic acid and ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. The product was purified by preparative HPLC (XBridge C18, MeCN/H$_2$O, 0.4% NH$_4$OH) to provide the title compound as a colorless oil. $^1$H NMR (500 MHz, CDCl$_3$) δ 8.04 (d, J=1.8 Hz, 1H), 7.25-7.23 (m, 1H), 7.22 (d, J=1.8 Hz, 1H), 3.84 (s, 3H), 3.38-3.26 (m, 2H), 2.89 (s, 2H), 2.86-2.79 (m, 4H), 2.53-2.42 (m, 2H), 2.30-2.24 (m, 2H), 2.11-2.04 (m, 2H), 1.72-1.63 (m, 1H), 1.60-1.53 (m, 2H), 1.19-1.16 (m, 7H), 1.15-1.13 (m, 3H), 1.12-1.08 (m, 1H). MS (ESI) m/z: [M+H]$^+$ Found 579.0.

Example 126

2-Ethyl-1-(3-methoxy-5-(3,3,3-trifluoro-2,2-dimethylpropyl)pyridin-2-yl)-5-methyl-N-(((1r,4r)-4-(methylsulfonyl)cyclohexyl)methyl)-1H-imidazole-4-carboxamide

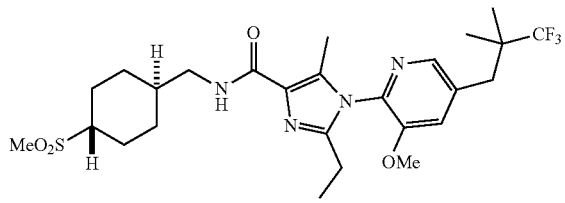 [SMILES: CCc1nc(C(=O)NC[C@H]2CC[C@H](S(C)(=O)=O)CC2)c(C)n1-c1ncc(CC(C)(C)C(F)(F)F)cc1OC]

The title compound was prepared as described for Example 1, using 2-ethyl-1-(3-methoxy-5-(3,3,3-trifluoro-2,2-dimethylpropyl)pyridin-2-yl)-5-methyl-1H-imidazole-4-carboxylic acid (Intermediate 185) in place of 5-cyano-2-ethyl-1-(2-methoxy-4-(3,3,3-trifluoro-2-methylpropyl)phenyl)-1H-imidazole-4-carboxylic acid and ((1r,4r)-4-(methylsulfonyl)cyclohexyl)methanamine hydrochloride (Intermediate 13) in place of (1s,4s)-1-(aminomethyl)-4-(methylsulfonyl)cyclohexanol hydrochloride. The product was purified by preparative HPLC (XBridge C18, MeCN/H$_2$O, 0.4% NH$_4$OH) to provide the title compound as a colorless oil. $^1$H NMR (500 MHz, CDCl$_3$) δ 8.04 (d, J=1.9 Hz, 1H), 7.34-7.29 (m, 1H), 7.21 (d, J=1.9 Hz, 1H), 3.82 (s, 3H), 3.34-3.25 (m, 2H), 2.89 (s, 2H), 2.85-2.79 (m, 4H), 2.48-2.42 (m, 2H), 2.31 (s, 3H), 2.29-2.24 (m, 2H), 2.12-2.05 (m, 2H), 1.70-1.53 (m, 4H), 1.17 (s, 6H), 1.15-1.11 (m, 4H). MS (ESI) m/z: [M+H]$^+$ Found 559.1.

Example 127

2-Ethyl-N-(((1s,4s)-1-hydroxy-4-(methylsulfonyl)cyclohexyl)methyl)-1-(3-methoxy-5-(3,3,3-trifluoro-2,2-dimethylpropyl)pyridin-2-yl)-5-methyl-1H-imidazole-4-carboxamide

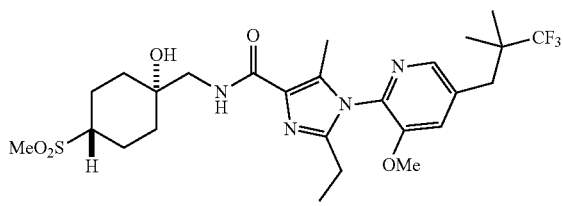 [SMILES: CCc1nc(C(=O)NC[C@]2(O)CC[C@@H](S(C)(=O)=O)CC2)c(C)n1-c1ncc(CC(C)(C)C(F)(F)F)cc1OC]

The title compound was prepared as described for Example 1, using 2-ethyl-1-(3-methoxy-5-(3,3,3-trifluoro-2,2-dimethylpropyl)pyridin-2-yl)-5-methyl-1H-imidazole-4-carboxylic acid (Intermediate 185) in place of 5-cyano-2-ethyl-1-(2-methoxy-4-(3,3,3-trifluoro-2-methylpropyl)phenyl)-1H-imidazole-4-carboxylic acid. The product was purified by preparative HPLC (XBridge C18, MeCN/H$_2$O, 0.4% NH$_4$OH) to provide the title compound as a colorless foam. $^1$H NMR (500 MHz, CDCl$_3$) δ 8.04 (d, J=1.9 Hz, 1H), 7.60-7.53 (m, 1H), 7.23-7.20 (m, 1H), 4.25 (s, 1H), 3.83 (s, 3H), 3.48-3.34 (m, 2H), 2.90 (s, 2H), 2.82 (s, 3H), 2.81-2.74 (m, 1H), 2.47-2.41 (m, 2H), 2.29 (s, 3H), 2.16-2.09 (m, 2H), 2.04-1.94 (m, 4H), 1.41-1.32 (m, 2H), 1.17 (s, 6H), 1.13 (t, J=7.5 Hz, 3H). MS (ESI) m/z: [M+H]$^+$ Found 575.1.

Example 128

N-(((1s*,4s*)-1-Cyano-4-(methylsulfonyl)cyclohexyl)methyl)-2-ethyl-1-(3-methoxy-5-(3,3,3-trifluoro-2,2-dimethylpropyl)pyridin-2-yl)-5-methyl-1H-imidazole-4-carboxamide

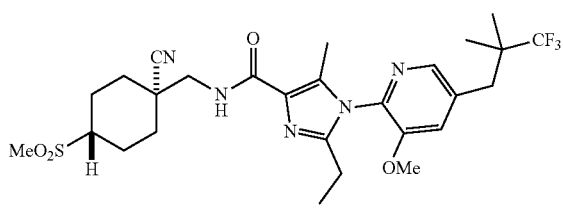 [SMILES: CCc1nc(C(=O)NC[C@]2(C#N)CC[C@@H](S(C)(=O)=O)CC2)c(C)n1-c1ncc(CC(C)(C)C(F)(F)F)cc1OC]

The title compound was prepared as described for Example 1, using 2-ethyl-1-(3-methoxy-5-(3,3,3-trifluoro-2,2-dimethylpropyl)pyridin-2-yl)-5-methyl-1H-imidazole-4-carboxylic acid (Intermediate 185) in place of 5-cyano-2-ethyl-1-(2-methoxy-4-(3,3,3-trifluoro-2-methylpropyl)phenyl)-1H-imidazole-4-carboxylic acid and (1s*,4s*)-1-(aminomethyl)-4-(methylsulfonyl)cyclohexane-1-carbonitrile hydrochloride (Intermediate 51) in place of (1s,4s)-1-(aminomethyl)-4-(methyl sulfonyl)cyclohexanol hydrochloride. The product was purified by preparative HPLC (XBridge C18, MeCN/H$_2$O, 0.4% NH$_4$OH) to provide the title compound as a colorless solid. $^1$H NMR (500 MHz, CDCl$_3$) δ 8.04 (d, J=1.8 Hz, 1H), 7.66-7.61 (m, 1H), 7.22 (d, J=1.8 Hz, 1H), 3.84 (s, 3H), 3.72-3.58 (m, 2H), 2.90 (s, 2H), 2.85 (s, 3H), 2.83-2.77 (m, 1H), 2.47-2.41 (m, 2H), 2.38-2.32 (m, 2H), 2.30-2.24 (m, 5H), 1.96-1.84 (m, 2H), 1.61-1.53 (m, 2H), 1.17 (s, 6H), 1.16-1.13 (m, 3H). MS (ESI) m/z: [M+H]$^+$ Found 584.1.

Example 129

1-(2-Methoxy-4-(3,3,3-trifluoro-2,2-dimethylpropyl)phenyl)-2-methyl-N-(((1r,4r)-4-(methylsulfonyl)cyclohexyl)methyl)-1H-imidazole-4-carboxamide

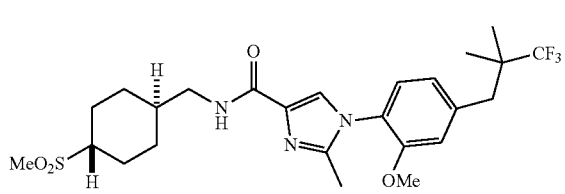 [SMILES: COc1cc(CC(C)(C)C(F)(F)F)ccc1-n1cc(C(=O)NC[C@H]2CC[C@H](S(C)(=O)=O)CC2)nc1C]

The title compound was prepared as described for the synthesis of Example 1, using ethyl 1-(2-methoxy-4-(3,3,3-trifluoro-2,2-dimethylpropyl)phenyl)-2-methyl-1H-imidazole-4-carboxylate (Intermediate 196) and ((1r,4r)-4-(methylsulfonyl)cyclohexyl)methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, MeOD) δ=7.56 (s, 1H), 7.26 (d, J=8.0 Hz, 1H), 7.07 (d, J=1.6 Hz, 1H), 6.97 (dd, J=1.6, 8.0 Hz, 1H), 3.84 (s, 3H), 3.27 (d, J=6.9 Hz, 2H), 3.05-2.98 (m, 1H), 2.92-2.89 (m, 5H), 2.26-2.18 (m, 5H), 2.04-1.98 (m, 2H), 1.67-1.61 (m, 1H), 1.59-1.49 (m, 2H), 1.20-1.12 (m, 9H). MS (ESI) m/z: [M+H]$^+$ Found 530.2.

Example 130

N-(((1s,4s)-1-hydroxy-4-(methylsulfonyl)cyclohexyl)methyl)-1-(2-methoxy-4-(3,3,3-trifluoro-2,2-dimethylpropyl)phenyl)-2-methyl-1H-imidazole-4-carboxamide

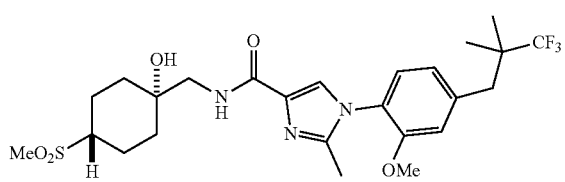 [SMILES: COc1cc(CC(C)(C)C(F)(F)F)ccc1-n1cc(C(=O)NC[C@]2(O)CC[C@@H](S(C)(=O)=O)CC2)nc1C]

The title compound was prepared as described for the synthesis of Example 1, using ethyl 1-(2-methoxy-4-(3,3,3-trifluoro-2,2-dimethylpropyl)phenyl)-2-methyl-1H-imidazole-4-carboxylate (Intermediate 196) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 7.55 (br s, 1H), 7.13 (d, J=8.0 Hz, 1H), 6.88-6.82 (m, 2H), 3.80 (s, 3H), 3.61-3.39 (m, 3H), 2.88-2.77 (m, 6H), 2.25-2.16 (m, 3H), 2.14-2.06 (m, 2H), 2.04-1.94 (m, 4H), 1.46-1.35 (m, 2H), 1.33-1.16 (m, 1H), 1.13 (s, 6H). MS (ESI) m/z: [M+H]$^+$ Found 546.3.

Example 131

1-(2-(Difluoromethoxy)-4-(3,3,3-trifluoro-2,2-dimethylpropyl)phenyl)-2-methyl-N-(((1r,4r)-4-(methylsulfonyl)cyclohexyl)methyl)-1H-imidazole-4-carboxamide

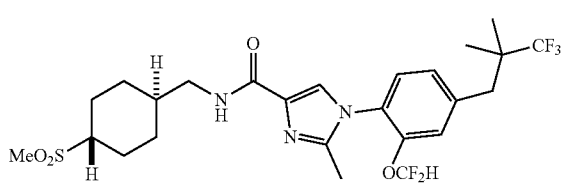

The title compound was prepared as described for the synthesis of Example 1, using ethyl 1-(2-(difluoromethoxy)-4-(3,3,3-trifluoro-2,2-dimethylpropyl)phenyl)-2-methyl-1H-imidazole-4-carboxylate (Intermediate 200) and ((1r,4r)-4-(methylsulfonyl)cyclohexyl) methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (500 MHz, CDCl$_3$) δ 7.54 (s, 1H), 7.27-7.16 (m, 3H), 6.57-6.23 (m, 1H), 3.33 (t, J=6.6 Hz, 2H), 2.89-2.80 (m, 6H), 2.29-2.23 (m, 5H), 2.11-2.04 (m, 2H), 1.70-1.54 (m, 3H), 1.18-1.12 (m, 9H). MS (ESI) m/z: [M+H]$^+$ Found 566.3.

Example 132

1-(2-(Difluoromethoxy)-4-(3,3,3-trifluoro-2,2-dimethylpropyl)phenyl)-N-(((1s,4s)-1-hydroxy-4-(methylsulfonyl)cyclohexyl)methyl)-2-methyl-1H-imidazole-4-carboxamide

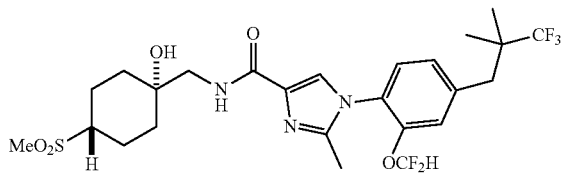

The title compound was prepared as described for the synthesis of Example 1, using ethyl 1-(2-(difluoromethoxy)-4-(3,3,3-trifluoro-2,2-dimethylpropyl)phenyl)-2-methyl-1H-imidazole-4-carboxylate (Intermediate 200) in place of ethyl 5-cyano-2-ethyl-1-(2-methoxy-4-(3,3,3-trifluoro-2-methylpropyl)phenyl)-1H-imidazole-4-carboxylate. $^1$H NMR (500 MHz, CDCl$_3$) δ 7.57 (s, 1H), 7.57 (d, J=6.4 Hz, 1H), 7.29-7.26 (m, 1H), 7.20 (s, 1H), 7.19-7.16 (m, 1H), 6.60-6.25 (m, 1H), 4.00 (br s, 1H), 3.45 (d, J=6.3 Hz, 2H), 2.87 (s, 2H), 2.85-2.78 (m, 4H), 2.23 (s, 3H), 2.14-2.06 (m, 2H), 2.05-1.94 (m, 4H), 1.49-1.37 (m, 2H), 1.13 (s, 6H). MS (ESI) m/z: [M+H]$^+$ Found 582.2.

Example 133

5-Chloro-1-(3-(difluoromethoxy)-5-(3,3,3-trifluoro-2,2-dimethylpropyl)pyridin-2-yl)-2-methyl-N-(((1r,4r)-4-(methylsulfonyl)cyclohexyl)methyl)-1H-imidazole-4-carboxamide

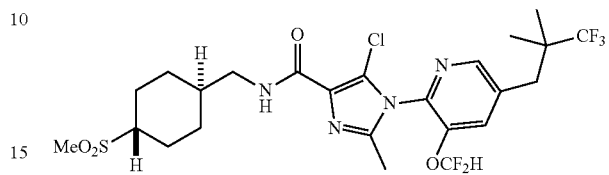

The title compound was prepared as described for the synthesis of Example 1, using ethyl 5-chloro-1-(3-(difluoromethoxy)-5-(3,3,3-trifluoro-2,2-dimethylpropyl)pyridin-2-yl)-2-methyl-1H-imidazole-4-carboxylate (Intermediate 204) and ((1r,4r)-4-(methylsulfonyl) cyclohexyl) methanamine hydrochloride (Intermediate 13) in place of ethyl 5-cyano-2-ethyl-1-(2-methoxy-4-(3,3,3-trifluoro-2-methylpropyl)phenyl)-1H-imidazole-4-carboxylate and (1s,4s)-1-(aminomethyl)-4-(methylsulfonyl)cyclohexanol hydrochloride. $^1$H NMR (600 MHz, CDCl$_3$) δ 8.35 (d, J=1.9 Hz, 1H), 7.68-7.65 (m, 1H), 7.24-7.19 (m, 1H), 6.64-6.37 (m, 1H), 3.33-3.29 (m, 2H), 2.95-2.92 (m, 2H), 2.82 (s, 4H), 2.30-2.24 (m, 2H), 2.22 (s, 3H), 2.10-2.04 (m, 2H), 1.72-1.63 (m, 1H), 1.63-1.53 (m, 2H), 1.19-1.16 (m, 6H), 1.16-1.09 (m, 2H). MS (ESI) m/z: [M+H]$^+$ Found 600.8.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS 1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Development, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data
RORγt (Full-Length Human) Reporter Assay:

Two similar reporter assay protocols, shown below, have been used to test the functional activity of RORγt modulatory compounds on transcriptional activation driven by full-length human RORγt. Both provide similar data and can be used interchangeably.

Conditions A

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and *Renilla* luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM_001001523.1 (SEQ ID NO: 1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 L Glo Lysis Buffer (Promega) for 10-15 minutes followed by 10 minute incubation with 50 µL Dual Glo reagent (Promega) at room temperature. Firefly luciferase luminescence was measured using a BMG Pherastar plate reader. To each well, 50 µL Stop and Glo reagent was added and incubated for 10 minutes at room temperature. *Renilla* luminescence was measured using a BMG Pherastar plate reader. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Conditions B

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and *Renilla* luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM_001001523.1 (SEQ ID NO: 1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 µL Glo Lysis Buffer (Promega) for 10-15 minutes followed by 10 minute incubation with 20 µL Dual Glo reagent (Promega) at room temperature. Firefly luciferase luminescence was measured using a BMG Pherastar plate reader. To each well, 20 µL Stop and Glo reagent was added and incubated for 10 minutes at room temperature. *Renilla* luminescence was measured using a BMG Pherastar plate reader. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total CD4+ T cells were isolated from the peripheral blood mononuclear cells (PBMC) of healthy donors using a CD4+ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

| Example # | ThermoFluor® Assay, Kd (μM) | RORγt (FL) Reporter Assay A or B, $IC_{50}$ (μM) | RORγt (FL) Reporter Assay A or B, % inhibition @ 6 μM | Human Th17 Assay, $IC_{50}$ (μM) |
|---|---|---|---|---|
| 1 | 0.0046 | 0.040 | 103** | ND |
| 2 | 0.0024 | 0.012 | 84*** | 0.085 |
| 3 | 0.0035 | 0.036 | 101** | 0.031 |
| 4 | 0.47 | 0.35 | 87** | ND |
| 5 | 1.3 | 0.26 | 43**** | ND |
| 6 | 0.00017 | 0.0060 | 99**** | 0.0020 |
| 7 | 0.0010 | 0.012 | 91****** | 0.0070 |
| 8 | ND | 0.16 | 66**** | ND |
| 9 | 0.0026 | 0.035 | 101 | ND |
| 10 | 0.0061 | 0.057 | 104** | ND |
| 11 | 0.0010 | 0.039 | 102 | ND |
| 12 | 0.012 | 0.16 | 109 | 0.22 |
| 13 | 0.025 | 0.14 | 95 | ND |
| 14 | 0.083 | 0.32 | 83 | ND |
| 15 | 0.0039 | 0.055 | 103 | ND |
| 16 | 0.0013 | 0.016 | 103** | ND |
| 17 | 0.075 | 0.40 | 74** | ND |
| 18 | 0.028 | 0.23 | 93** | ND |
| 19 | 0.050 | 0.36 | 80** | ND |
| 20 | 0.021 | 0.17 | 94** | ND |
| 21 | 0.014 | 0.094 | 101 | ND |
| 22 | 0.020 | 0.015 | 38****** | 0.042 |
| 23 | 0.049 | 0.037 | 41 | ND |
| 24 | 0.0053 | 0.033 | 104 | ND |
| 25 | 0.084 | 0.37 | 101 | ND |
| 26 | 0.024 | 0.054 | 96 | ND |
| 27 | 0.00076 | 0.018 | 97**** | 0.013 |
| 28 | 0.0025 | 0.033 | 102** | ND |
| 29 | 0.015 | 0.087 | 95 | ND |
| 30 | 0.044 | 0.32 | 96 | ND |
| 31 | 0.014 | 0.078 | 101** | ND |
| 32 | 0.012 | 0.071 | 99** | ND |
| 33 | 0.0048 | 0.015 | 94**** | ND |
| 34 | 0.0035 | 0.037 | 98** | ND |
| 35 | 0.011 | 0.028 | 97 | ND |
| 36 | 0.0016 | 0.013 | 101** | 0.0080 |
| 37 | 0.00087 | 0.0053 | 105**** | ND |
| 38 | 0.0044 | 0.019 | 97**** | ND |
| 39 | 0.00042 | 0.0079 | 101**** | ND |
| 40 | 0.00073 | 0.0032 | 105** | ND |
| 41 | 0.00019 | 0.0027 | 106**** | ND |
| 42 | 0.0011 | 0.0062 | 66****** | ND |
| 43 | 0.0022 | 0.0032 | 86**** | ND |
| 44 | 0.0041 | 0.031 | 75****** | ND |
| 45 | 0.0077 | 0.011 | 77**** | ND |
| 46 | 0.0031 | 0.028 | 97 | ND |
| 47 | 0.087 | 0.34 | 98 | ND |
| 48 | 0.015 | 0.050 | 104 | ND |
| 49 | 0.0058 | 0.014 | 94 | ND |
| 50 | 0.023 | 0.12 | 90 | ND |
| 51 | 0.12 | 0.14 | 84 | ND |
| 52 | 0.55 | 0.64 | 78 | ND |
| 53 | 0.0025 | 0.011 | 84* | ND |
| 54 | 0.011 | 0.035 | 83*** | ND |
| 55 | 0.020 | 0.066 | 93* | ND |
| 56 | 0.032 | 0.063 | 102* | ND |
| 57 | 0.022 | 0.040 | 98* | ND |
| 58 | 0.012 | 0.16 | 121* | ND |
| 59 | 0.012 | 0.065 | 104* | ND |
| 60 | 0.034 | 0.19 | 86* | ND |
| 61 | 0.046 | 0.11 | 90* | ND |
| 62 | 0.019 | 0.089 | 100* | ND |
| 63 | 0.0073 | 0.047 | 95* | ND |
| 64 | 0.035 | 0.21 | 101* | ND |
| 65 | 0.028 | 0.11 | 105* | ND |
| 66 | 0.073 | 0.79 | 70* | ND |
| 67 | 0.053 | 0.17 | 103* | ND |
| 68 | 0.0037 | 0.050 | 103* | ND |
| 69 | 0.0072 | 0.039 | 102* | ND |
| 70 | 0.32 | 0.35 | 88* | ND |
| 71 | 0.028 | 0.16 | 90* | ND |
| 72 | 0.0098 | 0.075 | 98* | ND |
| 73 | 0.038 | 0.11 | 80*** | ND |
| 74 | 0.034 | 0.092 | 116* | ND |
| 75 | 0.0083 | 0.059 | 110* | ND |
| 76 | 0.11 | 0.44 | 76* | ND |
| 77 | 0.020 | 0.077 | 101* | ND |
| 78 | 0.0070 | 0.096 | 94*** | ND |
| 79 | 0.026 | 0.22 | 84* | ND |
| 80 | 0.058 | 0.054 | 113* | ND |
| 81 | 0.26 | 1.2 | 27 | ND |
| 82 | 0.15 | 0.37 | 44** | ND |
| 83 | 0.0026 | 0.12 | 23** | >6 |
| 84 | 2.2 | 2.0 | 35 | ND |
| 85 | 0.0082 | 0.023 | 63****** | ND |
| 86 | 0.0053 | 0.023 | 68**** | ND |
| 87 | 0.0038 | 0.018 | 66**** | ND |
| 88 | 0.017 | 0.046 | 67**** | ND |
| 89 | 0.00020 | 0.016 | 66**** | ND |
| 90 | 0.00031 | 0.021 | 67** | ND |
| 91 | 0.62 | 0.36 | 42** | ND |
| 92 | 0.00028 | 0.0070 | 72 | ND |
| 93 | 0.093 | 0.33 | 65** | ND |
| 94 | 0.25 | 0.49 | 47** | ND |
| 95 | 0.29 | 1.2 | 72 | ND |
| 96 | 0.45 | 1.4 | 75 | ND |
| 97 | 0.014 | 0.022 | 53**** | ND |
| 98 | 0.033 | 0.033 | 43** | ND |
| 99 | 0.0040 | 0.016 | 99****** | ND |
| 100 | 0.0021 | 0.0067 | 100****** | 0.058 |
| 101 | 0.0040 | 0.018 | 65****** | ND |
| 102 | 0.0080 | 0.036 | 74**** | ND |
| 103 | 0.0044 | ND | ND | ND |
| 104 | 0.0054 | ND | ND | ND |
| 105 | ND | 0.053 | 80****** | ND |
| 106 | 0.055 | 0.17 | 40****** | ND |
| 107 | 0.018 | 0.075 | 85* | ND |
| 108 | 0.10 | 0.34 | 99 | ND |
| 109 | 0.0065 | 0.022 | 97**** | 0.079 |
| 110 | 0.0033 | 0.0018 | 90******* | ND |

| Example # | ThermoFluor® Assay, Kd (μM) | RORγt (FL) Reporter Assay A or B, IC$_{50}$ (μM) | RORγt (FL) Reporter Assay A or B, % inhibition @ 6 μM | Human Th17 Assay, IC$_{50}$ (μM) |
|---|---|---|---|---|
| 111 | 0.024 | 0.086 | 99 | 0.069 |
| 112 | 0.0019 | 0.017 | 89** | ND |
| 113 | 0.0083 | 0.044 | 88** | ND |
| 114 | 0.11 | 0.66 | 66 | ND |
| 115 | 0.10 | 0.19 | 74 | ND |
| 116 | 5.0 | 3.0 | 30 | ND |
| 117 | 0.56 | 1.5 | 88 | ND |
| 118 | ND | 2.4 | 54 | ND |
| 119 | 0.19 | 0.72 | 96 | ND |
| 120 | 0.83 | 1.4 | 57 | ND |
| 121 | 0.30 | 1.7 | 76 | ND |
| 122 | 0.012 | 0.048 | 101** | ND |
| 123 | 0.031 | 0.24 | 102 | ND |
| 124 | 0.037 | 0.084 | 105 | ND |
| 125 | 0.0018 | 0.011 | 99** | ND |
| 126 | 0.0086 | 0.076 | 100 | ND |
| 127 | 0.021 | 0.14 | 98 | ND |
| 128 | 0.037 | 0.31 | 105 | ND |
| 129 | 0.045 | 0.13 | 47****** | ND |
| 130 | 0.065 | 0.54 | 73** | ND |
| 131 | 0.097 | 0.47 | 73* | ND |
| 132 | 0.34 | 0.80 | 87* | ND |
| 133 | 0.0095 | 0.037 | 72* | ND |

ND: value not determined.
*% inhibition is shown at 3 μM compound concentration,
**% inhibition is shown at 2 μM compound concentration,
***% inhibition is shown at 1 μM compound concentration,
****% inhibition is shown at 0.67 μM compound concentration,
*****% inhibition is shown at 0.33 μM compound concentration,
******% inhibition is shown at 0.22 μM compound concentration,
*******% inhibition is shown at 0.07 μM compound concentration While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

We claim:

1. A compound of Formula I

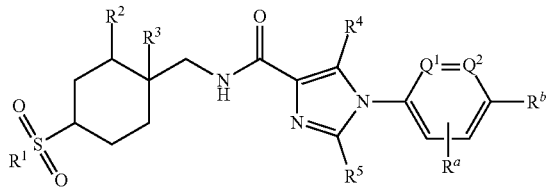

Formula I and pharmaceutically acceptable salts thereof
wherein
$R^1$ is —$C_{(1-4)}$alkyl, —$NH_2$, —$NHC_{(1-4)}$alkyl, —$N(C_{(1-4)}$alkyl$)_2$, —$NHC(O)NH_2$, $NHC(O)C_{(1-4)}$alkyl, —NHC(O)H, or —NHC(O)NH$C_{(1-4)}$alkyl;
$R^2$ is H, —OH, or —$NH_2$;
$R^3$ is —H, —OH, —CN, —$NH_2$, —$CONH_2$, —$CO_2$H, —$CO_2C_{(1-4)}$alkyl, —$CH_2$OH, —$CH_2NH_2$, —$CH_2$CN, —$NHC_{(1-4)}$alkyl, or —$CONHC_{(1-4)}$alkyl;
$R^4$ is —H, —Cl, —$C_{(1-4)}$alkyl, —F, —CN, —C(O)$NH_2$, or

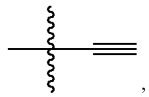

;

wherein said —$C_{(1-4)}$alkyl is optionally substituted with up to six fluorine atoms;
$R^5$ is —$C_{(1-4)}$alkyl, wherein said —$C_{(1-4)}$alkyl is optionally substituted with —CN, —OH, —$OCH_3$, —$OCF_3$, or up to six fluorine atoms;
$Q^1$ is N or $CR^c$;
$Q^2$ is N or CH; provided that $Q^2$ is not N if $Q^1$ is N;
$R^a$ is —F, —Cl, —$OCD_3$, —CN, —$OC_{(1-3)}$alkyl, or —$C_{(1-3)}$alkyl, wherein said —$C_{(1-3)}$alkyl and said $OC_{(1-3)}$alkyl are optionally substituted with up to three fluorine atoms;
$R^b$ is —$NA^1A^2$, —$C_{(3-6)}$alkyl, or —$OC_{(1-3)}$alkyl, wherein said —$C_{(3-6)}$alkyl is optionally substituted with —OH or oxo, and the —$C_{(3-6)}$alkyl may additionally be substituted with up to six fluorine atoms, and said —$OC_{(1-3)}$alkyl is optionally substituted with up to three fluorine atoms;

$R^c$ is —H, —$OCH_3$, —F, —$CH_3$, —$CF_3$, —$OCF_3$, or —Cl;
$A^1$ is —$C_{(2-3)}$alkyl, wherein said —$C_{(2-3)}$alkyl is optionally substituted with up to six fluorine atoms;
$A^2$ is H, or $A^1$ and $A^2$ are taken together with their attached nitrogen to form

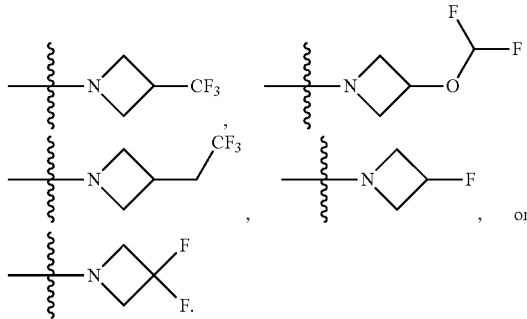

, or

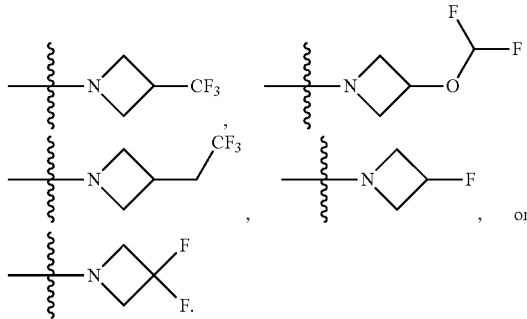

.

2. The compound of claim 1 wherein
$R^1$ is —$C_{(1-3)}$alkyl, —$NH_2$, —$NHC_{(1-2)}$alkyl, —$N(C_{(1-2)}$alkyl$)_2$, —$NHC(O)NH_2$, $NHC(O)C_{(1-2)}$alkyl, —NHC(O)H, or —NHC(O)NH$CH_3$;
$R^3$ is —H, —OH, —CN, —$NH_2$, —$CONH_2$, —$CO_2$H, —$CO_2CH_2CH_3$, or —$CH_2$OH;
$R^4$ is —H, —Cl, —$C_{(1-4)}$alkyl, —F, —CN, —C(O)$NH_2$,

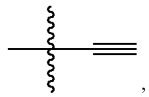

, or —$CF_3$;
$R^5$ is —$C_{(1-4)}$alkyl, wherein said —$C_{(1-4)}$alkyl is optionally substituted with —CN, —OH, or —$OCH_3$;
$R^c$ is —H, —$OCH_3$, —F, —$CH_3$, —$CF_3$, or —$OCF_3$;
$A^2$ is H.

3. The compound of claim 2 wherein
$R^1$ is —$C_{(1-3)}$alkyl, —$NH_2$, —$NHC_{(1-2)}$alkyl, or —$N(C_{(1-2)}$alkyl$)_2$;
$R^2$ is —H or —OH;
$R^3$ is —H, —OH, —CN, or —$NH_2$;
$R^5$ is —$C_{(1-4)}$alkyl;
$R^a$ is —F, —$OCD_3$, —$OC_{(1-3)}$alkyl, or —$C_{(1-3)}$alkyl, wherein said —$C_{(1-3)}$alkyl and said $OC_{(1-3)}$alkyl are optionally substituted with up to three fluorine atoms;

$R^b$ is

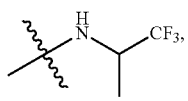

—$C_{(3-6)}$alkyl, or —$OC_{(1-3)}$alkyl, wherein said —$C_{(3-6)}$alkyl is optionally substituted with —OH or oxo, and the —$C_{(3-6)}$alkyl may additionally be substituted with up to six fluorine atoms, and said —$OC_{(1-3)}$alkyl is optionally substituted with up to three fluorine atoms;
$R^c$ is —H, —$OCH_3$, —F, or —$CH_3$.

4. The compound of claim 3 wherein
$R^1$ is —$C_{(1-2)}$alkyl, —$NH_2$, —$NHC_{(1-2)}$alkyl, or —$N(C_{(1-2)}alkyl)_2$;
$R^4$ is —H, —Cl, —$C_{(1-4)}$alkyl, —F, —CN, —$C(O)NH_2$, or

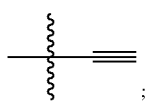

$R^a$ is —F, —$OCH_3$, —$OCD_3$, —$OCHF_2$, —$OCF_3$, or —$C_{(1-3)}$alkyl, wherein said —$C_{(1-3)}$alkyl is optionally substituted with up to three fluorine atoms;
$R^b$ is

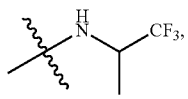

or —$C_{(3-6)}$alkyl, wherein said —$C_{(3-6)}$alkyl is optionally substituted with —OH or oxo, and the —$C_{(3-6)}$alkyl may additionally be substituted with up to six fluorine atoms;
$R^c$ is —H, —$OCH_3$, or —F.

5. The compound of claim 4 wherein
$R^1$ is —$CH_3$, —$NH_2$, —$NHCH_3$, or —$N(CH_3)_2$;
$R^3$ is —H, —OH, or —CN;
$R^4$ is —H, —Cl, —$CH_3$, —F, —CN, —$C(O)NH_2$, or

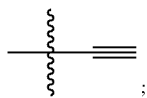

$R^a$ is —F, —$OCH_3$, —$OCD_3$, —$OCHF_2$, —$OCF_3$, or —$C_{(1-2)}$alkyl;
$R^b$ is

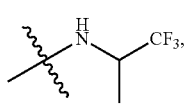 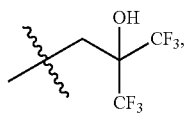

or —$C_{(3-6)}$alkyl, wherein said —$C_{(3-6)}$alkyl is optionally substituted with up to six fluorine atoms;
$R^c$ is —H, or —F.

6. The compound of claim 5 selected from the group consisting of:

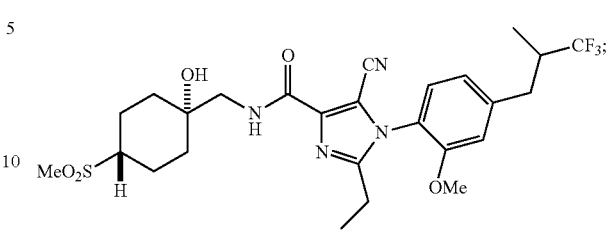

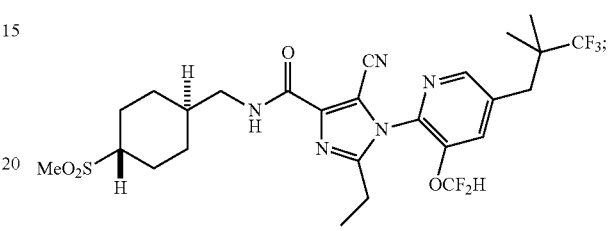

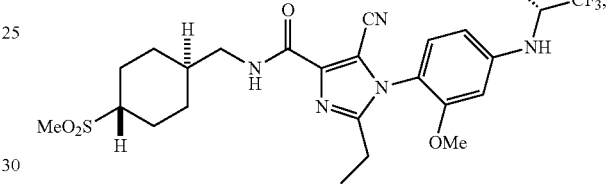

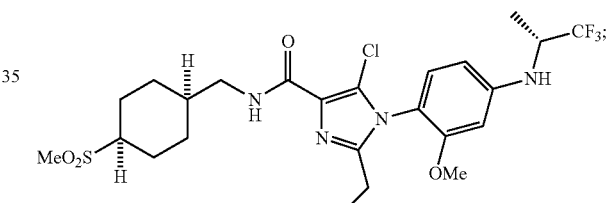

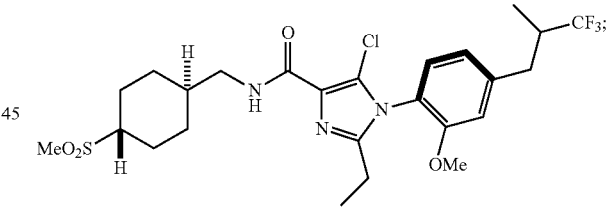

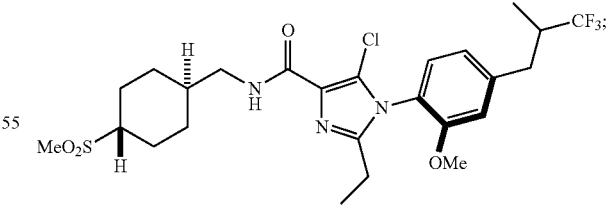

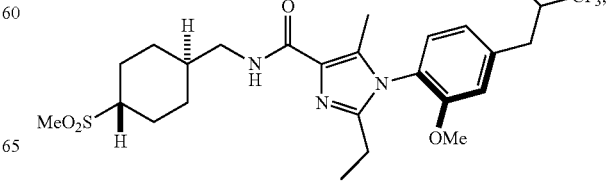

213
-continued
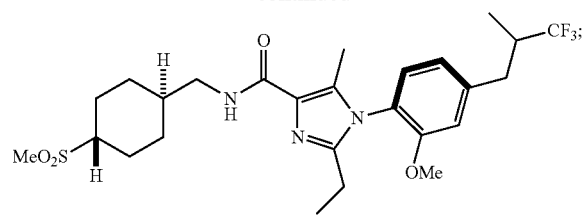
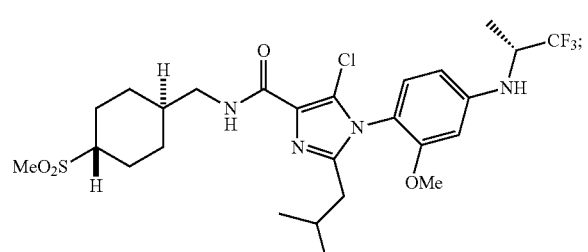
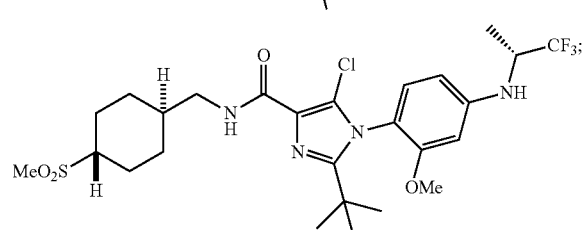
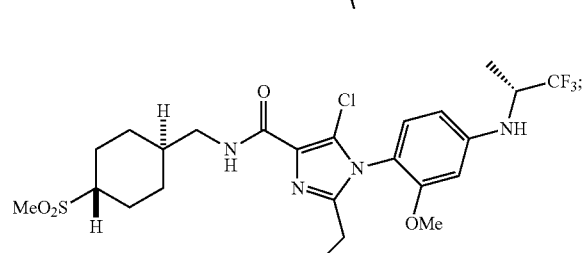
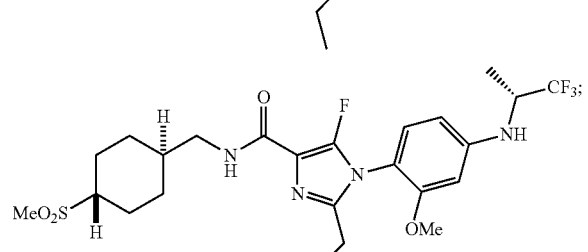
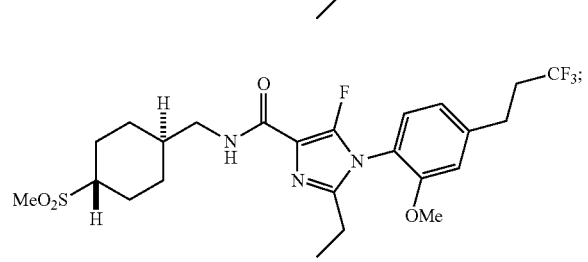
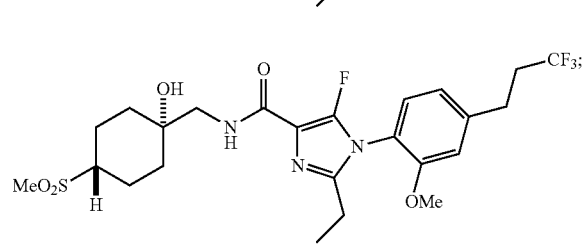
214
-continued
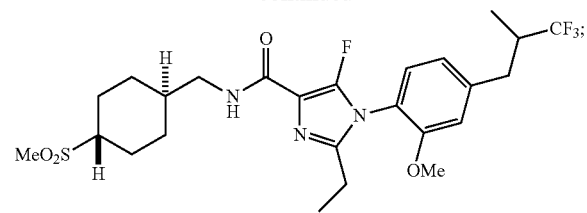
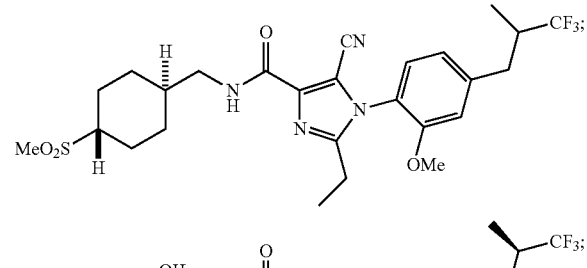
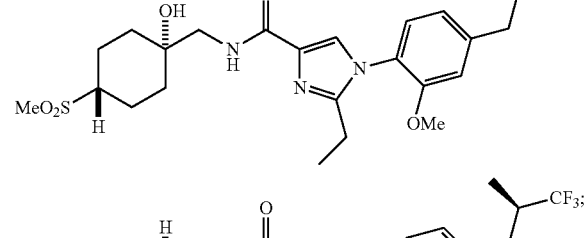
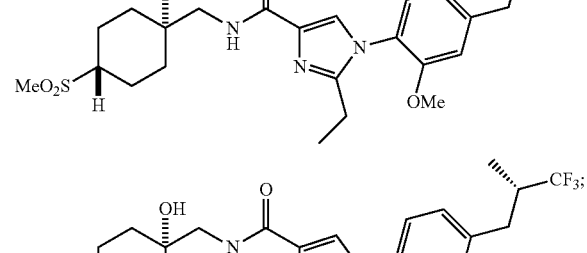
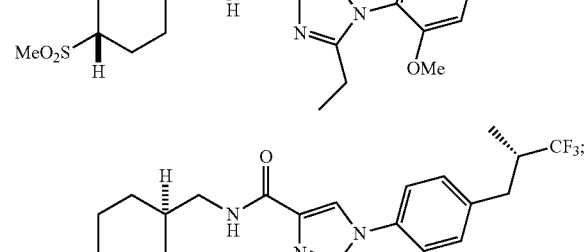
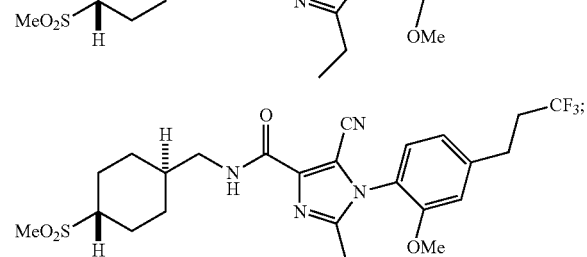
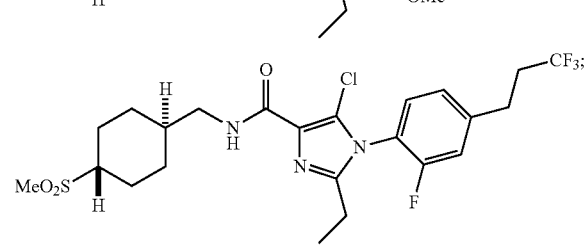

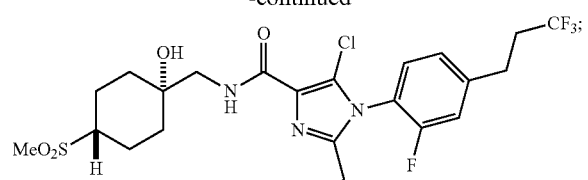
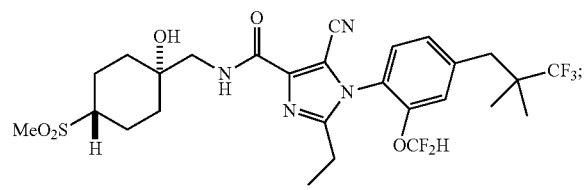
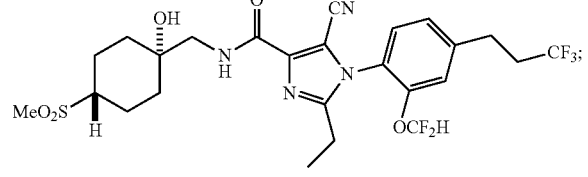
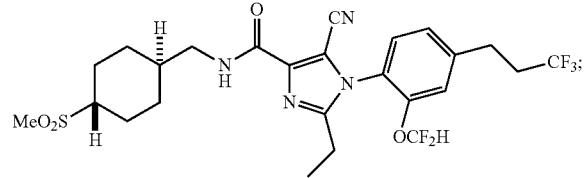
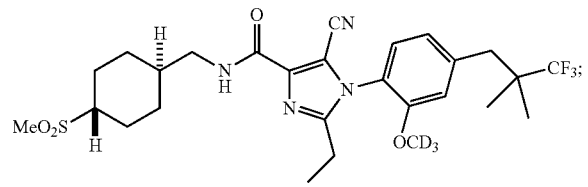
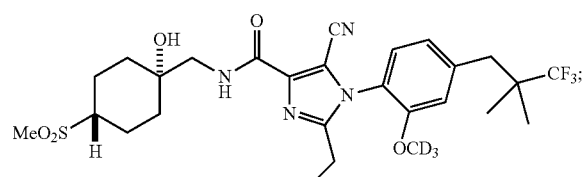
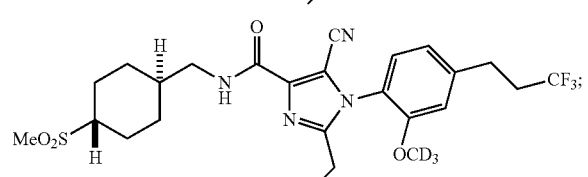
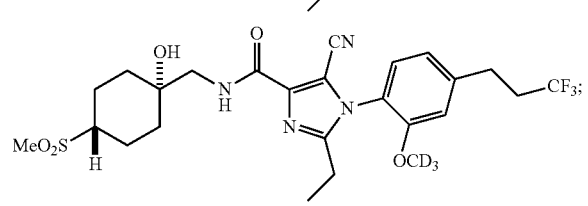
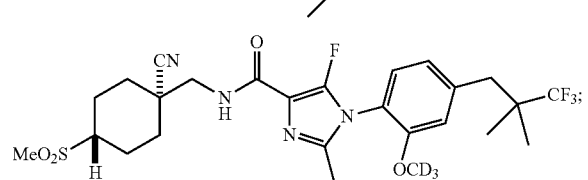
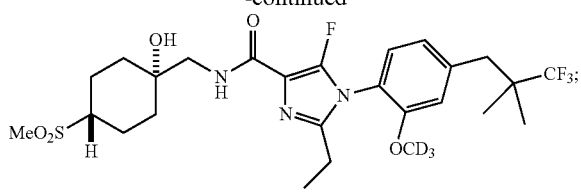
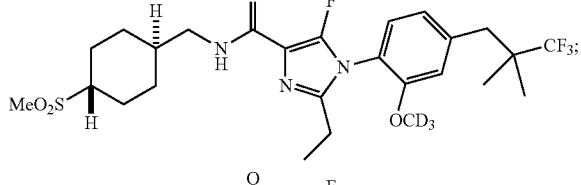
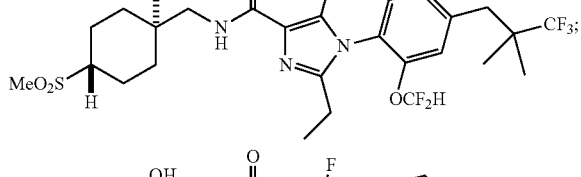
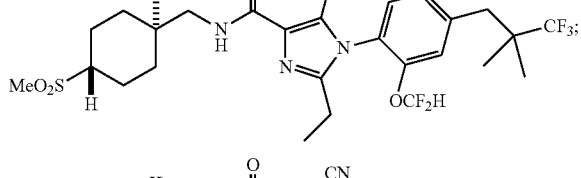
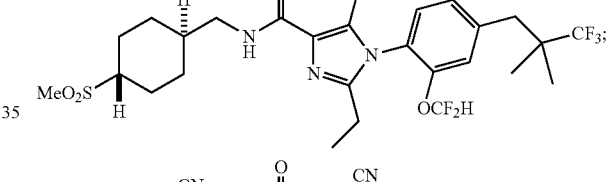
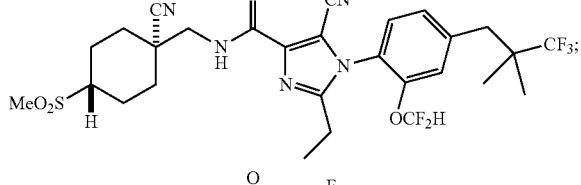
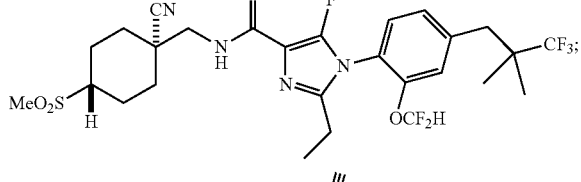
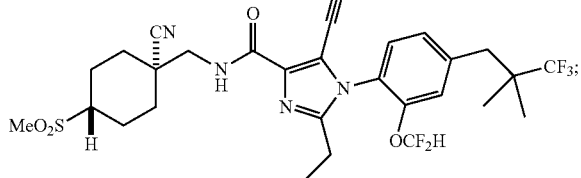
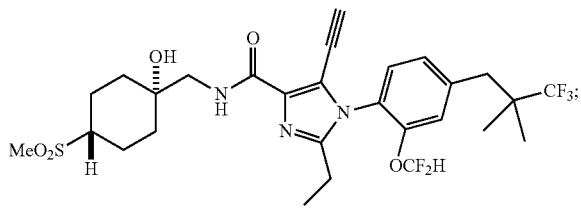

217
-continued
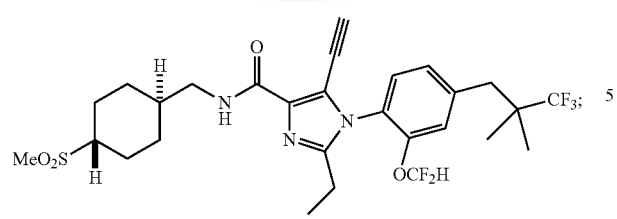
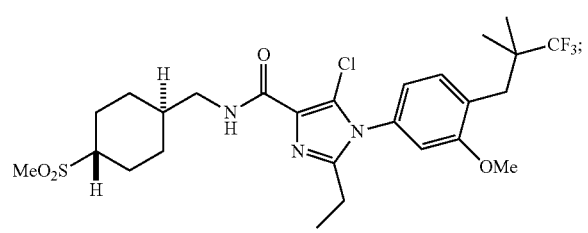
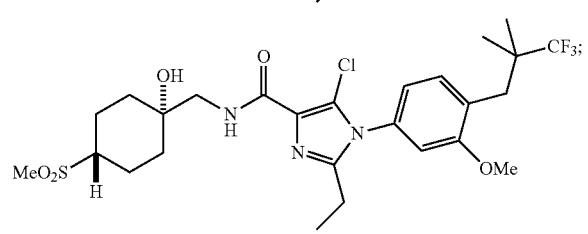
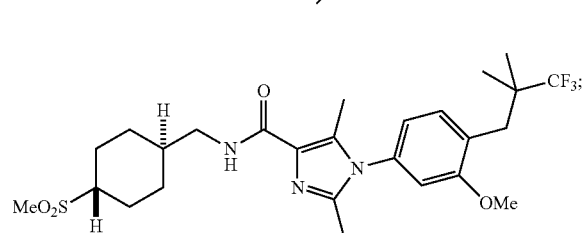
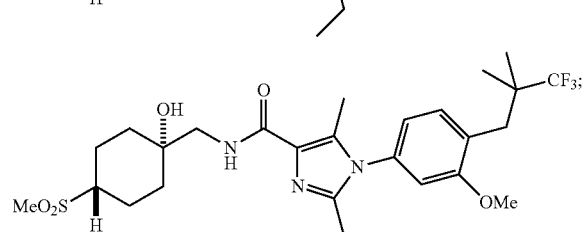
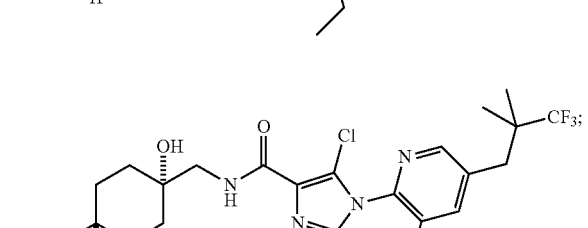
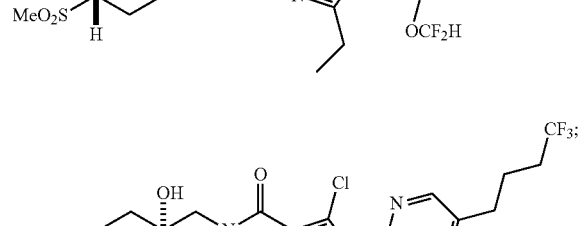
218
-continued
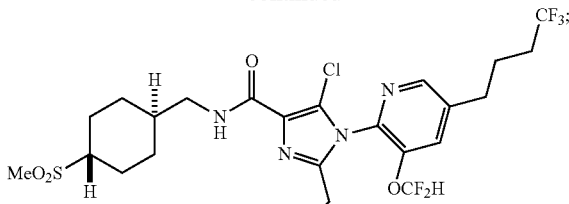
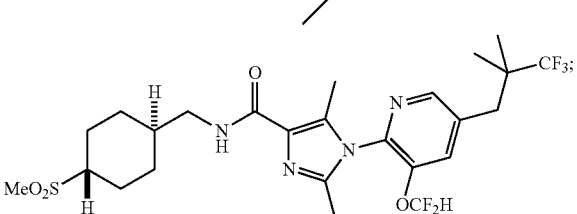
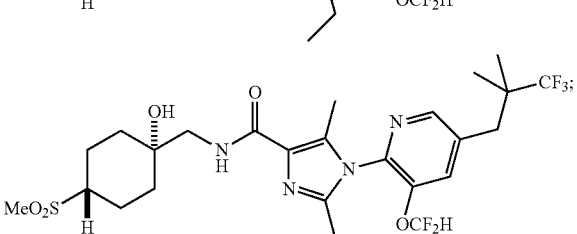
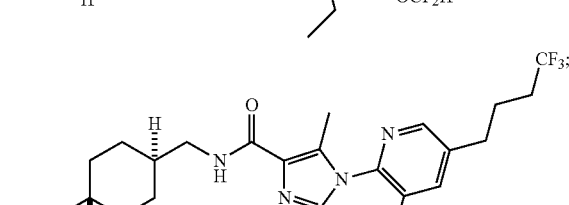
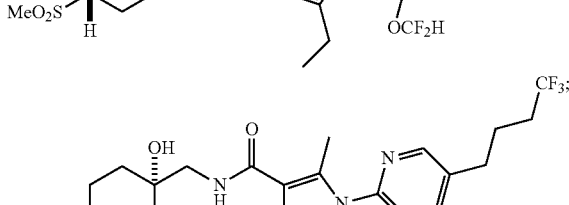
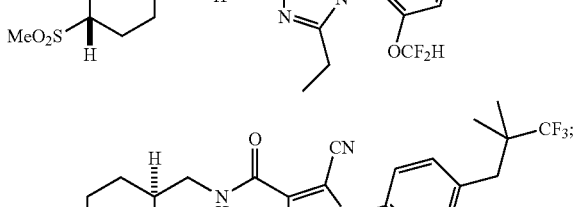
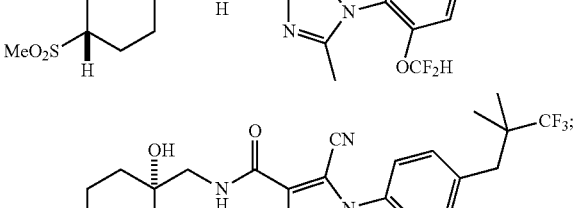
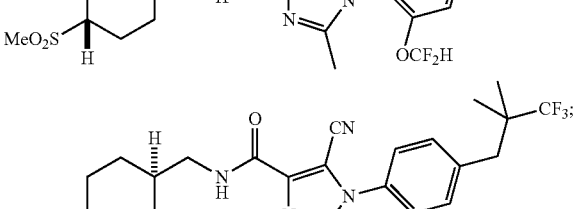

219
-continued
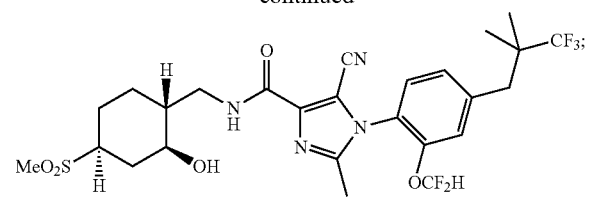
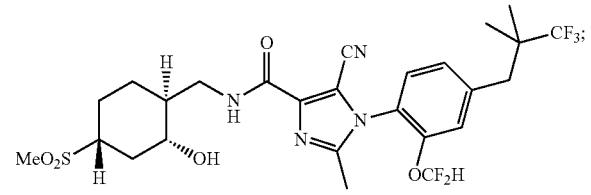
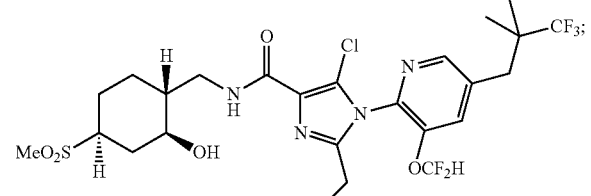
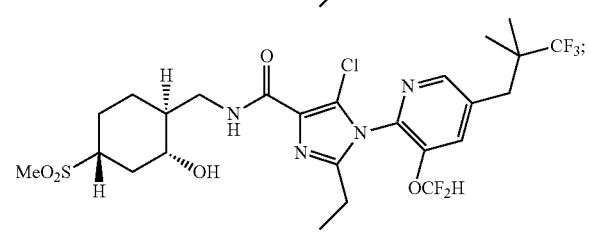
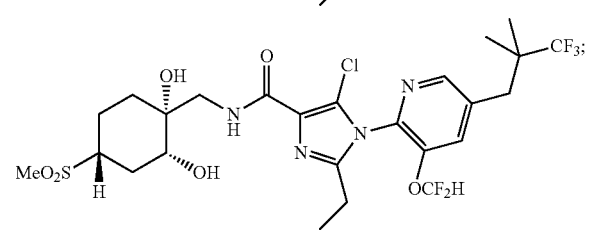
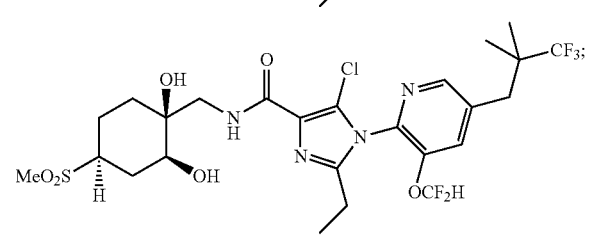
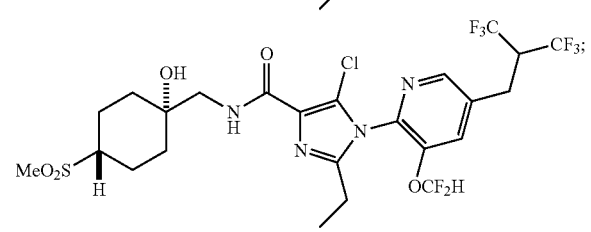
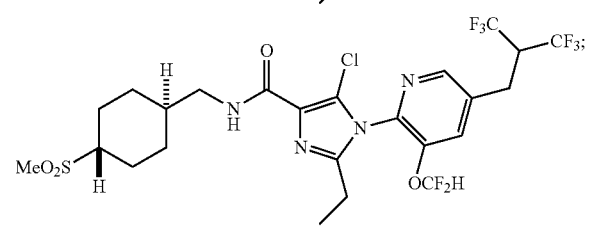
220
-continued
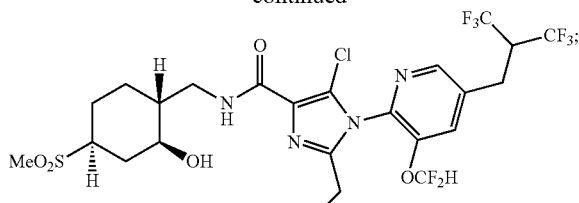
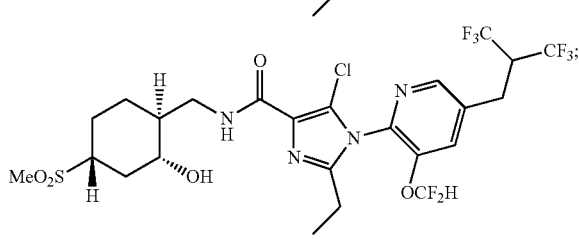
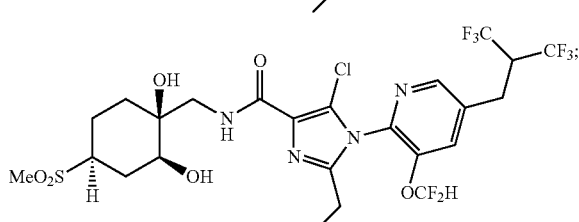
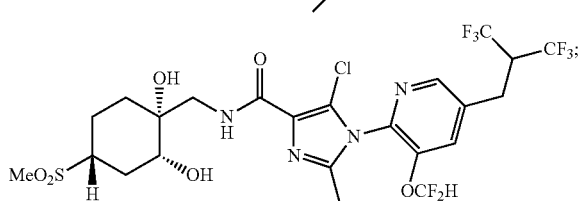
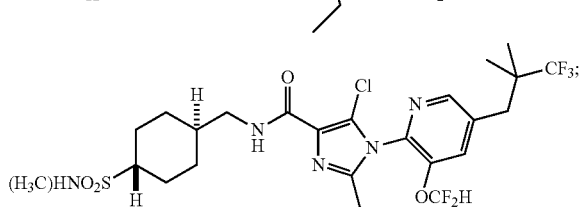
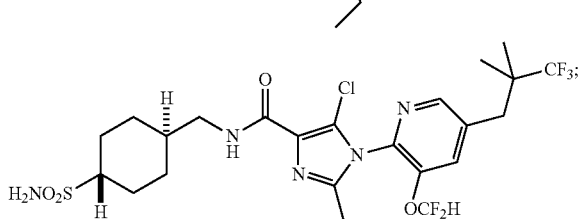
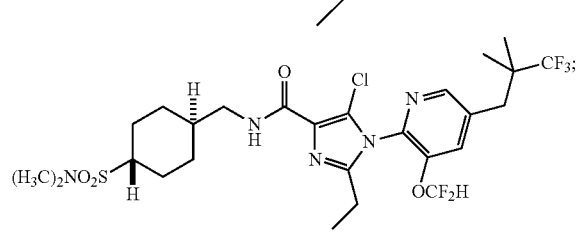
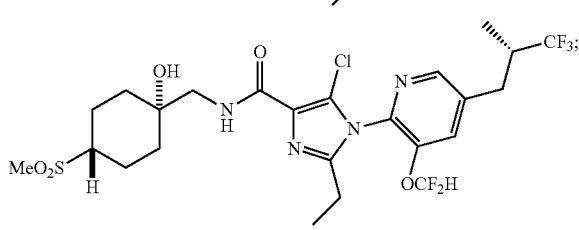

221
-continued
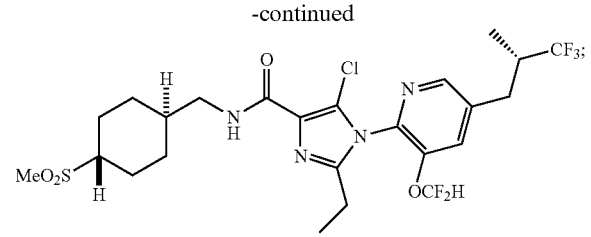
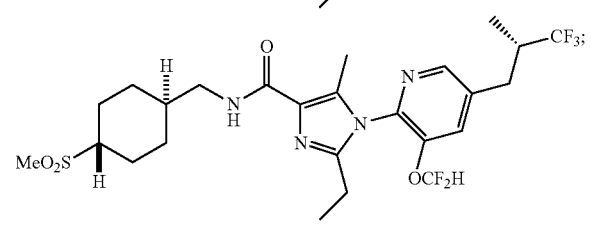
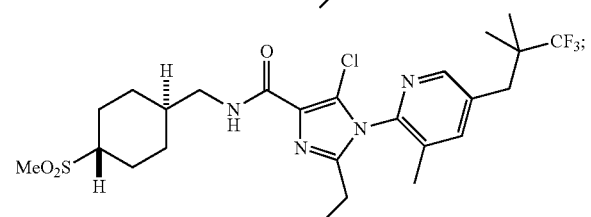
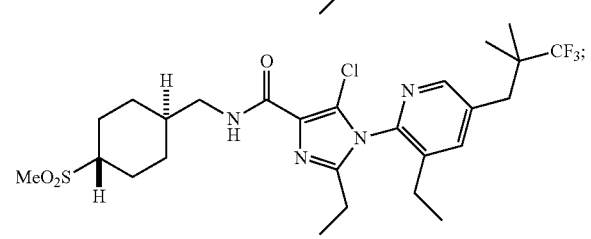
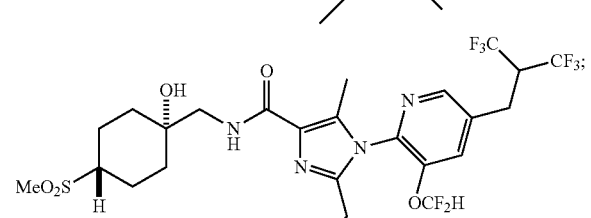
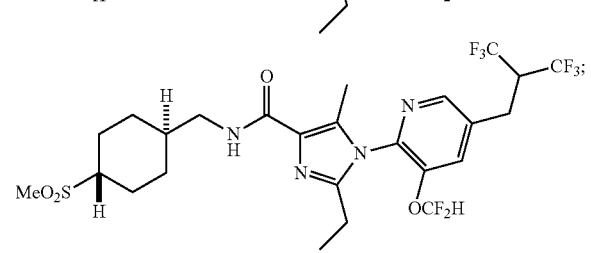
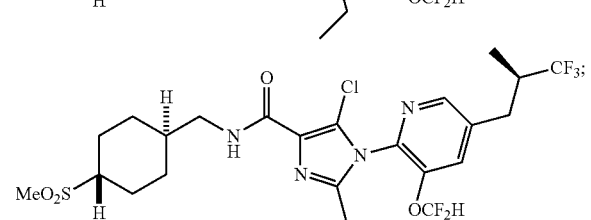
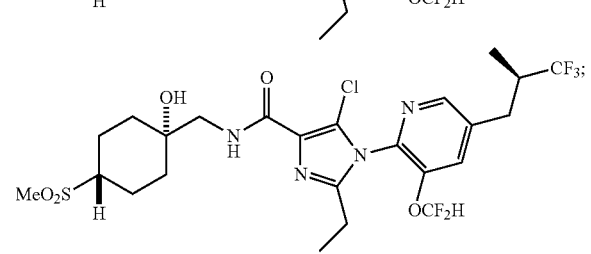
222
-continued
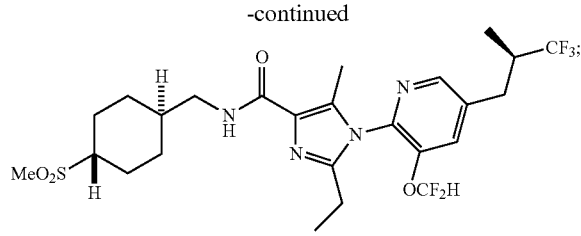
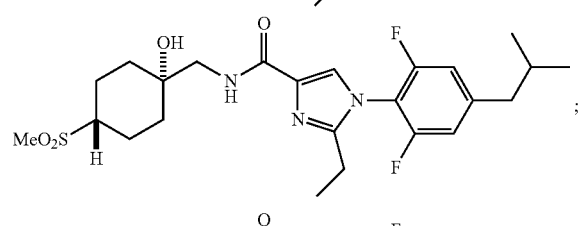
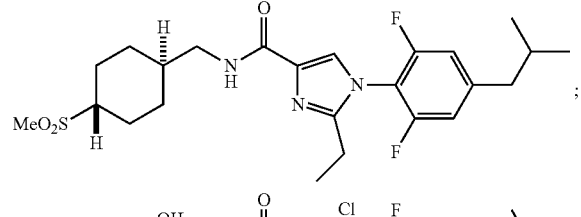
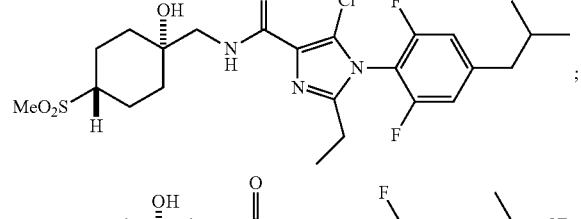
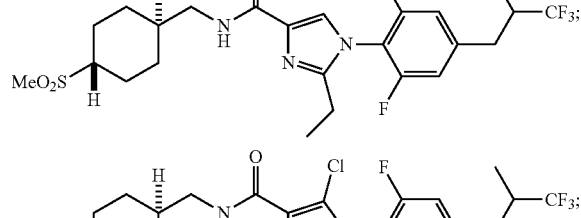
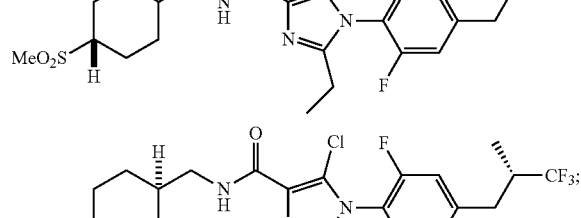
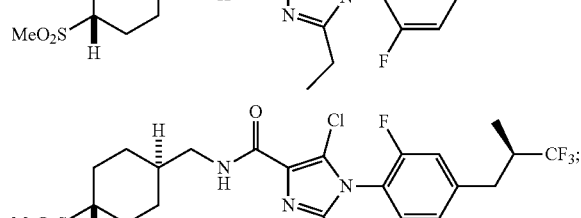
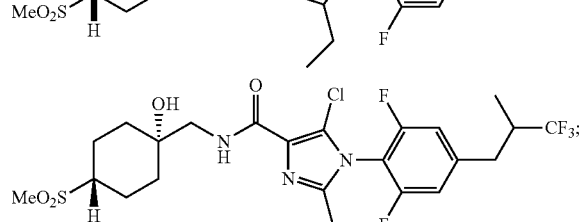

223
-continued
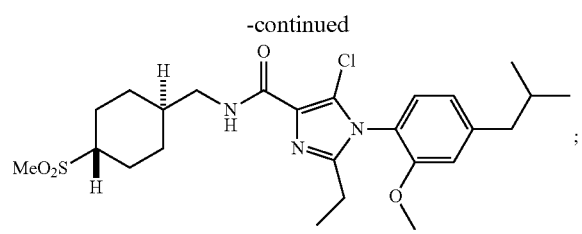
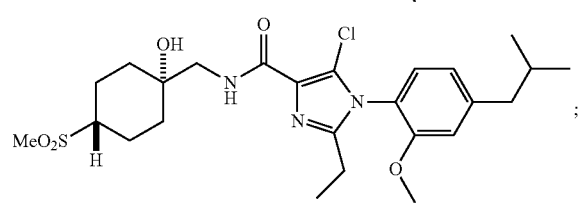
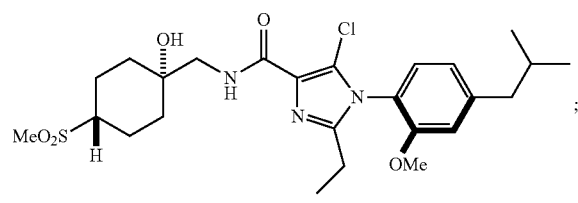
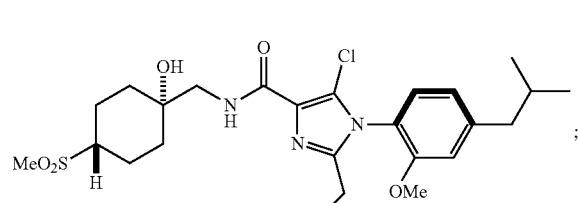
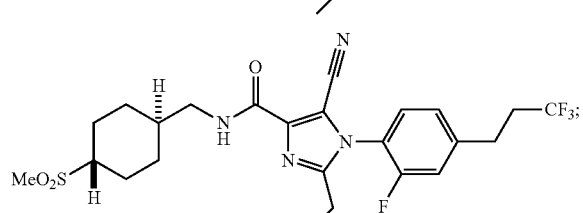
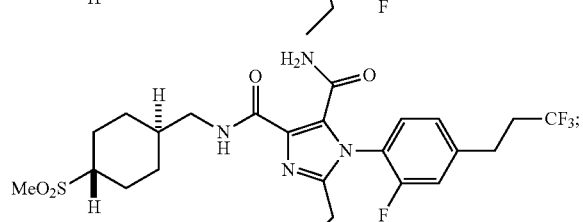
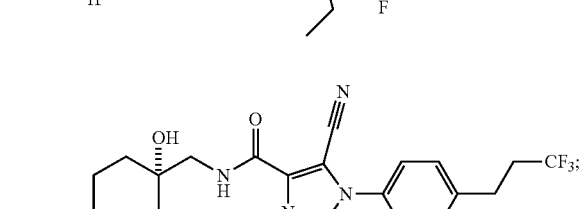
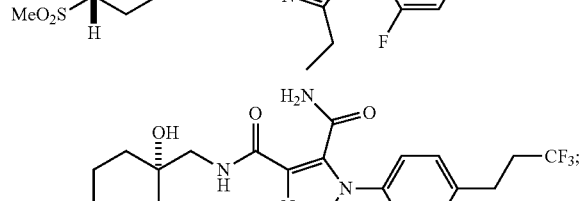
224
-continued
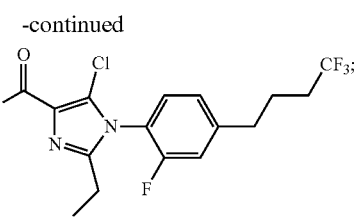
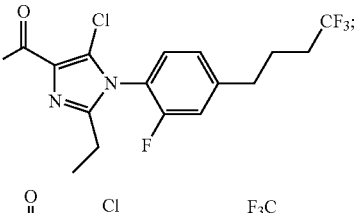
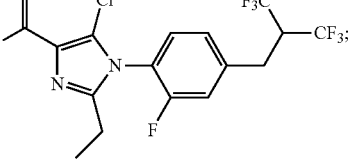
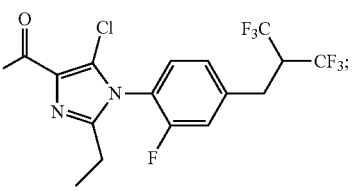
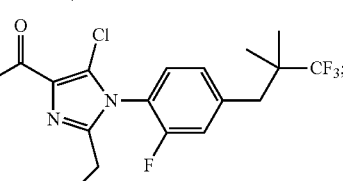
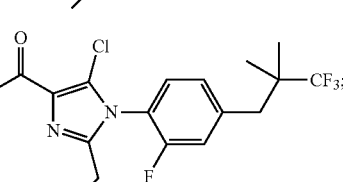
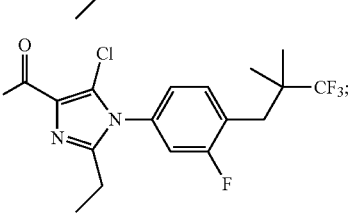
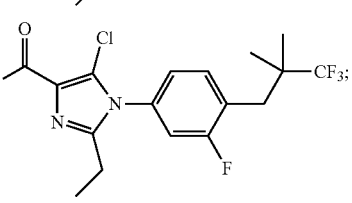
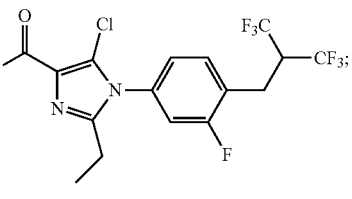

225
-continued
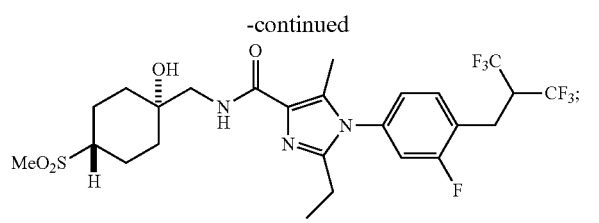
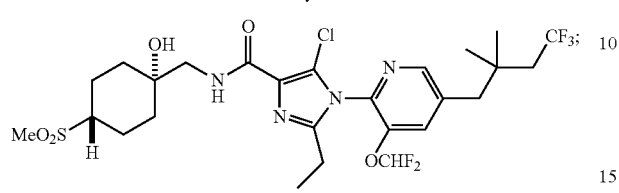
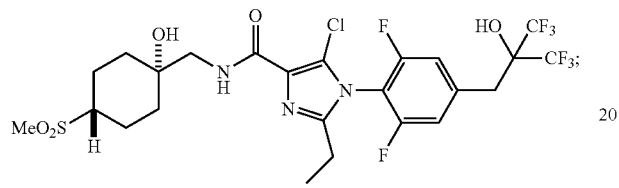
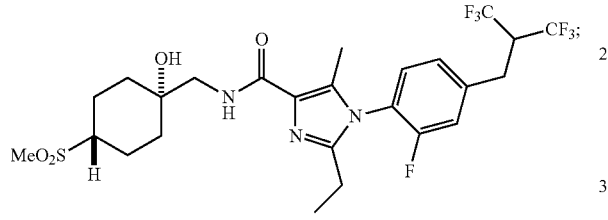
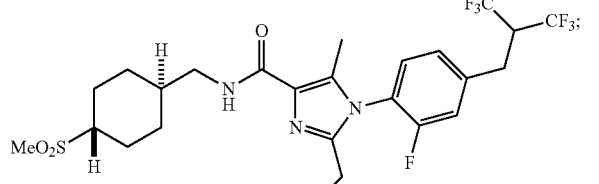
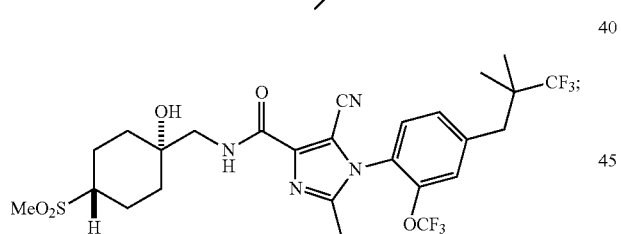
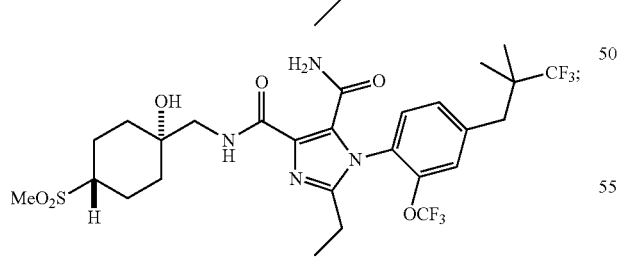
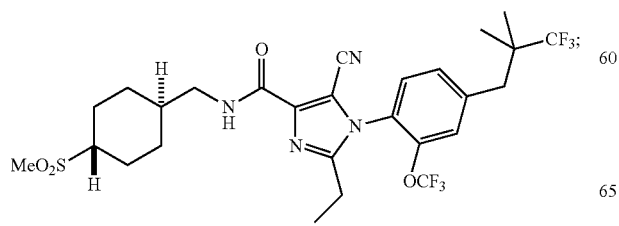
226
-continued
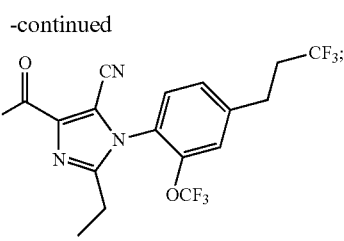
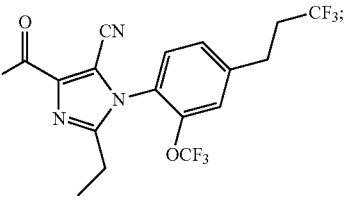
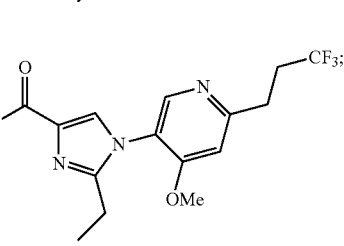
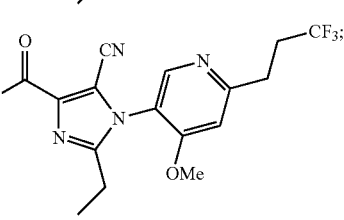
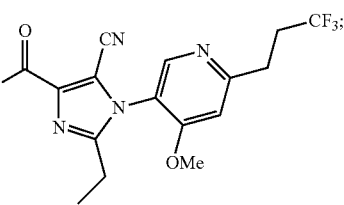
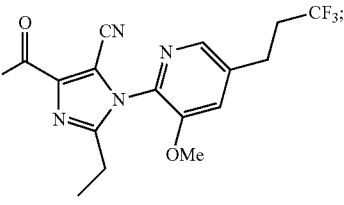
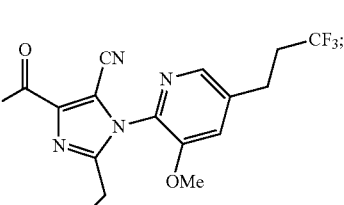
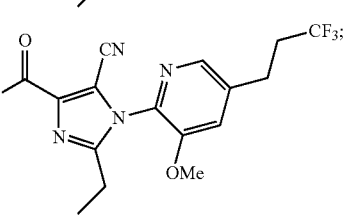

227
-continued
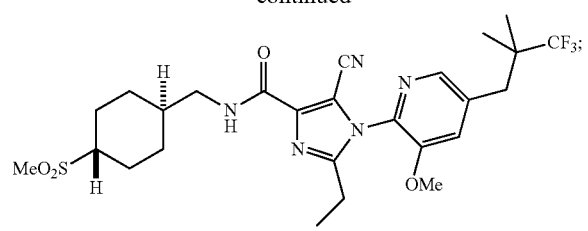
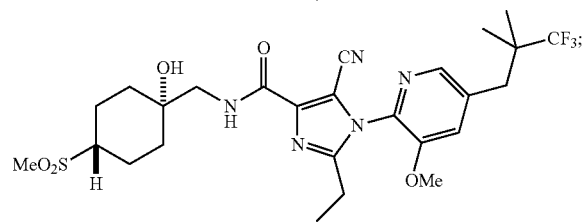
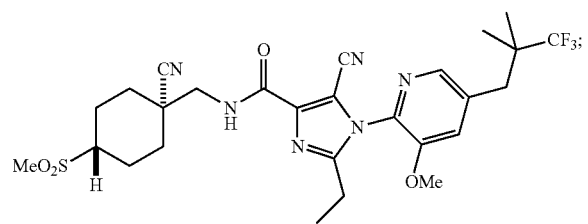
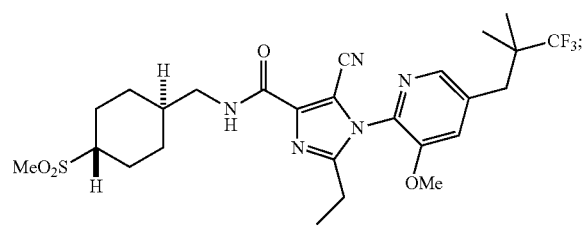
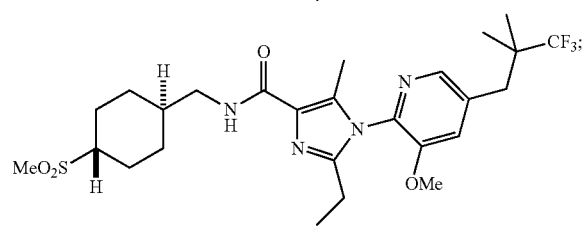
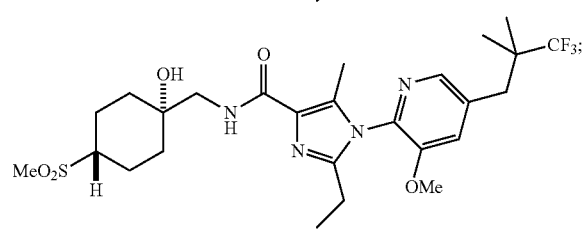
228
-continued
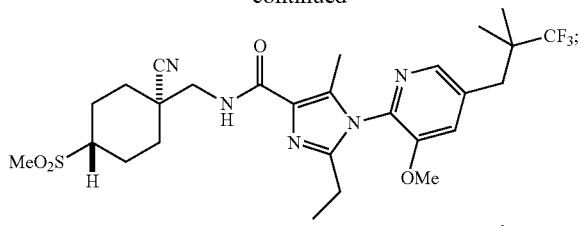
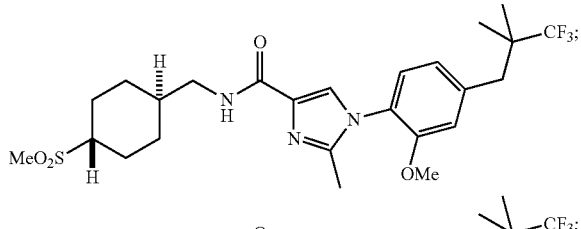
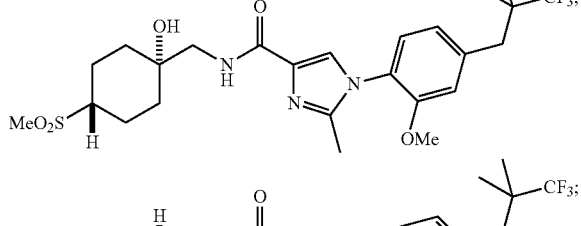
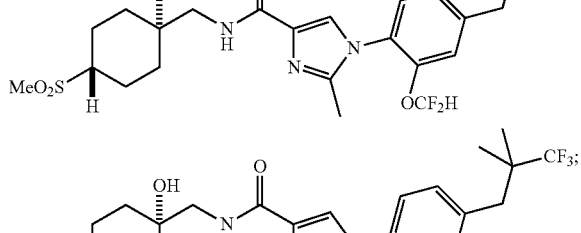
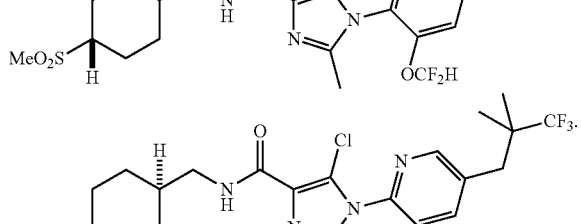
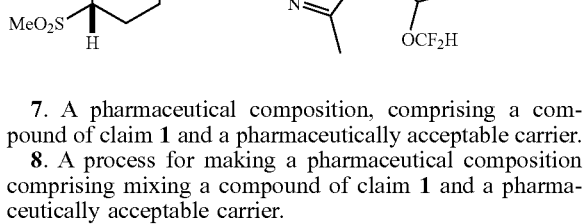
7. A pharmaceutical composition, comprising a compound of claim 1 and a pharmaceutically acceptable carrier.
8. A process for making a pharmaceutical composition comprising mixing a compound of claim 1 and a pharmaceutically acceptable carrier.
* * * * *

SEQUENCE LISTING

```
<160> NUMBER OF SEQ ID NOS: 4

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct      60
gccgccagct gcaccccact cctggaccac cccctgctga aaggacagg gagccaaggc     120 cggcagagcc aaggctcagt catgagaaca caaattgaag tgatcccttg caaaatctgt     180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480
aagacccctc cagcagggc ccaaggagca gatacctca cctacacctt ggggctccca     540
gacgggcagc tgccctggg ctcctcgcct gacctgcctg aggcttctgc ctgtccccct     600
ggcctcctga aagcctcagg ctctgggccc tcatattcca caacttggc caaggcaggg     660 ctcaatgggg cctcatgcca ccttgaatac agccctgagc ggggcaaggc tgagggcaga     720
gagagcttct atagcacagg cagccagctg accctgacc gatgtggact tcgtttgag     780 gaacacaggc atcctgggct tggggaactg ggacagggcc cagacagcta cggcagcccc     840
agtttccgca gcacaccgga ggcaccctat gcctccctga cagagataga gcacctggtg     900
cagagcgtct gcaagtccta cagggagaca tgccagctgc ggctggagga cctgctgcgg     960
cagcgctcca acatcttctc ccgggaggaa gtgactggct accagaggaa gtccatgtgg    1020
gagatgtggg aacggtgtgc ccaccacctc accgaggcca ttcagtacgt ggtggagttc    1080 gccaagagggc tctcaggctt tatggagctc tgccagaatg accagattgt gcttctcaaa    1140
```

| | |
|---|---|
| gcaggagcaa tggaagtggt gctggttagg atgtgccggg cctacaatgc tgacaaccgc | 1200 |
| acggtctttt ttgaaggcaa atacggtggc atggagctgt tccgagcctt gggctgcagc | 1260 |
| gagctcatca gctccatctt tgacttctcc cactccctaa gtgccttgca cttttccgag | 1320 |
| gatgagattg ccctctacac agcccttgtt ctcatcaatg cccatcggcc agggctccaa | 1380 |
| gagaaaagga agtagaaca gctgcagtac aatctggagc tggcctttca tcatcatctc | 1440 |
| tgcaagactc atcgccaaag catcctggca agctgccac ccaaggggaa gcttcggagc | 1500 |
| ctgtgtagcc agcatgtgga aaggctgcag atcttccagc acctccaccc catcgtggtc | 1560 |
| caagccgctt tccctccact ctacaaggag ctcttcagca ctgaaaccga gtcacctgtg | 1620 |
| gggctgtcca agtgacctgg aagagggact ccttgcctct ccctatggcc tgctggccca | 1680 |
| cctccctgga ccccgttcca ccctcaccct tttcctttcc catgaaccct ggagggtggt | 1740 |
| ccccaccagc tctttggaag tgagcagatg ctgcggctgg ctttctgtca gcaggccggc | 1800 |
| ctggcagtgg gacaatcgcc agagggtggg gctggcagaa caccatctcc agcctcagct | 1860 |
| ttgacctgtc tcatttccca tattccttca cacccagctt ctggaaggca tggggtggct | 1920 |
| gggatttaag gacttctggg ggaccaagac atcctcaaga aaacaggggc atccagggct | 1980 |
| ccctggatga atagaatgca attcattcag aagctcagaa gctaagaata agcctttgaa | 2040 |
| atacctcatt gcatttccct ttgggcttcg gcttggggag atggatcaag ctcagagact | 2100 |
| ggcagtgaga gcccagaagg acctgtataa aatgaatctg gagctttaca ttttctgcct | 2160 |
| ctgccttcct cccagctcag caaggaagta tttgggcacc ctaccctta cctggggtct | 2220 |
| aaccaaaaat ggatgggatg aggatgagag gctggagata attgttttat gggatttggg | 2280 |
| tgtgggacta gggtacaatg aaggccaaga gcatctcaga catagagtta aaactcaaac | 2340 |
| ctcttatgtg cactttaaag atagacttta ggggctggca caaatctgat cagagacaca | 2400 |
| tatccataca caggtgaaac acatacagac tcaacagcaa tcatgcagtt ccagagacac | 2460 |
| atgaacctga cacaatctct cttatccttg aggccacagc ttggaggagc ctagaggcct | 2520 |
| caggggaaag tcccaatcct gagggaccct cccaaacatt tccatggtgc tccagtccac | 2580 |
| tgatcttggg tctggggtga tccaaatacc acccagctc cagctgtctt ctaccactag | 2640 |
| aagacccaag agaagcagaa gtcgctcgca ctggtcagtc ggaaggcaag atcagatcct | 2700 |
| ggaggacttt cctggcctgc ccgccagccc tgctcttgtt gtggagaagg aagcagatgt | 2760 |
| gatcacatca ccccgtcatt gggcaccgct gactccagca tggaggacac cagggagcag | 2820 |
| ggcctgggcc tgtttcccca gctgtgatct tgcccagaac ctctcttggc ttcataaaca | 2880 |
| gctgtgaacc ctcccctgag ggattaacag caatgatggg cagtcgtgga gttgggggggg | 2940 |
| ttggggggtgg gattgtgtcc tctaagggga cgggttcatc tgagtaaaca taaaccccaa | 3000 |
| cttgtgccat tctttataaa atgattttaa aggcaaaaaa aaaaaaaaaa aaaa | 3054 |

<210> SEQ ID NO 2
<211> LENGTH: 786
<212> TYPE: DNA
<213> ORGANISM: Homo sapiens

<400> SEQUENCE: 2

| | |
|---|---|
| agcacaccgg aggcacccta tgcctccctg acagagatag agcacctggt gcagagcgtc | 60 |
| tgcaagtcct acagggagac atgccagctg cggctggagg acctgctgcg gcagcgctcc | 120 |
| aacatcttct cccgggagga agtgactggc taccagagga agtccatgtg ggagatgtgg | 180 |
| gaacggtgtg cccaccacct caccgaggcc attcagtacg tggtggagtt cgccaagagg | 240 |

-continued

```
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                                786
```

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
                20                  25                  30

Thr Glu Ile Glu His Leu Val Gln Ser Val Cys Lys Ser Tyr Arg Glu
            35                  40                  45

Thr Cys Gln Leu Arg Leu Glu Asp Leu Leu Arg Gln Arg Ser Asn Ile
        50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
            180                 185                 190

```
Ala His Arg Pro Gly Leu Gln Glu Lys Arg Lys Val Glu Gln Leu Gln
    195                 200                 205

Tyr Asn Leu Glu Leu Ala Phe His His His Leu Cys Lys Thr His Arg
    210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
                260                 265                 270

Thr Glu Thr Glu Ser Pro Val Gly Leu Ser Lys
    275                 280
```